(12) United States Patent
Okada et al.

(10) Patent No.: US 7,829,113 B2
(45) Date of Patent: Nov. 9, 2010

(54) LIPOSOME COMPOSITIONS

(75) Inventors: Kazushi Okada, Yokohama (JP); Tadayuki Ibuki, Funabashi (JP); Donghyun Kim, Ota-ku (JP); Tadashi Fujisawa, Minato-ku (JP)

(73) Assignee: Mebiopharm Co., Ltd., Yokohama-shi (JP)

( * ) Notice: Subject to any disclaimer, the term of this patent is extended or adjusted under 35 U.S.C. 154(b) by 0 days.

(21) Appl. No.: 11/371,586

(22) Filed: Mar. 8, 2006

(65) Prior Publication Data

US 2006/0222696 A1    Oct. 5, 2006

(30) Foreign Application Priority Data

Mar. 10, 2005    (JP)    ............... 2005-067469

(51) Int. Cl.
    *A61K 9/127*    (2006.01)
(52) U.S. Cl. .................................... 424/450
(58) Field of Classification Search ................ 424/450
    See application file for complete search history.

(56) References Cited

U.S. PATENT DOCUMENTS

| | | | |
|---|---|---|---|
| 4,169,846 A | 10/1979 | Kidani et al. | |
| 4,235,871 A | 11/1980 | Papahadjopoulos et al. | |
| 4,452,812 A | 6/1984 | Macquet | |
| 4,534,899 A | 8/1985 | Sears | |
| 4,565,696 A | 1/1986 | Heath et al. | |
| 4,789,633 A | 12/1988 | Huang et al. | |
| 4,925,661 A | 5/1990 | Huang | |
| 4,983,397 A | 1/1991 | Schroit et al. | |
| 5,013,556 A | 5/1991 | Woodle et al. | |
| 5,026,651 A | 6/1991 | Bowman et al. | |
| 5,049,390 A | 9/1991 | Wojdani | |
| 5,080,904 A | 1/1992 | Iga et al. | |
| 5,151,264 A | 9/1992 | Samain et al. | |
| 5,290,961 A | 3/1994 | Okamoto et al. | |
| 5,292,524 A | 3/1994 | Male et al. | |
| 5,298,642 A | 3/1994 | Tozawa et al. | |
| 5,338,874 A | 8/1994 | Nakanishi et al. | |
| 5,384,127 A | 1/1995 | Perez-Soler et al. | |
| 5,419,914 A * | 5/1995 | Sullivan .................. 424/450 | |
| 5,420,319 A | 5/1995 | Okamoto et al. | |
| 5,534,241 A | 7/1996 | Torchilin et al. | |
| 5,554,728 A | 9/1996 | Basava et al. | |
| 5,593,622 A | 1/1997 | Yoshioka et al. | |
| 5,648,478 A | 7/1997 | Henderson | |
| 5,676,928 A | 10/1997 | Klaveness et al. | |
| 5,676,971 A | 10/1997 | Yoshioka et al. | |
| 5,683,715 A | 11/1997 | Boni et al. | |
| 5,716,988 A | 2/1998 | Ibrahim et al. | |
| 5,736,155 A | 4/1998 | Bally et al. | |
| 5,756,069 A | 5/1998 | Torchilin et al. | |
| 5,780,052 A | 7/1998 | Khaw et al. | |
| 5,786,214 A | 7/1998 | Holmberg | |
| 5,804,552 A | 9/1998 | Basava et al. | |
| 5,834,012 A | 11/1998 | Perez-Soler et al. | |
| 5,846,458 A | 12/1998 | Yoshioka et al. | |
| 5,891,468 A | 4/1999 | Martin et al. | |
| 5,945,122 A | 8/1999 | Abra et al. | |
| 5,959,133 A | 9/1999 | Ohnishi | |
| 6,046,225 A | 4/2000 | Maddock | |
| 6,056,973 A * | 5/2000 | Allen et al. ................ 424/450 | |
| 6,057,299 A | 5/2000 | Henderson | |
| 6,063,780 A | 5/2000 | Dexter et al. | |
| 6,077,834 A | 6/2000 | Cheng | |
| 6,087,325 A * | 7/2000 | Meers et al. .................. 514/2 | |
| 6,120,797 A | 9/2000 | Meers et al. | |
| 6,126,966 A | 10/2000 | Abra et al. | |
| 6,153,596 A | 11/2000 | Liotta et al. | |
| 6,153,646 A | 11/2000 | Kidani et al. | |
| 6,177,059 B1 | 1/2001 | Matsuda et al. | |
| 6,197,333 B1 | 3/2001 | Onyuksel et al. | |
| 6,228,391 B1 | 5/2001 | Shimizu et al. | |
| 6,242,188 B1 | 6/2001 | Dattagupta et al. | |
| 6,245,427 B1 | 6/2001 | Düzgünes et al. | |
| 6,272,370 B1 | 8/2001 | Gillies et al. | |
| 6,284,277 B1 | 9/2001 | Bouloumie et al. | |
| 6,294,191 B1 | 9/2001 | Meers et al. | |
| 6,306,902 B1 | 10/2001 | Anderson et al. | |
| 6,316,024 B1 | 11/2001 | Allen et al. | |
| 6,319,923 B1 | 11/2001 | Dexter et al. | |
| 6,387,397 B1 | 5/2002 | Chen et al. | |
| 6,476,068 B1 | 11/2002 | Lauria et al. | |
| 6,511,453 B2 | 1/2003 | Georgieff | |

(Continued)

FOREIGN PATENT DOCUMENTS

AU    2252499 B2    3/2000

(Continued)

OTHER PUBLICATIONS

Oradd et al, Biophys. J. 83:2702-2704, 2002.*

(Continued)

*Primary Examiner*—Kevin K. Hill
(74) *Attorney, Agent, or Firm*—Morrison & Foerster LLP

(57) ABSTRACT

The present disclosure provides lipid-containing compositions, including targeted liposomes encapsulating drug, and pharmaceutical formulations thereof, as well as methods for the making and using the lipid-containing compositions, including the use of the targeted liposomes in the treatment of cancer and other diseases.

48 Claims, 30 Drawing Sheets

U.S. PATENT DOCUMENTS

| | | | |
|---|---|---|---|
| 6,518,278 B1 | 2/2003 | Oguro et al. | |
| 6,524,613 B1 | 2/2003 | Steer et al. | |
| 6,530,944 B2 | 3/2003 | West et al. | |
| 6,586,559 B2 | 7/2003 | Ansell | |
| 6,617,161 B2 | 9/2003 | Luyten et al. | |
| 6,627,218 B2 | 9/2003 | Huang et al. | |
| 6,703,524 B2 | 3/2004 | Lam et al. | |
| 6,723,338 B1 | 4/2004 | Sarris et al. | |
| 6,749,863 B1 | 6/2004 | Chang et al. | |
| 6,790,632 B2 | 9/2004 | Zweig | |
| 6,808,720 B2 * | 10/2004 | Unger | 424/450 |
| 6,866,857 B1 | 3/2005 | Mauverney | |
| 6,897,196 B1 | 5/2005 | Szoka, Jr. et al. | |
| 6,936,272 B2 | 8/2005 | Martin et al. | |
| 7,012,072 B2 * | 3/2006 | Ibrahim et al. | 514/186 |
| 7,034,006 B2 * | 4/2006 | Yedgar et al. | 514/42 |
| 2001/0006775 A1 | 7/2001 | Oku et al. | |
| 2001/0031473 A1 | 10/2001 | Dattagupta et al. | |
| 2001/0033860 A1 | 10/2001 | Gwathmey | |
| 2001/0038851 A1 | 11/2001 | Allen et al. | |
| 2001/0039050 A1 | 11/2001 | Luyten et al. | |
| 2001/0044147 A1 | 11/2001 | Sullivan et al. | |
| 2002/0025305 A1 | 2/2002 | Beach et al. | |
| 2002/0034537 A1 | 3/2002 | Schulze et al. | |
| 2002/0038464 A1 | 3/2002 | Charron et al. | |
| 2002/0068273 A1 | 6/2002 | Jacotot et al. | |
| 2002/0082392 A1 | 6/2002 | Beach et al. | |
| 2002/0136707 A1 | 9/2002 | Yu et al. | |
| 2002/0146773 A1 | 10/2002 | Graff et al. | |
| 2002/0164289 A1 | 11/2002 | McMurray et al. | |
| 2002/0164338 A1 | 11/2002 | Iversen | |
| 2002/0198164 A1 | 12/2002 | Henderson | |
| 2003/0027779 A1 | 2/2003 | Neuman et al. | |
| 2003/0059461 A1 | 3/2003 | Backer et al. | |
| 2003/0072794 A1 | 4/2003 | Boulikas | |
| 2003/0082228 A1 | 5/2003 | Flowers et al. | |
| 2003/0087845 A1 | 5/2003 | Nyce | |
| 2003/0096299 A1 | 5/2003 | Wittamer et al. | |
| 2003/0100489 A1 | 5/2003 | Beach et al. | |
| 2003/0104478 A1 | 6/2003 | Wittamer et al. | |
| 2003/0108986 A1 | 6/2003 | Communi et al. | |
| 2003/0113262 A1 | 6/2003 | Ikeda et al. | |
| 2003/0129223 A1 | 7/2003 | Wartchow et al. | |
| 2003/0130190 A1 | 7/2003 | Hallahan et al. | |
| 2003/0143742 A1 | 7/2003 | Goomer | |
| 2003/0162748 A1 | 8/2003 | Jorgensen et al. | |
| 2003/0165934 A1 | 9/2003 | Elledge et al. | |
| 2003/0166601 A1 | 9/2003 | Woodle et al. | |
| 2003/0175205 A1 | 9/2003 | Jorgensen et al. | |
| 2003/0175285 A1 | 9/2003 | Klinguer-Hamour et al. | |
| 2003/0175775 A1 | 9/2003 | LePoul et al. | |
| 2003/0180223 A1 | 9/2003 | McMurray et al. | |
| 2003/0190638 A1 | 10/2003 | West et al. | |
| 2003/0203865 A1 | 10/2003 | Harvie et al. | |
| 2003/0212031 A1 | 11/2003 | Huang et al. | |
| 2003/0215490 A1 | 11/2003 | Allen et al. | |
| 2003/0220284 A1 | 11/2003 | Yotnda et al. | |
| 2003/0224037 A1 | 12/2003 | Eriguchi et al. | |
| 2003/0228285 A1 | 12/2003 | Hung et al. | |
| 2003/0232756 A1 | 12/2003 | Brezillion et al. | |
| 2004/0009164 A1 | 1/2004 | Reeves et al. | |
| 2004/0022842 A1 | 2/2004 | Eriguchi et al. | |
| 2004/0029210 A1 | 2/2004 | Robillot et al. | |
| 2004/0044076 A1 | 3/2004 | Goldenberg | |
| 2004/0049022 A1 | 3/2004 | Nyce et al. | |
| 2004/0057902 A1 | 3/2004 | Gold et al. | |
| 2004/0071768 A1 | 4/2004 | Sarris et al. | |
| 2004/0072146 A1 | 4/2004 | Jacotot et al. | |
| 2004/0115193 A1 | 6/2004 | Hansen et al. | |
| 2004/0126431 A1 | 7/2004 | Lagarce et al. | |
| 2004/0132652 A1 | 7/2004 | Martin et al. | |
| 2004/0137487 A1 | 7/2004 | Chandy et al. | |
| 2004/0142025 A1 | 7/2004 | MacLachlan et al. | |
| 2004/0180380 A1 | 9/2004 | Lee et al. | |
| 2004/0186172 A1 | 9/2004 | Ibrahim | |
| 2004/0197770 A1 | 10/2004 | Sperber et al. | |
| 2004/0213833 A1 | 10/2004 | Penate Medina et al. | |
| 2004/0220078 A1 | 11/2004 | Ibrahim | |
| 2004/0234588 A1 | 11/2004 | Lu et al. | |
| 2004/0235065 A1 | 11/2004 | Hansen et al. | |
| 2004/0265392 A1 | 12/2004 | Tovar et al. | |
| 2005/0003403 A1 | 1/2005 | Rossi et al. | |
| 2005/0014207 A1 | 1/2005 | Goldenberg et al. | |
| 2005/0025709 A1 | 2/2005 | McBride et al. | |
| 2005/0070693 A1 | 3/2005 | Hansen et al. | |
| 2005/0100963 A1 | 5/2005 | Sato et al. | |
| 2005/0107287 A1 | 5/2005 | Pilkiewicz et al. | |
| 2005/0118103 A1 | 6/2005 | Lauffer et al. | |
| 2005/0136064 A1 | 6/2005 | Allen et al. | |
| 2005/0271588 A1 | 12/2005 | Medina et al. | |

FOREIGN PATENT DOCUMENTS

| | | |
|---|---|---|
| EP | 0 039 272 A2 | 11/1981 |
| EP | 0 039 272 A3 | 11/1981 |
| EP | 0 039 272 B1 | 11/1981 |
| EP | 0 322 319 A2 | 6/1989 |
| EP | 0 322 319 A3 | 6/1989 |
| EP | 0 322 319 B1 | 6/1989 |
| EP | 0 567 438 A1 | 10/1993 |
| EP | 0 567 438 B1 | 10/1993 |
| EP | 0 617 043 A1 | 9/1994 |
| EP | 0 617 043 B1 | 9/1994 |
| EP | 0 625 523 A1 | 11/1994 |
| EP | 0 625 523 B1 | 11/1994 |
| EP | 0 715 854 A2 | 6/1996 |
| EP | 0 715 854 A3 | 6/1996 |
| EP | 0 715 854 B1 | 6/1996 |
| EP | 0 774 963 B1 | 5/1997 |
| EP | 0 897 389 B1 | 2/1999 |
| EP | 0 943 331 A2 | 9/1999 |
| EP | 0 943 331 A3 | 9/1999 |
| EP | 0 943 331 B1 | 9/1999 |
| EP | 1 014 990 B1 | 7/2000 |
| EP | 1 121 117 B1 | 8/2001 |
| EP | 1 207 875 B1 | 5/2002 |
| EP | 1 209 469 A1 | 5/2002 |
| EP | 1 308 453 A2 | 5/2003 |
| EP | 1 308 453 A3 | 5/2003 |
| EP | 1 324 758 A1 | 7/2003 |
| EP | 1 324 758 B1 | 7/2003 |
| EP | 1 341 555 A0 | 9/2003 |
| EP | 1 368 022 A0 | 12/2003 |
| EP | 1 369 132 A1 | 12/2003 |
| EP | 1 369 166 A1 | 12/2003 |
| EP | 1 404 689 A0 | 4/2004 |
| EP | 1 568 360 A1 | 8/2005 |
| EP | 1 579 850 A2 | 9/2005 |
| JP | 62-207283 A2 | 9/1987 |
| JP | 5-331648 A2 | 12/1993 |
| JP | 5-345792 A2 | 12/1993 |
| JP | 7-501316 T | 2/1995 |
| JP | 7-082286 A2 | 3/1995 |
| JP | 9-040632 A | 2/1997 |
| JP | 9-040685 A | 2/1997 |
| JP | 2001-002592 A | 1/2001 |
| JP | 2001-261688 A | 9/2001 |
| JP | 2002-205945 A | 7/2002 |
| JP | 2005-154282 A | 6/2005 |
| WO | WO-86/01102 A1 | 2/1986 |
| WO | WO-86/04232 A1 | 7/1986 |
| WO | WO-91/04014 A1 | 4/1991 |
| WO | WO-92/07959 A1 | 5/1992 |
| WO | WO-93/01828 A1 | 2/1993 |

| | | | |
|---|---|---|---|
| WO | WO-94/12193 A1 | 6/1994 |
| WO | WO-94/23697 A1 | 10/1994 |
| WO | WO-95/19434 A1 | 7/1995 |
| WO | WO-95/33841 A1 | 12/1995 |
| WO | WO-96/04904 A1 | 2/1996 |
| WO | WO-96/10391 A1 | 4/1996 |
| WO | WO-96/13250 A1 | 5/1996 |
| WO | WO-96/21658 A1 | 7/1996 |
| WO | WO-96/33698 A1 | 10/1996 |
| WO | WO-97/33894 A1 | 9/1997 |
| WO | WO-98/01454 A1 | 1/1998 |
| WO | WO-98/07409 A2 | 2/1998 |
| WO | WO-98/33481 A1 | 8/1998 |
| WO | WO-98/39009 A1 | 9/1998 |
| WO | WO-99/25320 A1 | 5/1999 |
| WO | WO-99/30686 A1 | 6/1999 |
| WO | WO-99/40789 A1 | 8/1999 |
| WO | WO-99/43355 A2 | 9/1999 |
| WO | WO-99/43355 A3 | 9/1999 |
| WO | WO-00/21527 A2 | 4/2000 |
| WO | WO-00/74646 A2 | 12/2000 |
| WO | WO-00/74646 A3 | 12/2000 |
| WO | WO-01/15691 A1 | 3/2001 |
| WO | WO-01/34130 A1 | 5/2001 |
| WO | WO-01/37807 A1 | 5/2001 |
| WO | WO-01/49266 A2 | 7/2001 |
| WO | WO-01/49266 A3 | 7/2001 |
| WO | WO-02/28386 A1 | 4/2002 |
| WO | WO-02/41870 A2 | 5/2002 |
| WO | WO-02/41870 A3 | 5/2002 |
| WO | WO-02/47725 A2 | 6/2002 |
| WO | WO-02/069959 A1 | 9/2002 |
| WO | WO-03/004505 A1 | 1/2003 |
| WO | WO-2004/071518 A1 | 8/2004 |
| WO | WO-2006/099169 A2 | 9/2006 |
| WO | WO-2006/099169 A3 | 9/2006 |
| WO | WO-2008/030818 A2 | 3/2008 |
| WO | WO-2008/030818 A3 | 3/2008 |

OTHER PUBLICATIONS

Tardi et al, Cancer Res. 60:3389-3393, 2000.*

Culy et al, Drugs 60(4):895-924, 2000; Abstract only.*

International Search Report mailed on Dec. 28, 2006 for PCT Application No. PCT/US2006/008650 filed on Mar. 8, 2006, four pages.

Maruyama, K. et al. (2004). "Intracellular Targeting of Sodium Mercaptoundecahydrododecaborate (BSH) to Solid Tumors by Transferrin-PEG Liposomes, for Boron Neutron-Capture Therapy (BNCT)," *Journal of Controlled Release* 98(2):195-207.

Afzelius, P. et al. (1989). "Covalent Modification of Serum Transferrin with Phospholipid and Incorporation into Liposomal Membranes," *Biochimica et Biophysica Acta* 979:231-238.

Bogdanov Jr., A.A. et al. (Apr. 1988). "Protein Immobilization on the Surface of Liposomes via Carbodiimide Activation in the Presence of N-hydroxysulfosuccinimide," *FEBS Letters* 231(2):381-384.

Feero, W.G. et al. (1997). "Selection and Use of Ligands for Receptor-Mediated Gene Delivery to Myogenic Cells," *Gene Therapy* 4:664-674.

Hatakeyama, H. et al. (2004). "Factors Governing the In Vivo Tissue Uptake of Transferrin-Coupled Polyethylene Glycol Liposomes In Vivo," *International Journal of Pharmaceuticals* 281:25-33.

International Preliminary Report on Patentability mailed Sep. 12, 2007, for PCT Application No. PCT/US2006/008650, filed Mar. 8, 2006, nine pages.

Kakudo, T. et al. (2004). "Transferrin-Modified Liposomes Equipped with a pH-Sensitive Fusogenic Peptide: An Artificial Viral-like Delivery System," *Biochemistry* 43(19):5618-5628.

Khatri, K. et al. (Jul. 2005). "Hepatitis B Surface Protein Docked Vesicular Carrier for Site Specific Delivery to Liver," *Journal of Drug Targeting* 13(6):359-366.

Kinsky, S.C. et al. (Jan. 25, 1984). "Synthesis of N-Hydroxysuccinimide Esters of Phosphatidylethanolamine and Some Properties of Liposomes Containing These Derivatives," *Biochimica et Biophysica Acta* 769(2):543-550.

Kung, V.T. et al. (1986). "Synthesis of Carboxyacyl Derivatives of Phosphatidylethanolamine and Use as an Efficient Method for Conjugation of Protein to Liposomes," *Biochimica et Biophysica Acta* 862:435-439.

Maruyama, K. (2004). "Drug Delivery System by Stealth Liposome," *Pharm. Tech. Japan* 20(5):963-973. (Japanese Language Article, English Abstract only.).

Matsuo, H. et al. (2001). "Possibility of the Reversal of Multidrug Resistance and the Avoidance of Side Effects by Liposomes Modified with MRK-16, a Monoclonal Antibody to P-glycoprotein," *Journal of Controlled Release* 77:77-86.

Mori, A. et al. (1995). "Characterization of Organ-Specific Immunoliposomes for Delivery of 3',5'-O-dipalmitoyl-5-fluro-2'-deoxyuridine in a Mouse Lung-Metastasis Model," *Cancer Chemother. Pharmacol.* 35:447-456.

Muñoz, M. et al. (1998). "Physico-Chemical Characterization of Liposomes with Covalently Attached Hepatitis A VP3(101-121) Synthetic Peptide," *Analyst* 123:2223-2228.

Ng, K-Y. et al. (2000). "The Effects of Polyethyleneglycol (PEG)-Derived Lipid on the Activity of Target-Sensitive Immunoliposome," *International Journal of Pharmaceutics* 193:157-166.

Nishiya, T. et al. (2000). "Targeting of Liposomes Carrying Recombinant Fragments of Platelet Membrane Glycoprotein Ibα to Immobilized von Willebrand Factor under Flow Conditions," *Biochemical and Biophysical Research Communications* 270(3):755-760.

Pinnaduwage, P. et al. (1992). "Stable Target-Sensitive Immunoliposomes," *Biochemistry* 31 (11):2850-2855.

Soni, V. et al. (2005). "Potential of Transferrin and Transferrin Conjugates of Liposomes in Drug Delivery and Targeting," *Am. J. Drug. Deliv.* 3(3):155-170.

Soni, V. et al. (May 2005). "Transferrin Coupled Liposomes as Drug Delivery Carriers for Brain Targeting of 5-Florouracil," *Journal of Drug Targeting* 13(4):245-250.

Weissig, V. et al. (Jun. 1986). "A New Hydrophobic Anchor for the Attachment of Proteins to Liposomal Membranes," *FEBS Letters* 202(1):86-90.

Weissig, V. et al. (1989). "Covalent Coupling of Sugars to Liposomes," *Biochimica et Biophysica Acta* 1003:54-57.

International Search Report mailed on Mar. 21, 2008, for PCT Application No. PCT/US2007/77548 filed on Sep. 4, 2007, five pages.

Kobayashi, T. et al. (2007). "Effect of Transferrin Receptor-Targeted Liposomal Doxorubicin in P-Glycoprotein-Mediated Drug Resistant Tumor Cells," *International Journal of Pharmaceuticals* 329:94-102.

Lopez-Barcons, L.A. et al. (2005). "Targeted Adriamycin Delivery to MXT-B2 Metastatic Mammary Carcinoma Cells by Transferrin Liposomes: Effect of Adriamycin ADR-to-Lipid Ratio," *Oncology Reports* 14:1337-1343.

Mishra, V. et al. (Jan. 2006). "Targeted Brain Delivery of AZT via Transferrin Anchored Pegylated Albumin Nanoparticles," *Journal of Drug Targeting* 14(1):45-53.

Ahl, P.L. et al. (Oct. 1997). "Enhancement of the In Vivo Circulation Lifetime of L-alpha-Distearoylphosphatidylcholine Liposomes: Importance of Liposomal Aggregation Versus Complement Opsonization," *Biochimica Biophys. Acta* 1329(2):370-382.

Aliminaña, N. et al. (2004). "Biodistribution Study of Doxorubicin Encapsulated in Liposomes: Influence of Peptide Coating and Lipid Composition," *Prep. Biochem. Biotech.* 34(1):77-96.

Allen, T.M. et al. (Dec. 2004). "Advantages of Liposomal Delivery Systems for Anthracyclines" *Semin Oncol* 31(6)(suppl 13):5-15.

Avanti® Polar Lipids, Inc. "Structures for Avanti Product No. 870013," located at <http://www.avantilipids.com/ProductStructures.asp?n=870013> last visited on Mar. 1, 2006. (1 page).

Avanti® Polar Lipids, Inc. "Structures for Avanti Product No. 870245," located at <http://www.avantilipids.com/ProductStructures.asp?n=870245> last visited on Mar. 1, 2006. (1 page).

Avanti® Polar Lipids, Inc. "Synthetic Products: Phosphatidylethanolamine," located at <http://www.avantilipids.com/SyntheticPhosphatidylethanolamine.asp> last visited on Mar. 1, 2006. (4 pages).

Castagnola, J. et al. (Sep. 1987). "Effects of Epidermal Growth Factor on Transferrin Receptor Phosphorylation and Surface Expression in Malignant Epithelial Cells," *J. Cell Physiol.* 132(3):492-500.

Chaney, S.G. et al. (2005). "Recognition and Processing of Cisplatin- and Oxaliplatin-DNA Adducts," *Crit Rev Oncol./Hematol.* 53:3-11.

Doddoli, C. et al. (Jun. 2005). "In Vitro and In Vivo Methotrexate Disposition in Alveolar Macrophages: Composition of Pharmacokinetic Parameters of Two Formulations," *Int. J. Pharm.* 297(1-2):180-189.

Gabizon, A. et al. (Mar. 2002). "Folate Receptor Targeting of Pegylated (Stealth) Liposomal Cisplatin Enhances Anti-tumor Activity in Mouse Models without Increasing Toxicity," *Proceedings of the 93rd Annual Meeting of the American Assoc. for Cancer Research*, Apr. 6-10, 2002, San Francisco, California, 43(415):415.

Habeshaw, J.A. et al.(Mar. 1983). "Correlation of Transferrin Receptor Expression with Histological Class and Outcome in Non-Hodgkin Lymphoma," *Lancet* 1(8323): 498-501.

Harashima, H. et al. (1995). "Size Dependent Liposome Degradation in Blood: in Vivo/in Vitro Correlation by Kinetic Modeling," *J. Drug Target.* 3(4):253-261.

Holmberg, E. et al. (Dec. 29, 1989). "Highly Efficient Immunoliposomes Prepared with a Method which is Compatible with Various Lipid Compositions," *Biochem. Biophys. Res. Comm.* 165(3):1272-1278.

Hoshino, T. et al. (Feb. 1995). In vitro Cytotoxicities and in vivo Distribution of Transferrin-Platinum(II) Complex, *J. Pharm. Sci* 84(2):216-221.

Ishida, O. et al. (Jul. 2001). "Liposomes Bearing Polyethyleneglycol-Coupled Transferrin with Intracellular Targeting Property to the Solid Tumors in Vivo," *Pharmaceutical Research* 18(7):1042-1048.

Klausner, R.D. et al. (Apr. 1983). "Binding of Apotransferrin to K562 Cells: Explanation of the Transferrin Cycle," *Proc. Natl. Acad. Sci. USA* 80(8):2263-2266.

Klausner, R.D. et al. (Apr. 1983). "Receptor-Mediated Endocytosis of Transferrin in K562 Cells," *J. Biol. Chem* 258(8):4715-4724.

Iinuma, H. et al. (2002). "Intracellular Targeting Therapy of Cisplatin-Encapsulated Transferrin-Polyethylene Glycol Liposome on Peritoneal Dissemination of Gastric Cancer," *International Journal of Cancer* 99(1):130-137.

Liu, D. et al.(Feb. 1992). "Role of Liposome Size and RES Blockade in Controlling Biodistribution and Tumor Uptake of GM1-Containing Liposomes," *Biochim. Biophys. Acta* 1104(1):95-101.

Lloyd, J.M. et al. (1984)."Demonstration of an Epitope of the Transferrin receptor in Human Cervical Epithelium—a potentially useful cell marker," *J Clin Pathol.* 37(2):131-135.

Lowry, O.H. et al. (Nov. 1951). "Protein Measurement with the Folin Phenol Reagent," *J. Biol. Chem.* 193(1):265-275.

Maruyama, K. et al. (Nov. 1990). "Characterization of In Vivo Immunoliposome Targeting to Pulmonary Endothelium," *Journal of Pharmaceutical Sciences* 79(11):978-984.

Maruyama, K. et al. (1999). "Possibility of Active Targeting to Tumor Tissues with Liposomes," *Advanced Drug Delivery Reviews* 40(1/2):89-102.

Maruyama, K. et al. (1995). "Targetability of Novel Immunoliposomes Modified with Amphipathic Poly(Ethylene Glycol) s Conjugated at their Distal Terminals to Monoclonal Antibodies," *Biochimica et Biophysica Acta* 1234:74-80.

Mebiopharm. Co., Ltd. "Efficacy, Safety and PK Profile of Oxaliplatin-Encapsulated Transferrin-Conjugated PEG-Liposomes, MB324, in ColonCancer Xenograft Models by Intravenous Administration84,". Abstract No. 1384, 16 pages.

Mebiopharm. Co., Ltd. (Sep. 6, 2005). "Multinational Activity Global Development from Japan," Poster Presentations from the Japan Biotech Meeting, 22 pages.

Mebiopharm. Co., Ltd. (Sep. 6, 2005). "The Japan Biotech Meeting," Poster Presentations from the Japan Biotech Meeting, 24 pages.

Nag, A. et al. (1999). "Assessment of Targeting Potential of Galactosylated and Mannosylated Sterically Stabilized Liposomes to Different Cell Types of Mouse Liver," *J. Drug Target.* 6(6):427-438.

Nam, S-M. et al.(Jan. 1998). "Convenient Preparation of Tumor-specific Immunoliposomes Containing Doxorubicin," *J. Biochem. Mol. Biol.* 31(1):95-100.

NOF Corporation. (2005). "DDS Development: Product Information—Phospholipids," located at <http://nof.co.jp/english/business/dds/product02.htm> last visited on Oct. 11, 2005. (10 pages).

NOF Corporation. (Date unknown). "World-wide Leader in Drug Delivery Systems: PEG Derivatives, Phospholipids, and Drug Delivery Materials for Pharmaceutical Products and Formulations," Product Catalogue Version 7.1, 59 pages.

Papahadjopoulos, D. et al. (Dec. 1991). "Sterically Stabilized Liposomes: Improvements in Pharmacokinetics and Antitumor Therapeutic Efficacy," *Proc Natl Acad Sci U.S.A.* 88:11460-11464.

Park, Y.S. et al. (1992). "Some Negatively Charged Phospholipids Derivatives Prolong the Liposome Circulation in Vivo," *Biochimica et Biophysica Acta* 1108(2):257-260.

Pignatello, R. et al. (2003). "Effect of Liposomal Delivery on into Antitumor Activity of Lipophilic Conjugates of Methotrexate with Lipoamino Acids," *Drug Delivery* 10(2):95-100.

Roiron, D. et al. (Dec. 8, 1989). "Lactoferrin-Binding Sites at the Surface of HT29-D4 Cells. Comparison with Transferrin," *Eur. J. Biochem* 186(1-2):367-373.

Schreiber, G. et al. (1997). "The Evolution of Gene Expression Structure and Function of Transthyretin," *Comp. Biochem. Physiol.* 116B(2):137-160.

Shindelman, J.E. et al. (1981). "Demonstration of the Transferrin Receptor in Human Breast Cancer Tissue. Potential Marker for Identifying Dividing Cells." *Int J Cancer* 27(3):329-334.

Sommerman, E.F. et al. (Jul. 18, 1984). "$^{125}$I Labelled Inulin: A Convenient Marker for Deposition of Liposomal Contents in Vivo," *Biochem. Biophys. Res. Commun.* 122(1):319-324.

Trotta, M. et al. (2004). "Deformable Liposomes for Dermal Administration of Methotrexate," *Int J. Pharm.* 270(1-2):119-125.

Vail, D.M. et al. (2004). "Pegylated Liposomal Doxorubicin: Proof of Principle Using Preclinical Animal Models and Pharmacokinetic Studies." *Semin Oncol.* 31 (Suppl 13):16-35.

Vodovozova, E.L. et al. (2004). "Synthesis of a Lipid Derivative of the Antitumor Agent Methotrexate," *Russ. J. Bioorg. Chem.* 30(6):599-601.

Wang, S. et al. (Apr. 1995). "Delivery of antisense oligodeoxyribonucleotides against the human epidermal growth factor receptor into cultured KB cells with liposomes conjugated to folate via polyethylene glycol," *Proc. Natl. Acad. Sci. USA* 92(8):3318-3322.

Ware, B.R. et al. (1972). "Light Scattering in Mixtures of BSA, BSA Dimers, and Fibrinogen Under the Influence of Electric Fields," *J. Colloid and Interface Sci.* 39(3):670-675.

Weissig, V. et al. (Oct. 1998). "Accumulation of Protein-loaded Long-circulating Micelles and Liposomes in Subcutaneous Lewis Lung Carcinoma in Mice," *Pharm. Res.* 15(10):1552-1556.

Wilkes,G.M. (2002). "New Therapeutic Options in Colon Cancer: Focus on Oxaliplatin" *Clin J Oncol Nurs.* 6(3):131-137.

Extra, J.M. et al. (1990). "Phase I Study of Oxaliplatin in Patients with Advanced Cancer," *Cancer Chemother. Pharmacol.* 25:299-303.

NOF Corporation. (May 2008). "DDS: Drug Delivery Systems," Product Catalogue Version 10, 58 pages.

Sanofi-Synthelabo Inc. (2004). "Eloxatin," product insert description of Eloxatin™ (Oxaliplatin for injection), 43 pages.

Xu, L. et al. (Mar. 1, 1997). "Transferrin-Liposome-Mediated p53 Sensitization of Squamous Cell Carcinoma of the Head and Neck to Radiation In Vitro," *Human Gene Therapy* 8:467-475.

Xu, L. et al. (Dec. 10, 1999). "Transferrin-Liposome-Mediated Systemic p53 Gene Therapy in Combination with Radiation Results in Regression of Human Head and Neck Cancer Xenographs," *Human Gene Therapy* 10:2941-2952.

Singh, M. (Jun. 1999). "Transferrin as a Targeting Ligand for Liposomes and Anticancer Drugs," *Curr. Pharm. Des.* 5(6):443-451.

\* cited by examiner

LIPOSOME COMPOSITIONS

CROSS-REFERENCE TO RELATED APPLICATIONS

This application claims the benefit of Japanese patent application No. 2005-67469, filed Mar. 10, 2005, the disclosure of which is incorporated herein by reference in its entirety.

BACKGROUND OF THE INVENTION

The efficacy of treatments for many diseases, including cancer, has improved dramatically in the past few decades, however, many treatment regimens require the use of drugs with deleterious side effects, including, for example, alopecia, nausea, vomiting, tiredness, etc. Some treatment regimens may also entail the use of drugs that are not stable under physiological conditions, for example, bio-therapeutics (e.g., genes or gene products) and/or other drugs that are easily degraded or otherwise altered upon administration and thereby loose their effectiveness before achieving the desired therapeutic result. Such instability also makes the drugs more difficult and costly to store and prepare for administration.

There are a number of classes of anticancer agents, encompassing nearly 100 individual drugs, as well as numerous drug combination therapies, methods of delivery and treatment regimens. Anticancer agents may be classified according to several criteria, such as class of compound and disease state treated. Certain agents have been developed to take advantage of the rapid division of cancer cells and target specific phases in the cell cycle, providing another method of classification. Agents can also be grouped according to the type and severity of their side effects or method of delivery. However, the most common classification of non-biotherapeutic based anticancer agents is by class of chemical compound, which broadly encompasses the mechanism of action of these compounds.

Depending on the reference source consulted, there are slight differences in the classification of anticancer agents. The classes of compounds are described in the Physician's Desk Reference as follows: alkaloids; alkylating agents; antitumor antibiotics; antimetabolites; hormones and hormone analogs; immunomodulators; photosensitizing agents; and miscellaneous other agents.

The alkaloid class of compounds may also be referred to as mitotic inhibitors, as they are cell cycle phase specific and serve to inhibit mitosis or inhibit the enzymes required for mitosis. They are derived generally from plant alkaloids and other natural products and work during the M-phase of the cell cycle. This class of compounds is often used to treat neoplasias such as acute lymphoblastic leukemia, Hodgkin's and non-Hodgkin's lymphoma; neuroblastomas and cancers of the lung, breast and testes.

Alkylating agents make up a large class of chemotherapeutic agents, including of the following sub-classes, which each represent a number of individual drugs: alkyl sulfonates; aziridines; ethylenimines and methylmelamines; nitrogen mustards; nitrosoureas; and others, including platinum compounds. Alkylating agents attack neoplastic cells by directly alkylating the DNA of cells and therefore causing the DNA to be replication incompetent. This class of compounds is commonly used to treat a variety of diseases, including chronic leukemias, non-Hodgkin's lymphoma, Hodgkin's lymphoma, multiple myeloma and certain lung, breast and ovarian cancers.

Nitrosoureas are often categorized as alkylating agents, and have a similar mechanism of action, but instead of directly alkylating DNA, they inhibit DNA repair enzymes causing replication failure. These compounds have the advantage of being able to cross the blood-brain barrier and therefore can be used to treat brain tumors.

Antitumor antibiotics have antimicrobial and cytotoxic activity and also interfere with DNA by chemically inhibiting enzymes and mitosis or by altering cell membranes. They are not cell cycle phase specific and are widely used to treat a variety of cancers.

The antimetabolite class of anticancer agents interfere with the growth of DNA and RNA and are specific to the S-phase of the cell-cycle. They can be broken down further by type of compound, which include folic acid analogs, purine analogs, and pyrimidine analogs. They are often employed in the treatment of chronic leukemia, breast, ovary, and gastrointestinal tumors.

There are two classes of hormones or hormone analogs used as anticancer agents, the corticosteroid hormones and sex hormones. While some corticosteroid hormones can both kill cancer cells and slow the growth of tumors, and are used in the treatment of lymphoma, leukemias, etc., sex hormones function primarily to slow the growth of breast, prostate and endometrial cancers. There are numerous subclasses of hormones and hormone analogs, including, androgens, antiadrenals, antiandrogens, antiestrogens, aromatase inhibitors, estrogens, leutenizing hormone releasing hormone (LHRH) analogs and progestins.

An additional smaller class of anticancer agents is classified as immunotherapy. These are agents that are intended to stimulate the immune system to more effectively attack the neoplastic (cancerous) cells. This therapy is often used in combination with other therapies.

There are also a number of compounds, such as campothectins, which are generally listed as 'other' anticancer agents and can be used to treat a variety of neoplasias.

Combinations of anticancer agents are also utilized in the treatment of a number of cancers. For example, Sanofi Syntholabo markets ELOXATIN™ (oxaliplatin for injection) for the treatment of colorectal cancer for use in combination with 5-fluorouracil and leuvocorin. This combination of drugs is often used adjunctively with surgery in the treatment of colorectal cancer. Oxaliplatin is an alkylating agent that is believed to act by inhibiting both DNA replication and transcription. Unlike other platinum agents, oxaliplatin has demonstrated a decreased likelihood of resistance development. Oxaliplatin is further described in U.S. Pat. Nos. 4,169,846; 5,338,874; 5,298,642; 5,959,133; 5,420,319; 5,716,988; 5,290,961; and in Wilkes G M. "*New therapeutic options in colon cancer: focus on oxaliplatin*" *Clin J Oncol Nurs.* (2002) 6:131-137.

While there are a plethora of anticancer agents, the benefit of these compounds is often outweighed by the severity of the side effects produced by the agent. This comparison is often referred to as the therapeutic index, which describes the balance between the required dose to accomplish the destruction of the cancer cells compared to the dose at which the substance is unacceptably toxic to the individual. The drawback to most anticancer agents is the relatively small range of the therapeutic index, (i.e., the narrow dosage range in which cancer cells are destroyed without unacceptable toxicity to the individual). This characteristic limits the frequency and dosage where an agent is useful, and often the side effects become intolerable before the cancer can be fully eradicated.

The severe side effects experienced with the majority of cancer chemotherapeutics are a result of the non-specific nature of these drugs, which do not distinguish between healthy and cancerous cells, and instead destroy both. Certain cell cycle specific drugs attempt to lessen these effects, targeting phases of the cell cycle involved in cell replication and division. These drugs do not, however, distinguish between cancerous cells and healthy cells that are undergoing normal cell division. The cells most at risk from these types of chemotherapy are those which undergo cell division often, including blood cells, hair follicle cells, and cells of the reproductive and digestive tracts.

The most common side effects of anticancer agents are nausea and vomiting. A large proportion of individuals also suffer from myelosuppression, or suppression of the bone marrow, which produces red blood cells, white blood cells and platelets. These and other side effects are also exacerbated by the suppression of the immune system concomitant with the destruction and lack of production of white blood cells, and associated risk of opportunistic infection.

Other side effects common to a wide range of anticancer agents include: hair loss (alopecia); appetite loss; weight loss; taste changes; stomatitis and esophagitis (inflammation and sores); constipation; diarrhea; fatigue; heart damage; nervous system changes; lung damage; reproductive tissue damage; liver damage; kidney and urinary system damage.

The wide range of the side effects associated with most anticancer agents and their severity in individuals who are already debilitated with disease and possibly immune compromised has led researchers to search for mechanisms by which they can alleviate some of the side effects while maintaining the efficacy of the treatment. Several approaches to this problem have been taken. They include combination chemotherapy, where multiple anticancer agents are administered together; adjuvant therapies, where additional agents are prescribed along with the anticancer agent to fight the side effects of the anticancer agent; combined modality treatments, where chemotherapy is combined with radiation and/or surgery; and alternative delivery vehicles for the administration of anticancer agents, such as the encapsulation of anticancer agents in liposomes.

Liposomes are formed when phospholipids and their derivatives are dispersed in water. Upon dispersion in water the phospholipids form closed vesicles called "liposomes", which are characterized by lipid bilayers encapsulating an aqueous core. Various liposomes have been used as carriers for entrapped therapeutic agents, such as drugs, enzymes and genetic sequences for use in medical science, in pharmaceutical science and in biochemistry.

Examples of liposome compositions include U.S. Pat. Nos. 4,983,397; 6,476,068; 5,834,012; 5,756,069; 6,387,397; 5,534,241; 4,789,633; 4,925,661; 6,153,596; 6,057,299; 5,648,478; 6,723,338; 6,627218; U.S. Pat. App. Publication Nos: 2003/0224037; 2004/0022842; 2001/0033860; 2003/0072794; 2003/0082228; 2003/0212031; 2003/0203865; 2004/0142025; 2004/0071768; International Patent Applications WO 00/74646; WO 96/13250; WO 98/33481; Papahadjopolulos D, Allen T M, Gbizon A, et al. "*Sterically stabilized liposomes. Improvements in pharmacokinetics and antitumor therapeutic efficacy*" *Proc Natl Acad Sci U.S.A.* (1991) 88: 11460-11464; Allen T M, Martin F J. "*Advantages of liposomal delivery systems for anthracyclines*" *Semin Oncol* (2004) 31: 5-15 (suppl 13). Weissig et al. *Pharm. Res.* (1998) 15: 1552-1556.

In earlier stages of developing liposomes, naturally occurring phospholipids of the cell membrane such as egg-yolk phospholipids and soybean phospholipids were used. In the case of being intravenously administered, however, liposomes utilizing these phospholipids are likely to be incorporated into the reticuloendothelial system of liver or spleen, causing a problem of low blood retention time and thereby reducing the efficacy of the drug. Thereafter, as a means for solving this problem, synthetic phospholipids whose lipid portion contains only saturated bonds were used as a constituent of the liposome membrane in order to harden the liposome membrane.

In an effort to prolong the circulatory half-life of liposomes and avoid uptake by the reticuloendothelial system, researchers developed liposomes that were modified by the incorporation of polyethylene glycol or other hydrophilic polymers (e.g., a PEG liposome where one or more of the constituent lipids was modified by attachment of PEG). PEG-modified liposomes were also often referred to as "shielded" liposomes. Doxil™ (doxorubicin HCl liposome injection) is a liposome-enclosed doxorubicin, with adjunct polyethylene glycol (PEG) utilized to avoid the reticuloendothelial system (RES) and prolong drug circulation time. See Vail D M, Amantea M A, Colbern G T, et al., "*Pegylated Liposomal Doxorubicin. Proof of Principle Using Preclinical Animal Models and Pharmacokinetic Studies.*" *Semin Oncol.* (2004) 31 (Suppl 13): 16-35. However, adverse effects were also caused by prolonged blood retention (e.g., hand-foot syndrome, an adverse effect of Doxil® on the peripheral system, etc.) became recognized as a problem.

Examples of liposomes include U.S. Pat. Nos. 4,983,397; 5,013,556; 6,316,024; 6,056,973; 5,945,122; 5,891,468; 6,126,966; 5,593,622, 5,676,971; 6,586,559; and 5,846,458 U.S. Pat. App. Publication. Nos. 2003/0224037; 2004/0022842; 2003/0113262; 2002/0136707; International Patent Applications WO 99/30686; WO 02/41870 Alimiñana et al., *Prep. Biochem. Biotech.* (2004) 34(1): 77-96. Liposomes are also described in U.S. Pat. Nos. 6,228,391; 6,197, 333; 6,046,225; 5,292,524; and U.S. Pat. App. Pub. Nos. 20050271588; 20040213833; 20040029210; 20030175205; 20030162748; 20030130190; 20030059461; and 20020034537.

In addition to PEG-modified liposomes, researchers developed a variety of other derivatized lipids. These derivatized lipids could also be incorporated into liposomes. See, for example: International Patent Application WO 93/01828; Park Y S, Maruyama K, Huang L. "*Some negatively charged phospholipids derivatives prolong the liposome circulation in vivo.*" *Biochimica et Biophysica Acta* (1992) 1108: 257-260; Ahl et al., *Biochimica Biophys. Acta* (1997) 1329: 370-382.

Additional lipid compositions are described in U.S. Pat. Nos. 6,936,272; 6,897,196; 6,077,834; and U.S. Pat. App. Pub. Nos. 20050136064; 20040234588; 20030215490; 20030166601; and 20010038851.

In addition to modification of liposomes with PEG and other hydrophilic polymers, researchers also developed liposomes that aimed to specifically target particular cell types by incorporating targeting factors (also referred to as targeting ligands) for particular cell types. Examples of targeting factors/ligands include asialoglycoprotein, folate, transferrin, antibodies, etc. In some cases one or more of the constituent lipids could be modified by the attachment of a targeting factor.

Examples of lipid compositions including targeting factors include U.S. Pat. Nos. 5,049,390; 5,780,052; 5,786,214; 6,316,024; 6,056,973; 6,245,427; 6,524,613; 6,749,863; 6,177,059; 6,530,944; U.S. Pat. App. Publication. Nos. 2004/0022842; 2003/0224037; 2003/143742; 2003/0228285; 2002/0198164; 2003/0220284; 2003/0165934; 2003/0027779; International Patent Application Nos. WO 95/33841; WO 95/19434; WO 2001037807; WO 96/33698; WO 2001/49266; WO 9940789; WO 9925320; WO 9104014;

WO 92/07959; EP 1369132; JP 2001002592; Iinuma H, Maruyama K, et al., "*Intracellular targeting therapy of cisplatin-encapsulated transferrin-polyethylene glycol liposome on peritoneal dissemination of gastric cancer*" Int J Cancer (2002) 99 130-137; Ishida O, Maruyama K, Tanahashi H, Iwatsuru M, Sasaki K, et al., "*Liposomes bearing polyethylene glycol-coupled transferrin with intracellular targeting property to the solid tumors in vivo.*" Pharmaceutical Research (2001) 18: 1042-1048; Holmberg et al., *Biochem. Biophys. Res. Comm.* (1989) 165(3):1272-1278; Nam et al., *J. Biochem. Mol. Biol.* (1998) 31(1): 95-100; Nag et al., *J. Drug Target.* (1999) 6(6): 427-438.

In particular, Iinuma et al. developed a Tf-PEG-liposome, with transferrin (Tf) attached at the surface of the liposome. Iinuma et al., showed that a greater number of liposomes were bound to the surface of the tumor cells, and there was a greater uptake of liposomes by the tumor cells for Tf-PEG-liposome as compared to PEG-liposome (Inuma et al., ibid; Ishida et al., ibid).

However, despite recent advances made in the drug and labeled compound delivery field, including the use of liposome compositions, there is still a need for improved liposome compositions for the delivery of drugs and labeled compounds to specific cells and/or tissues that achieve a therapeutic or diagnostic effect. In particular in the cancer field, drug formulations with improved specificity and reduced toxicity are need to ensure therapeutic benefit without adversely effecting healthy cells and which also do not result in deleterious side effects for the individual being treated. Similarly, labeled compounds that can be used to detect conditions, particularly life-threatening conditions at an early stage (e.g., with high specificity and/or high sensitivity) and also accurately monitor the severity/extent of the condition (e.g., progression and/or regression with or without treatment) would also significantly improve the quality and success of therapy.

BRIEF SUMMARY OF THE INVENTION

The present invention relates to novel lipid-containing compositions (including liposomes (e.g., targeted liposomes, blank liposomes), lipid mixtures and liposome-containing compositions) that may optionally incorporate a drug or labeled compound, or may be used in the preparation of formulations that incorporate a drug or labeled compound, where the lipid-containing composition confers the benefit of reducing side effects from the drug or labeled compound and/or also prevents degradation and/or loss of efficacy of the drug or labeled compound. The invention also includes methods of making and using the lipid-containing compositions described herein. In certain aspects of the invention, the lipid-containing compositions may be used to treat or diagnose cancer (e.g., breast cancer, gastric cancer, colorectal cancer, colon cancer, cancer of the pancreas, non small cell lung cancer, small cell lung cancer, brain cancer, liver cancer, renal cancer, prostate cancer, bladder cancer, ovarian cancer, or hematological malignancies (e.g., leukemia, lymphoma, multiple myeloma, etc.).

In certain embodiments are provided targeted liposomes comprising one or more phospholipids, an N-(ω)-dicarboxylic acid-derivatized phosphatidyl ethanolamine, a targeting factor-modified N-(ω)-dicarboxylic acid-derivatized phosphatidyl ethanolamine, an encapsulated drug or labeled compound and, optionally, at least one additional lipid, wherein the targeting factor-modified N-(ω)-dicarboxylic acid-derivatized phosphatidyl ethanolamine comprises a targeting ligand linked to a second N-(ω)-dicarboxylic acid-derivatized phosphatidyl ethanolamine; and wherein the N-(ω)-dicarboxylic acid-derivatized phosphatidyl ethanolamine is represented by Formula 1,

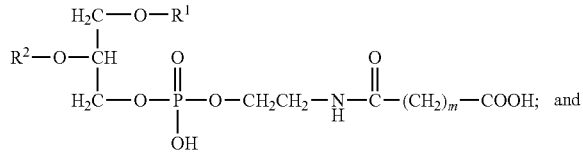

Formula 1 the second N-(ω)-dicarboxylic acid-derivatized phosphatidyl ethanolamine is represented by Formula 3,

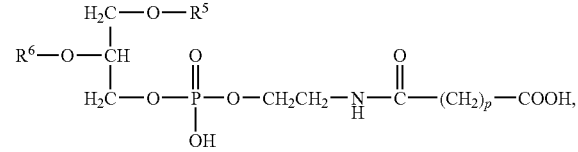

Formula 3 wherein $R^1$, $R^2$, $R^5$ and $R^6$ are each, independently, an acyl group, and m and p are, independently, an integer from 1 to 10; and, wherein the liposome does not comprise a non-derivatized phosphatidyl ethanolamine or polyethylene glycol, and wherein the targeting ligand is not an intact antibody.

In other embodiments are provided blank liposomes comprising one or more phospholipids, an N-(ω)-dicarboxylic acid-derivatized phosphatidyl ethanolamine, a targeting factor-modified N-(ω)-dicarboxylic acid-derivatized phosphatidyl ethanolamine, and, optionally, at least one additional lipid, wherein the targeting factor-modified N-(ω)-dicarboxylic acid-derivatized phosphatidyl ethanolamine comprises a targeting ligand linked to a second N-(ω)-dicarboxylic acid-derivatized phosphatidyl ethanolamine; and wherein the N-(ω)-dicarboxylic acid-derivatized phosphatidyl ethanolamine is represented by Formula 1,

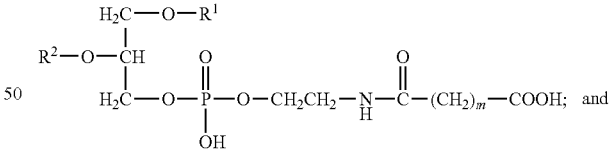

Formula 1 the second N-(ω)-dicarboxylic acid-derivatized phosphatidyl ethanolamine, where present, is represented by Formula 3,

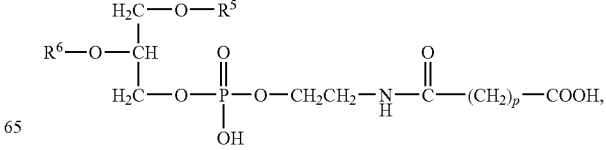

Formula 3 wherein R¹, R², R⁵ and R⁶ are each, independently, an acyl group, and m and p are, independently, an integer from 1 to 10; and, wherein the liposome does not comprise a non-derivatized phosphatidyl ethanolamine, polyethylene glycol, drug or labeled compound, and wherein the targeting ligand is not an intact antibody.

In certain embodiments of the targeted liposomes and blank liposomes, R¹, R², R⁵ and R⁶ are oleoyl or stearoyl, and m and p are 3. In certain embodiments, the targeting ligand is transferrin. In particular embodiments, the one or more phospholipids is DMPC or DSPC, and the at least one additional lipid is present and is cholesterol. In certain embodiments of the targeted liposomes and blank liposomes, R¹, R², R⁵ and R⁶ are oleoyl, m and p are 3, the one or more phospholipid is DMPC and the additional lipid is cholesterol.

In certain embodiments of the targeted liposomes and blank liposomes, m and p are each independently, an integer from 2 to 4. In some embodiments, m and p are equal and are an integer from 2 to 4. In particular embodiments, m and p are equal and are 3. In certain embodiments, R¹, R², R⁵ and R⁶ are each, independently, oleoyl, stearoyl, palmitoyl or myristoyl. In some embodiments, R¹ and are R² are the same, and R⁵ and R⁶ are the same. In other embodiments, R¹, R², R⁵ and R⁶ are the same. In particular embodiments, R¹, R², R⁵ and R⁶ are oleoyl or stearoyl. In certain embodiments, R¹, R², R⁵ and R⁶ are oleoyl.

In further embodiments are provided lipid mixtures comprising a mixture of one or more phospholipids, an N-(ω)-dicarboxylic acid-derivatized phosphatidyl ethanolamine, a succinimidyl ester of an N-(ω)-dicarboxylic acid-derivatized phosphatidyl ethanolamine, and, optionally, at least one additional lipid, wherein the N-(ω)-dicarboxylic acid-derivatized phosphatidyl ethanolamine is represented by Formula 1, Formula 1

$$\begin{array}{c} H_2C-O-R^1 \\ R^2-O-CH \quad\quad O \quad\quad\quad\quad O \\ H_2C-O-P-O-CH_2CH_2-\underset{H}{N}-C-(CH_2)_m-COOH, \text{ and} \\ OH \end{array}$$

the succinimidyl ester of the N-(ω)-dicarboxylic acid-derivatized phosphatidyl ethanolamine is represented by Formula 2, Formula 2

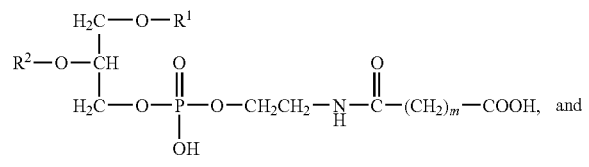

wherein R¹, R², R³ and R⁴ are each, independently, an acyl group, m and n are, independently, an integer from 1 to 10; and, wherein the mixture does not comprise a non-derivatized phosphatidyl ethanolamine or polyethylene glycol.

In certain embodiments of the lipid mixtures, m and n are each independently, an integer from 2 to 4. In some embodiments, m and n are equal and are an integer from 2 to 4. In particular embodiments, m and n are equal and are 3.

In certain embodiments of the lipid mixtures, R¹, R², R³ and R⁴ are each, independently, oleoyl, stearoyl, palmitoyl or myristoyl. In some embodiments, R¹ and are R² are the same, and R³ and R⁴ are the same. In particular embodiments, R¹, R², R³ and R⁴ are the same. In some embodiments, R¹, R², R³ and R⁴ are oleoyl or stearoyl. In certain embodiments, m and n are 3, where the one or more phospholipids is DMPC or DSPC and the at least one additional lipid is present and is cholesterol. In certain embodiments of the lipid mixtures, R¹, R², R³ and R⁴ are oleoyl, m and n are 3, the one or more phospholipid is DMPC and the additional lipid is cholesterol.

In further embodiments are provided lipid mixtures comprising a mixture of one or more phospholipids, an N-(ω)-dicarboxylic acid-derivatized phosphatidyl ethanolamine, a targeting factor-modified N-(ω)-dicarboxylic acid-derivatized phosphatidyl ethanolamine, and, optionally, at least one additional lipid, wherein the N-(ω)-dicarboxylic acid-derivatized phosphatidyl ethanolamine is represented by Formula 1, Formula 1

$$\begin{array}{c} H_2C-O-R^1 \\ R^2-O-CH \quad\quad O \quad\quad\quad\quad O \\ H_2C-O-P-O-CH_2CH_2-\underset{H}{N}-C-(CH_2)_m-COOH, \text{ and} \\ OH \end{array}$$

the targeting factor-modified N-(ω)-dicarboxylic acid-derivatized phosphatidyl ethanolamine comprises a targeting ligand linked to a second N-(ω)-dicarboxylic acid-derivatized phosphatidyl ethanolamine; and wherein the second N-(ω)-dicarboxylic acid-derivatized phosphatidyl ethanolamine is represented by Formula 3, Formula 3

$$\begin{array}{c} H_2C-O-R^5 \\ R^6-O-CH \quad\quad O \quad\quad\quad\quad O \\ H_2C-O-P-O-CH_2CH_2-\underset{H}{N}-C-(CH_2)_p-COOH, \\ OH \end{array}$$

wherein R¹, R², R⁵ and R⁶ are each, independently, an acyl group, m and p are, independently, an integer from 1 to 10; and, wherein the mixture does not comprise a non-derivatized phosphatidyl ethanolamine or polyethylene glycol, and wherein the targeting ligand is not an intact antibody.

In particular embodiments of the lipid mixtures, where a targeting factor-modified N-(ω)-dicarboxylic acid-derivatized phosphatidyl ethanolamine is present, m and p are each independently, an integer from 2 to 4. In certain embodiments, m and p are equal and are an integer from 2 to 4. In some embodiments, m and p are equal and are 3.

In particular embodiments of the lipid mixtures, where a targeting factor-modified N-(ω)-dicarboxylic acid-derivatized phosphatidyl ethanolamine is present, R¹, R², R⁵ and R⁶ are each, independently, oleoyl, stearoyl, palmitoyl or myristoyl. In some embodiments, wherein R¹ and are R² are the same, and R⁵ and R⁶ are the same. In further embodiments, R¹, R², R⁵ and R⁶ are the same. In some embodiments, R¹, R², $R^5$ and $R^6$ are oleoyl or stearoyl. In certain embodiments, $R^1$, $R^2$, $R^5$ and $R^6$ are oleoyl or stearoyl, m and p are 3, the one or more phospholipids is DMPC or DSPC, the at least one additional lipid is cholesterol, and the targeting ligand is transferrin. In certain embodiments of the lipid mixtures, $R^1$, $R^2$, $R^5$ and $R^6$ are oleoyl, m and p are 3, the one or more phospholipid is DMPC, the additional lipid is cholesterol and the targeting ligand is transferrin.

In certain embodiments are provided liposome-containing compositions comprising liposomes comprising one or more phospholipids, an N-(ω)-dicarboxylic acid-derivatized phosphatidyl ethanolamine, a succinimidyl ester of an N-(ω)-dicarboxylic acid-derivatized phosphatidyl ethanolamine, and, optionally, at least one additional lipid, wherein the N-(ω)-dicarboxylic acid-derivatized phosphatidyl ethanolamine is represented by Formula 1,

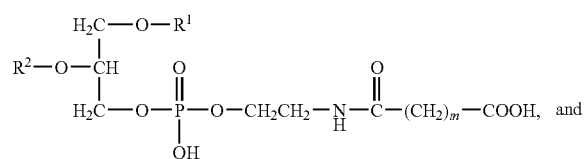

Formula 1 the succinimidyl ester of the N-(ω)-dicarboxylic acid-derivatized phosphatidyl ethanolamine is represented by Formula 2,

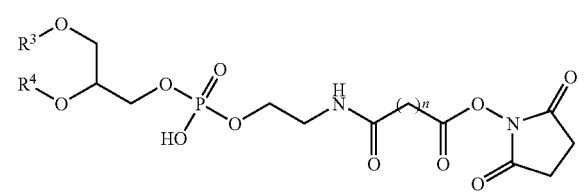

Formula 2 wherein $R^1$, $R^2$, $R^3$ and $R^4$ are each, independently, an acyl group, m and n are, independently, an integer from 1 to 10; and, wherein the composition does not comprise a non-derivatized phosphatidyl ethanolamine or polyethylene glycol.

In some embodiments of the liposome-containing compositions m and n are each independently, an integer from 2 to 4. In certain embodiments, m and n are equal and are an integer from 2 to 4. In particular embodiments, m and n are equal are 3.

In some embodiments of the liposome-containing compositions, $R^1$, $R^2$, $R^3$ and $R^4$ are each, independently, oleoyl, stearoyl, palmitoyl or myristoyl. In particular embodiments, $R^1$ and are $R^2$ are the same, and $R^3$ and $R^4$ are the same. In some embodiments, $R^1$, $R^2$, $R^3$ and $R^4$ are the same. In certain embodiments, $R^1$, $R^2$, $R^3$ and $R^4$ are oleoyl or stearoyl. In some embodiments, $R^1$, $R^2$, $R^3$ and $R^4$ are oleoyl or stearoyl, and m and n are 3 and the one or more phospholipids is DMPC, DSPC, POPC or DPPC. In certain embodiments, $R^1$, $R^2$, $R^3$ and $R4^6$ are oleoyl, m and n are 3, the one or more phospholipid is DMPC and the additional lipid is cholesterol.

In further embodiments of the liposome-containing compositions are provided liposome-containing compositions comprising liposomes comprising one or more phospholipids, an N-(ω)-dicarboxylic acid-derivatized phosphatidyl ethanolamine, a targeting factor-modified N-(ω)-dicarboxylic acid-derivatized phosphatidyl ethanolamine, and, optionally, at least one additional lipid, wherein the N-(ω)-dicarboxylic acid-derivatized phosphatidyl ethanolamine is represented by Formula 1,

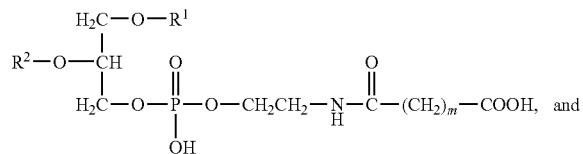

Formula 1 the targeting factor-modified N-(ω)-dicarboxylic acid-derivatized phosphatidyl ethanolamine comprises a targeting ligand linked to a second N-(ω)-dicarboxylic acid-derivatized phosphatidyl ethanolamine; and wherein the second N-(ω)-dicarboxylic acid-derivatized phosphatidyl ethanolamine is represented by Formula 3,

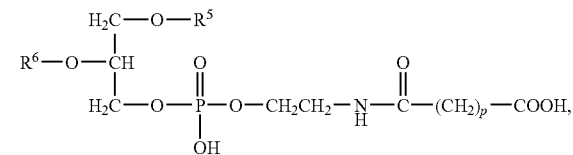

Formula 3 wherein $R^1$, $R^2$, $R^5$ and $R^6$ are each, independently, an acyl group, m and p are, independently, an integer from 1 to 10; and, wherein the composition does not comprise a non-derivatized phosphatidyl ethanolamine or polyethylene glycol, and wherein the targeting ligand is not an intact antibody.

In certain of the liposome-containing compositions, where a targeting-factor modified N-(ω)-dicarboxylic acid-derivatized phosphatidyl ethanolamine is present, m and p are each independently, an integer from 2 to 4. In particular embodiments, m and p are equal and are an integer from 2 to 4. In some embodiments, m and p are equal are 3.

In certain of the liposome-containing compositions, where a targeting-factor modified N-(ω)-dicarboxylic acid-derivatized phosphatidyl ethanolamine is present, $R^1$, $R^2$, $R^5$ and $R^6$ are each, independently, oleoyl, stearoyl, palmitoyl or myristoyl. In particular embodiments, $R^1$ and are $R^2$ are the same, and $R^5$ and $R^6$ are the same. In certain embodiments, wherein $R^1$, $R^2$, $R^1$ and $R^6$ are the same. In some embodiments, $R^1$, $R^2$, $R^5$ and $R^6$ are oleoyl or stearoyl. In particular embodiments, $R^1$, $R^2$, $R^5$ and $R^6$ are oleoyl or stearoyl, the one or more phospholipids is DMPC or DSPC, the at least one additional lipid cholesterol, and the targeting ligand is transferrin. In certain embodiments, $R^1$, $R^2$, $R^5$ and $R^6$ are oleoyl, m and p are 3, the one or more phospholipid is DMPC, the additional lipid is cholesterol and the targeting ligand is transferrin.

In further embodiments of the liposome-containing compositions a drug is included. In certain embodiments, the one or more phospholipid is DMPC or DSPC, $R^1$, $R^2$ and, where present, $R^5$ and $R^6$ are oleoyl or stearoyl, m and, where present, p are 3, the at least one additional lipid, where present, is cholesterol, the drug is oxaliplatin, and the targeting ligand, where present, is transferrin. In certain embodiments, the composition further includes a sugar at a concentration of from about 1 to about 20% percent sugar (v/v). In certain embodiments, the one or more phospholipid is DMPC or DSPC, $R^1$, $R^2$ and, where present, $R^5$ and $R^6$ are oleoyl, m and, where present, p are 3, the at least one additional lipid, where present, is cholesterol, the drug is oxaliplatin, and the targeting ligand, where present, is transferrin.

In further embodiments of the liposome-containing compositions a labeled compound is included. In certain embodiments, the labeled compound comprises a radioisotopic moiety.

In certain embodiments of the targeted liposomes, blank liposomes, lipid mixtures and liposome-containing compositions, the at least one additional lipid is present. In particular embodiments, the at least one additional lipid is cholesterol or a cholesterol derivative.

In particular embodiments of the targeted liposomes, blank liposomes, lipid mixtures and liposome-containing compositions, the one or more phospholipids is a phosphatidylcholine, phosphatidic acid, phosphatidylserine or phosphatidylglycerol. In particular embodiments, the one or more phospholipids is a neutral phospholipid. In some embodiments, the one or more phospholipids is a phosphatidylcholine. In particular embodiments, the phosphatidyl choline includes a moiety of a saturated fatty acid. In certain embodiments, the one or more phospholipids is DMPC, DSPC, POPC or DPPC. In particular of these embodiments, the at least one additional lipid is present. And in certain of these, the at least one additional lipid is cholesterol or a cholesterol derivative. In particular embodiments, DMPC and cholesterol, DSPC and cholesterol, POPC and cholesterol, or DPPC and cholesterol are incorporated. In certain embodiments, DMPC and cholesterol.

In particular embodiments of the targeted liposomes, blank liposomes, lipid mixtures and liposome-containing compositions, where present, targeting ligand is directed to a target cell. In some embodiments, the targeting ligand is directed to a cell surface receptor of a target cell. In particular embodiments, the targeting ligand is transferrin, folic acid, hyaluronic acid, a sugar chain or a fragment of a monoclonal antibody. In certain embodiments, the targeting ligand is transferrin, folic acid, hyaluronic acid or a sugar chain. In other embodiments, the targeting ligand is transferrin, folic acid, hyaluronic acid or a sugar chain. In some embodiments, the targeting ligand is transferrin. In particular embodiments, the transferrin is in a holo-form but not in an apo-form. In some embodiments, the transferrin is in a holo-form.

In certain embodiments of the targeted liposomes and blank liposomes, the mean diameter of the liposome is from about 50 nm to about 250 nm. In others, the mean diameter of the liposome is from about 90 nm to about 200 nm.

In particular embodiments of the targeted liposomes and blank liposomes, the zeta potential of the liposome is negative. In certain embodiments, the zeta potential is from about −75 mV to about −90 mV. In others, the zeta potential is from about −80 mV to about −85 mV.

In certain embodiments of the liposome-containing compositions, targeted liposomes and blank liposomes, the formulations further include a solution.

In particular embodiments of the targeted liposomes and liposome-containing compositions, the drug is present.

In particular embodiments of the targeted liposomes and liposome-containing compositions, the drug is oxaliplatin. In certain embodiments where the drug is oxaliplatin, the targeting ligand is transferrin. In certain embodiments, the at least one additional lipid is present and is cholesterol.

In certain embodiments, the drug is an anticancer agent. In particular embodiments, the drug is a cytotoxic drug. In some embodiments, the drug is a topoisomerase I inhibitor. In particular embodiments, the topoisomerase I inhibitor is topotecan or irinotecan. In other embodiments, the drug is a vinca alkaloid. In particular embodiments, the vinca alkaloid is vincristine, vinblastine, vinleurosine, vinrodisine, vinorelbine or vindesine. In some embodiments, wherein the drug is a nucleic acid. In certain embodiments, the nucleic acid is an antisense oligonucleotide or a ribozyme. In some embodiments, the drug is an alkylating agent. In particular embodiments, the drug is a taxanes. In other embodiments, the drug is a metabolic antagonist. In certain embodiments, the drug is an antitumour antibiotic. In some embodiments, the drug is a hormone therapy drug. In some embodiments, the drug is a molecular target drug.

In some embodiments of the targeted liposomes and liposome-containing compositions, the drug is a platinum compound. In particular embodiments, the platinum compound is biplatin, cisplatin, carboplatin, ormaplatin, oxaliplatin, zeniplatin, enloplatin, lobaplatin or spiroplatin. In some embodiments, the platinum compound is oxaliplatin.

In some embodiments where the drug is oxaliplatin, $R^1$, $R^2$, $R^5$ and $R^6$ are oleoyl or stearoyl, m and p are 3, the targeting ligand is transferrin, the one or more phospholipids is DMPC or DSPC, and the at least one additional lipid is present and is cholesterol. In certain embodiments where the drug is oxaliplatin, $R^1$, $R^2$, $R^5$ and $R^6$ are oleoyl, m and p are 3, the targeting ligand is transferrin, the one or more phospholipids is DMPC, and the at least one additional lipid is present and is cholesterol. In particular embodiments, the targeted liposomes and liposome-containing compositions are free of other lipid components.

In some embodiments where the drug is oxaliplatin, the oxaliplatin is dissolved in an aqueous solution of a sugar selected from the group consisting of trehalose, maltose, sucrose, mannose, lactose, mannitol, glycerol and dextrose. In certain embodiments, the sugar is at a concentration of from about 1 to about 20% percent sugar (v/v). In particular embodiments, the concentration of oxaliplatin is from about 0.1 mg/ml to about 25 mg/ml within the liposome. In other embodiments, the concentration of oxaliplatin is from about 0.5 mg/ml to about 10 mg/ml within the liposome. In still other embodiments, the concentration of oxaliplatin is from about 0.5 mg/ml to about 3 mg/ml.

In particular embodiments of the of the targeted liposomes and liposome-containing compositions, the labeled compound is present. In certain embodiments, the labeled compound includes a radioisotopic moiety. In particular embodiments, the radioisotopic moiety incorporates $^{125}I$.

In particular embodiments of the targeted liposomes and the liposome-containing compositions, the concentration of targeting ligand incorporated in the liposome is from about 1.0 mg/ml to about 3.0 mg/ml. In others, the concentration of targeting ligand incorporated in the liposome is from about 1.0 mg/ml to about 2.5 mg/ml.

In particular embodiments of the targeted liposomes and the liposome-containing compositions where drug is present and is oxaliplatin, the targeting ligand is transferrin. In particular embodiments, the transferrin is in a holo-form. In some embodiments, ferric iron is in a concentration of from about 0.4 to about 3.0 µg/ml. In other embodiments, ferric iron is in a concentration of from about 0.4 to about 1.5 µg/ml.

In particular embodiments of the targeted liposomes, blank liposomes, lipid mixtures and liposome-containing compositions, the liposomes, lipid mixtures or liposome-containing composition does not comprise a cationic lipid. In particular embodiments, the liposomes, lipid mixtures or liposome-containing composition do not comprise an anionic lipid. In some embodiments, the liposomes, lipid liposome, lipid mixtures or liposome-containing composition do not comprise either an anionic lipid or a cationic lipid.

In particular embodiments of the targeted liposomes, blank liposomes, lipid mixtures and liposome-containing compositions, the formulations further include a solution. In certain embodiments, the lipid mixtures are free of solution. In particular embodiments, the solution is an aqueous solution or a mixture of an aqueous solution and a water-miscible solvent.

In particular embodiments of the targeted liposomes, blank liposomes, lipid mixtures and liposome-containing compositions, the formulations further include sucrose.

In a further aspect of the invention are provided pharmaceutical formulations of the lipid-containing compositions described herein. Particular embodiments of the liposome-containing compositions, targeted liposomes and blank liposomes include the liposome-containing compositions, targeted liposomes or blank liposomes as described herein and one or more pharmaceutically acceptable carriers, excipients, diluents, stabilizers, or preservatives.

In yet another aspect of the invention are provided kits including the lipid-containing compositions described herein. Certain embodiments of the liposome-containing compositions, targeted liposomes and blank liposomes include the liposome-containing compositions, targeted liposomes or blank liposomes as described herein, packaging and contained in a second container.

In certain embodiments of the kits, the liposome-containing compositions, targeted liposomes or blank liposomes as described herein is contained in a first container and one or more pharmaceutically acceptable carriers, excipients, diluents, stabilizers, or preservatives are contained in a second container.

In particular embodiments are provided kits incorporating the pharmaceutical formulations described herein, packaging and instructions for use.

In another aspect of the invention are provided methods of making the lipid-containing compositions described herein.

In particular embodiments are provided methods of making targeted liposomes as described herein, comprising the steps of:

a) mixing the one or more phopsholipids, the N-(ω)-dicarboxylic acid-derivatized phosphatidyl ethanolamine, the targeting factor-modified N-(ω)-dicarboxylic acid-derivatized phosphatidyl ethanolamine, and, optionally, the at least one additional lipid, to form a lipid mixture;

b) adding a drug or labeled compound to the lipid mixture formed in step (a);

c) forming a liposome.

In a further embodiments of the method is provided a step (d), purifying the liposome of step (c). In particular embodiments, the drug in step (b) is in aqueous solution prior to mixing. In certain embodiments, step (c) comprises sonication or stirring. In some embodiments, step (c) comprises extrusion.

In other embodiments are provided methods of making targeted liposomes as described herein, comprising the steps of a) mixing the one or more phopsholipids, the N-(ω)-dicarboxylic acid-derivatized phosphatidyl ethanolamine, a succinimidyl ester of an N-(ω)-dicarboxylic acid-derivatized phosphatidyl ethanolamine, and, optionally, the at least one additional lipid, to form a lipid mixture wherein the succinimidyl ester of the N-(ω)-dicarboxylic acid-derivatized phosphatidyl ethanolamine is represented by Formula 2, Formula 2

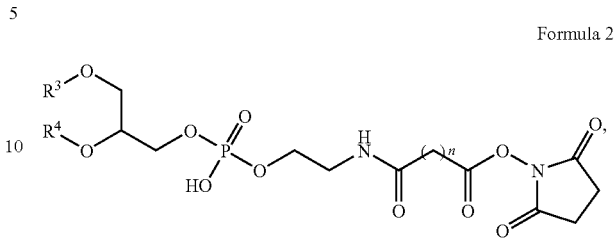

wherein $R^3$ and $R^4$ are each, independently, an acyl group, n is, independently, an integer from 1 to 10;

b) adding drug or labeled compound to the lipid mixture formed in step (a);

c) forming a liposome; and, d) linking a targeting ligand to the succinimidyl ester of an N-(ω)-dicarboxylic acid-derivatized phosphatidyl ethanolamine.

In certain embodiments of the above-described method, the method also includes a step (c), purifying the liposome of step (d).

In particular embodiments, the drug in step (b) is in aqueous solution prior to mixing. In some embodiments, step (c) comprises sonication or stirring. In certain embodiments, step (c) comprises extrusion. In particular embodiments, step (c) comprises stirring.

In certain embodiments are provided methods of making blank liposomes as described herein, comprising the steps of a) mixing the one or more phospholipids, the N-(ω)-dicarboxylic acid-derivatized phosphatidyl ethanolamine, the targeting factor-modified N-(ω)-dicarboxylic acid-derivatized phosphatidyl ethanolamine, and, optionally, the at least one additional lipid, to form a lipid mixture; and b) forming a liposome.

In certain embodiments of the methods of preparing the blank liposomes, the method further comprises a step (c), purifying the liposome of step (b).

In particular embodiments, step (b) comprises sonication or stirring. In some embodiments, step (b) comprises extrusion.

In other embodiments are provided methods of making blank liposomes as described herein, comprising the steps of a) mixing the one or more phopsholipids, the N-(ω)-dicarboxylic acid-derivatized phosphatidyl ethanolamine, and a succinimidyl ester of an N-(ω)-dicarboxylic acid-derivatized phosphatidyl ethanolamine, and, optionally, the at least one additional lipid, to form a lipid mixture, wherein the succinimidyl ester of the N-(ω)-dicarboxylic acid-derivatized phosphatidyl ethanolamine is represented by Formula 2, Formula 2 wherein $R^3$ and $R^4$ are each, independently, an acyl group, n is, independently, an integer from 1 to 10;

b) forming a liposome; and, c) linking a targeting ligand to the succinimidyl ester of an N-(ω)-dicarboxylic acid-derivatized phosphatidyl ethanolamine to form a targeting factor-modified N-(ω)-dicarboxylic acid-derivatized phosphatidyl ethanolamine.

In certain of the methods of preparing the blank liposomes, the methods further include a step (d), purifying the liposome of step (c).

In particular embodiments, step (b) comprises sonication or stirring. In some embodiments, step (b) comprises extrusion.

In other embodiments are provided methods of making the lipid-containing compositions as described herein, comprising the step of mixing the one or more phospholipids, the N-(ω)-dicarboxylic acid-derivatized phosphatidyl ethanolamine and the succinimidyl ester of an N-(ω)-dicarboxylic acid-derivatized phosphatidyl ethanolamine.

In further embodiments are provided methods of making the lipid-containing compositions where the at least one additional lipid is present, as described herein, comprising the step of mixing the one or more phospholipids, the at least one additional lipid, the N-(ω)-dicarboxylic acid-derivatized phosphatidyl ethanolamine and the succinimidyl ester of an N-(ω)-dicarboxylic acid-derivatized phosphatidyl ethanolamine.

In another embodiments are provided methods of making the lipid-containing composition as described herein, comprising the step of mixing the one or more phospholipids, the N-(ω)-dicarboxylic acid-derivatized phosphatidyl ethanolamine and the targeting factor-modified N-(ω)-dicarboxylic acid-derivatized phosphatidyl ethanolamine.

In further embodiments are provided methods of making the lipid-containing compositions, where the at least one additional lipid is present, as described herein, comprising the step of mixing the one or more phospholipids, the at least one additional lipid, the N-(ω)-dicarboxylic acid-derivatized phosphatidyl ethanolamine and the targeting factor-modified N-(ω)-dicarboxylic acid-derivatized phosphatidyl ethanolamine.

Also provided are methods of making the liposome-containing compositions described herein, comprising the steps of a) mixing the one or more phospholipid lipids, and the N-(ω)-dicarboxylic acid-derivatized phosphatidyl ethanolamine and, where present, the succinimidyl ester of an N-(ω)-dicarboxylic acid-derivatized phosphatidyl ethanolamine, or targeting-factor modified N-(ω)-dicarboxylic acid-derivatized phosphatidyl ethanolamine, and, optionally, where present, at least one additional lipid, to form a lipid mixture; and b) adding a drug to the lipid mixture formed in step (a); and, c) forming a liposome.

In certain embodiments of the methods of making the various lipid-containing compositions (targeted liposomes, blank liposomes, liposome-containing compositions), where a drug is present, the drug is in an aqueous solution. In certain embodiments, step a) is performed in the presence of organic solvent. In some embodiments, aqueous solution further comprises a sugar. In certain embodiments the aqueous solution may also include a water-miscible organic solvent.

In other embodiments are provided methods of making the liposome-containing compositions, comprising the steps of a) mixing the one or more phospholipid lipids, and the N-(ω)-dicarboxylic acid-derivatized phosphatidyl ethanolamine and, where present, the succinimidyl ester of an N-(ω)-dicarboxylic acid-derivatized phosphatidyl ethanolamine, or the targeting-factor modified N-(ω)-dicarboxylic acid-derivatized phosphatidyl ethanolamine, and, optionally, where present, the at least one additional lipid, to form a lipid mixture; and b) adding a labeled compound to the lipid mixture formed in step (a).

c) forming a liposome

In certain embodiments of the methods of making the various lipid-containing compositions (targeted liposomes, blank liposomes, liposome-containing compositions), where a labeled compound is present, the labeled compound is in an aqueous solution. In certain embodiments, step a) is performed in the presence of organic solvent. In certain embodiments the aqueous solution may also include a water-miscible organic solvent.

In certain embodiments are also provided methods of making the liposome-containing compositions as described herein, wherein the liposome-containing composition includes a targeting factor-modified N-(ω)-dicarboxylic acid-derivatized phosphatidyl ethanolamine, comprising the steps of a) mixing the one or more phospholipids, the N-(ω)-dicarboxylic acid-derivatized phosphatidyl ethanolamine and the targeting factor-modified N-(ω)-dicarboxylic acid-derivatized phosphatidyl ethanolamine and, optionally, at least one additional lipid, to form a lipid mixture; and b) adding solvent to the mixture formed in step (a) to form a liposome-containing composition.

In particular embodiments, the mixing step (a) is performed in the presence of an organic solvent. In particular embodiments, the solvent in step (b) is an aqueous solution or a mixture of aqueous solution and a water-miscible solvent.

In certain embodiments, step (b) comprises sonication or stirring. In some embodiments, step (b) comprises extrusion.

In particular embodiments of the methods of making the lipid-containing compositions, in step (a) the at least one additional lipid is present.

In some embodiments of the methods of making the lipid-containing compositions, in step (a) the succinimidyl ester of an N-(ω)-dicarboxylic acid-derivatized phosphatidyl ethanolamine is present.

In certain embodiments of the methods of making the lipid-containing compositions in step (a) the targeting factor-modified N-(ω)-dicarboxylic acid-derivatized phosphatidyl ethanolamine is present.

In an additional aspect of the invention are provided methods of treatment or diagnosis using the lipid-containing compositions described herein.

In particular embodiments are provided methods for treating cancer comprising, a) administering a targeted liposome as described herein to an individual in need thereof in an amount effective to treat cancer, wherein the targeted liposome comprises a drug, and the drug is an anticancer agent.

In certain embodiments of the method of treatment or diagnosis, the individual is a mammal. In particular embodiments, the individual is a human.

In certain embodiments of the methods of treatment, the cancer is breast, gastric, colon, solorectal cancer, cancer of the pancreas, non small cell lung cancer, small cell lung cancer, brain cancer, liver cancer, renal cancer, prostate cancer, bladder cancer, ovary cancer, or a hematological malignancies.

In some embodiments of the methods of treatment, step (a) is performed prior to, concurrently with or after combined modality cancer therapy. In particular embodiments, the combined modality cancer therapy comprises chemotherapy, radiation therapy, or surgery.

In particular embodiments of the methods of treatment, step (a) is performed prior to, concurrently with or after adjunctive cancer therapy. In particular embodiments, the adjunctive cancer therapy comprises administration of one or more agents to reduce hair loss, vomiting, immune suppression, nausea, diarrhea, rash, sensory disturbance, anemia, fatigue, stomatitis, or hand foot syndrome. In some embodiments, step (a) is performed prior to, concurrently with or after administration of one or more additional anticancer agents. In certain embodiments, the one or more additional anticancer agents comprise 5-fluorouracil, leucovorin, capecitabine, UFT/LV (tegafur-uracil and leucovorin), irinotecan, an-anti EGFR antibody, an anti-VEGF antibody, a tyrosine kinase inhibitor, or combinations thereof.

In some embodiments of the methods of treatment, the targeted liposome is administered via parenteral administration. In particular embodiments, the parenteral administration is via injected or intravenous infusion.

Also provided are methods of diagnosis comprising the steps of a) administering a targeted liposome as described herein to an individual in need thereof in an amount effective for detection, wherein the targeted liposome comprises a labeled compound; and, b) detecting the labeled compound.

In additional embodiments of the methods of diagnosis, the methods further comprise a step (c), comparing a level of labeled compound detected with the amount of labeled compound detected at a previous point in time.

In further embodiments of the methods of diagnosis, step (b) comprises detection via a gamma counter.

In a further aspect of the invention are provided transferrin-modified N-(ω)-dicarboxylic acid-derivatized phosphatidyl ethanolamines, where the N-(ω)-dicarboxylic acid-derivatized phosphatidyl ethanolamine is represented by Formula 3, Formula 3

$$\begin{array}{c} H_2C-O-R^5 \\ R^6-O-CH \quad O \quad\quad O \\ \phantom{R^6-O-}H_2C-O-\overset{\|}{\underset{OH}{P}}-O-CH_2CH_2-\underset{H}{N}-\overset{\|}{C}-(CH_2)_p-COOH, \end{array}$$

wherein $R^5$ and $R^6$ are each, independently, an acyl group and p is an integer from 1 to 10, and transferrin is liked linked to the N-(ω)-dicarboxylic acid-derivatized phosphatidyl ethanolamine.

In certain embodiments of the transferrin-modified N-(ω)-dicarboxylic acid-derivatized phosphatidyl ethanolamine, p is an integer from 2 to 4. In particular embodiments, p is 3.

In some embodiments of the transferrin-modified N-(ω)-dicarboxylic acid-derivatized phosphatidyl ethanolamine, $R^5$ and $R^6$ are each, independently, oleoyl, stearoyl, palmitoyl or myristoyl. In particular embodiments, $R^5$ and $R^6$ are the same. In some embodiments, $R^5$ and $R^6$ are oleoyl or stearoyl. In certain embodiments, $R^5$ and $R^6$ are oleoyl and p is 3.

Also provided in an additional aspect are a pharmaceutical formulations comprising the transferrin-modified N-(ω)-dicarboxylic acid-derivatized phosphatidyl ethanolamines as described herein and one or more pharmaceutically acceptable carriers, excipients, diluents, stabilizers, or preservatives.

In certain embodiments are provided lipid mixtures comprising a mixture of at least two different neutral lipids, an N-(ω)-dicarboxylic acid-derivatized phosphatidyl ethanolamine and a succinimidyl ester of an N-(ω)-dicarboxylic acid-derivatized phosphatidyl ethanolamine, wherein the N-(ω)-dicarboxylic acid-derivatized phosphatidyl ethanolamine is represented by Formula 1, Formula 1

$$\begin{array}{c} H_2C-O-R^1 \\ R^2-O-CH \quad O \quad\quad O \\ \phantom{R^2-O-}H_2C-O-\overset{\|}{\underset{OH}{P}}-O-CH_2CH_2-\underset{H}{N}-\overset{\|}{C}-(CH_2)_m-COOH; \text{ and} \end{array}$$

the succinimidyl ester of the N-(ω)-dicarboxylic acid-derivatized phosphatidyl ethanolamine is represented by Formula 2, Formula 2

$$R^3-O-\underset{R^4-O}{\overset{}{\bigg\langle}}-O-\overset{O}{\underset{HO}{\overset{\|}{P}}}-O-CH_2CH_2-\underset{H}{N}-\overset{O}{\overset{\|}{C}}-(CH_2)_n-O-N\underset{O}{\overset{O}{\bigg\langle}},$$

wherein $R^1$, $R^2$, $R^3$ and $R^4$ are each, independently, an acyl group, m and n are, independently, an integer from 1 to 10; and, wherein the mixture does not comprise a non-derivatized phosphatidyl ethanolamine or polyethylene glycol.

In certain embodiments are provided liposome-containing compositions comprising at least two different neutral lipids, an N-(ω)-dicarboxylic acid-derivatized phosphatidyl ethanolamine, a succinimidyl ester of an N-(ω)-dicarboxylic acid-derivatized phosphatidyl ethanolamine and an encapsulated drug or labeled compound, wherein the N-(ω)-dicarboxylic acid-derivatized phosphatidyl ethanolamine is represented by Formula 1, Formula 1

$$\begin{array}{c} H_2C-O-R^1 \\ R^2-O-CH \quad O \quad\quad O \\ \phantom{R^2-O-}H_2C-O-\overset{\|}{\underset{OH}{P}}-O-CH_2CH_2-\underset{H}{N}-\overset{\|}{C}-(CH_2)_m-COOH; \text{ and} \end{array}$$

the succinimidyl ester of the N-(ω)-dicarboxylic acid-derivatized phosphatidyl ethanolamine is represented by Formula 2, Formula 2

$$R^3-O-\underset{R^4-O}{\overset{}{\bigg\langle}}-O-\overset{O}{\underset{HO}{\overset{\|}{P}}}-O-CH_2CH_2-\underset{H}{N}-\overset{O}{\overset{\|}{C}}-(CH_2)_n-O-N\underset{O}{\overset{O}{\bigg\langle}},$$

wherein R¹, R², R³ and R⁴ are each, independently, an acyl group; m and n are, independently, an integer from 1 to 10; and, wherein the mixture does not comprise a non-derivatized phosphatidyl ethanolamine or polyethylene glycol.

In particular embodiments of the liposome-containing compositions and the lipid mixtures, m and n are each independently, an integer from 2 to 4. In certain embodiments, m and n are equal and are an integer from 2 to 4. In other embodiments, m and n are equal and are 3.

In some embodiments of the liposome-containing compositions and the lipid mixtures, R¹, R², R³ and R⁴ are each, independently, oleoyl, stearoyl, palmitoyl or myristoyl. In some embodiments, R¹ and are R² are the same, and R³ and R⁴ are the same. In particular embodiments R¹, R², R³ and R⁴ are the same. In some embodiments, R¹, R², R³ and R⁴ are oleoyl In particular embodiments of the liposome-containing compositions and the lipid mixtures, the molar ratio of neutral lipids:N-(ω)-dicarboxylic acid-derivatized phosphatidyl ethanolamine:succinimidyl ester of an N-(ω)-dicarboxylic acid-derivatized phosphatidyl ethanolamine is about 95:4:1.

In some embodiments of the liposome-containing compositions and the lipid mixtures, where the neutral lipids are DMPC and cholesterol, the molar ratio of DMPC:cholesterol: (N-(ω)-dicarboxylic acid-derivatized phosphatidyl ethanolamine+succinimidyl ester of an N-(ω)-dicarboxylic acid-derivatized phosphatidyl ethanolamine) is 50:45:5. In certain of these embodiments, the N-(ω)-dicarboxylic acid-derivatized phosphatidyl ethanolamine is NG-DOPE and the succinimidyl ester of an N-(ω)-dicarboxylic acid-derivatized phosphatidyl ethanolamine is NHS-NG-DOPE.

In certain embodiments are provided targeted liposomes comprising at least two different neutral lipids, a N-(ω)-dicarboxylic acid-derivatized phosphatidyl ethanolamine, a targeting factor-modified N-(ω)-dicarboxylic acid-derivatized phosphatidyl ethanolamine and an encapsulated drug or labeled compound, wherein the targeting factor-modified N-(ω)-dicarboxylic acid-derivatized phosphatidyl ethanolamine comprises a targeting ligand linked to a second N-(ω)-dicarboxylic acid-derivatized phosphatidyl ethanolamine; and, wherein the N-(ω)-dicarboxylic acid-derivatized phosphatidyl ethanolamine is represented by Formula 1, Formula 1

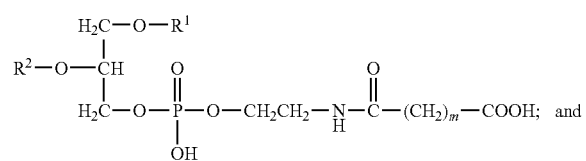

the second N-(ω)-dicarboxylic acid-derivatized phosphatidyl ethanolamine is represented by Formula 3, Formula 3

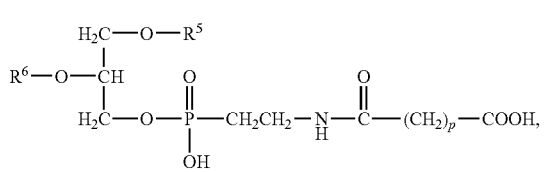

wherein R¹, R², R⁵ and R⁶ are each, independently, an acyl group, and m and p are, independently, an integer from 1 to 10; and, wherein the liposome does not comprise a non-derivatized phosphatidyl ethanolamine or polyethylene glycol, and wherein the targeting ligand is not an intact antibody.

In particular embodiments are provided targeted liposome comprising a neutral phosphatidyl choline, cholesterol or a cholesterol derivative, an N-(ω)-dicarboxylic acid-derivatized phosphatidyl ethanolamine, a transferrin-modified N-(ω)-dicarboxylic acid-derivatized phosphatidyl ethanolamine and encapsulated oxaliplatin, wherein the transferrin-modified N-(ω)-dicarboxylic acid-derivatized phosphatidyl ethanolamine comprises transferrin linked by a carboxylic acid amide bond to a second N-(ω)-dicarboxylic acid-derivatized phosphatidyl ethanolamine; and wherein the N-(ω)-dicarboxylic acid-derivatized phosphatidyl ethanolamine is represented by Formula 1, Formula 1

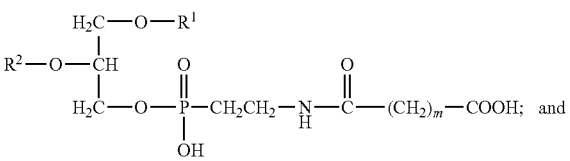

the succinimidyl ester of the N-(ω)-dicarboxylic acid-derivatized phosphatidyl ethanolamine is represented by Formula 2, and the second N-(ω)-dicarboxylic acid-derivatized phosphatidyl ethanolamine is represented by Formula 3, Formula 3

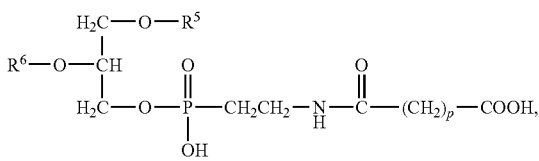

wherein R¹, R², R⁵ and R⁶ are each, independently, an acyl group, and m and p are, independently, an integer from 1 to 10; and, wherein the liposome does not comprise a non-derivatized phosphatidyl ethanolamine or polyethylene glycol. In certain embodiments, the targeted liposome is substantially free of EDC and/or DCC.

In certain embodiments of the targeted liposomes, m and p are each independently, an integer from 2 to 4. In some embodiments, m and p are equal and are an integer from 2 to 4. In particular embodiments, m and p are equal are 3.

In some embodiments of the targeted liposomes, R¹, R², R⁵ and R⁶ are each, independently, oleoyl, stearoyl, palmitoyl or myristoyl. In certain embodiments, R¹ and are R² are the same, and R⁵ and R⁶ are the same. In particular embodiments, R¹, R², R⁵ and R⁶ are the same. In some embodiments, R¹, R², R³ and R⁴ are oleoyl or stearoyl. In certain embodiments, R¹, R², R³ and R⁴ are oleoyl.

In certain embodiment of the targeted liposomes, the targeting ligand is directed to a target cell. In particular embodiments, the targeting ligand is directed to a cell surface receptor of a target cell. In some embodiments, the targeting ligand is transferrin, folic acid, hyaluronic acid, a sugar chain or a fragment of a monoclonal antibody. In certain embodiments, the targeting ligand is transferrin, folic acid, hyaluronic acid or a sugar chain. In particular embodiments, the targeting ligand is transferrin. In some of these embodiments, the transferrin is in a holo-form but not in an apo-form. In other embodiments, the transferring is in an apo-form.

In certain embodiments of the lipid mixtures, liposome-containing compositions and the targeted liposomes, the formulations do not comprise an anionic lipid. In some embodiments, the formulations do not comprise a cationic lipid. In some embodiments, the formulations do not comprise a cationic lipid or an anionic lipid. In certain embodiments, the formulation do not comprise a phosphatidyl glycerol or derivative thereof. In particular embodiments, the formulations do not comprise egg phosphatidylcholine.

In some embodiments of the lipid mixtures, liposome-containing compositions and the targeted liposomes, the at least two different neutral lipids are one or more phospholipids and cholesterol or a cholesterol derivatives. In some embodiments, at least one of the at least two different neutral lipids is a phospholipid. In certain embodiments of the lipid mixtures, liposome-containing compositions and the targeted liposomes, the at least two different neutral lipids are a phosphatidyl choline and cholesterol. In particular embodiments, one of the at least two different neutral lipids is DMPC, DSPC or DPPC. In some of the embodiments, one of the at least two different neutral lipids is cholesterol or a cholesterol derivative. In particular embodiments, the at least two different neutral lipids are DMPC and cholesterol, DSPC and cholesterol, or DPPC and cholesterol. In particular embodiments, the at least two different neutral lipids are DMPC and cholesterol.

In some embodiments of the targeted liposomes the mean diameter of the liposome is from about 50 nm to about 250 nm. In certain embodiments, the mean diameter of the liposome is from about 90 nm to about 200 nm. In particular embodiments, the mean diameter of the liposome is from about 100 nm to about 140 nm.

In certain embodiments of the targeted liposomes the zeta potential of the liposome is negative. In particular embodiments, the zeta potential is from about −75 mV to about −90 mV. In some embodiments, the zeta potential is from about −80 mV to about −85 mV.

In some embodiments of the lipid mixtures, liposome-containing compositions and the targeted liposomes, the N-(ω)-dicarboxylic acid-derivatized phosphatidyl ethanolamine is NG-DOPE (where NG-DOPE is equivalent to $R^1$ and $R^2$ being oleoyl and m being 3) and, where present, the succinimidyl ester of an N-(ω)-dicarboxylic acid-derivatized phosphatidyl ethanolamine is NHS-NG-DOPE (where NHS-NG-DOPE is equivalent to $R^3$ and $R^4$ being oleoyl and n being 3) or, where present the targeting-factor modified N-(ω)-dicarboxylic acid-derivatized phosphatidyl ethanolamine is TF-NG-DOPE (where TF-NG-DOPE is equivalent to $R^5$ and $R^6$ being oleoyl and p being 3).

In some embodiments of the liposome-containing compositions and the targeted liposomes, the formulations further include a solution.

In certain embodiments of the targeted liposomes, the molar ratio of neutral lipids:N-(ω)-dicarboxylic acid-derivatized phosphatidyl ethanolamine:targeting factor-modified N-(ω)-dicarboxylic acid-derivatized phosphatidyl ethanolamine is about 95:4:1.

In certain embodiments of the targeted liposomes, the molar ratio of DMPC:cholesterol:(N-(ω)-dicarboxylic acid-derivatized phosphatidyl ethanolamine+targeting-factor modified N-(ω)-dicarboxylic acid-derivatized phosphatidyl ethanolamine) is 50:45:5.

In particular embodiments of the liposome-containing compositions and the targeted liposomes, a labeled compound is present. In certain embodiments, the labeled compound includes a radioisotopic moiety. In particular embodiments, the labeled compound includes $^{125}I$.

In some embodiments of the liposome-containing compositions and the targeted liposomes, a drug is present. In particular embodiments, the drug is an anticancer agent. In some embodiments, the drug is a cytotoxic drug. In certain embodiments, the drug is a topoisomerase I inhibitor. In particular embodiments, the topoisomerase I inhibitor is topotecan or irinotecan. In other embodiments, the drug is a vinca alkaloid. In some embodiments, the vinca alkaloid is vincristine, vinblastine, vinleurosine, vinrodisine, vinorelbine or vindesine. In other embodiments, drug is a nucleic acid. In some of these embodiments, the nucleic acid is an antisense oligonucleotide or a ribozyme. In particular embodiments, the drug is a platinum compound. In certain embodiments, the platinum compound is biplatin, cisplatin, carboplatin, ormaplatin, oxaliplatin, zeniplatin, enloplatin, lobaplatin or spiroplatin. In particular embodiments, the platinum compound is oxaliplatin. In some embodiments drug is an alkylating agent. In particular embodiments, the drug is a taxanes. In other embodiments, the drug is a metabolic antagonist. In certain embodiments, the drug is an antitumour antibiotic. In some embodiments, the drug is a hormone therapy drug. In particular embodiments, the drug is a molecular target drug.

In particular embodiments, where oxaliplatin is present, the oxaliplatin is dissolved in an aqueous solution of a sugar selected from the group consisting of trehalose, maltose, sucrose, lactose, mannose, mannitol, glycerol and dextrose. In certain embodiments, the sugar is at a concentration of from about 1 to about 20% percent sugar (v/v). In some embodiments, the concentration of oxaliplatin is from about 0.1 mg/ml to about 25 mg/ml within the liposome. In other embodiments, the concentration of oxaliplatin is from about 0.5 mg/ml to about 10 mg/ml within the liposome. In still other embodiments, the concentration of oxaliplatin is from about 0.5 mg/ml to about 3 mg/ml.

In particular embodiments where targeting-factor modified N-(ω)-dicarboxylic acid-derivatized phosphatidyl ethanolamine is present, the concentration of targeting ligand incorporated in the liposome is from about 1.0 mg/ml to about 3.0 mg/ml. In certain embodiments, the concentration of targeting ligand incorporated in the liposome is from about 1.0 mg/ml to about 2.5 mg/ml.

In certain embodiments, where a targeting-factor modified N-(ω)-dicarboxylic acid-derivatized phosphatidyl ethanolamine is present, the targeting ligand is transferrin. In some embodiments, the transferrin is in a holo-form but not in an apo-form. In certain embodiments, the transferrin is in a holo-form. In some embodiments, the ferric iron is in a concentration of from about 0.4 to about 3.0 µg/ml. In other embodiments, the ferric iron is in a concentration of from about 0.4 to about 1.5 µg/ml.

In some embodiments of the lipid mixtures, liposome-containing compositions and the targeted liposomes, formulations are free of lipid components other than two different neutral lipids, the N-(ω)-dicarboxylic acid-derivatized phosphatidyl ethanolamine and the targeting-factor modified N-(ω)-dicarboxylic acid-derivatized phosphatidyl ethanolamine. In particular embodiments, the formulations are free of lipid components other than phosphatidyl choline, cholesterol or a cholesterol derivative, the N-(ω)-dicarboxylic acid-derivatized phosphatidyl ethanolamine and the transferrin-modified N-(ω)-dicarboxylic acid-derivatized phosphatidyl ethanolamine.

In another aspect are provided pharmaceutical formulations comprising a targeted liposome or liposome-containing composition as described herein and one or more pharmaceutically acceptable carriers, excipients, diluents, stabilizers, or preservatives.

In yet another aspect are provided kits containing one or more of the lipid mixtures, liposome-containing compositions or targeted liposomes described herein, packaging and instructions for use.

In certain embodiments, the kit includes targeted liposomes. In particular embodiments, the targeted liposome is contained in a first container and one or more pharmaceutically acceptable carriers, excipients, diluents, stabilizers, or preservatives are contained in a second container.

Unless otherwise noted, the lipid-containing compositions as described herein are intended for use in the methods of treatment and diagnosis as described herein and may be incorporated in the pharmaceutical formulations and kits described herein. The lipid-containing compositions described herein (including lipid mixtures, liposome-containing compositions), liposomes (including targeted liposomes, blank liposomes, etc.)) may, unless otherwise noted, be made by the methods of production as described herein.

In another aspect are provided methods for making the lipid-containing compositions described herein, comprising the step of mixing the at least two different neutral lipids, the N-($\omega$)-dicarboxylic acid-derivatized phosphatidyl ethanolamine and the succinimidyl ester of an N-($\omega$)-dicarboxylic acid-derivatized phosphatidyl ethanolamine.

In certain embodiments are provided methods for making the liposome-containing compositions described herein, comprising the steps of a) mixing the at least two different neutral lipids, the N-($\omega$)-dicarboxylic acid-derivatized phosphatidyl ethanolamine and the succinimidyl ester of an N-($\omega$)-dicarboxylic acid-derivatized phosphatidyl ethanolamine to form a lipid mixture;

b) adding a drug to the lipid mixture formed in step (a); and, c) forming a liposome.

In certain embodiments, the mixing step (a) is performed in the presence of an organic solvent.

In some embodiments, the drug in step (b) is in aqueous solution prior to mixing.

In certain embodiments, step (c) comprises sonication or stirring. In particular embodiments, step (c) comprises extrusion.

In further embodiments are provided methods of making a targeted liposome as described herein, comprising the steps of a) mixing the at least two different neutral lipids, the N-($\omega$)-dicarboxylic acid-derivatized phosphatidyl ethanolamine and the succinimidyl ester of an N-($\omega$)-dicarboxylic acid-derivatized phosphatidyl ethanolamine to form a lipid mixture;

b) adding drug or labeled compound to the lipid mixture formed in step (a);

c) forming a liposome; and, d) linking a targeting ligand to the succinimidyl ester of an N-($\omega$)-dicarboxylic acid-derivatized phosphatidyl ethanolamine.

In certain embodiments of the above method, the method further comprising a step (e), purifying the liposome of step (d). In particular embodiments, the drug in step (b) is in aqueous solution prior to mixing. In certain embodiments step (c) comprises sonication or stirring. In some embodiments, step (c) comprises extrusion.

Also provided are additional methods of making a targeted liposome comprising the steps of a) mixing the phosphatidyl choline, cholesterol or a cholesterol derivative, and N-($\omega$)-dicarboxylic acid-derivatized phosphatidyl ethanolamine to form a lipid mixture;

b) adding oxaliplatin to the lipid mixture formed in step (a);

c) forming a liposome; and, d) functionalizing a portion of the N-($\omega$)-dicarboxylic acid-derivatized phosphatidyl ethanolamine to form a succinimidyl ester of the N-($\omega$)-dicarboxylic acid-derivatized phosphatidyl ethanolamine; and e) linking transferrin to the succinimidyl ester of an N-($\omega$)-dicarboxylic acid-derivatized phosphatidyl ethanolamine.

In certain embodiments, the method further comprises a step (f) of purifying the liposome of step (e).

In particular embodiments of the method the drug in step (b) is in aqueous solution prior to mixing.

In some embodiments of the method step (c) comprises sonication or stirring.

In a further aspect of the invention is provided use of the lipid-containing compositions (including targeted liposomes) and formulations thereof as described herein in the manufacture of a medicament. Particularly, the manufacture of a medicament for use in the treatment or diagnosis of conditions as described herein. Further, the pharmaceutical formulations thereof, variously described herein, are also intended for use in the manufacture of a medicament for use in treatment and diagnosis of the conditions and, in accordance with the methods, described herein, unless otherwise noted.

In a further aspect of the invention is provide methods for treating cancer comprising the step of a) administering a targeted liposome as described herein to an individual in need thereof in an amount effective to treat cancer, wherein the drug is an anticancer agent.

In some embodiments, the individual is a mammal. In particular embodiments, the individual is a human.

In certain embodiments, the cancer is breast, gastric, colon, colorectal cancer, cancer of the pancreas, non small cell lung cancer, small cell lung cancer, brain cancer, liver cancer, renal cancer, prostate cancer, bladder cancer, ovary cancer, or a hematological malignancies.

In some embodiments of the methods of treatment, step (a) is performed prior to, concurrently with or after combined modality cancer therapy. In particular embodiments, the combined modality cancer therapy comprises chemotherapy, radiation therapy, or surgery.

In some embodiments of the methods of treatment, step (a) is performed prior to, concurrently with or after adjunctive cancer therapy. In particular embodiments, the adjunctive cancer therapy comprises administration of one or more agents to reduce hair loss, vomiting, immune suppression, nausea, diarrhea, rash, sensory disturbance, anemia, fatigue, stomatitis, or hand foot syndrome. In certain embodiments, step (a) is performed prior to, concurrently with or after administration of one or more additional anticancer agents. In particular embodiments, the one or more additional anticancer agents include 5-fluorouracil, leucovorin, capecitabine, UFT/LV (tegafur-uracil and leucovorin), irinotecan, an-anti EGFR antibody, an anti-VEGF antibody, a tyrosine kinase inhibitor, or combinations thereof.

In certain embodiments of the methods of treatment, the targeted liposome is administered via parenteral administration. In particular embodiments, the parenteral administration is via injection or intravenous infusion.

DETAILED DESCRIPTION OF THE INVENTION

Figure 1:
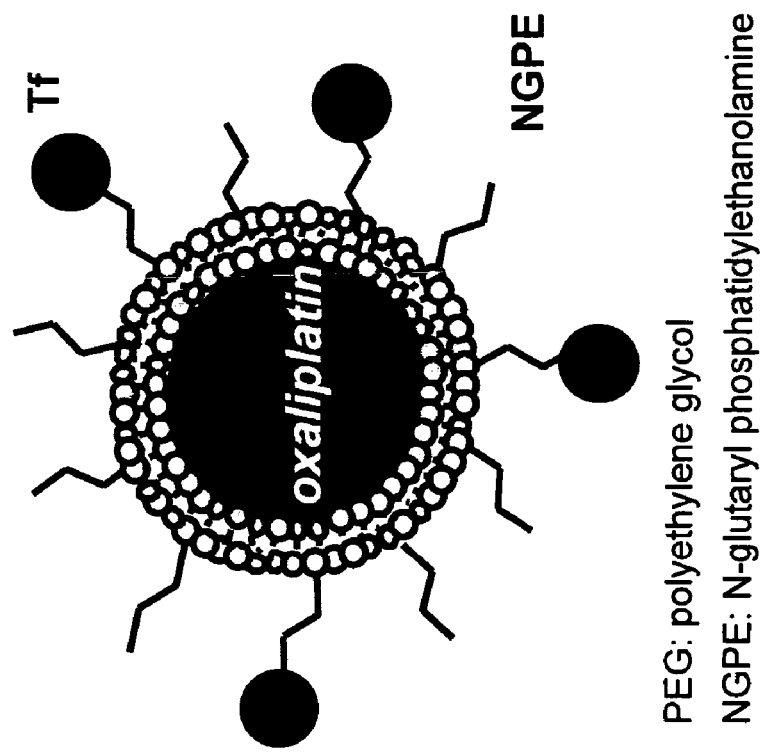
FIG. 1 shows a schematic representation of a targeted liposome.

Provided herein are lipid-containing compositions (including targeted liposomes, blank liposomes, liposome-containing compositions, lipid mixtures, etc.), and methods of making and using the lipid-containing compositions described herein. The lipid-containing compositions, and the liposomes in particular that are provide herein, are suitable for the preparation of pharmaceutical formulations and for use in the treatment or diagnosis of a variety of conditions, including cancer. The compositions, including the pharmaceutical formulations, provide for more effective treatment and diagnosis regimens with reduced adverse effects associated with the drug or labeled compound being delivered to the individual. The increased efficacy and reduced adverse effects should increase the therapeutic index of the drug formulation and provide an opportunity for successful treatment of a variety of conditions, including cancer and should also increase the efficacy and reduce the adverse effects associated with diagnosis. The increased specificity of the drug formulations with the concomitant reduction in adverse effects should ensure therapeutic benefit to a greater number and range of individuals being treated, thus, saving or prolonging lives and improving the quality of life of individuals in need of treatment. The increased specificity of the labeled compound formulations with the concomitant reduction in adverse effects should increase the number of individuals who can be successfully diagnosed, for example, able to tolerate the diagnosis formulation, and also increase the accuracy (e.g., sensitivity, etc.) of diagnosis, including allowing for earlier diagnosis of conditions and more effective monitoring of the severity of the disease (e.g., progression or regression with or without therapy).

Included in the compositions presently described are pharmaceutical formulations of the lipid-containing compositions. The lipid-containing compositions described herein include, but are not limited to, liposomes that encapsulate drugs and labeled compounds and can be used in the treatment or diagnosis of disease or other conditions requiring treatment or diagnosis, including, for example, cancer (e.g., breast, gastric, colorectal or colon cancer).

When conventional anticancer (including cytotoxic) agents are administered intravenously, the entire body is exposed and affected by the drug non-selectively. As a result, a number of adverse reactions may occur, the cancer is not targeted, and/or the drug effect may be lost during the circulation process. Encapsulation of a drug in a liposome composition prior to administration may result in a one or more benefits, including reducing the adverse effect(s) of the drug on a normal cell, protecting the drug until it arrives at a target pathological cell in the case where the drug may be unstable, prolonging the presence of the drug in the circulatory system to enable delivery to pathological cells, and/or in facilitating delivery of the drug to a particular target pathological cell. More specific targeting of the drug and the reduction of loss of drug by uptake in the RES also includes the benefit of reducing the amount of drug that needs to be administered and thereby also reduces the cost of therapy, as well as the other benefits described herein.

Similarly, many labeled compounds have adverse effects and/or may be degraded in the time between administration and diagnosis (e.g., the time at which the diagnostic technique is performed—for example, radioisotope detection, magnetic resonance imaging, ultrasound, etc.). Incorporation of the labeled compounds in the lipid-containing compositions described herein should increase the efficacy of the labeled compound, such as, for example, the threshold of detection may be achieved at lower doses of labeled compound, reducing the adverse effects of the agent, and/or extending the window of time in which the diagnosis can be performed.

The lipid-containing compositions also include lipids modified with targeting ligands (e.g., targeted liposomes, blank liposomes, liposome-containing compositions, lipid mixtures) or other derivatization. For example, liposomal compositions incorporating targeting factor (e.g., transferrin, folate, etc.) and derivatized lipids (e.g., N-($\omega$)-dicarboxylic acid-derivatized phosphatidyl ethanolamines) were developed to improve the safety and efficacy of anticancer agents (e.g., oxaliplatin, etc.) through the prolongation of drug circulation time in plasma (compared to drug administered in solution alone) and by targeting factor-specific receptors on tumor cells. This improved bioavailability and tumor-targeting, should result in improved safety and increased antitumor activity, and therefore a greater likelihood of effective treatment for individuals in need thereof, while also reducing the adverse effects associated with many drugs, particularly the severe adverse effects associated with most anticancer agents. Similarly, such derivatization and targeting factors may also be employed to efficiently target particular sites (e.g., tumor types, organs, tissues, etc.) for delivery of labeled compounds.

The invention also provides transferrin-modified N-($\omega$)-dicarboxylic acid-derivatized phosphatidyl ethanolamines, which can be used in the lipid-containing compositions and formulations thereof described herein.

The lipid-containing compositions, including the liposomes, described herein, may be made by the methods herein described, as well as methods for liposome manufacture known to the skilled artisan and appropriate in view of the teaching provide in the present specification. Unless otherwise noted, the liposomes and liposome-containing compositions described herein can be incorporated without limitation in pharmaceutical formulations and/or kits, including pharmaceutical formulations and/or kits as described herein and, additionally, those that would be apparent to a skilled artisan in view of the teaching provided in the present specification. Similarly the liposomes and liposome-containing compositions and pharmaceutical formulations incorporating the liposomes and liposome-containing compositions may be used without limitation, unless otherwise noted, in the methods of treatment or diagnosis consistent with the description provided throughout the present specification and in accordance with the practice of skill artisans in view of the teaching provided herein.

Figure 2:
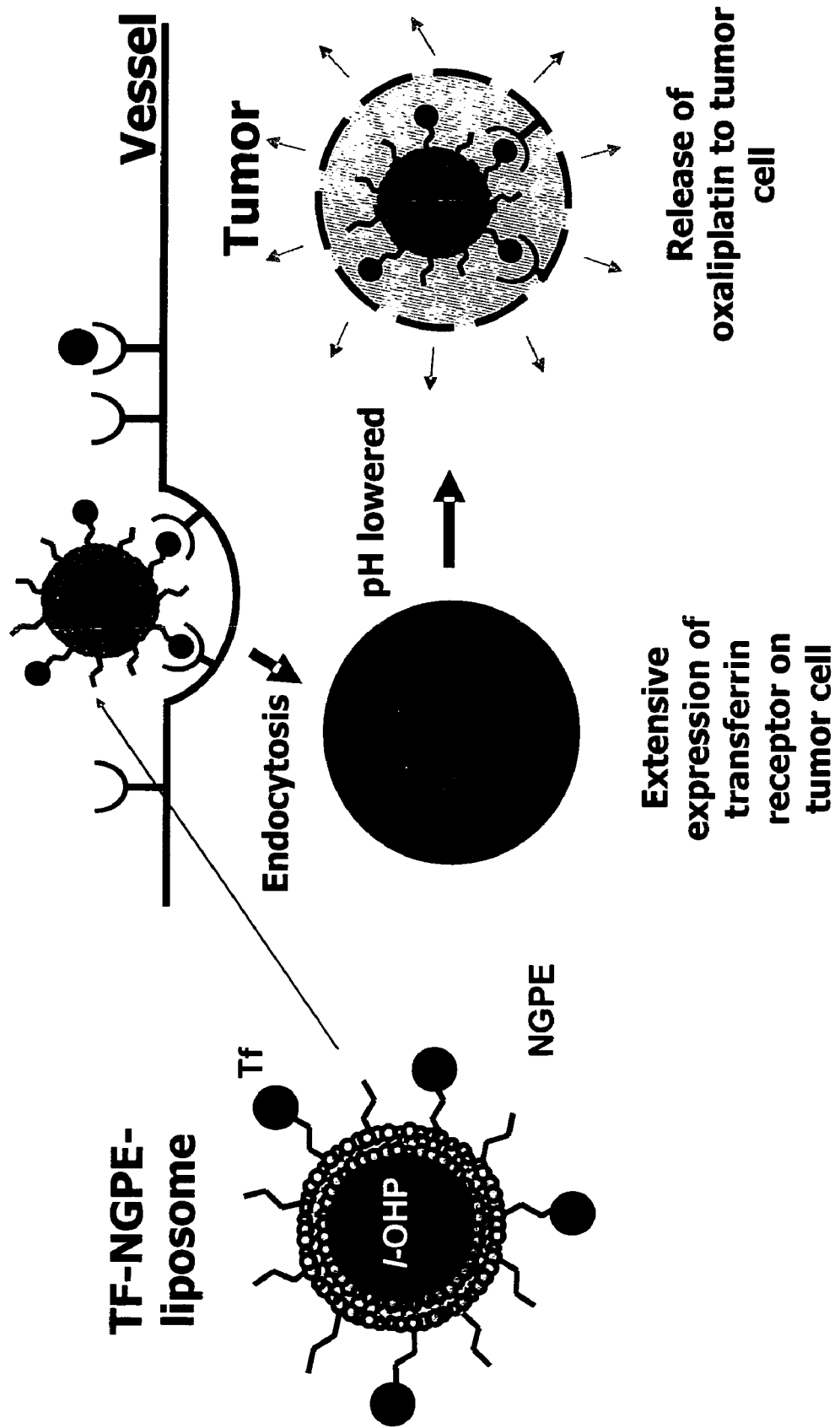
FIG. 2 shows a schematic representation of the active drug targeting of tumor cells using targeted liposomes.
Figure 3:
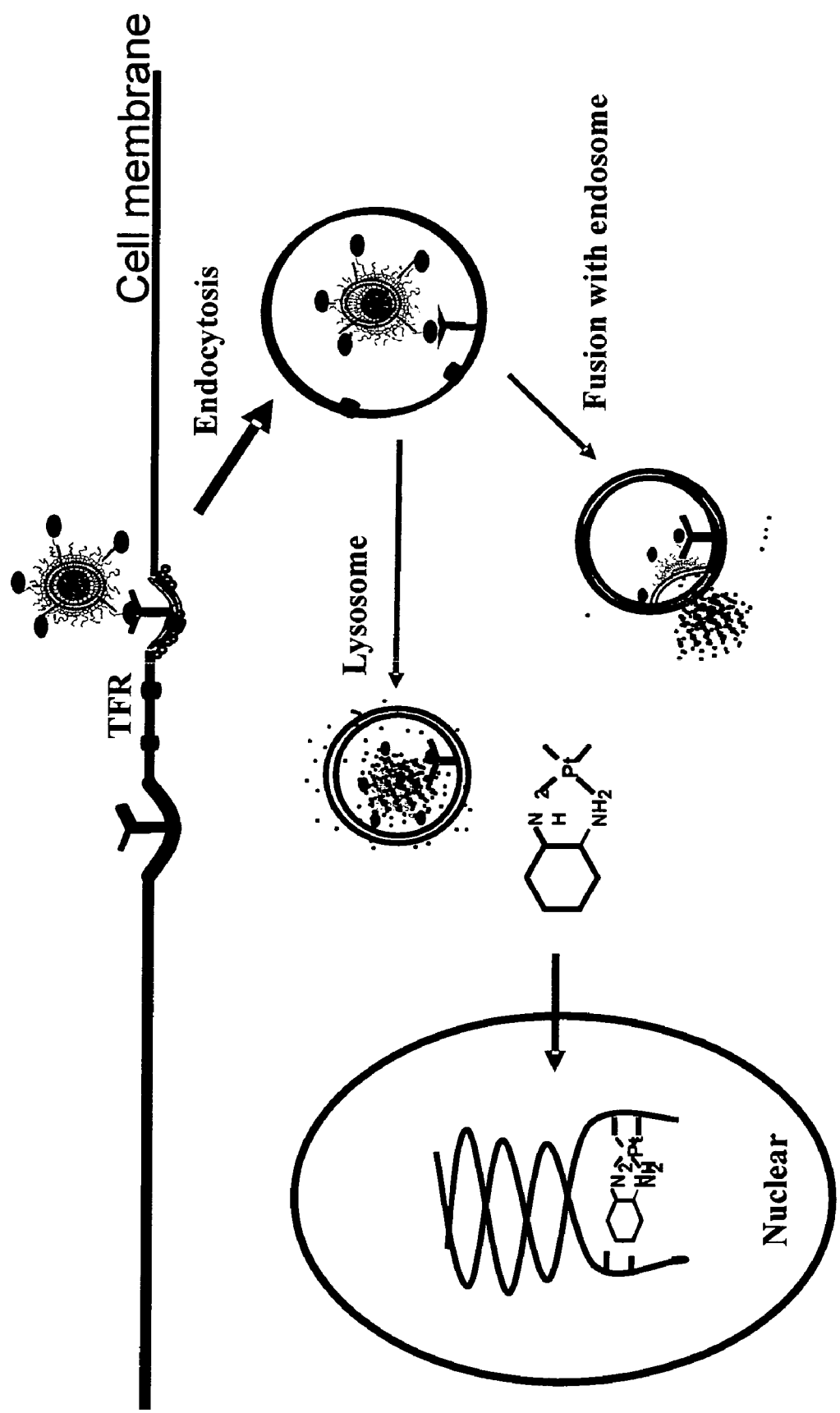
FIG. 3 shows a schematic representation of the proposed mode of action of targeted liposomes containing oxaliplatin.

An exemplary targeted liposome incorporating a drug (oxaliplatin) is represented schematically in FIG. 1. Proposed mechanisms of the uptake and mode of action of targeted liposomes are provided in FIGS. 2 and 3. As used herein, the term "targeted liposome" refers generally to a liposome with components including at least one or more phospholipid(s), N$\omega$PE, TF-N$\omega$PE and which also incorporates a drug or labeled compound as described herein. Each of these components as described throughout the specification, without limitation, can be incorporated into the targeted liposomes of the present invention in keeping with the teaching provided herein. It is noted that blank liposomes, described in greater detail herein, can also be "targeted," in that they can incorporate TF-modified N$\omega$PEs, but generally do not incorporate a drug or labeled compound.

N-(ω)-dicarboxylic acid-derivatized phosphatidyl ethanolamines

The lipid-containing compositions described herein incorporate at least one N-(ω)-dicarboxylic acid-derivatized phosphatidyl ethanolamine according to Formula 1, below:

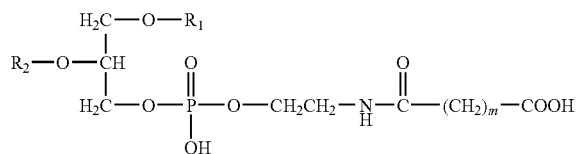

Formula 1 wherein $R^1$ and $R^2$ are, independently, an acyl group, and m is and integer from 1 to 10.

As used herein, the term "N-(ω)-dicarboxylic acid-derivatized phosphatidyl ethanolamine," and its cognates, refer to the N-(ω)-dicarboxylic acid-derivatized phosphatidyl ethanolamines encompassed by Formula 1 as provided herein. Similarly the abbreviation NωPE is used to refer to the N-(ω)-dicarboxylic acid-derivatized phosphatidyl ethanolamines encompassed by Formula I (e.g., Nω-DOPE, Nω-DSPE, NG-DOPE, etc.), and, for example NG-PE refers to N-glutaryl phosphatidyl ethanolamine(s) of Formula 1, unless otherwise noted.

It is intended that the only phosphatidyl ethanolamine(s) incorporated in the lipid-containing compositions (including targeted liposomes) described herein are N-(ω)-dicarboxylic acid-derivatized phosphatidyl ethanolamines of Formula 1 or succinimidyl esters of N-(ω)-dicarboxylic acid-derivatized phosphatidyl ethanolamines of Formula 2 or the targeting factor-modified N-(ω)-dicarboxylic acid-derivatized phosphatidyl ethanolamines of Formula 3, as described in greater detail below. As used herein, the term "non-derivatized phosphatidyl ethanolamine," and cognates thereof, refer to phosphatidyl ethanolamine, semi-synthetic phosphatidyl ethanolamine(s), synthetic phosphatidyl ethanolamine(s) and/or derivatives thereof that are not encompassed by Formula 1, Formula 2 or Formula 3.

A wide variety of acyl groups, represented by $R^1$ and $R^2$, may be used in Formula 1, as is well understood by those of ordinary skill in the field.

In some embodiments, the acyl group is derived from saturated or unsaturated aliphatic carboxylic acids having 12-22 carbon atoms. Exemplary acyl groups include, but are not limited to, acyl groups derived from lauric acid, tridecanoic acid, myristic acid, pentadecanoic acid, palmitic acid, margaric acid, stearic acid, nonadecanoic acid, arachic acid, heneicosanic acid, behenic acid, 2-lauroleic acid, 5-lauroleic acid, 11-lauroreic acid, 5-myristoleic acid, myristoleic acid, 2-palmitoleic acid, 7-palmitoleic acid, cis-9-palmitoleic acid, trans-9-palmitoleic acid, petroselinic acid, petroselidinic acid, oleic acid, elaidic acid, vaccenic acid, gondoic acid, trans-gondoic acid, erucic acid, linoleic acid, linoelaidic acid, α-eleostearic acid, β-eleostearic acid, linolenic acid, pseudoeleostearic acid, arachidonic acid, eicosapentaenic acid, or docosahexaenic acid.

In certain embodiments, the acyl group is derived from saturated or unsaturated aliphatic carboxylic acids having 14-18 carbon atoms. Exemplary acyl groups of this type include, but are not limited to those derived from oleic acid (18 carbons), palmitic acid (16 carbons), stearic acid (18 carbons), or myristic acid (14 carbons). As is recognized by those of skill, the corresponding acyl groups are oleoyl, palmitoyl, stearoyl, and myristoyl, respectively.

In other embodiments, the acyl groups are derived from saturated or unsaturated aliphatic carboxylic acids having 14-18, 14-20, 14-22, 16-18, 16-20, 16-22, 18-20, 18-22, 12, 14, 16, 18, 20 or 22 carbons. In certain embodiments, the acyl groups are derived from saturated or unsaturated aliphatic carboxylic acids having an even number of carbons.

In some embodiments, the acyl groups are derived from oleic acid (oleoyl), stearic acid (stearoyl), palmitic acid (palmitoyl), linoleic acid (linoleoyl, 18 carbons), or myristic acid (myristoyl). In other embodiments, the acyl groups are derived from oleic acid (oleoyl). In certain embodiments, the acyl groups are derived from stearic acid (stearoyl). In still other embodiments, the acyl groups are derived from palmitic acid (palmitoyl). In other embodiments, the acyl groups are derived from myristic acid (myristoyl).

In some embodiments, the acyl group is derived from a saturated aliphatic carboxylic acid, such as, but not limited to palmitic acid (16 carbons), stearic acid (18 carbons), or myristic acid (14 carbons).

In other embodiments, the acyl group is derived from an unsaturated aliphatic carboxylic acid, such as, but not limited to oleic acid (oleoyl, 18 carbons), linoleic acid (linoleoyl, 18 carbons) or linolenic acid (linolenoyl, 18 carbons). In some embodiments, the acyl group is derived from linoleic acid.

In certain embodiments, m is 1, 2, 3, 4, 5, 6, 7, 8, 9, or 10. In other embodiments, m is an integer from 1-8, 1-6, 1-5, 1-7, 1-3, 1-2, 2-8, 2-6, 2-5, 2-4, 2-3, 3-4, 3-5, or 3-6. In some embodiments, m is an integer from 2-4. In other embodiments, m is 1, 2 or 3.

In certain embodiments, m is an integer from 1 to 4. As is recognized by those of ordinary skill, m=1 corresponds to a malonic acid derivative of the phosphatidyl ethanolamine (PE), while m=2, 3, or 4, represent succinic acid, glutaric acid, and adipic acid derivatives of the PE, respectively. In some embodiments, m is 3 (glutaric acid).

In certain embodiments, $R^1$ and $R^2$ are the same acyl group. In other embodiments, $R^1$ and $R^2$ are different acyl groups. In certain embodiments, $R^1$ and $R^2$ are oleoyl, stearoyl, palmitoyl or myristoyl. In some embodiments, $R^1$ and $R^2$ are oleoyl. In other embodiments, $R^1$ and $R^2$ are stearoyl. In particular embodiments, $R^1$ and $R^2$ are palmitoyl. In other embodiments, $R^1$ and $R^2$ are myristoyl.

In some embodiments, the N-(ω)-dicarboxylic acid-derivatized phosphatidyl ethanolamine of Formula 1 is N-glutaryl-dioleoyl phosphatidyl ethanolamine (NG-DOPE (i.e., where $R^1$ and $R^2$ are oleoyl and m is 3)). In other embodiments, it is N-glutaryl-distearoyl phosphatidyl ethanolamine (NG-DSPE (i.e., where $R^1$ and $R^2$ are stearoyl and m is 3). In other embodiments, it is N-glutaryl-dimyristoyl phosphatidyl ethanolamine (NG-DMPE (i.e., where $R^1$ and $R^2$ are myristoyl and m is 3)). In other embodiments, it is N-glutaryl-dipalmitoyl phosphatidyl ethanolamine (NG-DPPE (i.e., where $R^1$ and $R^2$ are palmitoyl and m is 3)). In other embodiments, it is N-succinyl-distearoyl phosphatidyl ethanolamine (NS-DSPE (i.e., where $R^1$ and $R^2$ are stearoyl and m is 2)). In other embodiments, it is N-adipinyl-distearoyl phosphatidyl ethanolamine (NA-DSPE (i.e., where $R^1$ and $R^2$ are stearoyl and m is 4)). In certain embodiments the N-(ω)-dicarboxylic acid-derivatized phosphatidyl ethanolamine of Formula 1 is NG-DOPE or NG-DSPE.

Preparation of N-(ω)-dicarboxylic Acid-Derivatized Phosphatidyl Ethanolamines

The N-(ω)-dicarboxylic acid-derivatized phosphatidyl ethanolamines described herein can be obtained by binding a dicarboxylic acid to the amino group of phosphatidyl ethanol amine.

Phospholipids, including phosphatidyl ethanolamines and their derivatives utilized for the purposes described herein, must be of high purity and should ideally be homogeneous. Known methods for the preparation of high purity phospholipids include extraction of the lipid from a buffer solution and purification using column chromatography. For example, production methods for N-succinyl dipalmitoylphosphatidylethanolamine are described in International Patent Application Publication WO93/01828 (JPAH7-501316) and U.S. Pat. Nos. 5,804,552 and 5,554,728, the contents of which are hereby incorporated in their entirety. These production methods include the purification of phospholipid derivative from the reaction mixture by silica-gel 60 column chromatography of the reaction mixture. Dipalmitoyl phosphatidyl ethanolamine (DPPE) is reacted with succinic acid anhydride with triethylamine catalyst at room temperature under nitrogen gas for 16 hours.

Other production methods of N-(ω-carboxy) acylamido-phosphatidyl ethanolamine phospholipid derivatives are described in Japanese published patent application JPA2001-261688, which includes purification by separating a liquid layer after addition of pH3.5-7.5 buffer solution to the reaction mixture, and is herein incorporated by reference in its entirety. In this case, the PE was reacted with dicarboxylic acid anhydride with triethylamine alkali catalyst at 4° C. for 1 hr. This method may not work well for all phosphatidyl ethanolamine derivatives.

DOPE (dioleoyl-phosphatidyl ethanolamine) can also be commercially obtained or prepared by methods known to the skilled artisan. For example, briefly, lecithin (API Starting Material) can be chemically hydrolyzed to generate glycerol-phospho-choline that is isolated by precipitation. The lipid is then acylated using activated oleic acid, and DOPC (dioleoyl-phosphatidyl choline) is isolated by normal phase column chromatography and passed through ion exchange column to purify. DOPE can be prepared from DOPC by reacting with ethanolamine using phospholipase D.

The N-(ω-carboxy) acylamido-phosphatidylethanolamine phospholipid derivatives can also be prepared in such a manner as described in, for example, U.S. Pat. No. 4,534,899, which is hereby incorporated in its entirety. Briefly, a dicarboxylic anhydride is reacted with a phospholipid such as phosphatidylethanolamine to obtain a dicarboxylic acid-derivatized phosphatidylethanolamine.

Succinimidyl Esters of N-(ω)-dicarboxylic Acid-Derivatized Phosphatidyl Ethanolamines Succinimidyl esters of N-(ω)-dicarboxylic acid-derivatized phosphatidyl ethanolamines as described herein are represented by the following Formula 2:

Formula 2

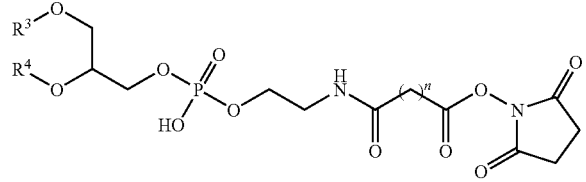

wherein $R^3$ and $R^4$ are, independently, an acyl group, and n is and integer from 1 to 10.

As used herein, the term "succinimidyl esters of N-(ω)-dicarboxylic acid-derivatized phosphatidyl ethanolamine," and its cognates, refer to the succinimidyl esters of N-(ω)-dicarboxylic acid-derivatized phosphatidyl ethanolamines encompassed by Formula 2 as provided herein. Similarly the abbreviation SuccNωPE can be used to refer to the succinimidyl esters of N-(ω)-dicarboxylic acid-derivatized phosphatidyl ethanolamines encompassed by Formula 2 (e.g., SuccNω-DOPE, SuccNω-DSPE, SuccNG-DOPE, etc.), and, for example NHS-NG-PE refers to a the succinimidyl ester of N-glutaryl phosphatidyl ethanolamine(s) of Formula 2 formed by reaction with NHS, unless otherwise noted.

A wide variety of acyl groups that are represented by $R^3$ and $R^4$ may be used, as is well understood by those of ordinary skill in the field and as described above for $R^1$ and $R^2$. Unless otherwise noted herein, it is expressly intended that the description provided herein of the acyl groups with respect to Formula 1 (e.g., $R^1$ and $R^2$) is equally applicable to the acyl groups with respect to Formula 2 (e.g., $R^3$ and $R^4$). Including, in particular, the description above in the section entitled "N-(ω)-dicarboxylic acid-derivatized phosphatidyl ethanolamines."

In certain embodiments, $R^3$ and $R^4$ are the same acyl group. In other embodiments, $R^3$ and $R^4$ are different acyl groups. In certain embodiments, $R^3$ and $R^4$ are oleoyl, stearoyl, palmitoyl or myristoyl. In some embodiments, $R^3$ and $R^4$ are oleoyl. In other embodiments, $R^3$ and $R^4$ are stearoyl. In certain embodiments, $R^3$ and $R^4$ are palmitoyl. In other embodiments, $R^3$ and $R^4$ are myristoyl.

In certain embodiments, n is 1, 2, 3, 4, 5, 6, 7, 8, 9, or 10. In other embodiments, n is an integer from 1-8, 1-6, 1-5, 1-7, 1-3, 1-2, 2-8, 2-6, 2-5, 2-4, 2-3, 3-4, 3-5, or 3-6. In some embodiments, n is an integer from 2-4. In other embodiments, n is 1, 2 or 3.

In certain embodiments, n is an integer from 1 to 4. As is recognized by those of ordinary skill, n=1 corresponds to a malonic acid derivative of the phosphatidyl ethanolamine (PE), while n=2, 3, or 4, represent succinic acid, glutaric acid, and adipic acid derivatives of the PE, respectively. In some embodiments, n is 3 (glutaric acid).

In some embodiments, the succinimidyl ester of the N-(ω)-dicarboxylic acid-derivatized phosphatidyl ethanolamine of Formula 2 is a succinimidyl ester of N-glutaryl-dioleoyl phosphatidyl ethanolamine (NG-DOPE). In other embodiments, it is a succinimidyl ester of N-glutaryl-distearoyl phosphatidyl ethanolamine (NG-DSPE). In certain embodiments the succinimidyl ester of the N-(ω)-dicarboxylic acid-derivatized phosphatidyl ethanolamine of Formula 2 is a succinimidyl ester of NG-DOPE or NG-DSPE.

In some embodiments, the succinimidyl ester of the N-(ω)-dicarboxylic acid-derivatized phosphatidyl ethanolamine of Formula 2 is the succinimidyl ester of the N-glutaryl-dioleoyl phosphatidyl ethanolamine (SuccNG-DOPE (i.e., where $R^3$ and $R^4$ are oleoyl and n is 3)). In other embodiments, it is the succinimidyl ester of N-glutaryl-distearoyl phosphatidyl ethanolamine (SuccNG-DSPE (i.e., where $R^3$ and $R^4$ are stearoyl and n is 3). In other embodiments, it is the succinimidyl ester of N-glutaryl-dimyristoyl phosphatidyl ethanolamine (SuccNG-DMPE (i.e., where $R^3$ and $R^4$ are myristoyl and n is 3)). In other embodiments, it is the succinimidyl ester of N-glutaryl-dipalmitoyl phosphatidyl ethanolamine (SuccNG-DPPE (i.e., where $R^3$ and $R^4$ are palmitoyl and n is 3)). In other embodiments, it is the succinimidyl ester of N-succinyl-distearoyl phosphatidyl ethanolamine (SuccNS-DSPE (i.e., where $R^3$ and $R^4$ are stearoyl and n is 2)). In other embodiments, it is the succinimidyl ester of N-adipinyl-distearoyl phosphatidyl ethanolamine (SuccNA-DSPE (i.e., where $R^3$ and $R^4$ are stearoyl and n is 4)). In certain embodiments the succinimidyl ester of the N-(ω)-dicarboxylic acid-derivatized phosphatidyl ethanolamine of Formula 2 is SuccNG-DOPE or SuccNG-DSPE.

In some embodiments, the N-(ω)-dicarboxylic acid-derivatized phosphatidyl ethanolamine is Nω-DOPE and the succinimidyl ester of the N-(ω)-dicarboxylic acid-derivatized phosphatidyl ethanolamine is SuccNω-DOPE. In other embodiments, the N-(ω)-dicarboxylic acid-derivatized phosphatidyl ethanolamine is Nω-DSPE and the succinimidyl ester of the N-(ω)-dicarboxylic acid-derivatized phosphatidyl ethanolamine is SuccNω-DSPE. In still other embodiments, the N-(ω)-dicarboxylic acid-derivatized phosphatidyl ethanolamine is Nω-DOPE and the succinimidyl ester of the N-(ω)-dicarboxylic acid-derivatized phosphatidyl ethanolamine is SuccNω-DSPE. In certain other embodiments, the N-(ω)-dicarboxylic acid-derivatized phosphatidyl ethanolamine is Nω-DSPE and the succinimidyl ester of the N-(ω)-dicarboxylic acid-derivatized phosphatidyl ethanolamine is SuccNω-DOPE. In certain of these embodiments, the succinimidyl ester may be NHS (e.g., NHS-Nω-DOPE, NHS-Nω-DSPE, etc.).

In some embodiments, the N-(ω)-dicarboxylic acid-derivatized phosphatidyl ethanolamine is NG-DOPE and the succinimidyl ester of the N-(ω)-dicarboxylic acid-derivatized phosphatidyl ethanolamine is SuccNG-DOPE. In other embodiments, the N-(ω)-dicarboxylic acid-derivatized phosphatidyl ethanolamine is NG-DSPE and the succinimidyl ester of the N-(ω)-dicarboxylic acid-derivatized phosphatidyl ethanolamine is SuccNG-DSPE. In still other embodiments, the N-(ω)-dicarboxylic acid-derivatized phosphatidyl ethanolamine is NG-DOPE and the succinimidyl ester of the N-(ω)-dicarboxylic acid-derivatized phosphatidyl ethanolamine is SuccNG-DSPE. In certain other embodiments, the N-(ω)-dicarboxylic acid-derivatized phosphatidyl ethanolamine is NG-DSPE and the succinimidyl ester of the N-(ω)-dicarboxylic acid-derivatized phosphatidyl ethanolamine is SuccNG-DOPE. In certain of these embodiments, the succinimidyl ester may be NHS (e.g., NHS-NG-DOPE, NHS-NG-DSPE, etc.).

Preparation of Succinimidyl Esters of N-(ω)-dicarboxylic Acid-Derivatized Phosphatidyl Ethanolamines The succinimidyl esters of N-(ω)-dicarboxylic acid-derivatized phosphatidyl ethanolamines described herein can be obtained by derivatization of the N-(ω)-dicarboxylic acid-derivatized phosphatidyl ethanolamines described herein, prepared as known in the art and described herein. Preparation of the succinimidyl esters of N-(ω)-dicarboxylic acid-derivatized phosphatidyl ethanolamines is also described in greater detail below, including in the Examples. In view of the teaching provided in the present specification, the skilled artisan will also be able to modify the methods described herein.

A method for the production of the succinimidyl esters of N-(ω)-dicarboxylic acid-derivatized phosphatidyl ethanolamines of the present inventions is as follows:

To 1 equivalent of N-(ω)-dicarboxylic acid-derivatized phosphatidyl ethanolamines represented by Formula 2 as described herein is added about 0.7-1.3 equivalents of NHS, which are dissolved in an organic solvent that does not have an active hydrogen. The mixture is then reacted with about 0.7-1.3 equivalents of a carbodiimide compound at 0-50° C., for about 1-7 days.

Exemplary, organic solvents that do not have an active hydrogen include, but are not limited to, esters (e.g., ethyl acetate, butyl acetate, etc.), aliphatic hydrocarbons (e.g., hexane, heptanes, etc.), aromatic hydrocarbons (e.g., toluene, xylene, etc.), halogenated hydrocarbone (e.g., chloroform, dichloromethane, dichloroethane, etc.), ethers (e.g., THF, dioxane, diethyl ether, etc.), cyclic hydrocarbons (e.g., cyclohexane, etc.), DMF and DMSO. The organic solvent may also be dehydrated.

A wide variety of carbodiimide compounds can be used, so long as the compounds posses a carbodiimide group (—N=C=N—). For example, carbodiimide compounds that made be used include, but are not limited to, carbodiimide groups such as N,N'-dicyclohexyl-carbodiimide (DCC), N,N'-diisopropyl-carbodiimide, N-ethyl-N'-(3-dimethylaminopropyl)-carbodiimide hydrochloride (EDC), etc. In certain embodiments, DCC used. In others EDC is used.

The above-described reaction may also be performed under conditions that minimize or eliminate production of by-products. Unwanted by-products include urea compounds (e.g., N,N'-dicyclohexylurea, N-ethyl-N'-(3-dimethylaminopropyl)urea, etc.), N-acylated urea compounds, carboxyanhydride compounds and 5-oxazolone compounds. Conditions and materials which disfavor or minimize the formation of by-products include, 1) slowly dissolving the carbodiimide compounds in organic solvent, 2) performing the reaction below 0 C.° to prevent heat evolution by the reaction, etc. Other means for optimizing the reaction and minimizing the production of by-products will be understood by those of ordinary skill in the field, particularly in view of the teaching provided herein.

The organic solvent that is capable of dissolving the carbodiimide compounds is the same as the organic solvent, which does not have an active hydrogen as described above. The solvent used to dissolve the carbodiimide and the organic solvent without active hydrogens may be the same or different.

The progress of the reaction can monitored by a thin-layer chromatography (TLC) systems, high-performance liquid chromatography (HPLC), and/or evaporated light scattering detectors. Other methods for monitoring the progress of the reaction will also be known by those of skill in the art.

Purification can be performed by silica gel column chromatography using a mixture of chloroform and methanol. Additional purification methods will be known to those of skill in the art.

In fully dehydrated organic solvents and in the absence of strong acidity or strong alkali, the succinimidyl esters of N-(ω)-dicarboxylic acid-derivatized phosphatidyl ethanolamines as described herein are usually stable.

Targeting Factor-Modified N-(ω)-dicarboxylic Acid-Derivatized Phosphatidyl Ethanolamines Targeting factor-modified N-(ω)-dicarboxylic acid-derivatized phosphatidyl ethanolamines include a targeting ligand linked to a second N-(ω)-dicarboxylic acid-derivatized phosphatidyl ethanolamine, where the second N-(ω)-dicarboxylic acid-derivatized phosphatidyl ethanolamine is represented by Formula 3, Formula 3

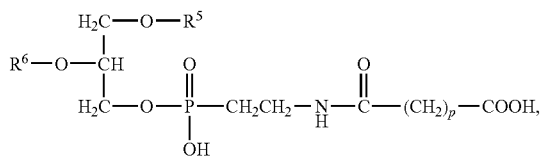

wherein $R^5$ and $R^6$ are, independently, an acyl group, and p is and integer from 1 to 10.

As used herein, the term "targeting factor-modified N-(ω)-dicarboxylic acid-derivatized phosphatidyl ethanolamine," and its cognates, refer to the N-(ω)-dicarboxylic acid-derivatized phosphatidyl ethanolamines encompassed by Formula 3 and modified with a targeting factor as provided herein. Similarly the abbreviation TF-NωPE can be used to refer to the targeting factor-modified N-(ω)-dicarboxylic acid-derivatized phosphatidyl ethanolamines (e.g., TF-Nω-DOPE, TF-Nω-DSPE, TF-NG-DOPE, etc.), and, for example TF-NG-PE refers to a targeting ligand linked to N-glutaryl phosphatidyl ethanolamine(s) of Formula 3.

A wide variety of acyl groups that are represented by $R^5$ and $R^6$ may be used, as is well understood by those of ordinary skill in the field and as described above for $R^1$ and $R^2$. Unless otherwise noted herein, it is expressly intended that the description provided herein of the acyl groups with respect to Formula 1 (e.g., $R^1$ and $R^2$) is equally applicable to the acyl groups with respect to Formula 3 (e.g., $R^5$ and $R^6$). Including, in particular, the description above in the section entitled "N-(ω)-dicarboxylic acid-derivatized phosphatidyl ethanolamines."

In certain embodiments, $R^5$ and $R^6$ are the same acyl group. In other embodiments, $R^5$ and $R^6$ are different acyl groups. In certain embodiments, $R^5$ and $R^6$ are oleoyl, stearoyl, palmitoyl or myristoyl. In some embodiments, $R^5$ and $R^6$ are oleoyl. In other embodiments, $R^5$ and $R^6$ are stearoyl. In certain embodiments, $R^5$ and $R^6$ are palmitoyl. In other embodiments, $R^5$ and $R^6$ are myristoyl.

In certain embodiments, p is 1, 2, 3, 4, 5, 6, 7, 8, 9, or 10. In other embodiments, p is an integer from 1-8, 1-6, 1-5, 1-7, 1-3, 1-2, 2-8, 2-6, 2-5, 2-4, 2-3, 3-4, 3-5, or 3-6. In some embodiments, p is an integer from 2-4. In other embodiments, p is 1, 2 or 3.

In certain embodiments, p is an integer from 1 to 4. As is recognized by those of ordinary skill, p=1 corresponds to a malonic acid derivative of the phosphatidyl ethanolamine (PE), while p=2, 3, or 4, represent succinic acid, glutaric acid, and adipic acid derivatives of the PE, respectively. In some embodiments, p is 3 (glutaric acid).

In some embodiments, the targeting factor-modified N-(ω)-dicarboxylic acid-derivatized phosphatidyl ethanolamine of Formula 3 is targeting factor-modified N-glutaryl-dioleoyl phosphatidyl ethanolamine (TF-NG-DOPE). In other embodiments, the targeting factor-modified N-glutaryl-distearoyl phosphatidyl ethanolamine is (TF-NG-DSPE). In certain embodiments the targeting factor-modified N-(ω)-dicarboxylic acid-derivatized phosphatidyl ethanolamine of Formula 3 is TF-NG-DOPE or TF-NG-DSPE.

In some embodiments, the N-(ω)-dicarboxylic acid-derivatized phosphatidyl ethanolamine of Formula 3 is N-glutaryl-dioleoyl phosphatidyl ethanolamine (NG-DOPE (i.e., where $R^5$ and $R^6$ are oleoyl and p is 3)). In other embodiments, it is N-glutaryl-distearoyl phosphatidyl ethanolamine (NG-DSPE (i.e., where $R^5$ and $R^6$ are stearoyl and p is 3). In other embodiments, it is N-glutaryl-dimyristoyl phosphatidyl ethanolamine (NG-DMPE (i.e., where $R^5$ and $R^6$ are myristoyl and p is 3)). In other embodiments, it is N-glutaryl-dipalmitoyl phosphatidyl ethanolamine (NG-DPPE (i.e., where $R^5$ and $R^6$ are palmitoyl and p is 3)). In other embodiments, it is N-succinyl-distearoyl phosphatidyl ethanolamine (NS-DSPE (i.e., where $R^5$ and $R^6$ are stearoyl and p is 2)). In other embodiments, it is N-adipinyl-distearoyl phosphatidyl ethanolamine (NA-DSPE (i.e., where $R^5$ and $R^6$ are stearoyl and p is 4)). In certain embodiments the N-(ω)-dicarboxylic acid-derivatized phosphatidyl ethanolamine of Formula 3 is NG-DOPE or NG-DSPE.

In certain embodiments the targeting ligand is transferrin (Tf), which is described in greater detail below, and the N-(ω)-dicarboxylic acid-derivatized phosphatidyl ethanolamine incorporated in the transferrin-modified N-(ω)-dicarboxylic acid-derivatized phosphatidyl ethanolamine is of Formula 3, as described herein.

In some embodiments, the N-(ω)-dicarboxylic acid-derivatized phosphatidyl ethanolamine is Nω-DOPE and the targeting ligand is transferrin (Tf), and the targeting factor-modified N-(ω)-dicarboxylic acid-derivatized phosphatidyl ethanolamine is Tf-Nω-DOPE. In other embodiments, the N-(ω)-dicarboxylic acid-derivatized phosphatidyl ethanolamine is Nω-DSPE and the targeting ligand is transferrin (Tf), and the targeting factor-modified N-(ω)-dicarboxylic acid-derivatized phosphatidyl ethanolamine is Tf-Nω-DSPE. In still other embodiments, the N-(ω)-dicarboxylic acid-derivatized phosphatidyl ethanolamine is Nω-DOPE and the targeting ligand is transferrin (Tf), and the targeting factor-modified N-(ω)-dicarboxylic acid-derivatized phosphatidyl ethanolamine is Tf-Nω-DSPE. In certain other embodiments, the N-(ω)-dicarboxylic acid-derivatized phosphatidyl ethanolamine is Nω-DSPE and the targeting ligand is transferrin (Tf), and the targeting factor-modified N-(ω)-dicarboxylic acid-derivatized phosphatidyl ethanolamine is Tf-Nω-DOPE. In certain of these embodiments, m may be 3 and the N-(ω)-dicarboxylic acid-derivatized phosphatidyl ethanolamine is a NG-PE according to Formula 1.

In some embodiments, the N-(ω)-dicarboxylic acid-derivatized phosphatidyl ethanolamine is NG-DOPE and the targeting factor-modified N-(ω)-dicarboxylic acid-derivatized phosphatidyl ethanolamine is TF-NG-DOPE. In other embodiments, the N-(ω)-dicarboxylic acid-derivatized phosphatidyl ethanolamine is NG-DSPE and the targeting factor-modified N-(ω)-dicarboxylic acid-derivatized phosphatidyl ethanolamine is TF-NG-DSPE. In still other embodiments, the N-(ω)-dicarboxylic acid-derivatized phosphatidyl ethanolamine is NG-DOPE and the targeting factor-modified N-(ω)-dicarboxylic acid-derivatized phosphatidyl ethanolamine is TF-NG-DSPE. In certain other embodiments, the N-(ω)-dicarboxylic acid-derivatized phosphatidyl ethanolamine is NG-DSPE and the targeting factor-modified N-(ω)-dicarboxylic acid-derivatized phosphatidyl ethanolamine is TF-NG-DOPE.

The targeting-factor modified N-(ω)-dicarboxylic acid-derivatized phosphatidyl ethanolamines may be prepared from the SuccNωPE by reaction with the targeting ligand and other reactants as described herein in greater detail. The TF-NωPE may either be prepared prior to mixture with other lipid components of the lipid-containing compositions described herein (and optionally purified) or may be prepared in situ from the reaction of the pre-prepared SuccNωPE that has been incorporated in a lipid-containing composition.

Additional Lipid Components

The lipid-containing compositions as described herein also contain one or more additional lipid components in addition to the NωPEs, SuccNωPEs and/or TF-NωPEs described herein. A variety of additional lipid components can be used, however, the term "additional lipid component(s)" is not intended to include non-derivatized phosphatidyl ethanolamines (PEs) or derivatives of PEs as in Formulae 1, 2 or 3. In some embodiments, the one or more additional lipid component(s) may be a phospholipid or one or more phospholipids. In certain embodiments, the one or more additional lipid components may include at least two neutral lipids. In other embodiments, one or more phospholipids may be present and, optionally, an "additional lipid" (which is not a phospholipid). A variety of neutral lipids can be used, however, the at least two neutral lipids are not intended to include non-derivatized phosphatidyl ethanolamines (PEs) or derivatives of PEs as in Formulae 1, 2 or 3. It is not intended that the term "phospholipid," as used herein, should include PEs or derivatives thereof, as in Formulae 1, 2 or 3. Similarly, the term "additional lipid" does not include PEs or derivatives thereof, as in Formulae 1, 2 or 3, nor does it include other phospholipids.

In particular embodiments, phospholipid(s) may be used in the lipid-containing compositions and formulations described herein. For example, one or more, at least two, at least three, at least four phospholipids; or, two, three, or four phospholipids. In particular embodiments there is one phospholipid. In certain embodiments the lipid components of the compositions are limited to one phospholipid, the NωPE, and the SuccNωPE (or TF-modified NωPE, where the reaction with the targeting factor has been performed).

In particular embodiments, two or more neutral lipids may be used in the lipid-containing compositions and formulations described herein. For example, at least two, at least three, at least four neutral lipids; or, two, three, or four neutral lipids. In particular embodiments there are two neutral lipids. In certain embodiments the lipid components of the compositions are limited to two neutral lipids, the NωPE, and the SuccNωPE (or TF-modified NωPE, where the reaction with the targeting factor has been performed).

In some embodiments, where the additional lipid components(s) includes a phospholipid, the phospholipid may be a phosphatidylcholine, including naturally occurring, semi-synthetic or synthetic phosphatidylcholines (e.g., DSPC, DMPC, etc.). In some embodiments, the phosphatidylcholine is a non-naturally occurring phosphatidylcholine (e.g., not egg phosphatidylcholine). In particular embodiments, the phosphatidylcholine is an acyl phosphatidylcholine (e.g., DMPC, DPPC, POPC, DSPC, etc.). In some embodiments, the phospholipid is cationic. In other embodiments the phospholipid is anionic. In still other embodiments, the phospholipid is neutral. In particular embodiments, the one or more phospholipid(s) is not anionic. In other embodiments, the one or more phospholipid(s) is not cationic. In certain embodiments where more than one phospholipid is present, an anionic and neutral lipid may be included. Exemplary phospholipids include, but are not limited to, phosphatidylcholines (PCs), phosphatidic acid, phosphatidylserine, phosphatidylglycerol, etc. In some embodiments, the lipid-containing compositions do not include phosphatidylserine or phosphatidylglycerol.

In certain embodiments, at least one of the at least two neutral lipids may be a phospholipid. In some embodiments, the phospholipid may be a phosphatidylcholine, including naturally occurring, semi-synthetic or synthetic phosphatidylcholines (e.g., DSPC, DMPC, etc.). In some embodiments, the phosphatidyl choline is a non-naturally occurring phosphatidyl choline (e.g., not egg phosphatidyl choline). In particular embodiments, the phosphatidyl choline is an acyl phosphatidyl choline (e.g., DMPC, DPPC, POPC, DSPC, etc.).

In some embodiments, at least one of the at least two neutral lipids may be cholesterol or a cholesterol derivative (e.g., cholesterol pullulan, positively-charged cholesterol (e.g., DC-Chol)), incorporating a moiety of a radioisotope (e.g., $^{3}H$, $^{14}C$, $^{125}I$, $^{131}I$, etc.), having a functional moiety (e.g., a fluorescent moiety, etc.).

In certain embodiments, where the lipid-containing compositions include one or more phospholipid, the compositions may additionally comprise an additional neutral, non-phospholipid as the additional lipid. For example, cholesterol or a cholesterol derivative as described above.

Phospholipids (non-PEs) for use in the lipid-containing compositions described herein include synthetic, semi-synthetic and naturally occurring phospholipids. Exemplary phospholipids include, but are not limited to, phosphatidylcholine (PC), phosphatidic acid, phosphatidylserine, phosphatidylglycerol, etc. In other embodiments, the one or more phospholipids include phosphatidylcholine (PC) or phosphatidic acid and do not include phosphatidylserine or phosphatidylglycerol.

In some embodiments, the phospholipid is a phosphatidylcholine. In certain embodiments, the phosphatidylcholine may be, e.g., distearoyl phosphatidyl choline (DSPC), dimyristoyl phosphatidylcholine (DMPC), dipalmitoyl phosphatidylcholine (DPPC), palmitoyl oleoyl phosphatidylcholine (POPC), egg phosphatidylcholine (EPC), hydrogenated soya phosphatidylcholine (HSPC), etc. In particular embodiments, at least one phospholipid is a phosphatidylcholine. In certain of these embodiments, the phosphatidylcholine is DMPC. In other embodiments, the phosphatidylcholine is DSPC. In other embodiments, the phosphatidylcholine is DPPC. In other embodiments, the phosphatidylcholine is POPC. In other embodiments, the phosphatidylcholine is EPC. In other embodiments, the phosphatidylcholine is HSPC. In some embodiments, one phospholipid is included and is DMPC, DSPC, DPPC, POPC, EPC or HSPC. In particular embodiments where there are lipid-containing composition includes a single phospholipid (non-PE phospholipid), the phospholipid is DMPC. In other embodiments where the lipid-containing composition includes a single phospholipid (non-PE phospholipid), the phospholipid is DSPC. In other embodiments where the lipid-containing composition includes a single phospholipid (non-PE phospholipid), the phospholipid is DPPC. In other embodiments where the lipid-containing composition includes a single phospholipid (non-PE phospholipid), the phospholipid is POPC. In other embodiments where the lipid-containing composition includes a single phospholipid (non-PE phospholipid), the phospholipid is EPC. In other embodiments where the lipid-containing composition includes a single phospholipid (non-PE phospholipid), the phospholipid is HSPC.

In certain embodiments, the additional lipid components(s) may include at least one phospholipid and, optionally, an additional lipid such as cholesterol or a cholesterol derivative. In particular embodiments, the additional lipid component(s) are a single phospholipid and cholesterol. In certain embodiments, the additional lipid component(s) include at least one phosphatidylcholine and cholesterol. In particular embodiments, the additional lipid component(s) include a single phosphatidylcholine and cholesterol. In certain embodiments where cholesterol is included, the phospholipid is DSPC, DMPC, DPPC, POPC, EPC or HSPC. In some embodiments, the additional lipid component(s) include cholesterol and DMPC. In other embodiments, the additional lipid component(s) include cholesterol and DSPC. In certain embodiments, the additional lipid component(s) are cholesterol and one of DMPC or DSPC. In certain embodiments, the additional lipid component(s) are cholesterol and DMPC. In other embodiments, the additional lipid component(s) are cholesterol and DSPC. In other embodiments, the additional lipid component(s) include cholesterol and DPPC. In other embodiments, the additional lipid component(s) include cholesterol and POPC. In other embodiments, the additional lipid component(s) include cholesterol and EPC. In other embodiments, the additional lipid component(s) include cholesterol and HSPC. In certain embodiments, the additional lipid component(s) are cholesterol and one of DMPC, DSPC, DPPC, POPC, EPC or HSPC. In certain embodiments, the additional lipid component(s) are cholesterol and DMPC. In other embodiments, the additional lipid component(s) are cholesterol and DSPC. In other embodiments, the additional lipid component(s) are cholesterol and DPPC. In other embodiments, the additional lipid component(s) are cholesterol and POPC. In other embodiments, the additional lipid component(s) are cholesterol and EPC. In other embodiments, the additional lipid component(s) are cholesterol and HSPC.

In particular embodiments, there is one phospholipid and the phospholipid is not HSPC or EPC.

In particular embodiments, there are one or more phospholipids. In certain embodiments, the one or more phospholipid includes a phosphatidyl choline. In particular embodiments, are included one or more phospholipids and cholesterol (or a cholesterol derivative). In certain embodiments, the phospholipid is a phosphatidyl choline and the composition additionally includes a cholesterol (or a cholesterol derivative). In particular embodiments, the phosphatidylcholine is a phosphatidylcholine which includes a moiety of saturated fatty acid (e.g., DMPC, DSPC or DPPC). In certain embodiments the phosphatidylcholine is not egg phosphatidylcholine. In particular embodiments, the phosphatidylcholine is not HSPC.

In particular embodiments, there are two neutral lipids. In some embodiments, the two neutral lipids are cholesterol (or a cholesterol derivative) and a phosphatidyl choline. In particular embodiments, the phosphatidylcholine is a phosphatidylcholine which includes a moiety of saturated fatty acid (e.g., DMPC, DSPC or DPPC). In certain embodiments the phosphatidylcholine is not egg phosphatidylcholine.

The additional lipid component(s) as described herein, and those known to the skilled artisan, are commercially available from a number of suppliers, including, for example Avanti Polar Lipids, Inc. (Alabaster, Ak.), Northern Lipid Inc. (Canada), Lipoid GmbH (Germany), NOF Corporation (Japan), Nippon Fine Chemical Co., Ltd (Japan).

Drugs

A variety of drugs may be included in the lipid-containing compositions of the present invention, for example, a compound or a gene. In certain embodiments, the drug may be an anticancer agent, for example, an anticancer agent suitable for encapsulation in a liposome. The amount of drug to be included in the lipid-containing compositions, and formulations thereof, as described herein can be readily determined by the skilled artisan in view of the teaching herein provided and depending on the drug selected and the use intended for the composition or formulation, taking into account factors specific to both the drug and the individual to be treated, as described further herein.

In certain embodiments, the drug may be a nucleic acid, for example, nucleic acid encoding for sequences with anticancer properties. For example, but not limited to, antisense oligonucleotides, ribozymes, etc.

In some embodiments, the anticancer agent can be a cytotoxic drug, including those known by skill in the art and medical practitioners. Exemplary anticancer agents include topoisomerase I inhibitors, vinca alkaloids, alkylating agents (including platinum compounds), taxanes and others known to those of skill in the art.

In some embodiments, the anticancer drug may be a topoisomerase I inhibitor, for example, but not limited to, topotecan, irinotecan, etc.

The anticancer drug may also be a vinca alkaloid, for example, vincristine, vinblastine, vinleurosine, vinrodisine, vinorelbine, vindesine, etc.

Further, the anticancer drug may also be a platinum compound. Non-limiting examples of platinum compounds include biplatin, cisplatin, carboplatin, ormaplatin, oxaliplatin, zeniplatin, enloplatin, lobaplatin, spiroplatin, etc.

Oxaliplatin (platinum (II) cis-oxalato complex of trans-1-1,2-diaminocyclohexane) is a platinum, more specifically, an oragnoplatinum, complex having a structure represented by the following formula shown below. Oxaliplatin is also known as the following: diaminocyclohexane platinum, DACH-platinum, and cis-[(1R,2R)-1,2-cyclohexanediamine-N,N'][oxalato(2)-O,O']platinum ($C_8H_{14}N_2O_4Pt$; MW 397.4 g/mol). As mentioned previously, oxaliplatin is the active pharmaceutical ingredient in Eloxatin™.

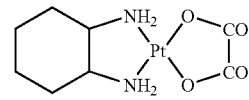

Oxaliplatin is useful as an antitumor agent, since it has a therapeutic activity similar to that of cisplatin and relatively low nephrotoxicity and emetogenicity (vomiting). Production processes for oxaliplatin is well known in the art (e.g., JP-A-9-40685; U.S. Pat. Nos. 4,169,846, 5,338,874; 5,959,133; 5,298,642; and 5,290,961 (the disclosures of which are hereby incorporated in their entirety). Oxaliplatin is further described in Chaney S G et al. "*Recognition and processing of cisplatin-and oxaliplatin-DNA adducts.*" Crit Rev Oncol Hematol. (2005) 53: 3-11 (herein incorporated by reference in its entirety).

In certain embodiments, the oxaliplatin concentration encapsulated within the liposome is about 1 mg/ml, for example about 0.8 mg/ml.

Generally, the liposome composition of the present invention contains from about 1 to about 50 μg oxaliplatin/mg lipid and from about 1 to about 150 μg TF/mg lipid. For example, from about 10 to about 50 μg oxaliplatin/mg lipid and from 10 to about 150 μg TF/mg lipid.

In certain embodiments, the compositions contain from about 1 to about 45 μg oxaliplatin/mg lipid, from about 1 to about 40 μg oxaliplatin/mg lipid, from about 1 to about 35 μg oxaliplatin/mg lipid, from about 1 to about 30 μg oxaliplatin/mg lipid, from about 1 to about 25 μg oxaliplatin/mg lipid, from about 1 to about 20 μg oxaliplatin/mg lipid, from about 1 to about 15 μg oxaliplatin/mg lipid, from about 1 to about 10 μg oxaliplatin/mg lipid, from about 1 to about 5 μg oxaliplatin/mg lipid, from about 5 to about 50 μg oxaliplatin/mg lipid, from about 5 to about 45 μg oxaliplatin/mg lipid, from about 5 to about 35 μg oxaliplatin/mg lipid, from about 5 to about 25 μg oxaliplatin/mg lipid, from about 5 to about 20 μg oxaliplatin/mg lipid, from about 5 to about 15 μg oxaliplatin/mg lipid, from about 5 to about 10 μg oxaliplatin/mg lipid, about 1 μg oxaliplatin/mg lipid, about 2 μg oxaliplatin/mg lipid, about 4 μg oxaliplatin/mg lipid, about 5 μg oxaliplatin/mg lipid, about 10 μg oxaliplatin/mg lipid, about 15 μg oxaliplatin/mg lipid, about 20 μg oxaliplatin/mg lipid, about 30 μg oxaliplatin/mg lipid, about 40 μg oxaliplatin/mg lipid, or about 50 μg oxaliplatin/mg lipid.

In certain embodiments, the compositions contain from about 1 to about 145 μg TF/mg lipid, from about 1 to about 120 μg TF/mg lipid, from about 1 to about 115 μg TF/mg lipid, from about 1 to about 100 μg TF/mg lipid, from about 1 to about 90 μg TF/mg lipid, from about 1 to about 70 μg TF/mg lipid, from about 1 to about 60 μg TF/mg lipid, from about 1 to about 50 μg TF/mg lipid, from about 1 to about 25 μg TF/mg lipid, from about 10 to about 150 μg TF/mg lipid, from about 10 to about 140 μg TF/mg lipid, from about 10 to about 125 μg TF/mg lipid, from about 10 to about 100 μg TF/mg lipid, from about 10 to about 80 μg TF/mg lipid, from about 10 to about 50 μg TF/mg lipid, from about 10 to about 25 μg TF/mg lipid, about 1 μg TF/mg lipid, about 5 μg TF/mg lipid, about 10 μg TF/mg lipid, about 25 μg TF/mg lipid, about 40 μg TF/mg lipid, about 50 μg TF/mg lipid, about 70 μg TF/mg lipid, about 100 μg TF/mg lipid, about 120 μg TF/mg lipid, about 140 μg TF/mg lipid, or about 150 μg TF/mg lipid.

In some embodiments, from about 0.5 to about 50 μg oxaliplatin/mg lipid and from about 1 to about 150 μg TF/mg lipid. In some embodiments, from about 5 to about 50 μg oxaliplatin/mg lipid and from about 10 to about 100 μg/mg. In certain embodiments, from about 2 to about 50 μg oxaliplatin/mg lipid and from about 5 to about 150 μg TF/mg lipid; from about 3 to about 50 μg oxaliplatin/mg lipid and from about 5 to about 150 μg TF/mg lipid; from about 4 to about 50 μg oxaliplatin/mg lipid and from about 5 to about 150 μg TF/mg lipid; from about 2 to about 40 μg oxaliplatin/mg lipid and from about 5 to about 150 μg TF/mg lipid; from about 3 to about 40 μg oxaliplatin/mg lipid and from about 5 to about 150 μg TF/mg lipid; from about 4 to about 40 μg oxaliplatin/mg lipid and from about 5 to about 150 μg TF/mg lipid; from about 2 to about 50 μg oxaliplatin/mg lipid and from about 10 to about 150 μg TF/mg lipid; from about 3 to about 50 μg oxaliplatin/mg lipid and from about 10 to about 150 μg TF/mg lipid; from about 4 to about 50 μg oxaliplatin/mg lipid and from about 10 to about 150 μg TF/mg lipid; from about 5 to about 50 μg oxaliplatin/mg lipid and from about 5 to about 100 μg TF/mg lipid; from about 5 to about 50 μg oxaliplatin/mg lipid and from about 5 to about 100 μg TF/mg lipid; or from about 0.5 to about 50 μg oxaliplatin/mg lipid and from about 5 to about 100 μg TF/mg lipid.

In certain embodiments, the oxaliplatin concentration in the liposome formulation is 0.8+/−10% mg/ml.

In certain embodiments, where the drug is oxaliplatin, the oxaliplatin may be dissolved in a solution (e.g., an aqueous solution). In some embodiments, the solution includes a sugar (e.g., trehalose, maltose, sucrose, lactose, mannose, mannitol, glycerol, dextrose, fructose, etc.) The concentration of the sugar may be of several percent. For example sugar concentrations (v/v) of about 0.1-12%; 0.5-12%, 1%-12%, 2%-8%, 2%-6%, 2%-5%, 2%-4%, 2%-5%, 2%-6%, 2%-8%, 2%-9%, 2%-10%, 4%-10%, 4%-9%, 4%-8%, 4%-6%, 3%-4%, about 2%, about 3%, about 4%, about 5%, about 6%, about 7%, about 8%, about 9% or about 10%. In certain embodiments the solution includes a sugar and is aqueous. It is intended that the solution in which oxaliplatin is dissolved can also contain additional components, including those known to the skilled artisan.

In certain embodiments, the sugar concentration is about 5%, about 7%, about 8%, about 9% or about 10%. In other embodiments, the sugar concentration is about 5% to about 10%. In some embodiments, the sugar is dextrose and the concentration of dextrose in the oxaliplatin solution is about 5%. In some embodiments, the sugar is dextrose and the concentration of dextrose in the oxaliplatin solution is about 9%. In certain embodiments, the sugar is sucrose and the concentration of sucrose in the oxaliplatin solution is about 9%. In certain embodiments, the sugar is sucrose and the concentration of sucrose in the oxaliplatin solution is about 10%.

In some embodiments, the concentration of sugar in solution may be, for example about 50 mg/ml to about 150 mg/ml, about 50 mg/ml to about 130 mg/ml, about 50 mg/ml to about 120 mg/ml, about 50 mg/ml to about 100 mg/ml, about 80 mg/ml to about 100 mg/ml, about 90 mg/ml to about 150 mg/ml, about 90 mg/ml to about 130 mg/ml, about 60 mg/ml, about 80 mg/ml, about 90 mg/ml, about 100 mg/ml, about 110 mg/ml, about 105 mg/ml, about 120 mg/ml, or about 140 mg/ml.

The solution may also contain other ingredients known to those of skill in the art, such as, but not limited to, salts, buffers, sugar alcohol, etc. In certain embodiments, the solution in which oxaliplatin is dissolved contains sodium phosphate (e.g., monobasic and/or dibasic sodium phosphate).

In certain embodiments, the concentration of sodium phosphate may be about 5 to about 15 mM. For example, from about 5 to about 12 mM, from about 5 to about 10 mM, from about 5 to about 7 mM, from about 7 to about 12 mM, from about 7 to about 15 mM, from about 9 to about 12 mM, about 5 mM, about 7 mM, about 10 mM, about 12 mM or about 15 mM.

In certain embodiments, the sugar solution may additionally include about 1.0 to about 1.5 mg/ml sodium phosphate. For example, about 1.2 to about 1.5 mg/ml, 1.0 to about 1.7 mg/ml, 1.0 to about 2 mg/ml, 1.0 to about 2.5 mg/ml, 1.0 to about 3 mg/ml, 0.5 to about 3.5 mg/ml sodium phosphate.

In some embodiments, the solution pH will be about 6.5 to about 7.5, be about 6.7 to about 7.5, be about 7 to about 7.5, about 7, about 7.5, about 6.8, or about 6.5.

In some embodiments, the drug is oxaliplatin, and is contained in a solution of about 9% sucrose. In some embodiments, the drug is oxaliplatin, and is contained in a solution of about 9% sucrose in an oxaliplatin concentration of about 1 mg/ml. In some embodiments, the drug is oxaliplatin, and is contained in a solution of about 105 mg/ml sucrose. In some embodiments, the drug is oxaliplatin, and is contained in a solution of about 105 mg/ml sucrose in an oxaliplatin concentration in liposome solution of about 1 mg/ml. In certain of these embodiments, the solution further contains sodium phosphate. In certain embodiments, oxaliplatin is in a concentration of about 0.8+/−10% mg/ml of liposome solution.

Labeled Compounds

A variety of labeled compounds may also be included in the lipid-containing compositions of the present invention. Generally, the labeled compound may be an agent useful in carrying out in vivo diagnostic procedures.

As with the incorporation and use of drugs as described herein, the amount of labeled compound to be included in the lipid-containing compositions, and formulations thereof, as described herein can be readily determined by the skilled artisan in view of the teaching herein provided and depending on the labeled compound selected and the use intended for the composition or formulation, taking into account factors specific to both the labeled compound and the individual to be diagnosed, as described further herein.

Exemplary labeled compounds include, for example, materials comprising radioisotopes (e.g., $^3$H, $^4$C, $^{67}$Ga, $^{111}$In, $^{125}$I, $^{131}$I, $^{133}$Xe, etc.), material comprising fluorescent moieties (e.g., fluorescein, fluorescein isothiocyanate, etc.), material comprising enzyme (e.g., peroxidase, alkaline phosohatase, etc.), as well as additional labeled compounds known to those of skill in the art.

As will be appreciated by the skilled artisan, the selection of the labeled compound and methods used in diagnosis will depend upon the organ (e.g., liver, pancreas, prostate, etc.), tissue (e.g., malignant or non-malignant or tissue type (e.g., breast, etc.)) to be investigated. For example, lipid-containing compositions (e.g., targeted liposomes, liposome-containing compositions, etc.) incorporating $^{125}$I are particularly useful for identifying the presence and determining the severity (e.g., initially, during a course of treatment, after treatment) of various cancers (e.g., breast cancer, gastric cancer, colorectal cancer, colon cancer, etc.) by gamma-counter.

Targeting Factors

Unless otherwise noted, the terms "targeting factor" and "targeting ligand" may be used interchangeably herein.

The lipid-containing compositions described herein are characterized by incorporating an N-(ω)-dicarboxylic acid-derivatized phosphatidyl ethanolamine modified with a targeting factor (i.e., TF-NωPE) directed to a particular target cell. The term "targeting factor" refers to a moiety that can bind to a receptor or a surface antigen present on the surface of a target cell. In certain embodiments, the targeting factors are directed to cell surface receptors on a particular target cell. The targeting factor is often a protein or a peptide that can be attached to a lipid component of the lipid-containing composition.

Most effectively, targeting factors are selected such that the targeted receptor or antigen is present only on cells that are targeted for the delivery of the drug or labeled compound (e.g., pathogenic cells) and not present on healthy cells. Alternatively, a greater number of receptors or antigens are expressed on the target cells (e.g., pathogenic or diseased cells) compared to non-targeted (e.g., healthy) cells. Preferably, the receptor or antigen that binds the targeting factor is either not present or present in low numbers on healthy cells such that binding with the targeting factor does not occur with frequency. In other words, targeting factors need to selectively deliver the liposomes as described herein (including encapsulated drug) to the targeted cells (e.g., pathogenic, unhealthy, etc.). Selective delivery of the encapsulated drug to the targeted cells thus reduces the occurrence of adverse effects due to the effect of encapsulated drug or labeled compound on non-targeted (e.g., healthy) cells, thereby also reducing the adverse effects experienced by the individual to whom the composition, or formulation thereof, is administered.

Exemplary targeting factors include, but are not limited to, transferrin, folic acid, folate, hyaluronic acid, sugar chains (e.g., galactose, mannose, etc.), fragments of monoclonal antibodies, asialoglycoprotein, etc., as well as other targeting factors known to the skilled artisan.

In particular embodiments, the targeting factor is a protein or peptide directed to a cell surface receptor (e.g., transferrin, folate, folic acid, asialoglycoprotein, etc.).

In other embodiments, the targeting factor is directed to an antigen (e.g., fragments of monoclonal antibodies (e.g., Fab, Fab', F(ab')$_2$, Fc, etc.)). It is not intended that targeting factors include intact or whole monoclonal antibodies. The term "whole antibody" or "intact antibody," and cognates thereof, as used herein generally refer to antibody IgG of immune globulin. A fragment of a monoclonal antibody generally refers to a decomposition product of the monoclonal antibody, for example, a fragment obtained by using protease digestion, such as pepsin, etc.

In certain embodiments, the targeting factor is not directed to an antigen (e.g., is not a fragment of a monoclonal antibody, e.g., Fab, Fab', F(ab')$_2$, Fc, etc).

In a certain embodiments, the targeting factor is transferrin.

Transferrin (Tf) is an iron binding protein with a molecular weight of 80,000, which is synthesized in hepatocytes and found in the blood. Transferrin supplies iron (Fe) to the cells through Tf receptors on the surface of each cell. The transferrin receptor is generally expressed in tumor tissues in a larger amount compared with normal tissues regardless of the types of the tumors. Tumor cell membranes are known to over-express transferrin receptors to maintain cell proliferation. See Shindelman J E, Ortmeyer A E, Sussman H H. "Demonstration of the transferrin receptor in human breast cancer tissue. Potential marker for identifying dividing cells." Int J Cancer. (1981) 27(3):329-34; Lloyd J M, O'Dowd T, Driver M, Tee D E. "Demonstration of an epitope of the transferrin receptor in human cervical epithelium—a potentially useful cell marker." J Clin Pathol. (1984) 37(2):131-5; and Habeshaw J A, Lister T A, Stansfeld A G, Greaves M F. "Correlation of transferrin receptor expression with histological class and outcome in non-Hodgkin lymphoma." Lancet. (1983) 1(8323): 498-501. Binding of the therapeutic agents to transferrin will therefore enhance the uptake of the drug into tumor cells through the transferrin receptor. While not being limited to a mechanism of action, the likely route of uptake of transferrin liposomes as described herein is represented schematically in FIGS. 2 and 3. Transferrin is commercially available, or can be produced recombinantly as described in, for example, U.S. Pat. No. 5,026,651, which is hereby incorporated by reference in its entirety.

While not being bound by theory, it is believed that the conjugation of transferrin (Tf) to the NωPE occurs by the reaction of a primary amine with the NωPE which results in the formation of a carboxylic acid amide bond between the lipid anchor and the protein.

In certain embodiments, the molar ratio of Tf to total lipid present in the targeted liposome product is approximately 0.00014:1 mol/mol (Tf:total lipid) (0.015, wt/wt). In other embodiments, the molar ratio of Tf:total lipid is from about 0.016 to about 0.029:about 126 about 158 mM/mM.

Lipid-Containing Compositions

The lipid-containing compositions described herein include targeted liposomes incorporating derivatized lipids, additional lipids and encapsulated drug or labeled compound, as well as the intermediates used to prepare the targeted liposomes, including lipid mixtures and liposome-containing compositions, as described herein, where the lipid-containing compositions (including targeted liposomes) are free of non-derivatized phosphatidyl ethanolamine and hydrophilic polymers, such as, but not limited to, polyethylene glycol. The lipid-containing compositions also include liposomes which incorporate a TF, but do not include a drug or labeled compound (e.g., blank liposomes).

As used herein, the term "hydrophilic polymer" and cognates thereof, refers to polymers such as polyethylene glycol (PEG) and other polyethoxylated polymers that are used in the liposome field to shield liposomes in an attempt to enhance the circulatory half-life of the liposome. It is intended that this term encompasses free hydrophilic polymers associated non-covalently with the liposomes as well as hydrophilic polymers that are in some way conjugated or covalently linked to a particular component of the liposome (e.g. PEG-modified lipids, etc.). Such hydrophilic polymers are also alternatively referred to in the field as "water-soluble" polymers. Additional exemplary hydrophilic polymers include, but are not limited to, polyvinyl alcohol, polylactic acid, polyglycolic acid, polyvinylpyrrolidone, polyacrylamide, polyglycerol, polyaxozlines, etc.

As used herein, the term "lipid mixture," and cognates thereof, refer to mixtures of lipid components as described herein, where the lipid mixture does not incorporate solution, for example, aqueous solution (e.g., water, buffer or a mixture of water and a water-miscible solvent (e.g., sugar (e.g., trehalose, sucrose, lactose, mannose, dextrose, fructose, etc.), sugar alcohol (e.g., sorbitol, maltitol, lactitol, glycerol, mannitol, etc), alcohol (e.g., ethanol, t-butanol, etc.), etc.)) or organic solvent.

The term "liposome-containing composition," and cognates thereof, refers to mixtures of lipids and, optionally, drug(s) or labeled compound(s), in which aqueous solution (e.g., water, buffer (e.g., acetate buffer, phosphate buffer, citrate buffer, borate buffer, tartrate buffer, etc.) or mixture of water and a water-miscible solvent) has been incorporated by mixing (e.g., one, or more of, stirring, shaking, etc.). The aqueous solution may also include additional components such as one or more sugars (e.g., trehalose, maltose, sucrose, lactose, mannose, dextrose, fructose, etc.), sugar alcohol (e.g., sorbitol, maltitol, lactitol, mannitol, glycerol, etc.), alcohol (e.g., ethanol, t-butanol, etc.), etc. And the aqueous solution may also include organic solvent ((e.g., esters (e.g., ethyl acetate, butyl acetate, etc.), aliphatic hydrocarbons (e.g., hexane, heptane, etc.), aromatic hydrocarbons (e.g., toluene, xylene, etc.), halogenated hydrocarbons (e.g., chloroform, dichloromethane, dichloroethane, etc.), ethers (e.g., THF, dioxane, diethyl ether, isopropyl ether, etc.), cyclic hydrocarbons (e.g., cyclohexane, etc.), DMF, DMSO, etc.) or mixtures thereof). The liposome-containing composition will generally contain a non-homogenous mixture of lipids, aqueous solution, and liposomes having a broad distribution around 100-10,000 nm and a mean diameter of 500-2,000 nm. Characterization of exemplary liposome-containing compositions is further provided in the Examples.

In certain embodiments, the lipid-containing compositions do not incorporate hydrophilic polymers. In particular embodiments, the lipid-containing compositions do not incorporate PEG.

In some embodiments, the intermediate lipid mixtures include at least two different neutral lipids or one or more phospholipids, and an N-(ω)-dicarboxylic acid-derivatized phosphatidyl ethanolamine, wherein the lipid components are described in greater detail herein and wherein the mixture is free of non-derivatized phosphatidyl ethanolamine and hydrophilic polymers, such as polyethylene glycol. Optionally, an aqueous solution as herein described may be mixed with the lipid components to form a liposome-containing composition. In certain embodiments, the lipid mixture does not include a drug or labeled compound. In particular embodiments, the lipid-mixture may be treated to form a liposome-containing composition or a liposome formulation.

In some embodiments, the intermediate lipid mixtures include at least two different neutral lipids or one or more phospholipids, an N-(ω)-dicarboxylic acid-derivatized phosphatidyl ethanolamine and a drug or labeled compound, wherein the lipid components and drug/labeled compound are described in greater detail herein and wherein the mixture is free of non-derivatized phosphatidyl ethanolamine and hydrophilic polymers, such as polyethylene glycol. Optionally, an aqueous solution as herein described may be mixed with the lipid components to form a liposome-containing composition, for example, as where the drug or labeled compound is added as an aqueous solution of drug/labeled compound. In certain embodiments, the liposome-containing composition can be treated (e.g., by one or more of extrusion, size exclusion chromatography, etc. or methods known in the art) to form a liposome.

In some embodiments, the lipid mixtures include one or more phospholipids or at least two different neutral lipids, an N-(ω)-dicarboxylic acid-derivatized phosphatidyl ethanolamine and a succinimidyl ester of an N-(ω)-dicarboxylic acid-derivatized phosphatidyl ethanolamine, wherein the lipid components are described in greater detail herein and wherein the mixture is free of non-derivatized phosphatidyl ethanolamine and hydrophilic polymers, such as polyethylene glycol. The mixtures may also be substantially free of non-NHS starting material, byproduct and/or decomposition product associated with synthesis of the succinimidyl ester of an N-(ω)-dicarboxylic acid-derivatized phosphatidyl ethanolamine (e.g., carbodiimmides (e.g., DCC, EDC, etc.), acylated urea compounds, etc.). Optionally, an aqueous solution as herein described may be mixed with the lipid components to form a liposome-containing composition.

In some embodiments, the intermediate lipid mixtures include one or more phospholipids or at least two different neutral lipids, an N-(ω)-dicarboxylic acid-derivatized phosphatidyl ethanolamine and a targeting factor-modified N-(ω)-dicarboxylic acid-derivatized phosphatidyl ethanolamine, wherein the lipid components are described in greater detail herein and wherein the mixture is free of non-derivatized phosphatidyl ethanolamine and hydrophilic polymers, such as polyethylene glycol. The mixtures may also be substantially free of non-NHS starting material, byproduct and/or decomposition product associated with synthesis of the succinimidyl ester of an N-(ω)-dicarboxylic acid-derivatized phosphatidyl ethanolamine (e.g., carbodiimmides (e.g., DCC, EDC, etc.), acylated urea compounds, etc.). Optionally, an aqueous solution as herein described may be mixed with the lipid components to form a liposome-containing composition. In some embodiments, the lipid mixture does not include a drug or labeled compound. The lipid mixture may be treated to form a liposome-containing composition or a liposome formulation.

In some embodiments, the intermediate lipid mixtures include one or more phospholipids or at least two different neutral lipids, an N-(ω)-dicarboxylic acid-derivatized phosphatidyl ethanolamine and a succinimidyl ester of an N-(ω)-dicarboxylic acid-derivatized phosphatidyl ethanolamine and a drug or labeled compound, wherein the lipid and drug/labeled compound components are described in greater detail herein and wherein the composition is free of non-derivatized phosphatidyl ethanolamine and hydrophilic polymers, such as polyethylene glycol. The mixtures may also be substantially free of non-NHS starting material, byproduct and/or decomposition product associated with synthesis of the succinimidyl ester of an N-(ω)-dicarboxylic acid-derivatized phosphatidyl ethanolamine (e.g., carbodiimmides (e.g., DCC, EDC, etc.), acylated urea compounds, etc.). Optionally, an aqueous solution as herein described may be mixed with the lipid components to form a liposome-containing composition.

In certain embodiments, the intermediate lipid-containing compositions include a liposome containing one or more phospholipids or at least two different neutral lipids, an N-(ω)-dicarboxylic acid-derivatized phosphatidyl ethanolamine and a succinimidyl ester of an N-(ω)-dicarboxylic acid-derivatized phosphatidyl ethanolamine and an encapsulated drug, wherein the lipid and drug components are described in greater detail herein and wherein the liposome is free of non-derivatized phosphatidyl ethanolamine and hydrophilic polymers, such as polyethylene glycol. The liposomes may also be substantially free of non-NHS starting material, byproduct and/or decomposition product associated with synthesis of the succinimidyl ester of an N-(ω)-dicarboxylic acid-derivatized phosphatidyl ethanolamine (e.g., carbodiimides (e.g., DCC, EDC, etc.), acylated urea compounds, etc.). In some embodiments, the lipid mixture does not include a drug or labeled compound. The lipid mixture may be treated to form a liposome-containing composition or a liposome formulation.

In certain embodiments, the lipid mixtures include one or more phospholipids or at least two different neutral lipids, an N-(ω)-dicarboxylic acid-derivatized phosphatidyl ethanolamine, a targeting-factor-modified N-(ω)-dicarboxylic acid-derivatized phosphatidyl ethanolamine and an encapsulated drug or labeled compound, wherein the lipid, targeting factor and drug/labeled compound components are described in greater detail herein and wherein the liposome is free of non-derivatized phosphatidyl ethanolamine and hydrophilic polymers, such as polyethylene glycol. In some embodiments of the lipid mixtures, the liposomes are substantially free of non-NHS starting material, byproduct or decomposition products associated with synthesis of the succinimidyl ester of an N-(ω)-dicarboxylic acid-derivatized phosphatidyl ethanolamine (e.g., carbodiimmides (e.g., DCC, EDC, etc.), acylated urea compounds, etc.). In particular embodiments, the lipid mixture is a liposome-containing composition (e.g., where drug or labeled compound is added as an aqueous solution). Optionally, an aqueous solution as herein described may be mixed with the lipid components to form a liposome-containing composition.

In certain embodiments, the targeted liposomes include liposomes containing one or more phospholipids or at least two different neutral lipids, an N-(ω)-dicarboxylic acid-derivatized phosphatidyl ethanolamine and a targeting-factor modified N-(ω)-dicarboxylic acid-derivatized phosphatidyl ethanolamine and an encapsulated drug or labeled compound, wherein the lipid, targeting factor and drug or labeled compound components are described in greater detail herein and wherein the liposome is free of non-derivatized phosphatidyl ethanolamine and hydrophilic polymers, such as polyethylene glycol. In some embodiments of the targeted liposomes, the liposomes are substantially free of non-NHS starting material, byproduct or decomposition products associated with synthesis of the succinimidyl ester of an N-(ω)-dicarboxylic acid-derivatized phosphatidyl ethanolamine (e.g., carbodiimmides (e.g., DCC, EDC, etc.), acylated urea compounds, etc.). However, in some embodiments, the succinimidyl ester of an N-(ω)-dicarboxylic acid-derivatized phosphatidyl ethanolamine may be present in the initial stages in the preparation of the targeted liposomes (e.g., NHS-NG-PEs (e.g., NHS-NG-DOPE, NHS-NG-DSPE, etc.), for example, prior to hydrolysis of the succinimidyl ester which may yield, for example NHS and NG-DOPE in the final formulation. In certain embodiments, where SuccNωPE is not incorporated into the interior of the liposome, the liposome or liposome-containing composition can also be free or substantially free of NHS, as in when TF-NωPE is pre-formed and used as starting material. In particular embodiments, the targeted liposomes are substantially free of DCC and EDC. In certain embodiments, the targeted liposomes are substantially free of DCC.

Additionally, each of the liposome-containing compositions as described herein can be treated to produce liposomes. The production of liposomes is well known in the art and, additionally, can be accomplished according to the methods described herein, for examples as described for production methods A and B, described in greater detail below. Production methods for liposomes from liposome-containing compositions include, but are not limited to, extrusion, sonication, reverse phase vesicle, freeze-thaw, size exclusion chromatography, ultrafiltration, etc. and combinations thereof. The liposomes formed from the liposome-containing compositions herein described may incorporate drug or labeled compound or may be free of drug or labeled compound (e.g., for liposomes also referred to herein also as "blank liposomes"). In particular embodiments, the liposome-containing compositions, liposomes (including blank liposomes) and targeted liposomes maybe formulated as pharmaceutical formulations and, additionally, may be used in the methods of treatment or diagnosis and/or kits described herein.

The term "substantially free" refers to levels of materials that are undetectable or minimally detectable by routine analytical methods used in the field. For example, HPLC (see e.g., *European Phmaracopoeia* 5$^{th}$ Ed.), TLC, gas chromatography, etc., as well as other analytical methods known to the skilled artisan.

For example, the lipid-containing compositions may contain less than about 0.1%, less than about 0.5%, less than about 1%, less than about 2%, less than about 3%, less than about 4%, less than about 5%, or less than about 6% by weight of a particular starting material, byproduct or decomposition product associated with synthesis of the succinimidyl ester of an N-(ω)-dicarboxylic acid-derivatized phosphatidyl ethanolamine to the total lipid content. In particular embodiments, the compositions will contain less than about 10%, less than about 7%, less than about 5%, less than about 3%, less than about 2%, or less than about 1% total impurities (e.g., % sum of starting material, byproduct and decomposition product associated with synthesis of the succinimidyl ester of an N-(ω)-dicarboxylic acid-derivatized phosphatidyl ethanolamine).

In some embodiments, the targeted liposomes include liposomes containing a phosphatidylcholine (e.g., neutral, anionic or cationic), cholesterol or a cholesterol derivative, an N-(ω)-dicarboxylic acid-derivatized phosphatidyl ethanolamine, a targeting factor-modified N-(ω)-dicarboxylic acid-derivatized phosphatidyl ethanolamine and an encapsulated drug or labeled compound, wherein the lipid, targeting factor and drug components are described in greater detail herein and wherein the liposome is free of non-derivatized phosphatidyl ethanolamine and hydrophilic polymers, such as polyethylene glycol. In particular embodiments, the phosphatidyl choline is a neutral phosphatidyl choline.

In particular embodiments, the targeted liposomes include liposomes containing a phosphatidyl choline (e.g., neutral, anionic or cationic), cholesterol or a cholesterol derivative, an N-(ω)-dicarboxylic acid-derivatized phosphatidyl ethanolamine, a transferrin-modified N-(ω)-dicarboxylic acid-derivatized phosphatidyl ethanolamine and encapsulated drug or labeled compound, wherein the lipid components and drug or labeled compound are described in greater detail herein and wherein the liposome is free of non-derivatized phosphatidyl ethanolamine and hydrophilic polymers, such as polyethylene glycol. In particular embodiments, the phosphatidyl choline is a neutral phosphatidyl choline.

In particular embodiments, the targeted liposomes include liposomes containing a phosphatidyl choline (e.g., neutral, anionic or cationic), cholesterol or a cholesterol derivative, an N-(ω)-dicarboxylic acid-derivatized phosphatidyl ethanolamine, a transferrin-modified N-(ω)-dicarboxylic acid-derivatized phosphatidyl ethanolamine and encapsulated oxaliplatin, wherein the lipid components are described in greater detail herein and wherein the liposome is free of non-derivatized phosphatidyl ethanolamine and hydrophilic polymers, such as polyethylene glycol. In particular embodiments, the phosphatidyl choline is a neutral phosphatidyl choline.

In certain embodiments, the lipid-containing compositions (including targeted liposomes and blank liposomes), and formulations thereof, described herein may further contain lipids obtained by derivatizing phosphatidylglycerol, sphingosine, ceramide, a cholesterol derivative or the like with a dicarboxylic acid. These dicarboxylic acid-derivatives may be prepared as described herein for the N-(ω)-dicarboxylic acid-derivatized phosphatidyl ethanolamines and according to preparation methods known to the skilled artisan.

In some embodiments, the lipid-containing compositions (including targeted liposomes and blank liposomes), and formulations thereof, described herein do not include anionic lipids (e.g., phosphatidylserines, phosphatidylinsitosols, phosphatidylglycerols, etc.) or cationic lipids (e.g., sphingosine, DOTAP, DOTMA, DC-CHOL, etc.). In particular embodiments, the compositions are free of anionic lipids. In other embodiments, the compositions are free of cationic lipids. In certain embodiments, the compositions are free of cationic and anionic lipids.

In some embodiments, the lipid-containing compositions, the composition comprises a drug. In other embodiments, the lipid-containing compositions comprise a labeled compound.

In certain embodiments of the lipid-containing compositions, the drug is oxaliplatin, the targeting factor (TF) is transferrin (Tf) and the lipid components include: DMPC or DSPC, and, cholesterol or a cholesterol derivative, and an N-(ω)-dicarboxylic acid-derivatized phosphatidyl ethanolamine, and a transferrin-modified N-(ω)-dicarboxylic acid-derivatized phosphatidyl ethanolamine, wherein the transferrin-modified N-(ω)-dicarboxylic acid-derivatized phosphatidyl ethanolamine comprises a transferrin linked to an N-(ω)-dicarboxylic acid-derivatized phosphatidyl ethanolamine by a carboxylic acid amide bond.

In some embodiments, the N-(ω)-dicarboxylic acid-derivatized phosphatidyl ethanolamine and targeting factor-modified N-(ω)-dicarboxylic acid-derivatized phosphatidyl ethanolamine are NG-DOPE or NG-DSPE.

In particular embodiments, the lipid components of the lipid-containing compositions are DMPC, cholesterol, NG-DOPE and TF-modified NG-DOPE. In other embodiments, the lipid components are DSPC, cholesterol, NG-DOPE and TF-modified NG-DOPE. In still other embodiments, the lipid components are DMPC, cholesterol, NG-DSPE, and TF-modified NG-DSPE. In certain other embodiments, the lipid components are DSPC, cholesterol, NG-DSPE, and TF-modified NG-DSPE. In certain of these embodiments, the targeting factor (TF) is transferrin and the drug is oxaliplatin.

In particular embodiments, the lipid components are DPPC, cholesterol, NG-DOPE and TF-modified NG-DOPE. In other embodiments, the lipid components are POPC, cholesterol, NG-DOPE and TF-modified NG-DOPE. In still other embodiments, the lipid components are DPPC, cholesterol, NG-DSPE, and TF-modified NG-DSPE. In certain other embodiments, the lipid components are POPC, cholesterol, NG-DSPE, and TF-modified NG-DSPE. In certain of these embodiments, the targeting factor (TF) is transferrin and the drug is oxaliplatin.

In particular embodiments, the lipid components are HSPC, cholesterol, NG-DOPE and TF-modified NG-DOPE. In other embodiments, the lipid components are EPC, cholesterol, NG-DOPE and TF-modified NG-DOPE. In still other embodiments, the lipid components are HSPC, cholesterol, NG-DSPE, and TF-modified NG-DSPE. In certain other embodiments, the lipid components are EPC, cholesterol, NG-DSPE, and TF-modified NG-DSPE. In certain of these embodiments, the targeting factor (TF) is transferrin and the drug is oxaliplatin.

Ratios of Lipid Components

Generally, the molar percent of starting materials NG-DOPE will be between about 2.5 mole % to about 4.5 mol %, compared to the total lipid content. Additionally, the molar percent of starting materials NHS-NG-DOPE will be between about 0.5 mole % to about 2.5 mol %, compared to the total lipid content.: In some embodiments, the relative mole ratio of NG-DOPE to NHS-NG-DOPE will be about 3.4:1. In certain embodiments, the relative mole % ratio of NG-DOPE to NHS-NG-DOPE may be about 4:1. In particular embodiments, where a neutral phospholipid and a neutral lipid are present, the molar ratio of (e.g., DMPC:Chol:NG-DOPE:NHS-NG-DOPE) may be 43.0:38.5:3.42:1, which can also be expressed as 50:45:4:1 by mol %.

In certain embodiments, the relative mol % of additional lipid(s) to NωPE to SccNωPE (e.g., at least two neutral lipids: NωPE:SuccNωPE or one or more phospholipids:NωPE:SuccNωPE or (one or more phospholipids+neutral lipid(s)): NωPE:SuccNωPE) may be from about 98 mol % to about 87 mol % additional lipids:from about 1 mol % to about 12 mol % NωPE:about 0.5 mol % to about 1% SuccNωPE; where the total mol % of all components is 100 mol %. For example, additional lipids:NωPE:SuccNωPE may be approximately 95:4:1, 90:9:1, 92:7:1, 93:6:1, etc.

In particular embodiments, where the additional lipids include a phospholipid and another lipid such as cholesterol, cholesterol derivatives, etc., the range of mol % for each lipid component is from about 30 mol % to about 64%, where the total of additional lipids is from about 98 mol % to about 87 mol %.

In certain embodiments, where the additional lipids are two different neutral lipids, the range of mol % for each neutral lipid is from about 30 mol % to about 64%, where the total of neutral lipids is from about 98 mol % to about 87 mol %.

In an exemplary embodiment, where one additional lipid is a phosphatidyl choline and a second additional lipid is cholesterol or a cholesterol derivative, the mol % of the phosphatidyl choline is from about 30 to about 70 mol %, (e.g., from about 50 to about 64 mol %, from about 40 to about 65 mol %, from about 40 to about 60 mol %, from about 50 to about 62 mol %, from about 55 to about 60 mol %, from about 35 to about 55 mol %, about 30 mol %, about 40 mol %, about 45 mol %, about 50 mol %, about 55 mol %, about 60 mol %, about 65 mol %, about 70 mol %) and the mol % of the cholesterol or cholesterol derivative is from about 30 to about 60 mol % (e.g., from about 32 to about 45 mol %, from about 32 to about 42 mol %, from about 32 to about 40 mol %, from about 40 to about 60 mol %, from about 35 to about 55 mol %, from about 35 to about 60 mol %, from about 45 to about 60 mol %, from about 35 to about 45 mol %, about 30 mol %, about 35 mol %, about 40 mol %, about 45 mol %, about 50 mol %, about 55 mol % or about 60 mol %). In some embodiments, the phosphatidyl choline is about 50 mol %, about 52 mol %, about 55 mol %, about 58 mol %, about 60 mol %, about 62 mol % and the cholesterol or cholesterol derivatives is from about 30 mol %, about 32 mol %, about 34 mol %, about 35 mol %, about 37 mol %, about 38 mol %, about 40 mol %, about 42 mol %, about 43 mol %, about 45 mol %.

In particular embodiments, the mol % of NωPE is about 1 to about 11 mol %, about 1 to about 10 mol %, about 1 to about 8 mol %, about 1 to about 6 mol %, about 1 to about 5 mol %, about 1 to about 4 mol %, about 1 to about 3 mol %, about 1 to about 2 mol %, about 2 to about 10 mol %, about 2 to about 5 mol %, about 1 mol %, about 2 mol %, about 3 mol %, about 4 mol %, about 5 mol %, about 7 mol %, about 8 mol %, about 9 mol % about 10 mol %, about 11 mol %, or about 12 mol %.

In certain embodiments, the relative mol % of the first additional lipid:second additional lipid:NωPE:SuccNωPE is, for example 50:45:4:1. In some embodiments, the first additional lipid is a phosphatidylcholine (e.g., DMPC, DOPC, DPPC, DSPC, etc.) and the second additional lipid is cholesterol. In some embodiments, the PE of the NωPE is DOPE or DSPE. In particular embodiments, the NωPE is NG-DOPE or NG-DSPE. In some embodiments, the lipids are DMPC:Chol:NG-DOPE:NHS-NG-DOPE and their relative mol % is 50:45:4:1. In other embodiments, the lipids are DSPC:Chol:NG-DSPE:NHS-NG-DSPE and their relative mol % is 50:45:4:1. In other embodiments, the lipids are DSPC:Chol:NG-DSPE:NHS-NG-DSPE and their relative mol % is 62:33:4:1.

In some embodiments, the total mol % of NωPE and TF-NωPE (NωPE+TF-NωPE) is about 2 to about 13 mol % of total lipid content. For example, about 2 to about 12 mol %, about 2 to about 10 mol %, about 2 to about 8 mol %, about 2 to about 6 mol %, about 2 to about 4 mol %, about 2 mol %, about 3 mol %, about 4 mol %, about 5 mol %, about 6 mol %, about 7 mol %, about 8 mol %, about 9 mol %, about 10 mol %, about 11 mol %, or about 12 mol %.

Generally, the total mol % of TF-NωPE is about 0.002 to about 0.2 mol % relative to total lipid content. For example, in some embodiments, the total mol % of TF-NωPE is about 0.002 to about 0.15 mol %, total mol % of TF-NωPE is about 0.002 to about 0.1 mol %, 0.002 to about 0.05 mol %, 0.01 to about 0.03 mol %, about 0.005 to about 0.2 mol %, about 0.007 to about 0.2 mol %, about 0.007 to about 0.05 mol %, about 0.01 to about 0.025 mol %, about 0.015 to about 0.025 mol %, about 0.01 to about 0.2 mol %, about 0.02 to about 0.2 mol %, about 0.04 to about 0.2 mol %, about 0.06 to about 0.2 mol %, about 0.08 to about 0.2 mol %, about 0.002 mol %, about 0.008 mol %, about 0.01 mol %, about 0.02 mol %, about 0.03 mol %, about 0.025 mol %, about 0.015 mol %, about 0.06 mol %, about 0.08 mol %, about 0.1 mol %, about 0.15 mol %, or about 0.2 mol %.

Characterization of Liposomes and Liposome-Containing Compositions

In addition to characterizing the lipid-containing compositions by the ratios of components (e.g., ratios of lipids, ratio of drug/labeled compound to lipid, etc.), the liposome-containing compositions as described herein may also be characterized (e.g., physicochemical properties, etc.) using standard analytical methods, as will be appreciated by the skilled artisan. Such analytical methods include, but are not limited to and where appropriate, determination of mean diameter, encapsulated volume, net charge (zeta potential), amount of entrapped (i.e., encapsulated) drug, particle size, stability under various conditions (e.g., in storage, as prepared for administration, in vitro), osmotic properties, amount of conjugated targeting factor, etc. Exemplary analytical methods for such characterization are set forth below, as well as in the Examples, and additional methods known to the skilled artisan may also be used to characterize the compositions.

As will be appreciated by the skilled artisan, the drug content of liposomes can be determined using established methods for HPLC analysis, with appropriate controls, as routinely practiced in the art and, additionally, as described in the Examples. Using appropriate controls, the identity of the encapsulated drug can also be determined by HPLC or, for certain drugs (e.g., platinum containing drugs) by analytical methods such as ICP-MS (Inductively Coupled Plasma-Mass Spectrometry) as is practiced by those of skill in the field.

In certain embodiments, the amount of drug (e.g., oxaliplatin, etc.) or labeled compound encapsulated within the liposome or liposome-containing composition may be from about 0.1 mg/ml to about 15 mg/ml within the liposome. For example, the drug concentration may be from about 0.5 mg/ml to about 15 mg/ml, about 0.5 mg/ml to about 10 mg/ml, about 0.1 mg/ml to about 10 mg/ml, about 0.5 mg/ml to about 5 mg/ml; about 0.5 mg/ml to about 3 mg/ml, about 0.5 mg/ml to about 2 mg/ml, about 0.5 mg/ml to about 1.5 mg/ml, about 0.8 mg/ml to about 3 mg/ml, about 0.8 mg/ml to about 2 mg/ml, about 0.8 mg/ml to about 1.5 mg/ml, about 0.7 mg/ml to about 3 mg/ml, about 0.7 mg/ml to about 2 mg/ml, about 0.7 mg/ml to about 1.7 mg/ml, about 0.7 mg/ml to about 1.5 mg/ml, about 0.7 mg/ml to about 1.4 mg/ml, about 0.7 mg/ml to about 1.3 mg/ml, about 0.5 mg/ml, about 0.7 mg/ml, about 0.8 mg/ml, about 0.9 mg/ml, about 1 mg/ml, about 1.1 mg/ml, about 1.2 mg/ml, about 1.3 mg/ml, about 1.4 mg/ml, about 1.5 mg/ml, about 1.6 mg/ml, about 2 mg/ml, about 3 mg/ml, about 4 mg/ml, about 5 mg/ml, about 6 mg/ml, about 7 mg/ml, about 8 mg/ml, about 9 mg/ml, about 10 mg/ml or about 15 mg/ml within the liposome.

The electric potential at the shear plane is called the zeta potential of a liposome. As is known the skilled artisan, the zeta potential of liposomes can be experimentally determined using appropriate instrumentation, for example as measured by an ELS-6000 (Otsuka Electronics, Japan) with the laser-Doppler microelectrophoresis method or other instrumentation and protocols available to the skilled artisan. For example, *J. Colloid and Interface Sci.*, 39, 670-675(1972), nition.com/en/products/zeecom_s.htm, etc.

In certain embodiments, the liposomes (including the targeted liposomes and the liposomes of the liposome-containing composition) as described herein will exhibit an overall net negative zeta potential. In some embodiments, the zeta potential is from about −10 mV to about −200 mV. For example, from about −50 mV to about −150 mV, from about −50 mV to about −130 mV, from about −60 to about −120 mV, from about −50 to about −100 mV, from about −75 mV to about −90 mV, from about −80 mV to about −90 mV, from about −80 mV to about −85 mV, from about −85 mV to about −90 mV, from about −75 mV to about −85 mV, from about −70 mV to about −90 mV, about −75 mV, about −80 mV, about −85 mV, about −83 mV, about −90 mV, about −100 mV, about −120 mV.

After the intravenous injection of small liposomes, they are thought to pass through the fenestrae of the liver sinusoids and will rapidly come into contact with hepatocytes. Liposomes of intermediate size are thought to be retained within the blood compartment and can circulate for a considerable length of time. However, large liposomes pass more slowly through the liver sinusoids, and are rapidly taken up by Kupffer cells. Thus the size of the liposome is very important to determine the behavior in vivo. See, for example, Liu et al., *Biochim. Biophys. Acta* (1992) 1104(1):95-101; Harashima et al., *J. Drug Target*. (1995) 3(4):253-261; (which are hereby incorporated by reference in their entirety) etc.

Liposome particle size can be obtained from the correlation function by using various algorithms using Photon Correlation Spectroscopy (PCS; Dynamic Light Scattering or Quasi-Elastic Light Scattering (QELS)). The particle size obtained by these techniques is comparable to the mean diameter determined by PCS. PCS uses standard deviation and $\chi 2$ to describe the size distribution. In PCS systems, $\chi^2$ determines whether the system is unimodal (Gaussian distribution) or multimodal (Nicomp distribution). The mean particle size can be determined using intensity weighted measurements and is reported from the Gaussian distribution if $\chi 2 \leq 5$. If $\chi 2 > 5$, then the mean of the principal peak in a Nicomp distribution. Such analysis will be familiar to the skilled artisan, as will suitable hardware, for example Nicomp QELS Particle Sizer, PSS Model 380ZLS, S/N 0103301; pssnicomp.com/zetaspec.htm.

In certain embodiments of the liposomes, particularly the targeted liposomes, described herein the liposome mean diameter will be from about 50 to about 275 nm. For example, the liposome mean diameter may be from about 50 to about 200 nm, from about 50 to about 265 nm, from about 50 to about 250 nm, from about 50 to about 225 nm, from about 50 to about 175 nm, from about 50 to about 150 nm, from about 50 to about 120 nm, from about 50 to about 100 nm, from about 75 to about 250 nm, from about 75 to about 200 nm, from about 75 to about 175 nm, from about 75 to about 150 nm, from about 75 to about 120 nm, from about 75 to about 100 nm, from about 90 to about 100 nm, from about 90 to about 120 nm, from about 90 to about 150 nm, from about 90 to about 200 nm, from about 95 to about 100 nm, from about 95 to about 120 nm, from about 95 to about 125 nm, from about 95 to about 130 nm, from about 95 to about 150 nm, from about 95 to about 175 nm, about 90 nm, about 95 nm, about 100 nm, about 120 nm, about 130 nm, or about 150 nm. For a particular liposome composition, the targeted liposome will be approximately about 15 to about 25 nm greater in diameter than the a liposome formed of the same components but with the targeting factor not incorporated.

The liposomes (e.g., targeted liposomes, blank liposomes, liposomes in liposome-containing compositions) described herein can also be characterized by the concentration of targeting ligand that is incorporated into the liposome. Depending on the targeting ligand selected, various means of quantifying the amount of targeting ligand will be apparent to the skilled artisan. For example, as described in the examples, the transferrin (Tf) content of liposomes can be determined by use of electrophoretic migration (e.g., as measured by SDS-PAGE) the liposome compared to appropriate controls.

In brief, confirmation of transferrin content in liposomes can be evaluated using two assays for the content and/or identity of transferrin conjugated to liposomes. Firstly, the electrophoretic migration of transferrin the liposome as analyzed by SDS-PAGE can be compared to the migration pattern of purified conjugated transferrin, e.g., TF-NωPE. In addition, the electrophoretic migration of conjugated transferrin in can also be compared to free transferrin reference standard. Additional support for the identity of transferrin in liposomes can be obtained using ELISA, a research-grade formulation that demonstrates specific binding of anti-transferrin antibody to the targeted liposomes. The concentration of transferrin-targeted liposomes can be measured using colorimetric protein quantification assays, such as a BCA, an assay well known to the skilled artisan. The skilled artisan in view of the teachings herein will also appreciate similar methods and others known in the field for determining the amount of a variety of targeting factors.

Briefly, the amount of transferrin in a liposome can be analyzed using the bicinchoninic acid (BCA) assay reagent. Copper (II) is reduced to copper (I) by protein under alkaline conditions. The copper (I) ion generated forms a soluble, intensely colored complex with BCA. The total microparticle-bound protein is measured by the reaction of a known amount of microparticle suspension with the BCA reagents. Once color formation occurs, the microparticles are removed by filtration and the color is measured spectrophotometrically.

In some embodiments, the concentration of targeting ligand incorporated in the liposome will be from about 0.5 mg/ml to about 5.0 mg/ml, from about 0.5 mg/ml to about 2.0 mg/ml, from about 1.0 mg/ml to about 2.0 mg/ml, from about 1.0 mg/ml to about 3.0 mg/ml, from about 1.0 mg/ml to about 2.5 mg/ml, from about 1.0 mg/ml to about 2.0 mg/ml, or from about 1.3 mg/ml to about 2.5 mg/ml.

The role of ferric ion is very important in binding transferrin to the surface of tumor cells. Therefore, the ferric ion content of targeted liposomes incorporating Tf is another meaningful way of characterizing the liposomes. While a number of methods for determining ferric ion content will be known to those of skill in the art, one method is ICP-MS.

Where the a liposome contains transferrin, the ferric ion content of the liposome may be, for example, from about 0.25 µg/mL to about 3 µg/mL, 0.4 µg/mL to about 3 µg/mL, 0.25 µg/mL to about 2 µg/mL, 0.25 µg/mL to about 1.5 µg/mL, 0.25 µg/mL to about 1 µg/mL, 0.4 µg/mL to about 2 µg/mL, 0.4 µg/mL to about 1.5 µg/mL, 0.5 µg/mL to about 2 µg/mL, about 0.5 µg/mL to about 1.4 µg/mL, or about 0.5 µg/mL to about 1.5 µg/mL.

The liposomes, including targeted liposomes and blank liposomes, may also be characterized by their osmotic pressure at a given temperature. The osmotic pressure at a given temperature depends upon the molar concentration of sugar (sucrose) solution. And it also depends on the total ion density and the size of the molecules within the solution. Normally osmotic pressure can be measured using an instrument known as an osmometer, which measures osmotic pressure in suitable pressure units, as will be appreciated by the skilled artisan.

In certain embodiments the osmotic pressure of the liposomes, particularly the targeted liposomes and blank liposomes, at room temperature will be from about 310 to about 410 mOsm/kg. For example, the osmotic pressure may be from about from about 310 to about 400 mOsm/kg, from about 310 to about 380 mOsm/kg, from about 320 to about 360 mOsm/kg, from about 315 to about 375 mOsm/Kg, from about 320 to about 375 mOsm/Kg, from about 315 to about 370 mOsm/Kg, from about 320 to about 370 mOsm/Kg, about 360 mOsm/Kg, about 350 mOsm/Kg, about 340 mOsm/Kg, about 370 mOsm/Kg or about 380 mOsm/Kg at room temperature.

Under the various conditions described herein (e.g., conditions for storage, prepared for administration and/or in vitro conditions) the osmotic pressure may vary less than about 25%, less than about 20%, less than about 15% when monitored over a particular time period associated with the various conditions as described herein. For example, 360+/−50 mOsm/kg.

Production of Lipid-Containing Compositions

There are three main requirements for drugs and labeled compounds intended for administration to individuals in the course of therapy, namely, efficacy, safety, and assurance of quality. Despite proven efficacy and safety, the ability to use a drug in therapy is undermined if its quality (e.g., purity, homogeneity, reproducibility of dosage, stability over time, etc.) cannot be consistently guaranteed during manufacture and distribution. Methods of production of drugs or labeled compound that do not assure consistently high quality drug also increase the likelihood of adverse reactions in the individuals to whom the drug is administered. Throughout the lifetime of a drug or labeled compound, it is important that the product that is manufactured and distributed meet the same standards as the product that initially received regulatory approval. Thus, the ability to consistently produce drugs or labeled compounds of high quality is necessary for producing safe drug or labeled compound products and drugs or labeled compound that can be routinely and easily manufactured and purified are advantageous from both a commercial and a safety perspective. Where, for example, efficacy of a labeled compound refers to its ability to be useful in the diagnosis of a particular disease or conditions in conjunction with the particular diagnostic methods (e.g., the activity of the labeled compound (for example, ability to be visualized by gamma counter, etc.) is not impaired by an unacceptable level batch to batch or during storage.

Described below are general methods for the production of the compositions described herein that can be used to consistently produce high quality (e.g., of high purity, homogeity, etc.) targeted liposomes (and intermediates thereof) and blank liposomes. These methods are also represented schematically in FIGS. 4 (production method A) and 5 (production method B).

The succinimidyl esters of N-(ω)-dicarboxylic acid-derivatized phosphatidyl ethanolamines and N-(ω)-dicarboxylic acid-derivatized phosphatidyl ethanolamines as described herein are useful as components of phospholipid complexes such as liposomes, polymer micelles, micro- and nanospheres, emulsions and water-soluble polymers. The preparation of these PE derivatives is described herein and methods for their production are also known in the art, as mentioned previously.

In particular, the succinimidyl esters of N-(ω)-dicarboxylic acid-derivatized phosphatidyl ethanolamines and N-(ω)-dicarboxylic acid-derivatized phosphatidyl ethanolamines are also useful as components of the lipid-containing compositions as described herein. The lipid-containing compositions can be prepared according to the methods described herein, though modifications of these methods will also be apparent to the skilled artisan. For example, various methods known to the skilled artisan may be used in liposome formation from lipid components (e.g., sonication, stirring, extrusion, dehydration, etc.) As, for example, as described in U.S. Pat. App. Pub. No. 2004/0142025, the contents of which are hereby incorporated by reference in its entirety.

Use of the general methods described herein, including in the Examples, to produce the targeted liposomes also encompasses methods for the production of the other lipid-containing compositions (e.g., lipid mixtures, liposome-containing compositions, blank liposomes, and intermediate liposomes), as described herein.

Production Method A

Figure 4:
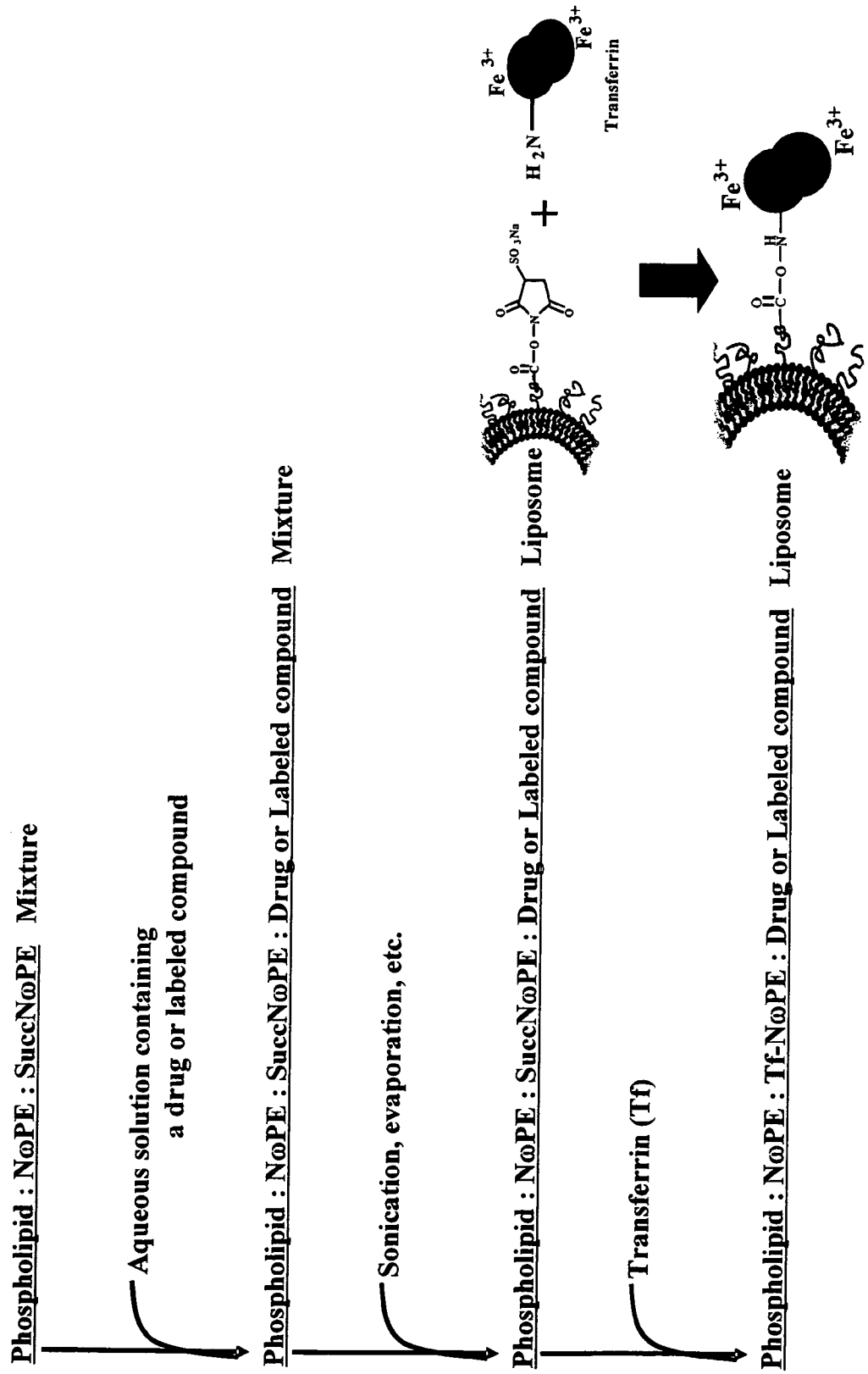
FIG. 4 shows a schematic depiction of production process A for targeted liposomes.

Production method A is depicted schematically in FIG. 4.

A: Production of NωPE:SuccNωPE:Additional Lipid Mixture (Intermediate 1)

The succinimidyl esters of N-(ω)-dicarboxylic acid-derivatized phosphatidyl ethanolamines (SuccNωPE) and N-(ω)-dicarboxylic acid-derivatized phosphatidyl ethanolamines (NωPE) as described herein are mixed with additional lipid(s) ((e.g., at least one phospholipid(s) (e.g. PC (e.g., DMPC, DSPC, etc.), PI, sphingomyelin, phosphatidic acid, etc.) and at least one other additional lipid (e.g., cholesterol)), then dissolved in a suitable solvent (e.g., ethanol, t-BuOH, chloroform, isopropylether, etc.). The amount of the solvent is generally 1 to 100 v/w (vs. total lipid weight). In certain embodiments, this is 2 to 20 v/w.

The SuccNωPE and NωPE used as described in the preceding paragraph can be prepared and purified by methods described herein or by methods known to the skilled artisan. The SuccNωPE and NωPE, as well as other components described herein for the production of the targeted liposomes and intermediates thereof, should be of sufficient purity and homogeneity to ultimately yield targeted liposomes of sufficient purity and homogeneity to fall within regulatory guidelines for administration of the targeted liposomes to individuals and in accordance with good laboratory practice (GLP) and good manufacturing practice (GMP) guidelines.

Where an additional lipid(s) (in additional to one or more phospholipids) is used in combination with the phospholipid, the ratio of phospholipid(s) to other additional lipid(s) is about 2:1. A mixing ratio of the SuccNωPE derivatives to the phospholipids is from about 1 to about 12% (1:99 to 12:88), or about 3-6% (3:97 to 6:94) of the total concentration/ratio of (NHS-NGPE+NGPE) to (CHOL+Phospholipid). For example, exemplary ratio include 50:45:4:1 (e.g., PC:Chol:NG-PENHS-NG-PE), where, for example 17.5 mg of NHS-NG-DOPE, 63.1 mg of NG-DOPE, 312 mg of chol and 607 mg of phospholipids in 1 g of mixture.

B: Production of Drug:NωPE:SuccNωPE:Additional Lipid Mixture (Intermediate 2)

The NωPE:SuccNωPE:additional lipid mixture prepared in step A is then mixed with aqueous solution (e.g., buffer, etc.) containing the drug or labeled compound to be encapsulated (e.g., anticancer agent (e.g., oxaliplatin, topoisomerase I inhibitor, vinca alkaloid, etc.)) to obtain the drug:NωPE:SuccNωPE:neutral lipid mixture (Intermediate 2).

Where the drug is oxaliplatin (l-OHP), the concentration of the oxaliplatin solution is about 8 mg/ml in an approximately 9% sucrose solution. For example, the concentration of oxaliplatin in the targeted liposome is about 0.8 mg/mL+/−10%.

C: Production of Drug:NωPE:SuccNωPE:Additional Lipid Liposome (Intermediate 3)

The drug:NωPE:SuccNωPE:additional lipid mixture (Intermediate 2) obtained in step B is then sonicated or stirred followed by evaporation of the solvent to form the drug:NωPE:SuccNωPE:additional lipid liposome (Intermediate 3). Methods and conditions for performing sonication, stirring and evaporation and means for accomplishing these steps are well understood by the skilled artisan and are also further described in the Examples. See for example, methods of production by reverse phase vesicle (REV) methods, U.S. Pat. No. 4,235,871 (incorporated by reference in its entirety). General liposome production methods such as simple hydration methods and ethanol injection methods, known to the skilled artisan, can be also used.

The drug:NωPE:SuccNωPE:additional lipid liposome formed as described above is then extruded by size and the drug:NωPE:SuccNωPE:additional lipid liposome is isolated. Optionally, ultrafiltration can then be used to concentrate the liposome solution.

Where the liposome contains l-OHP (drug), DMPC (additional lipid/phospholipid (neutral)), cholesterol (CHOL, additional lipid/neutral lipid), N-glutaryl-DOPE (NG-DOPE) and NHS-NG-DOPE, a liposome with a mean diameter of about 0.2 micrometer (200 nm) can be isolated. Similarly sized liposomes can also be obtained for liposomes containing l-OHP (drug), DSPC (additional lipid/phospholipid (neutral), cholesterol, N-glutaryl-DSPE (NG-DSPE) and NHS-NG-DSPE. Exemplary target amounts of the lipid components are, for example, about 40 mg/mL DMPC (an additional lipid/phosphatidyl choline/phospholipid/neutral lipid), about 20 mg/mL CHOL (additional lipid/neutral lipid) and about 5 mg/mL NG-DOPE (combined amount of NG-PE and NHS-NG-PE). An exemplary ratio for the lipid components is 50:45:5 (additional lipid 1 (e.g. a phosphatidyl choline)):additional lipid 2 (e.g., CHOL):NG-PE (e.g., NG-DOPE+NHS-NG-DOPE).

D: Production of Drug:NωPE:TF-NωPE:Additional Lipid Liposome (Targeted Liposome)

The drug:NωPE:SuccNωPE:additional lipid liposome formed as described in step C can then be functionalized with the targeting factor of choice to produce the drug:NωPE:TF-NωPE:additional lipid liposome (also referred to as the "targeted liposome").

Attachment of the targeting factor (TF) (e.g., functionalization of the intermediate liposome (Intermediate 3) with targeting factor) is accomplished by covalently binding the targeting factor to SuccNωPE by reaction of the succinimidyl moiety with the targeting factor. Through appropriate reaction conditions, succinimidyl groups on the exposed surface of the liposome (on the exterior of the lipid bilayer, where the drug or labeled compound is encapsulated in the interior of the liposome) can be covalently modified to form targeting factor-modified N-(ω)-dicarboxylic acid-derivatized phosphatidyl ethanolamines (TF-NωPE). Attachment of the targeting factor to the liposome results in the formation of the drug:NωPE:TF-NωPE:additional lipid liposome (targeted liposome).

More specifically, under appropriate conditions, the succinyl carboxyl moiety of the SuccNωPE as described herein is functionalized. If the targeting factor has an amino group(s), the amino group(s) on the targeting factor is reacted with the succinyl carboxyl moiety and forms carboxylic acid amide bond. Conditions appropriate for this reaction are further described herein, including in the Examples, and will also be well understood by the skilled artisan. The skilled artisan will also be able to modify the reaction conditions to optimize conditions for particular combinations of targeting factor and liposomes without undue experimentation given the teaching herein.

Various targeting factors as described herein and known to the skilled artisan can be obtained commercially or produced by methods known to the artisan of ordinary skill.

When, for example, transferrin is selected as the targeting factor, transferrin is can be commercially obtained as purified protein, for example, from Celliance Corp., GA, USA. Transferrin can also be obtained using recombinant methods well understood in the art (e.g., by using prokaryotic cell (*E. coli*, etc.), by using eukaryotic cell (CHO, BHK, etc.), etc.). As is well understood, transferrin can be obtained and used in the targeted liposomes in either its apo or holo forms. Alternatively, targeted liposomes incorporating apo-transferrin can be treated with ferric compounds, such as ferric citrate, iron (III) chloride, etc., to produce targeted liposomes incorporating holo-transferrin derivatized liposome.

An exemplary amount of transferrin as targeting factor is, for example, about 2 mg/mL transferrin. Such an amount would be appropriate for an exemplary targeted liposome containing about 40 mg/mL DMPC, about 20 mg/mL CHOL and about 5 mg/mL NG-DOPE (combined amount of NG-PE and NHS-NG-PE).

Upon functionalization of the liposome (intermediate 3) with targeting factor as described above to obtain the targeted liposomes, the resulting liposomes can optionally be further purified using methods known to those of skill in the art, including those purification methods described herein, particularly those described in connection with step C, above.

Where the liposome contains l-OHP (drug), DMPC, cholesterol (CHOL), N-glutaryl-DOPE (NG-DOPE) and Tf-NG-DOPE, a liposome with a mean diameter of about 0.05 micrometer to about 0.2 micrometer (about 50 nm to about 200 nm) can be isolated. Similarly sized liposomes can also be obtained for liposomes containing l-OHP (drug), DSPC, cholesterol, N-glutaryl-DSPE (NG-DSPE) and NHS-NG-DSPE.

Production of the targeted liposomes by the above-described method (referred to for convenience as production method A) reproducibly produces targeted liposomes of high purity and homogeneity. In particular, the targeted liposomes are substantially free of the non-NHS starting materials (described herein) and by-products (e.g., acylated urea compounds, etc.) associated with the generation of SuccNωPEs. In particular, preparation and purification of Succ NωPEs prior to liposome formation yields liposomes (intermediate 3) and targeted liposomes substantially free of carbodiimide starting materials (e.g., DCC, EDC, etc.) used to functionalize NωPEs to form SuccNωPEs. As mentioned previously, drugs and labeled compounds, including targeted liposomes incorporating drugs or labeled compounds, which are intended for administration to individuals in the course of therapy or diagnosis, must necessarily be of high quality.

Optionally, the lipid mixtures described in A (intermediate 1) can be treated with targeting factor to form a lipid mixture containing TF-NωPE. Further, this lipid mixture may be mixed with aqueous solution to form a liposome-containing composition. Finally, the liposome-containing composition may be treated to produce a liposome formulation. Optionally, the aqueous solution may include a drug or labeled compound.

Alternative Production Method (Method B)

Figure 5:
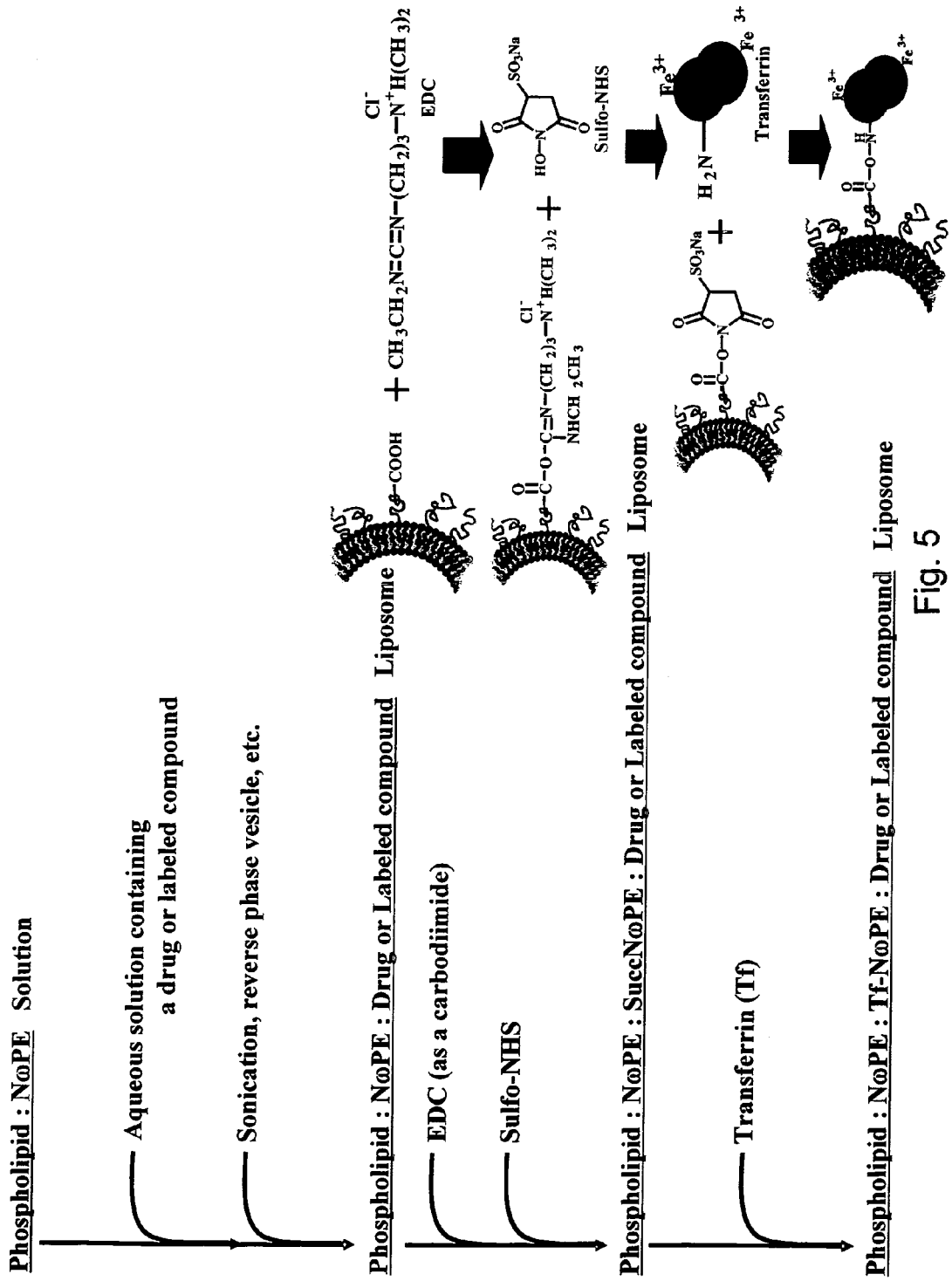
FIG. 5 shows a schematic of production process B for targeted liposomes.

Production method B is depicted schematically in FIG. 5.

A. Production of Drug:NωPE:Additional Lipids Liposome

The targeted liposomes as described herein can also be produced by dissolving the additional lipids and NωPE in a suitable solvent (e.g., ethanol, t-BuOH, chloroform, isopropylether, etc.), dispersing the resultant solution in an aqueous solution optionally containing a drug or labeled compound, and then performing ultrasonication or reverse phase vesicle of the resultant dispersion to form a liposome (drug:NωPE: neutral lipids). The liposome solution may be concentrated by ultrafiltration.

As a non-limiting example, the liposomes can be produced by reverse phase vesicle (REV) method (U.S. Pat. No. 4,235, 871, incorporated by reference). Of course, general liposome composition methods such as simple hydration methods and ethanol injection methods can be also used.

In order to stably retain the NωPE(s) in the lipid bilayer, the NωPE(s) can be prepared and purified, and then NωPE(s), together with the additional lipids (e.g., phospholipid(s), cholesterol, etc.) are used to prepare the liposome according to methods known to the skilled artisan.

As a non-limiting example, additional lipids (e.g., one or more phospholipid (e.g., DSPC, DMPC, etc.), and, optionally, another additional lipid (e.g., cholesterol, etc.) and at least one NωPE are mixed together and dissolved in a suitable organic solvent.

Where the additional lipids are a phospholipid and cholesterol, the mixing ratio of the phospholipid and the cholesterol may be, for example, about 1:1, for example, about 1.1:1, about 1.2:1, about 0.9:1 (e.g., DMPC and cholesterol, 50:45 (mol %). The content of the NωPE(s) as a proportion of total lipid content is, for example, 6% relative to the phospholipid. Then, the resultant solution is mixed with a solution of oxaliplatin in an aqueous buffer. The NωPE can be about 0.8 mol % to about 12 mol % to total lipid content. For example, from about 1 mol % to about 10 mol %, about 1 mol % to about 8 mol %, about 1 mol % to about 6 mol %, about 1 mol % to about 5 mol %, about 1 mol % to about 4 mol %, about 1 mol % to about 3 mol %, about 1 mol % to about 2 mol %, about 2 mol % to about 12 mol %, about 2 mol % to about 10 mol %, about 3 mol % to about 8 mol %, about 1 mol %, about 2 mol %, about 3 mol %, about 4 mol %, about 5 mol %, about 6 mol %, about 8 mol %, about 10 mol %, or about 12 mol %.

The concentration of drug or labeled compound in solution can be as described herein, and, in particular as above for production method A. Similarly, the solution containing the drug or labeled compound includes the solution components as described herein.

Liposomes incorporating l-OHP (drug), DSPC, cholesterol and N-glutaryl-DSPE (NG-DOPE) prepared by this method can be isolated to provide an oxaliplatin-containing liposome (e.g., by gel-filtration, by size exclusion chromatography, by ultrafiltration, by ultracentrifugation, etc.) having a mean diameter of about 0.2 m.

B. Production of Drug:SuccNωPE:NωPE:Additional Lipids Liposome

Following step A, a portion of the NωPE present in the liposome prepared in step A (drug:NωPE:additional lipids liposome) is functionalized to yield a liposome incorporating SuccNωPE (i.e., drug:SuccNωPE:NωPE:additional lipids liposome), which can later be modified to form TF-NωPE.

In order to form SuccNωPE, the carboxyl group at a terminus of the NωPE is modified to form a succinimidyl group. Such functionalization can be accomplished using the methods described for the production of SuccNωPE(s).

For example, a carbodiimmide (e.g., EDC, DCC, etc.) and N-hydroxysulfosuccinimide (NHS) are reacted in the presence of the liposome to yield drug:SuccNωPE:NωPE:additional lipids liposome.

C. Production of Drug:TF-NωPE:NωPE:Additional Lipids Liposome

After step B, the drug:SuccNωPE:NωPE:additional lipids liposome prepared in step B is reacted with targeting factor to form drug:TF-NωPE:NωPE:additional lipids liposome. The methods and conditions for the reaction are as described for production method A, step D.

The drug:TF-NωPE:NωPE:additional lipids liposomes obtained by production method B can be purified and concentrated using methods as described herein and known to the skilled artisan.

Comparison of Production Methods

Production method A has several advantages over production method B, though both can be used to obtain drug:TF-NωPE:NωPE:additional lipids liposomes (targeted liposomes, optionally containing either drug or labeled compound). Most notably, the liposomes obtained by method A will be free or substantially free of impurities (e.g., non-NHS starting materials and/or by-products) related to the production of the SuccNωPEs. In particular, as noted previously, targeted liposomes prepared by production method A will be free, or substantially free, of e.g., carbodiimmides (e.g., EDC, DCC, etc.), and acylated ureas. In certain embodiments, where SuccNωPE is not incorporated into the interior of the liposome, the liposome or liposome-containing composition can also be free or substantially free of NHS. Additionally, the larger a scale of reaction, the more a preparation time. The time for production method A is substantially shorter than production method B.

While purification of the drug:TF-NωPE:NωPE:additional lipids liposomes prepared by production method B will reduce the amount of such impurities, it is more difficult to purify liposomes (e.g., the drug:SuccNωPE:NωPE:additional lipids liposomes obtained in step B of production method B) than lipids (e.g., SuccNωPEs prepared and purified prior to step A of production method A). As some of the SuccNωPE is likely oriented to the interior of the liposomes (e.g., the succinimidyl ester functionality is on the interior of the lipid bilayer and inaccessible to reaction with targeting factor), it is likely that targeted liposomes prepared by production method A might have some residual SuccNωPE incorporated therein.

An additional advantage of production method A is that the relative content of TF-NωPE vs. NωPE in the final drug:TF-NωPE:NωPE:additional lipids liposomes can be controlled more accurately when production method A is used. The relative amounts of these lipids are directly related to the relative amounts of the SuccNωPE and NωPE used as starting materials in step A of production method A. Thus, the amount of TF-modified SuccNωPE can also be controlled more accurately.

When production method B is used, the relative amounts of NωPE vs. SuccNωPE are dependent upon the reaction efficiency of method B step B. This reaction is believed to go to completion for about approximately 10% of the NωPE present in the liposome, but experimental variation would be expected from batch to batch. The low reaction efficiency is likely due, in part, to the steric hindrance of the pre-formed liposome. When SuccNωPE is formed from isolated NωPE (lipid only), there is far less steric hindrance and the reaction goes farther to completion. Also, subsequent to formation of the SuccNωPE (in lipid only form), the resultant product can be purified from the reaction mixture, thus removing unreacted NωPE, carbodiimmide and NHS, as well as other by-products that may form during the reaction.

The liposomes formed by either method appear to be more homogeneous (and therefore can be used to produce a more reproducible drug/diagnostic product) than liposomes that incorporate PEG or other hydrophilic polymers, such as those described in the Background section of the present specification. In general, when PEG or other hydrophilic polymers are used to increase the circulation time of liposomes (e.g., to shield the liposomes from uptake by the RES), their use results in liposomes with a distribution of molecular size=due to the broad distribution of the PEG or hydrophilic polymers themselves. This distribution increases the difficulties associated with manufacture (e.g., reproducibility and/or purification) and may also increase the variability in clinical efficacy. Targeted liposomes prepared by either method A or B should be superior in these respects.

Additional Production Methods

Lipid mixtures and liposome-containing compositions (which may be used to prepare liposomes) may also be prepared by modification of production methods A and B. For example, in some embodiments, lipid mixtures and liposome-containing compositions incorporating additional lipid component(s):NωPE:TF-NωPE or additional lipid component(s):NωPE:TF-NωPE:drug/labeled compound (where "additional lipid component(s)" refers to one or more phospholipids (e.g., one or more neutral, one or more anionic, one or more cationic phospholipids or combinations of two or more of the foregoing), optionally additionally comprising one or more additional lipids as described herein (e.g., cholesterol or a derivative thereof); or at least two different neutral lipids as described herein, (e.g., at least one phospholipid(s) (e.g. PCs (e.g., DMPC, DSPC, etc.), PI, sphingomyelin, phosphatidic acid, etc.) and at least one other neutral lipid (e.g., cholesterol)) may be prepared by the production methods described below, as well as other modifications of the methods envisioned by the skilled artisan in view of the teaching of the present specification. The additional lipids, NωPE, TF-NωPE and, where present, drug or labeled compound components may be as described throughout the present specification. Similarly, the relative amounts of the components are also as described through the present specification.

In certain embodiments, the lipid mixture produced in the first step of production method B (the lipid mixture produced by dissolving the additional lipids and NωPE in a suitable organic solvent) may be modified to incorporate NHS and then modified with a TF to produce a additional lipid component(s):NωPE:TF-NωPE lipid mixture. This lipid mixture can then be mixed with aqueous solution (optionally containing drug or labeled compound) to form a liposome-containing composition. Alternatively, a drug or labeled compound can be incorporated after the liposome-containing composition has been prepared. In some embodiments, drug or labeled compound free of aqueous solution can be incorporated in the lipid mixture, formed after modification with NHS and TF, to form a additional lipid component(s):NωPE:TF-NωPE:drug/labeled compound lipid mixture. This lipid mixture can subsequently be mixed with an aqueous solution to form a liposome-containing composition.

In some embodiments, the lipid mixture produced in the first step of production method B (the lipid mixture produced by dissolving the additional lipid component(s) and NωPE in a suitable solvent) may be mixed with aqueous solution to form a liposome-containing composition (additional lipid component(s):NωPE). This liposome-containing composition may then either be treated with NHS and TF and subsequently mixed with drug or labeled compound to form a additional lipid component(s):NωPE:TF-NωPE:drug/labeled compound liposome-containing composition. Alternatively, the additional lipid component(s):NωPE liposome-containing composition may be treated with drug or labeled compound and then modified with NHS followed by TF.

In some embodiments, the lipid mixture produced in the first step of production method B (the lipid mixture produced by dissolving the additional lipid component(s) and NωPE in a suitable solvent) may then be mixed with drug or labeled compound (optionally including aqueous solution) to form a lipid mixture (where the drug or labeled compound does not include aqueous solution) or liposome-containing composition. Where a lipid mixture is formed, the lipid mixture can then be treated with NHS and TF to form a additional lipid component(s):NωPE:TF-NωPE:drug/labeled compound lipid mixture, which can then be mixed with aqueous solution to form a liposome-containing composition. Alternatively, where a liposome-containing composition is formed (e.g., when the drug or labeled compound is incorporated in aqueous solution), this liposome-containing composition can subsequently be treated with NHS and TF to also yield a additional lipid component(s):NωPE:TF-NωPE:drug/labeled compound liposome-containing composition.

In a further alternative production method, method C, individual components are simultaneous mixed in organic solvent to form a lipid mixture (C-1) (e.g., components: additional lipid component(s); NωPE; TF-NωPE or components:additional lipid component(s):NωPE:TF-NωPE:drug or labeled compound), where the TF-NωPE is prepared and optionally purified prior to admixture. Lipid mixture C-1 can then be mixed with aqueous solution to form a liposome-containing composition C-2 (additional lipid component(s):NωPE:TF-NωPE (optionally containing drug or labeled compound). Where the liposome-containing composition so formed does not contain drug or labeled compound, the drug or labeled compound may be added after formation of the liposome-containing composition (C2-A). Alternatively, where a drug or labeled compound including an aqueous solution is used as an initial starting component, the liposome-containing composition can be formed simultaneously upon the mixing of all the starting components.

C-2 (optionally containing drug or labeled compound) or C2-A, may then be treated to form a liposome (C-3). Where C-3 does not include a drug or labeled compound, the liposome will be an blank liposome, as previously described (e.g., additional lipid component(s):NωPE:TF-NωPE liposome). Where C-3 includes a drug or labeled compound, the liposome will be a targeted liposome as described herein. Where C-3 is an blank liposome, a drug or labeled compound may, as previously described, be added to the blank liposome in a subsequent step to form a targeted liposome, which may be performed immediately after preparation of C-3 or after a delay, which may include storage of the C-3 blank liposome for a period of time.

In a further alternative production method, method D, individual components are simultaneous mixed in organic solvent to form a lipid mixture (D-1) (e.g., components:additional lipid component(s); NωPE; or components:additional lipid component(s):NωPE:drug or labeled compound). Lipid mixture D-1 can then be mixed with aqueous solution to form a liposome-containing composition D-2 (additional lipid component(s):NωPE: (optionally containing drug or labeled compound). Liposome-containing composition D-2 can then be mixed with TF-NωPE to form a liposome-containing composition D-3 (additional lipid component(s):NωPE:TF-NωPE (optionally containing drug or labeled compound)), where the TF-NωPE is prepared and optionally purified prior to admixture. Where the liposome-containing composition so formed does not contain drug or labeled compound, the drug or labeled compound may be added after formation of the liposome-containing composition (D3-A). Alternatively, where a drug or labeled compound including an aqueous solution is used as an initial starting component, the liposome-containing composition can be formed simultaneously upon the mixing of all the components.

D-3 (optionally containing drug or labeled compound) or D3-A, may then be treated to form a liposome (D-4). Where D-4 does not include a drug or labeled compound, the liposome will be an blank liposome, as previously described (e.g., additional lipid component(s):NωPE:TF-NωPE liposome). Where D-4 includes a drug or labeled compound, the liposome will be a targeted liposome as described herein. Where D-4 is an blank liposome, a drug or labeled compound may, as previously described, be added to the blank liposome in a subsequent step to form a targeted liposome, which may be performed immediately after preparation of D-4 or after a delay, which may include storage of the D-4 blank liposome for a period of time.

As with lipid mixtures, liposome-containing compositions, and liposomes (including targeted liposomes, blank liposomes, etc.) formed by production method A, the lipid-containing compositions prepared by production method C or method D will be substantially free of non-NHS starting material, byproduct and/or decomposition product associated with synthesis of the succinimidyl ester of an N-(ω)-dicarboxylic acid-derivatized phosphatidyl ethanolamine (e.g., carbodiimmides (e.g., DCC, EDC, etc.), acylated urea compounds, etc.), so long as the starting material (e.g., TF-NG-PE) is substantially free of these substances prior to the initial step of production method C or method D. Where SuccNωPE is not incorporated as a starting material (and therefore not incorporated into the interior of the liposome), the liposome or liposome-containing composition can also be free or substantially free of NHS, as in when TF-NωPE is pre-formed and used as starting material. In particular embodiments, the lipid-containing compositions prepared by production method C or method D are substantially free of DCC and EDC. In certain embodiments, the lipid-containing compositions prepared by production method C or method D are substantially free of DCC.

In certain embodiments, the additional lipid component(s) includes one or more phospholipid (e.g., a phosphatidyl choline, etc.) and a cholesterol or cholesterol derivative. In particular embodiments, the phosphatidyl choline is DMPC, POPC, DSPC, etc. as herein described. In certain embodiments, the phosphatidyl choline is DMPC or DSPC. In particular embodiments, the additional lipid(s) are a phospholipid and cholesterol. In certain embodiments, the phospholipid is a neutral phospholipid.

In certain embodiments, the additional lipid component(s) include at least two different neutral lipids, which include a phospholipid (e.g., a phosphatidyl choline, etc.) and a cholesterol or cholesterol derivative. In particular embodiments, the phosphatidyl choline is DMPC, POPC, DSPC, etc. as herein described. In certain embodiments, the phosphatidyl choline is DMPC or DSPC. In particular embodiments, the at least two different neutral lipids are a phospholipid and cholesterol.

In some embodiments, the NωPE is an NG-PE. In particular embodiments, the NωPE is Nω-DOPE or Nω-DSPE. In certain embodiments, the NωPE is NG-DOPE or NG-DSPE.

In particular embodiments, the TF is for example, asialoglycoprotein, folate, transferrin, etc. In certain embodiments, the TF is transferrin (Tf). In some embodiments, the TF-NωPE is a Tf-NωPE (e.g., Tf-NG-DOPE or Tf-NG-DSPE).

In particular embodiments, the drug is, for example, an anticancer agent (e.g., oxaliplatin, topoisomerase I inhibitor, vinca alkaloid, etc.). In other embodiments, the lipid mixture or liposome-containing composition includes a labeled compound. In some embodiments, the lipid mixture or liposome-containing composition does not include a labeled compound or drug.

As mentioned previously, each of the lipid mixtures may be mixed with an aqueous solution to form liposome-containing compositions and each of the liposome-containing compositions may be treated to form the corresponding liposomes (e.g., targeted liposomes (e.g., incorporating drug or labeled compound), intermediate liposomes, blank liposomes, etc.), as described in detail herein.

With respect to the variations of the production methods described herein, it is intended that the modification of NωPE with NHS, the modification of NHS-NωPE with TF, the preparation of liposome-containing compositions from lipid mixtures, and the preparation of liposomes from liposome-containing compositions may be accomplished by the skilled artisan as described herein without undue experimentation given the teaching provided in the present specification, including, in particular, the detailed description of production methods A and B and as presented in the examples.

Pharmaceutical Formulations

In another aspect, the present invention provides pharmaceutical formulations for treatment or diagnosis of individuals in need thereof, comprising lipid-containing compositions as described herein and one or more pharmaceutically acceptable carriers, excipients, diluents, stabilizers, preservatives, or other inactive ingredients, including combinations of the foregoing, known to skilled artisans and described further herein.

In certain embodiments of the pharmaceutical formulations, the lipid-containing composition is a targeted liposome as described herein. In other embodiments, the lipid-containing composition is a liposome-containing composition. In some embodiments, the lipid-containing composition is an blank liposome. In certain embodiments, the composition comprises a drug. In other embodiments, the composition comprises a labeled compound.

In certain embodiments, the carrier may include one or more of sterile water, a buffer solution or saline, diluent, and combinations thereof.

The pharmaceutical formulations may further comprise one or more of different salts, sugars, proteins, starch, gelatin, plant oils, polyethylene glycol and the like, including combinations of two or more of the foregoing.

An additional aspect of the invention includes use of the compositions and formulations thereof as described herein in the manufacture of a medicament. Particularly, the manufacture of a medicament for use in the treatment or diagnosis of conditions as described herein. Further, the active compositions and formulations thereof, variously described herein, are also intended for use in the manufacture of a medicament for use in treatment or diagnosis of the conditions and, in accordance with the methods, described herein, unless otherwise noted.

Use of the Compositions

Administration

As noted previously, in one aspect is provided methods of treatment or diagnosis of conditions as described herein using the drug- or labeled compound-containing lipid-containing compositions (e.g., targeted liposomes, drug-/labeled compound-containing liposome-containing compositions) and pharmaceutical formulations as described herein.

In one embodiment, the methods may be practiced as a therapeutic approach towards the treatment of the conditions described herein. Thus, in a specific embodiment, the drug-containing lipid-containing compositions or pharmaceutical formulations may be used to treat the conditions described herein in individuals in need thereof, including humans. The methods generally comprise administering to the individual an amount of a composition, or formulation described herein, effective to treat the condition.

In another embodiment, the methods may practiced as a diagnostic approach towards the diagnosis of the conditions described herein. Thus, in a specific embodiment, the labeled compound-containing lipid-containing compositions or pharmaceutical formulations may be used to diagnosis the conditions described herein in individuals in need thereof, including humans. The methods generally comprise administering to the individual an amount of a composition, or formulation described herein, effective to diagnosis the condition. Such administration is generally undertaken in conjunction with methods to detect the condition.

In some embodiments, the individual is a mammal, including, but not limited to, human, bovine, horse, feline, canine, rodent, or primate. In other embodiments, the individual is a human.

The terms, "pharmaceutically effective amount" or "therapeutically effective amount" refer to an amount of a composition sufficient to treat a specified disorder, condition or disease or one or more of its symptoms and/or to prevent the occurrence of the disease or disorder. In reference to cancers, a pharmaceutically or therapeutically effective amount comprises an amount sufficient to, among other things, cause a tumor to shrink or to decrease the growth rate of the tumor.

The terms "an amount effective to diagnose" or "diagnostically effective amount" or "amounts effective for diagnosis" cognates thereof, refer to an amount of a composition sufficient to diagnose a specified disorder, condition or disease, and/or one or more of its manifestations, where diagnosis includes identification of the existence of the disease and/or detection of the extent or severity of the disease. For example, in reference to cancers, a "diagnostically effective amount" comprises an amount sufficient to detect, for example, the presence and/or concentration of one or more of malignant cells, tumor(s) or other manifestation of the cancer. Often, diagnosis will be carried out with reference to a baseline or background detection level observed for individuals without the condition. Levels of detection above background or baseline levels (elevated levels of detection) are indicative of the presence and, in some cases, the severity of the condition.

When used with respect to methods of treatment and the use of drug-containing lipid-containing compositions, an individual "in need thereof" may be an individual who has been diagnosed with or previously treated for the condition to be treated. With respect to methods of diagnosis and the use of labeled compound-containing compositions, an individual "in need thereof" may be an individual who is suspected to have a condition, is at risk for a condition (e.g., a family history of the condition, life-style factors indicative of risk for the condition (e.g., smoking as a risk factor for lung cancer, etc.)) or has previously been diagnosed with the condition (e.g., diagnosis can include monitoring of the severity (e.g., progression/regression) of the disease over time and/or in conjunction with therapy).

In certain embodiments, the condition to be treated or diagnosed is cancer. In some embodiments the cancer may be a gastric, colon, colorectal or breast cancer. In certain embodiments, the cancer is a colon cancer. In other embodiments, the cancer is a breast cancer. In still other embodiments, the cancer is a gastric cancer. In some embodiments the cancer is cancer of the pancreas, non small cell lung cancer, small cell lung cancer, brain cancer, liver cancer, renal cancer, prostate cancer, bladder cancer, ovarian cancer, or hematological malignancies (e.g., leukemia, lymphoma, multiple myeloma, etc.).

The drug-containing compositions, including formulations described herein, may be used alone or in conjunction with (e.g., prior to, concurrently with, or after) other modes of treatments (e.g., adjunctive cancer therapy, combined modality treatments). For example, in combination with other therapeutic agents (e.g., cancer chemotherapeutic agents as described herein and known to those of skill in the art (e.g., alkylating agents, taxanes, metabolic antagonist, antitumour antibiotic, plant alkaloids, hormone therapy drug, molecular target drug, etc.)), surgery, and/or radiation therapy. Where the condition being treated is cancer, the compositions described herein can be administered in conjunction with one or more of other anticancer agents or cytotoxic compounds as described herein and as know in the art, one or more additional agents to reduce the occurrence and/or severity of adverse reactions and/or clinical manifestations thereof, surgery (e.g., to remove a tumor or lymph nodes, etc.) or radiation. Where one or more of surgery or radiation are part of the treatment regimen, the compositions may be administered before, concurrently, or after the radiation therapy or surgery. Likewise, the compositions, and formulations thereof, as described herein may be administered before, concurrently, or after the administration of one or more anticancer agents. The targeted liposomes and formulations thereof described herein may also be administered in conjunction with (e.g., prior to, concurrently with, or after) drugs to alleviate the symptoms associated with the condition or the treatment regimen (e.g., drugs to reduce vomiting, hair loss, immunosuppression, diarrhea, rash, sensory disturbance, anemia, fatigue, stomatitis, hand foot syndrome, etc.). The targeted liposomes may also be administered at more than one stage of (including throughout) the treatment regimen (e.g., after surgery and concurrently with and after radiation therapy, etc.).

The labeled compound-containing compositions, including formulations described herein, may be used alone or in conjunction with (e.g., prior to, concurrently with, or after) modes of treatments (e.g., adjunctive cancer therapy, combined modality treatments). For example, the compositions may be used to monitor the progress of treatment. For example, to determined if the condition being treated is detectable before, after or concurrently with a treatment regimen (as described above with respect to methods of treatment).

In certain embodiments, the compositions are administered prior to or after surgery (e.g., removal of a tumor or lymph nodes, etc.). In other embodiments, the compositions are administered after surgery and prior to, concurrently with or after radiation therapy. The optimal combination of one or more of surgery and/or radiation therapy in conjunction with administration of the compositions described herein, and, optionally, additional one or more chemotherapeutic agents, can be determined by an attending physician based on the individual and taking into consideration the various factors effecting the particular individual, including those described herein.

In particular embodiments, the drug-containing compositions or pharmaceutical formulations may be administered in combination with one or both of 5-fluorouracil and/or leucovorin. In other embodiments, the drug-containing composition or pharmaceutical formulations may be administered in combination with one or more other anti cancer drugs such as capecitabine, UFT/LV (tegafur-uracil and leucovorin), irinotecan, anti EGFR antibody (e.g., cetuximab, etc.), anti VEGF antibody (e.g., avastin, etc.), tyrosine kinase inhibitor (e.g., erlotinib), etc. Such administration may also be combined with a treatment regimen including radiation therapy and/or surgery. In certain embodiments, the encapsulated drug in the targeted liposome is oxaliplatin.

In conjunction with the methods of use described herein, the lipid-containing compositions or pharmaceutical formulations of the present invention may be administered parenterally. Parenteral administration may be accomplished via bolus injection (IV), infusion (IV), intraperitoneal injection, or via local injection (such as intracranial injection). In some embodiments, the administration is via a bolus injection or continuous infusion.

Continuous intravenous infusion may be administered over a period of minutes or hours. For example, but not limited to, from about 10 minutes to about 5 hours, from about 15 minutes to about 4 hours; from about 30 minutes to about 4 hours; from about 45 minutes to about 4 hours, from about 60 minutes to about 4 hours, from about 45 minutes to about 3 hours, from about 60 minutes to about 2 hours, from about 90 minutes to about 3 hours, from about 90 minutes to about 2 hours, about 10 minutes, about 15 minutes, about 20 minutes, about 30 minutes, about 45 minutes, about 50 minutes, about 60 minutes, 80 minutes, about 1.5 hours, about 2 hours, about 2.5 hours, about 3 hours, about 3.5 hours, about 4 hours, about 5 hours, about 12 hours, about 24 hours, about 36 hours, or about 48 hours.

Formulation and Dosage

As noted previously, the lipid-containing compositions and pharmaceutical formulations as described herein may be administered to individuals in need thereof for the treatment or diagnosis of conditions as described herein in conjunction with the methods of use described herein.

The lipid-containing compositions described herein, and, in particular the targeted liposomes described herein, will generally be used in an amount effective to achieve the intended result, for example in an amount effective to treat or prevent the particular condition being treated. The composition(s) may be administered therapeutically to achieve therapeutic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also includes halting or slowing the progression of the disease, regardless of whether improvement is realized.

In some embodiments, where the condition being treated is a cancer, an effective amount is an amount sufficient to reduce tumor growth (e.g., as measured by rate of increase of mean tumor volume prior to and/or after treatment). In certain embodiments, an effective amount is an amount sufficient to decrease mean tumor volume (e.g., where mean tumor volume after treatment is reduced compared to mean tumor volume prior to treatment).

The amount of compositions administered in order to administer an effective amount of encapsulated drug (e.g., oxaliplatin) will depend upon a variety of factors, including, for example, the particular condition being treated, the mode of administration, the severity of the condition being treated and the age and weight of the patient, the bioavailability of the composition, the adverse effects experienced by the individual being treated, etc. Determination of an effective dosage is well within the capabilities of those skilled in the art in view of the teachings provided herein.

In certain embodiments, the dose of encapsulated oxaliplatin administered at a particular time point will be in the range from about 1 to about 400 mg/m$^2$/day. For example, in the range from about 1 to about 350 mg/m$^2$/day, 1 to about 300 mg/m$^2$/day, 1 to about 250 mg/m$^2$/day, 1 to about 200 mg/m$^2$/day, 1 to about 150 mg/m$^2$/day, 1 to about 100 mg/m$^2$/day, from about 5 to about 80 mg/m$^2$/day, from about 5 to about 70 mg/m$^2$/day, from about 5 to about 60 mg/m$^2$/day, from about 5 to about 50 mg/m$^2$ day, from about 5 to about 40 mg/m$^2$/day, from about 5 to about 20 mg/m$^2$/day, from about 10 to about 80 mg/m$^2$/day, from about 10 to about 70 mg/m$^2$/day, from about 10 to about 60 mg/m$^2$/day, from about 10 to about 50 mg/m$^2$/day, from about 10 to about 40 mg/m$^2$/day, from about 10 to about 20 mg/m$^2$/day, from about 20 to about 40 mg/m$^2$/day, from about 20 to about 50 mg/m$^2$/day, from about 20 to about 90 mg/m$^2$/day, from about 30 to about 80 mg/m$^2$/day, from about 40 to about 90 mg/m$^2$/day, from about 40 to about 100 mg/m$^2$/day, from about 80 to about 150 mg/m$^2$/day, from about 80 to about 140 mg/m$^2$/day, from about 80 to about 135 mg/m$^2$/day, from about 80 to about 130 mg/m$^2$/day, from about 80 to about 120 mg/m$^2$/day, from about 85 to about 140 mg/m$^2$/day, from about 85 to about 135 mg/m$^2$/day, from about 85 to about 135 mg/m$^2$/day, from about 85 to about 130 mg/m$^2$/day, or from about 85 to about 120 mg/m$^2$/day. The does admintestered at a particular time point may also be about 130 mg/m$^2$/day, about 120 mg/m$^2$/day, about 100 mg/m$^2$/day, about 90 mg/m$^2$/day, about 85 mg/m$^2$/day, about 80 mg/m$^2$/day, about 70 mg/m$^2$/day, about 60 mg/m$^2$/day, about 50 mg/m$^2$/day, about 40 mg/m$^2$/day, about 30 mg/m$^2$/day, about 20 mg/m$^2$/day, about 15 mg/m$^2$/day, or about 10 mg/m$^2$/day.

The dose administered may be higher or lower than the dose ranges described herein, depending upon, among other factors, the bioavailability of the composition, the tolerance of the individual to adverse side effects, the mode of administration and various factors discussed above. Dosage amount and interval may be adjusted individually to provide plasma levels of the composition that are sufficient to maintain therapeutic effect, according to the judgment of the prescribing physician. Skilled artisans will be able to optimize effective local dosages without undue experimentation in view of the teaching provided herein.

Dosages may also be estimated using in vivo animal models, as will be appreciated by those skill in the art.

Multiple doses (e.g., continuous or bolus) of the compositions as described herein may also be administered to individuals in need thereof of the course of hours, days, weeks, or months. For example, but not limited to, daily, every other day, every 10 days, weekly, monthly, twice weekly, three times a week, twice monthly, three times a month, four times a month, five times a month, every other month, every third month, every fourth month, etc.

Kits

Also provided are kits for administration of the compositions described herein, including pharmaceutical formulations comprising the compositions.

In certain embodiments the kits may include a dosage amount (e.g., as used for therapy or diagnosis) of at least one lipid-containing composition, or pharmaceutical formulation thereof, as disclosed herein. Kits may further comprise suitable packaging and/or instructions for use of the composition. Kits may also comprise a means for the delivery for the composition, or pharmaceutical formulation thereof, such as a syringe for injection or other device as described herein and known to those of skill in the art.

In some embodiments the kits may include a dosage amount (e.g., as used for therapy or diagnosis) of a blank liposome, or pharmaceutical formulation thereof, as disclosed herein. Kits may further comprise suitable packaging and/or instructions for use of the composition. Kits may also comprise a means for the delivery for the composition, or pharmaceutical formulation thereof, such as a syringe for injection or other device as described herein and known to those of skill in the art. Additionally, in certain embodiments, the kit may contain a separate dosage amount of the drug or labeled compound to be incorporated into the blank liposome.

Additionally, the lipid-containing composition, or pharmaceutical formulation thereof may be assembled in the form of kits. The kit provides the lipid-containing composition, or pharmaceutical formulation thereof and reagents to prepare a composition for administration. The composition may be in a dry or lyophilized form, or in a solution, particularly a sterile solution. When the composition is in a dry form, the reagent may comprise a pharmaceutically acceptable diluent for preparing a liquid formulation. Such diluents include those known to those of skill in the art, for example, sugar solutions, e.g., dextrose, sucrose, etc. In certain embodiments the kits may includes sugar solutions of about 1% to about 20%, about 1% to about 18%, about 1% to about 15%, about 1% to about 10%, about 3% to about 10%, about 3% to about 6%, about 1%, about 2%, about 3%, about 4%, about 5%, about 6%, about 7%, about 8%, about 9%, about 10%, about 12%, about 15%, about 18%, or about 20% sugar. In certain embodiments, the solution may be a dextrose solution (e.g., about 1%, about 2%, about 5% dextrose, etc.). In certain embodiments, the lipid-containing composition may be, for example, a targeted liposome, blank liposome, lipid mixture, or liposome-containing composition (optionally containing drug or labeled compound).

The kit may also contain a device for administration or for dispensing the compositions, including, but not limited to syringe, pipette, or other device known to those of skill. When in a wet form, the composition may be stored in an ampoule or other sterile sealed container, including those known to persons of skill in the art.

The kits may include other therapeutic compounds for use in conjunction with the compounds described herein. In one embodiment, the therapeutic agents are other anticancer agents. These agents may be provided in a separate form, or mixed with the compounds of the present invention, provided such mixing does not reduce the effectiveness of either the additional therapeutic agent of the compositions and formulations described herein. Similarly the kits may include additional agents for adjunctive therapy. For example, agents to reduce the adverse effects of the drug (e.g., anti-nausea agents, anti-alopecia agents, immuno-enhancing agents, etc.).

The kits will include appropriate instructions for preparation and administration of the composition, side effects of the compositions, and any other relevant information. The instructions may be in any suitable format, including, but not limited to, printed matter, videotape, computer readable disk, or optical disc.

In another aspect of the invention, kits for treating an individual who suffers from or is susceptible to the conditions described herein are provided, comprising a first container comprising a dosage amount of a lipid-containing composition or formulations thereof as disclosed herein, and instructions for use. The container may be any of those known in the art and appropriate for storage and delivery of intravenous formulations. In certain embodiments the kit further comprises a second container comprising a pharmaceutically acceptable carrier, diluent, adjuvant, etc. for preparation of the composition to be administered to the individual.

Kits may also be provided that contain sufficient dosages of the compositions or formulations thereof as disclosed herein to provide effective treatment for an individual for an extended period, such as a week, 2 weeks, 3, weeks, 4 weeks, 6 weeks, 8 weeks, 3 months, 4 months, 5 months, 6 months, 7 months, 8 months, 9 months or more.

Kits may also include multiple doses of the lipid-containing composition or formulations thereof and instructions for use and packaged in quantities sufficient for storage and use in pharmacies, for example, hospital pharmacies and compounding pharmacies.

All patents, patent applications and publications referred to herein are hereby incorporated herein by reference in their entirety.

EXAMPLES

The present invention is further described with reference to the following Examples; however, these Examples are not limiting the scope of the present invention.

Example 1

Cytotoxicity Test for Oxaliplatin

An oxaliplatin (l-OHP) solution was prepared by dissolving oxaliplatin in a 9% sucrose solution (sucrose/distilled water) at a concentration of 8 mg/ml. The cell viability was determined using a commercially available cytotoxicity assay kit (WST-1 kit, Wako Pure Chemical Industries, Ltd., Japan).

AsPC-1 cells (provided by Dr. Hironobu Yanagie of Research Center for Advanced Science and Technology, the University of Tokyo, Japan) cultured in RPMI 1640 medium supplemented with 10% FCS (fetal calf serum; SIGMA, USA) were treated with concentrations of l-OHP solutions $[200\times(½)^{(0-10)}$ nM] at 37° C. in 5% $CO_2$ for 48 hours. Then, the medium was removed and a substrate (WST-1, Cell Counting Kit, Dojindo Laboratories, Japan) was added to the cells which were incubated at 37° C. in 5% $CO_2$ for 2 hours to develop the colored product. The developed color was measured at an absorbance of 450 nm (reference wavelength: 620 nm) on an Immuno Mini NJ-2300 (Cosmo Bio Co., Ltd., Japan).

Figure 6:
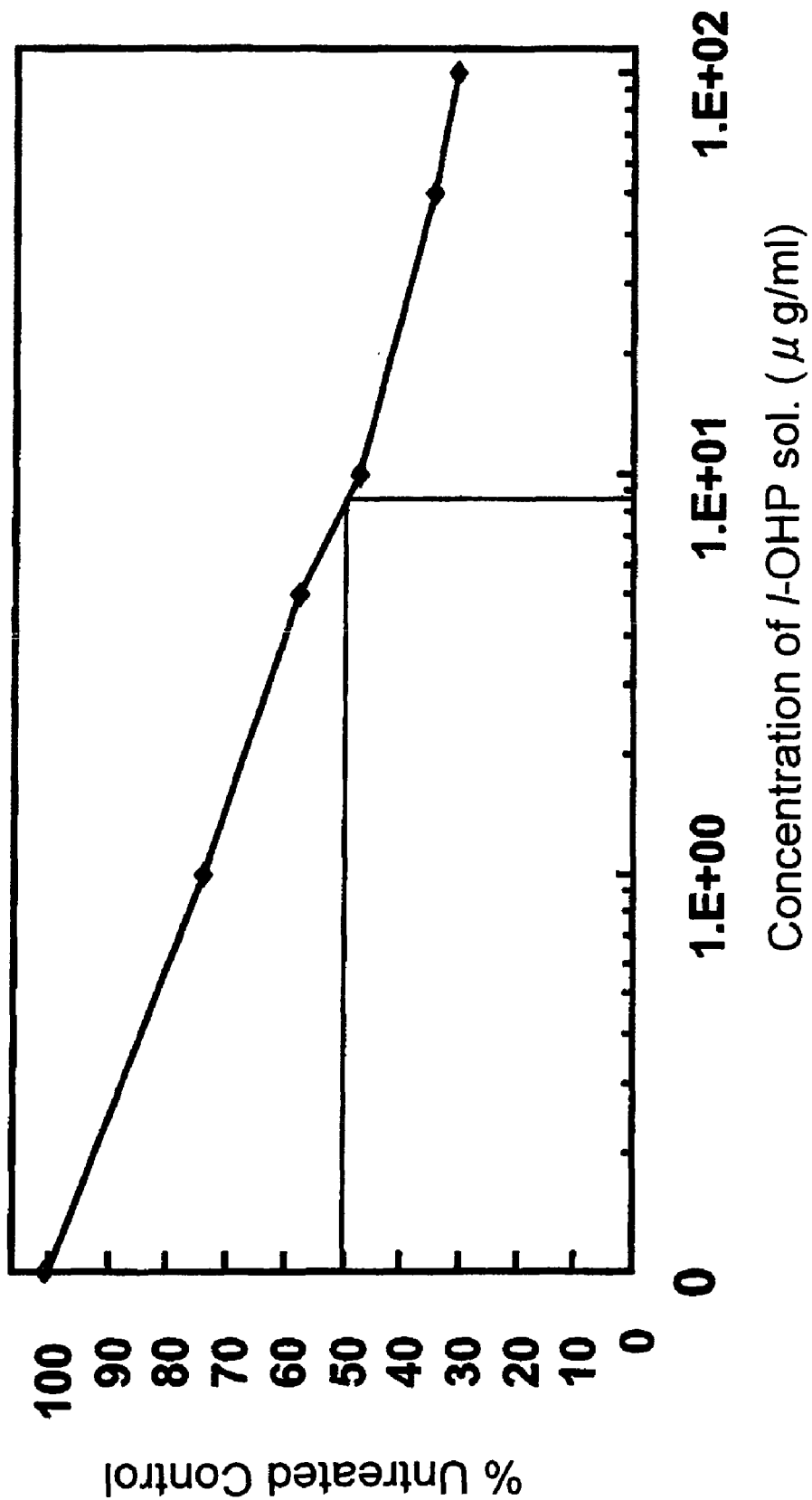
FIG. 6 shows the cytotoxicity of oxaliplatin on AsPC-1 cells at various oxalipatin concentrations.

The results are shown in FIG. 6. The cytotoxicity of l-OHP was found to be $LD_{50}$>8 µg/ml.

Example 2

Determination of the Number of Transferrin Receptors on the Cell Surface

Human normal leukocytes and human malignant tumor-derived cell lines (K562, MKN45P and HL60) were used in the experiment and obtained as follows: K562:TKG0210 (Cell Resource Center for Biomedical Research, Institute of Department, Aging and Cancer, Tohoku University, Japan); MKN45P: Dr. Hisae Iinuma, Teikyo University School of Medicine, Japan; HL60:TKG0345 (Cell Resource Center for Biomedical Research, Institute of Department, Aging and Cancer, Tohoku University, Japan).

The number of Tf (transferrin) receptors on the cell surface of each was determined by Scatchard analysis (Comp. Biochem. Physiol., 116B, 137-160 (1949), using Microsoft Excel). A solution of $^{125}$I-labeled Tf (Na-$^{125}$I (PerkinElmer Japan Co., Ltd., Japan) and h-Tf (T-4132, SIGMA, USA) were combined by iodogen method (Biochem. Biophys. Res. Commun., 122, 319-325 (1984)) was added to each cell culture at different concentrations ranging from $[300\times(½)^{(0-9)}$ nM] at 4° C. and incubated for 1 hour.

The concentration of $^{125}$I-labeled Tf was determined by protein quantification assay by the Lowry method (*J. Biol. Chem.*, 193, 265-270 (1951)) and the radioactivity was measured using a gamma counter (Auto Well Gamma System ARC-300, Aloka Co., Ltd., Japan]. Briefly, the solution was centrifuged to precipitate the cells, and the cell fraction was washed with an ice-cooled PBS (180×g (gravity), for 3 min, which was repeated 3 times, followed by the measurement of radioactivity with a gamma counter to determine the concentration of Tf bound to the cell surface. The number of cells was determined by protein quantification assay, using the Lowry method (*J. Biol. Chem.*, 193, 265-270 (1951)).

For each data point, the concentration of unbound Tf was determined by subtracting the concentration of bound Tf from the known concentration of Tf added. The Scatchard plot was drawn by plotting the concentration of bound Tf on the horizontal axis and the ratio of the concentration of bound Tf to the concentration of unbound Tf on the vertical axis. The number of the bound Tf (i.e., the number of the receptors) was determined from the x intercept of the graph, as described in *Proc. Natl. Acad. Sci. USA,* 80 2263-2266 (1983); *J. Cell Physiol.,* 132, 492-500 (1987); *Proc. Natl. Acad. Sci. USA,* 92 3318-3322 (1995); *J. Pharm. Sci.,* 84, 216-220 (1995); *Eur. J.*

Biochem., 186, 367-373 (1989); J. Biol., Chem., 258, 4715-4724 (1983), which are hereby incorporated by reference in their entirety.

Figure 7:
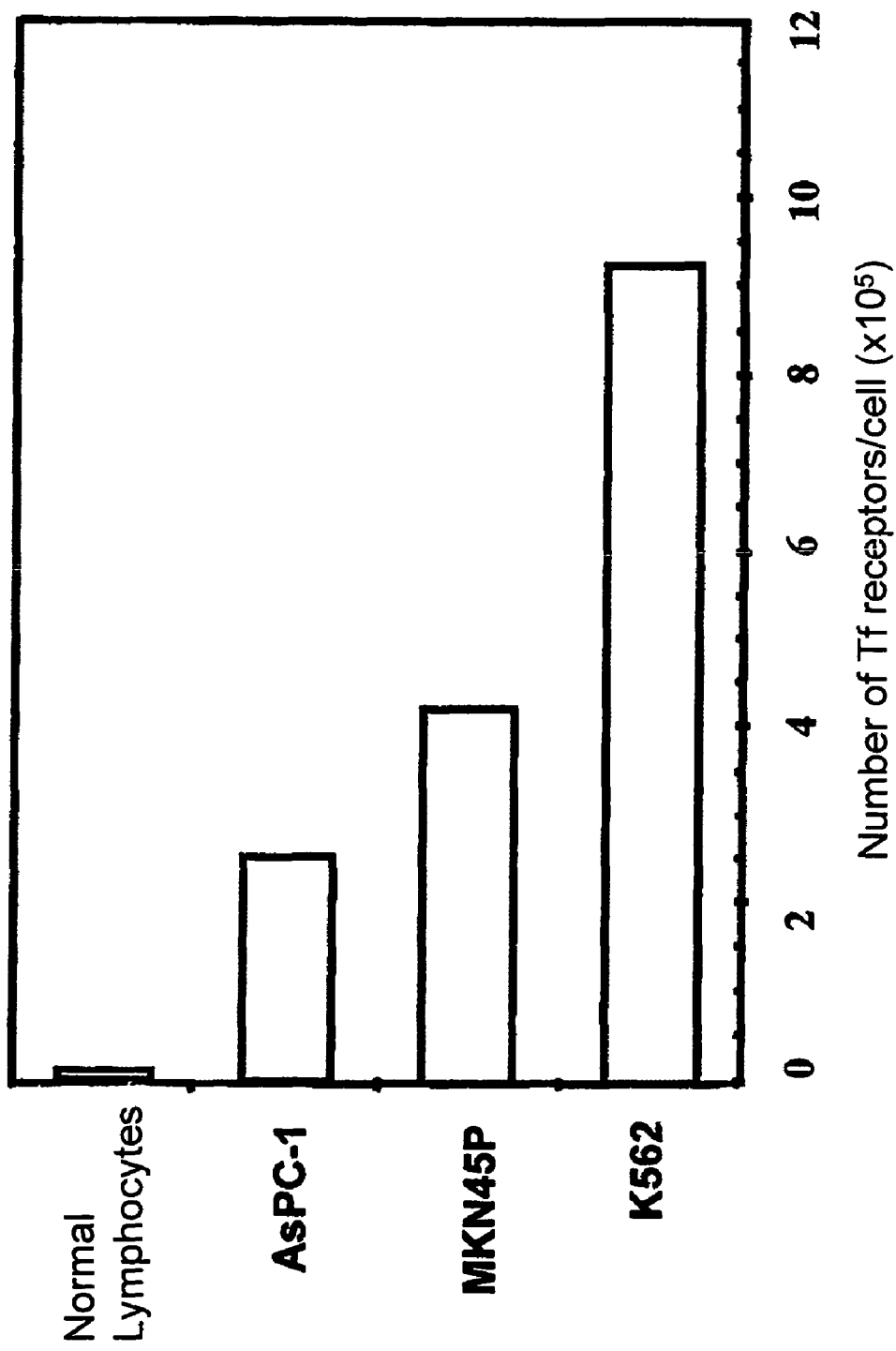
FIG. 7 shows the number of transferrin receptors present on the cell surface of normal leukocytes and tumor-derived cell lines.
Figure 8A:
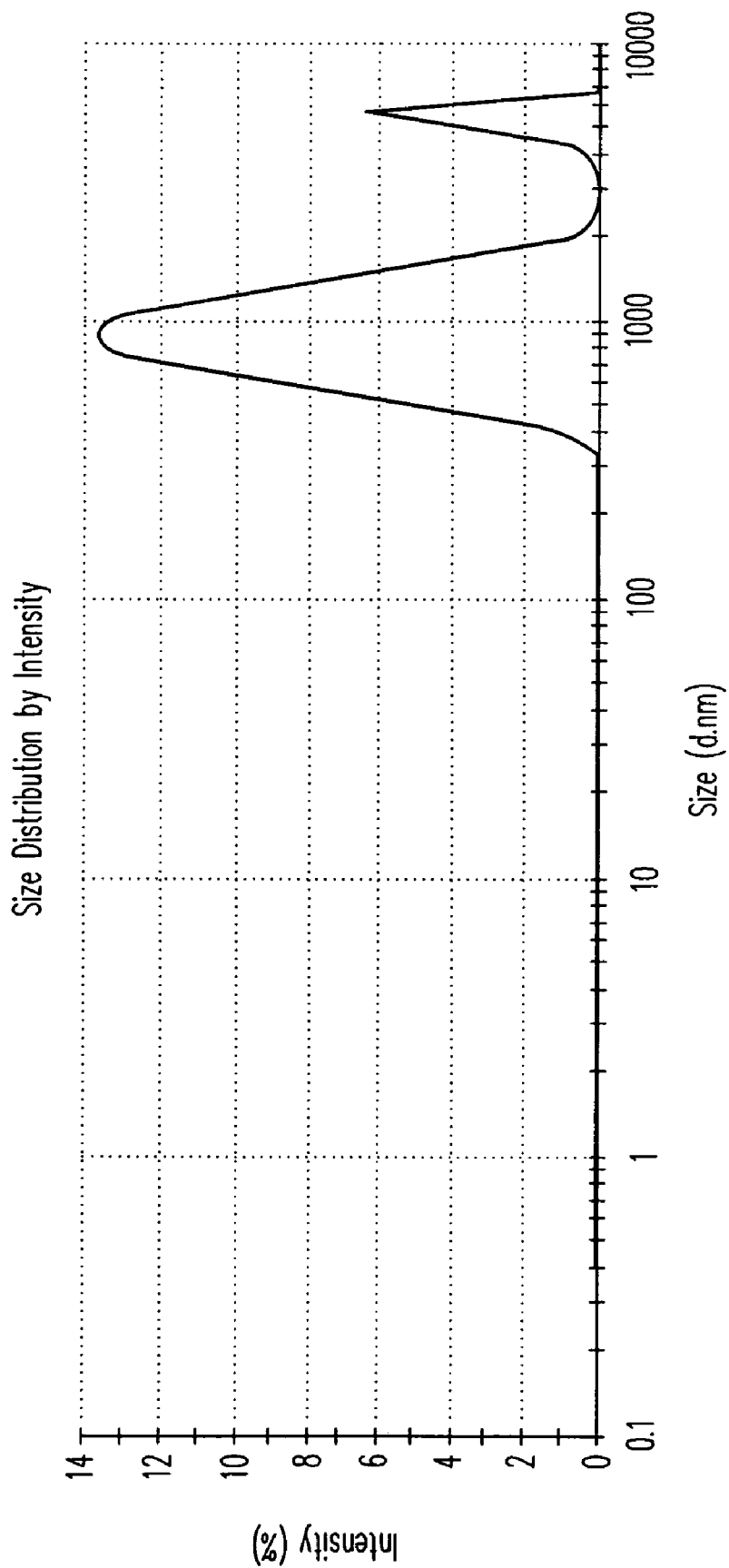
FIG. 8 shows the results of size distribution for the liposome-containing mixtures prepared in Example 6 and obtained by QELS; A) Entry 1, B) Entry 2, C) Entry 3, D) Entry 4, E) Entry 5, F) Entry 6.
Figure 8B:
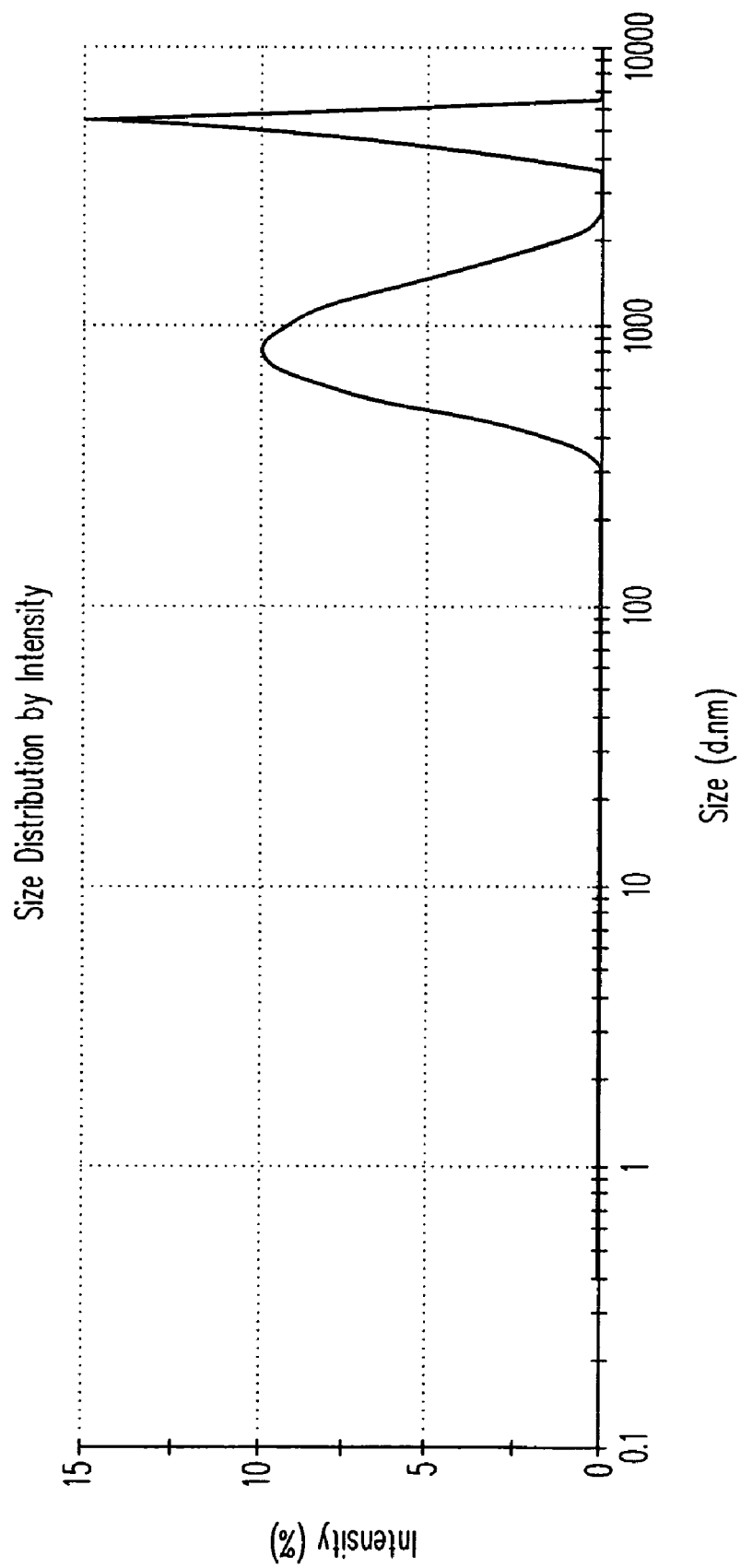
Figure 8C:
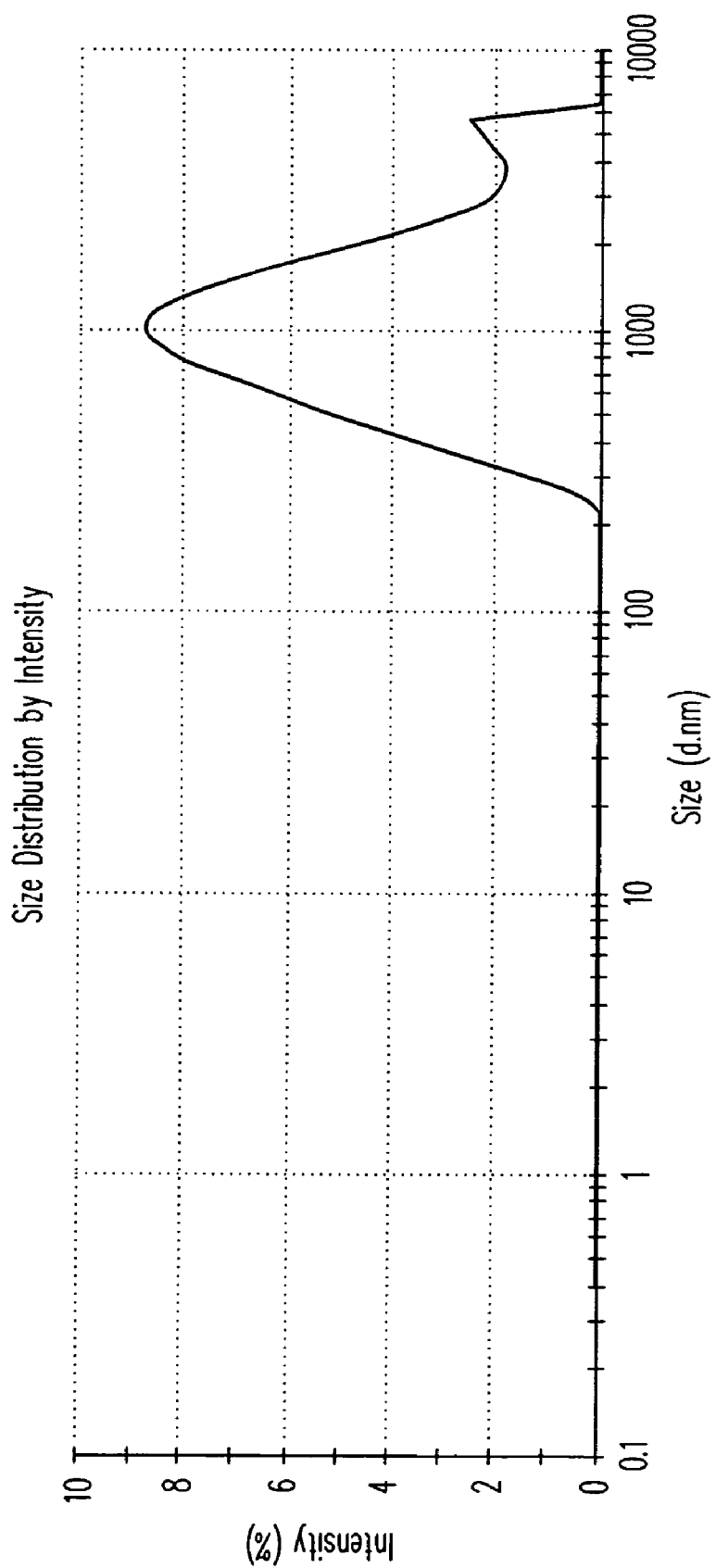
Figure 8D:
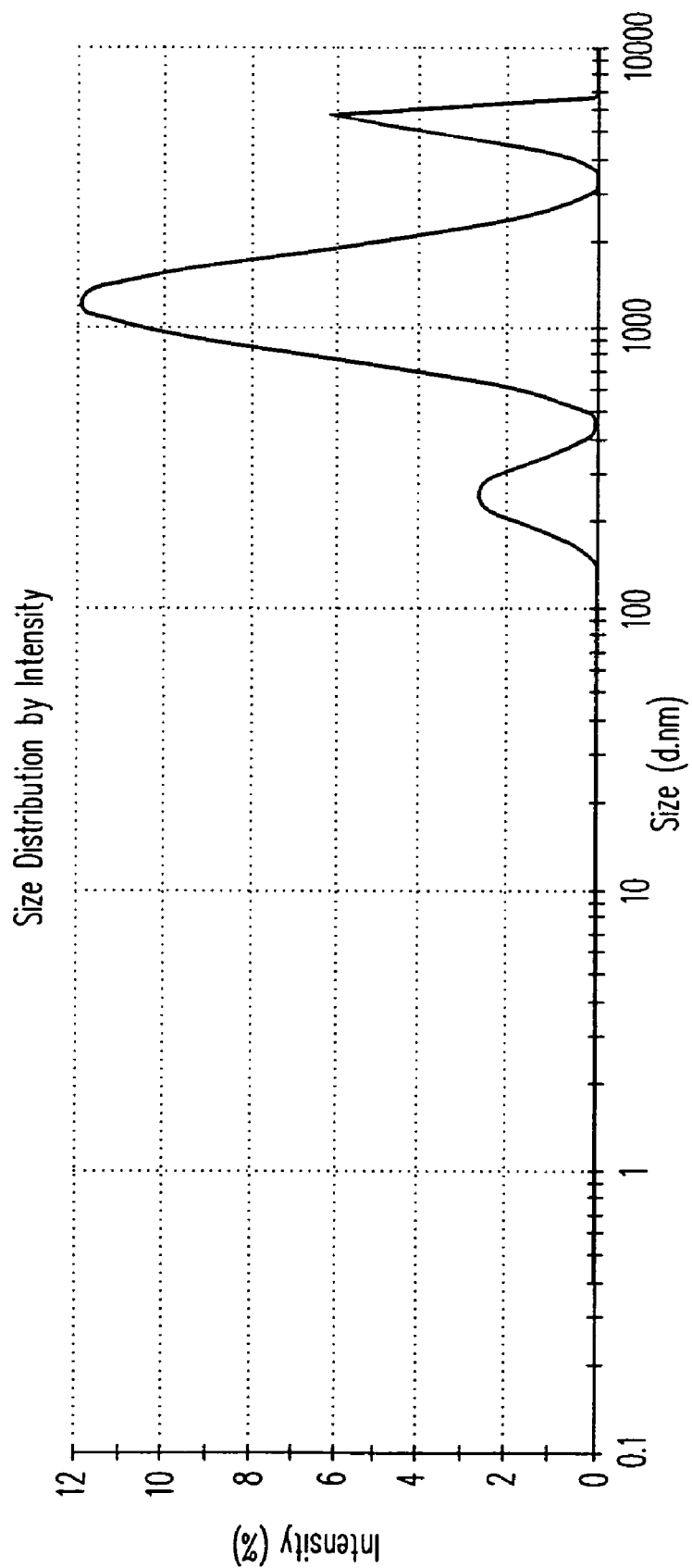
Figure 8E:
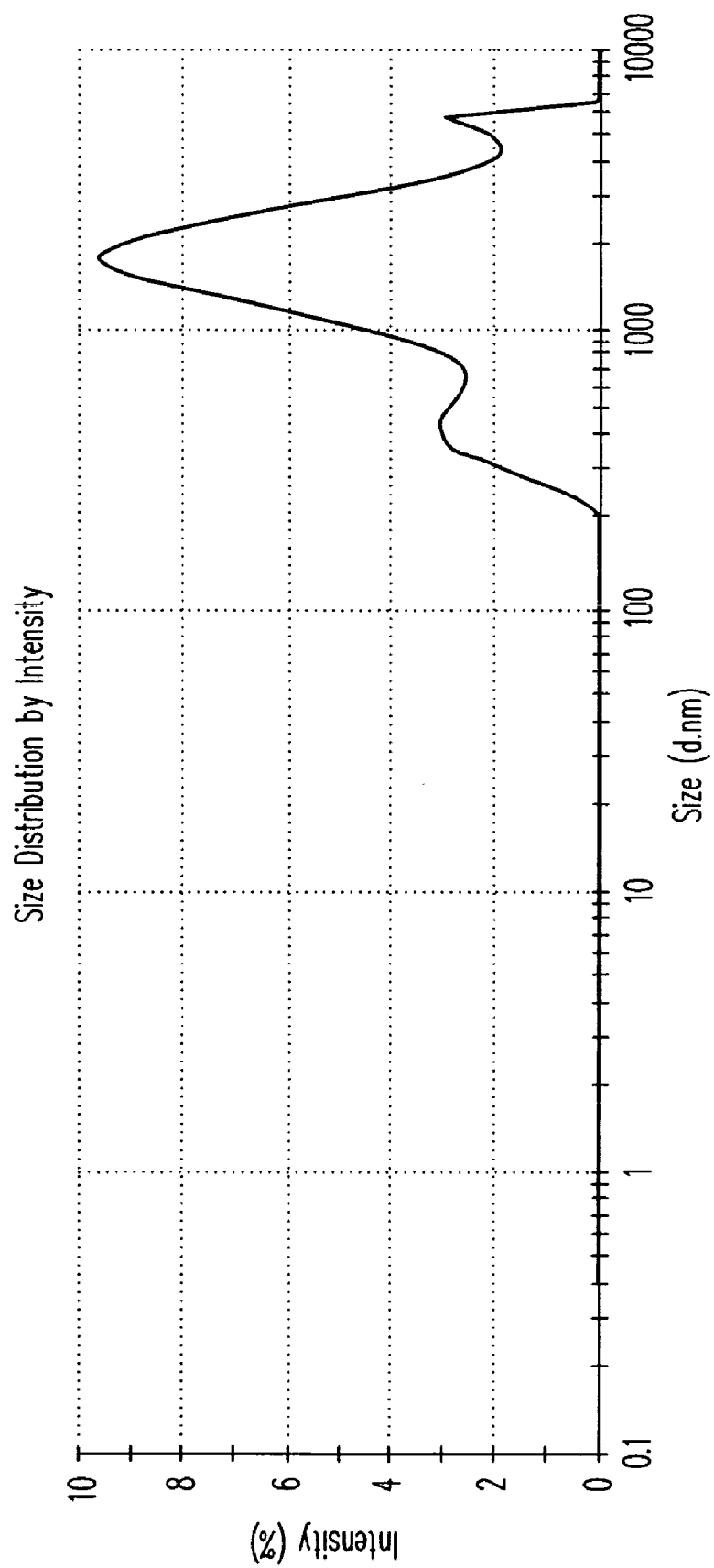
Figure 8F:
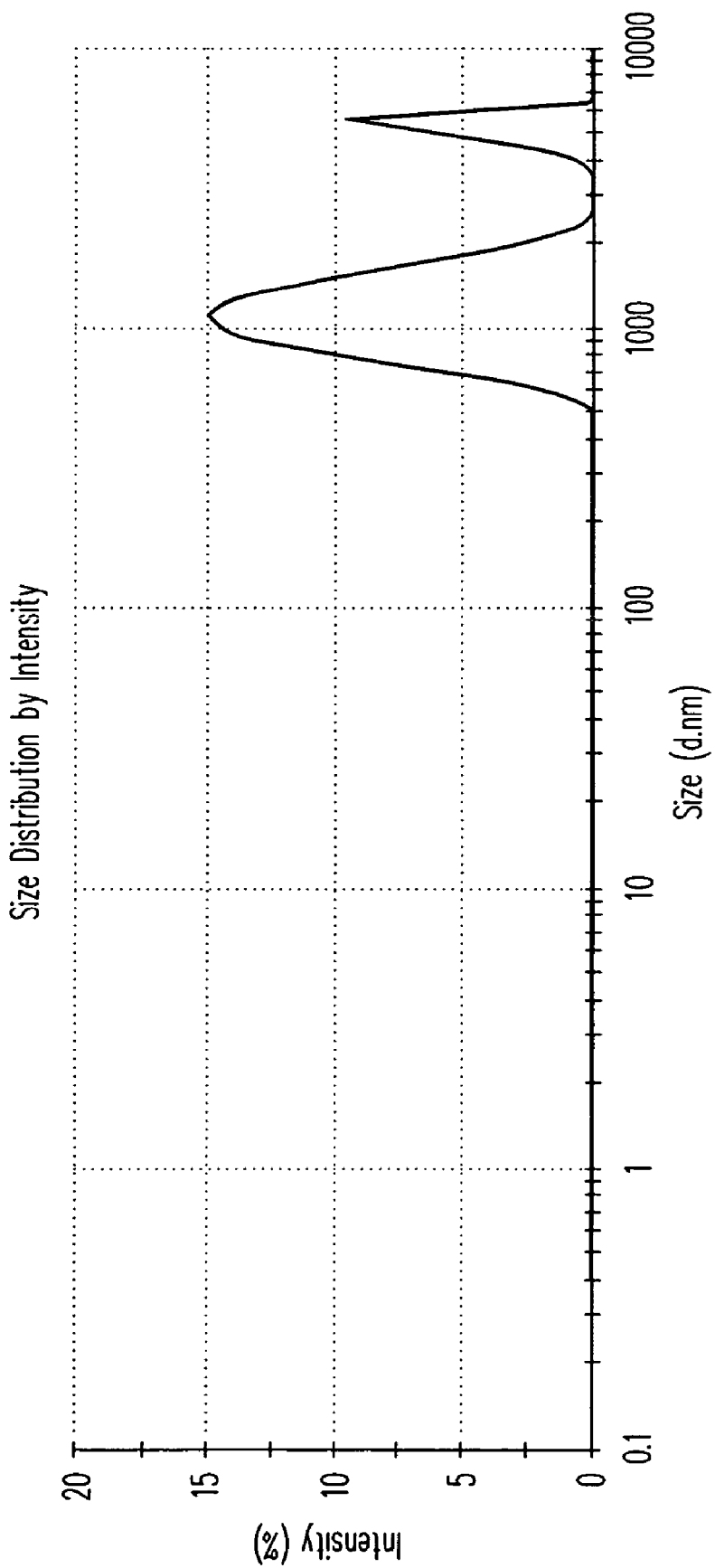

The number of $^{125}$I-Tf bound to the cell surface in the different cell types are shown in FIG. 7. It was determined that the number of transferrin (Tf) receptors on the cell surface of the cell lines derived from human malignant tumors was significantly higher than that in normal leukocytes.

Example 3

Preparation of NHS-NG-DOPE

A mass of 200 mg of NG-DOPE (Avanti Polar Lipids, Inc., USA) (Cat. No. 870242, MW 880.13)) was weighed into a conical flask with 2 legs. To the flask was added 39.2 mg NHS (Sigma, USA, MW=115.09). Next, 5 mL of chloroform/Ethyl acetate (1:1 (v/v), Wako Pure Chemical Industries, Ltd., Japan) was added and swirled to begin dissolving the NG-DOPE and NHS. Slight cloudiness observed.

Following initial mixing, a stir bar was added and the flask set up (balloon filled with nitrogen gas) to blow nitrogen gas gently into one leg of the flask and sealed with rubber stopper. Stirring under nitrogen was accomplished using a stir bar and stir plate. The second leg was sealed with a tube. The reaction was performed at ambient temperature (20-23° C.). The mixture was stirred for 5-10 minutes. A 20 µL sample of Lipid+NHS reaction mixture was set aside for use as a TLC control.

In a separate flask, a solution of DCC (99%, Aldrich, USA, MW: 206.33 g/mol) was prepared by dissolving 70 mg of DCC in 5 mL ethyl acetate. The DCC dissolved quickly in the solvent to yield a clear solution. The DCC solution so prepared (approximately 5 mL) was then added dropwise to the lipid/NHS reaction mixture over 10-15 minute period. The reaction mixture became more cloudy upon addition of DCC.

TLC was performed on the control (lipid/NHS) and on an aliquot of lipid/NHS/DCC at time 0 for reference, as follows. Sample was spotted 50 µg (2.5 µL of 20 mg/mL) on TLC plate (aluminum sheet—silica gel 60F$_{254}$ from EM Science (Gibbstown, N.J., USA) Cat No. SP05554M), dried and then placed in the developing chamber where solvent (70% chloroform, 28% methanol, 2% water) was allowed to migrate. The solvent front was marked and then the TLC plate was dipped in ammonium molybdate (5% ammonium molybdate in 10% $H_2SO_4$) and dehydrated with dryer.

The lipid/NHS/DCC reaction mixture was stirred under nitrogen flow and the formation of product was monitored (Rf 0.3-0.4) over time.

After 18 hours, conversion to NHS-NG-DOPE was not complete conversion after 18 hours, and more NHS (26 mg in 2 mL ethyl acetate) and DCC (47 mg in 1 mL ethyl acetate) were added. Reaction progression was again tested by TLC at T=20 hr.

The reaction was allowed to proceed over the weekend at ambient temperature with nitrogen flow and stirring (protected from light). Some starting materials remained prior to purification.

Purification: The reaction mixtures was chilled reaction on ice for ~30 minutes. The chilled reaction mixture was then filtered through a Buckner funnel and then washed 3 times with 2×5 mL chloroform. All of the liquid obtained was collected and dried by rotary evaporation. A semi-solid paste was obtained after evaporation. The paste was then resuspended in 2-3 mL chloroform.

Silica gel for purification of the suspended paste was prepared using silica (400 mesh) 4 g—hydrated in chloroform. The silica gel was packed onto a 1 cm×28 cm column with stopcock. The approximate size of the bed was 1 cm×14 cm. The column was equilibrated with chloroform (gravity packed).

Sample was loaded onto the equilibrated (but not dried) silica gel column. Added 10 chloroform to column (5×2 mL). Collected 5×2 mL fractions. Flow rate was a function of gravity, but 5×10 mL fractions collected in 10-20 min and designated fractions 1-5.

Next, 50 mL chloroform/methanol (90/10, vol/vol) was added to the column (5×10 mL). And 5×10 mL fractions were collected and designated fractions 6-10.

After collection of fractions 6-10, a volume of 100 mL chloroform/methanol (5/1 (v/v)) was added to the column (10×10 mL). And additional 10×10 mL fractions were collected and designated fractions 11-15.

Fractions 6-15 were assayed (5 µL aliquot) by TLC as described above.

Following TLC of fractions 6-15, fractions 7-11 were pooled and dried to a thin film using rotary evaporation. The final product obtained after evaporation was 130 mg (65% yield), as determined by by TLC against the unpurified reaction product and comparison with a standard product (NHS-NG-DOPE) obtained from NOF (Japan).

Example 4

Preparation of NHS-NG-DOPE

Pre-prepared and purified NG-DOPE (200 mg) (NOF Corporation Japan) and NHS (N-hydroxysulfosuccinimide; 34 mg) were weighed and placed in a 5 mL conical flask with 2 openings. One opening was sealed with a rubber stopper and a stir bar was added through the remaining opening.

The flask was then placed under vacuum and filled with nitrogen gas flowing gently (repeat at three times). The flask was then kept under nitrogen using a nitrogen balloon.

After placing under nitrogen, to the flask was added 2.5 mL dry chloroform, was then stirred using the stir bar and stir plate. The reaction was performed at ambient temperature for approximately 30 minutes and swirling was used to dissolve the starting materials. A 20 µL sample of Lipid+NHS was set aside for use in the TLC control/monitoring of the reaction.

A solution of 61 mg of DCC (1,3-dicyclohexylcarbodiimide) dissolved in 2.5 mL dry chloroform (clear, dissolved quickly) was prepared then prepared. The DCC solution was added dropwise to the lipid/NHS mixture over a 15 minute period. The solution turned cloudy upon addition of DDC.

At time 0, a TLC (70% chloroform, 30% methanol, 5% water) on lipid/NHS and lipid/NHS/DCC was performed to monitor the reaction by spotting 50 mg of chloroform on the TLC plate, allowing to dry, which was then placed in the reaction chamber (70% chloroform, 30% methanol, 5% water) to migrate.

The reaction mixture continued with stirring under nitrogen flow and the formation of product (Rf 0.3-0.4) was monitored over time.

The reaction was allowed to proceed over a time period of 2-3 days at ambient temperature with nitrogen flow and stirring.

The reaction mixture was then filtered through a Bruchner funnel and washed twice with 2×5 mL chloroform. The entire solution was collected and dried by rotary-evaporation. A semi-solid paste was obtained.

The semi-solid paste was resuspended in 2×3 mL chloroform, and then filtered and dried. This process was repeated three times. Finally, after three times the product was resuspended in 2×3 mL chloroform.

Column silica gel was prepared by mixing silica in chloroform which was then packed on a 1 cm×28 cm column with stopcock. The approximate size of the column bed was 1 cm×14 cm. The column was equilibrated with chloroform (gravity packed).

Samples were loaded onto equilibrated (but not dried) silica gel column. Then, was added 100 mL chloroform to column and aliquots were collected in 100 mL fractions. The flow rate was a function of gravity. (Fraction 1)

Fraction 1. Added 100 mL chloroform/methanol (90/10, vol/vol) to column. Collected 100 mL fractions. (Fraction 2)

Added 200 mL chloroform/methanol (50/10, vol/vol) to column (20×10 mL). Collected 20×10 mL fractions. (Fraction 3-23.)

Fractions 1 to 23 were assayed using 5 mL aliquots via TLC.

Fractions 9 through 22 were pooled and dried to a thin film using rotary-evaporation and lyophlization. The final weight of NHS-NG-DOPE from these fractions was 61.9 mg (27.9% yield).

Example 5

Preparation of Lipid Mixture
(NG-DOPE:Tf-NG-DOPE:DMPC:CH)

583 mg of DMPC(NOF corporation, Japan), 299 mg of cholesterol (Wako Pure Chemical Industries, Ltd., Japan) and 75.7 mg of NG-DOPE (NOF corporation, Japan) were mixed and dissolved in t-BuOH (10 v/w vs. lipids (10 mL)) at 45-50° C.

The resulting solution was poured into a vial and frozen for about 8 hours on a shelf at −40° C. It was depressurized to about 0.1 mmHg and kept at reduced pressure for 2 days with rising the temperature from −40° C. to 25° C. stepwise, from which process a lyophilized lipid mixture was obtained.

A powder of the lyophilized lipid mixture as obtained above was mixed with 20 mg of powdery Tf-NG-DOPE (as prepared in Example 29) and crashed. A homogeneous powder of lipid mixture was thus obtained, with a lipid ratio of 50:45:5 (DMPC:Chol:NG-DOPE+Tf-NG-DOPE).

Example 6

Preparation of Liposome-Containing Compositions

Lipid mixtures were prepared according to the previous examples with the components as detailed below:
Entry 1: DMPC/Chol/NG-DOPE (155 mg/79.4 mg/16.1 mg)
Entry 2: DMPC/Chol/NG-DOPE (155 mg/79.4 mg/16.1 mg)
Entry 3: DMPC/Chol/NG-DOPE/NHS-NG-DOPE (152 mg/77.9 mg/15.8 mg/4.38 mg)
Entry 4: DMPC/Chol/NG-DOPE/NHS-NG-DOPE (152 mg/77.9 mg/1 5.8 mg/4.38 mg)
Entry 5: DMPC/Chol/NG-DOPE/Tf-NG-DOPE (148 mg/76.0 mg/15.4 mg/4.8 mg)
Entry 6: DMPC/Chol/NG-DOPE/Tf-NG-DOPE (148 mg/76.0 mg/15.4 mg/4.8 mg)

Entries 1, 3 and 5 were each hydrated and stirred with 300 mM of aqueous sucrose solution (20 v/w vs. lipids (5 mL) (5 mL of sucrose solution (20 v/w) was added to the dry lipid mixture and stirred) for 30 min. at 40-45° C. Entries 2, 4 and 6 were each hydrated and stirred with an aqueous solution of l-OHP (8 mg l-OHP/mL, 20 v/w vs. lipids (5 mL) in a 300 mM sucrose solution) for 30 min. at 40-45° C. A liposome-containing mixture was thus obtained.

Liposome diameter was determined by QELS and the results are shown in FIG. 8. The liposomes present in the liposome-containing mixture have a mean diameter of 500-2,000 nm and have a broad distribution of sizes around 100-10,000 nm.

Example 7

Preparation of Oxaliplatin-Containing Liposome
(NG-DOPE:Tf-NG-DOPE:DMPC:CH)

The composition of the liposome was as follows:

Dimyristoyl phosphatidylcholine (1,2-dimyristoyl-sn-glycero-3-phosphocholine:DMPC) (NOF Corporation, Japan)

Cholesterol (CH) (Solvay Pharmaceuticals B.V., Netherlands)

N-glutaryl-dioleoyl phosphatidyl ethanolamine (N-glutaryl-1,2-dioleoyl-sn-glycero-3-phosphoethanolamine, sodium salt:DOPE-CO—(CH$_2$)$_3$—COOH; hereinafter represented by NG-DOPE) (NOF Corporation, Japan)

Succ-N-glutaryl-dioleoyl phosphatidyl ethanolamine (N-(succinimidyl-glutaryl)-1,2-dioleoyl-sn-glycero-3-phosphoethanolamine, sodium salt:DOPE-CO—(CH$_2$)$_3$—CO—OSu; hereinafter represented by NHS-NG-DOPE) (NOF Corporation, Japan)

DMPC:CH:NG-DOPE:NHS-NG-DOPE=50:45:4:1 (m/m).

As the aqueous phase, an aqueous solution of l-OHP (8 mg/ml, in a 300 mM sucrose solution) was used.

A mixture of DMPC, CH, NG-DOPE and NHS-NG-DOPE (at the mole ratio of 50:45:4:1) was dissolved in 4 v/w (vs. total lipid weight) of warm ethanol/t-butanol/water solvent. The lipid solution was injected into 300 mM sucrose solution containing about 8 mg/ml l-OHP at about 45° C., so that the concentration of the solvent became about 14% v/v.

The suspension was passed through an Extruder that was lapped over five pieces of 100 nm filters (Cat. No. 112105, Whatman plc, UK) under pressure of about 200-800 psi at about 45° C. The liposome was thus obtained, having an average diameter in the vicinity of 100 nm. Liposome diameter was determined using QELS.

6 L of phosphate buffered saline (pH 7.9), 6 L of transferrin (Cat. No. 4455, Selorogicals, GA, USA) solution (20 mg/ml), and 18 L of liposome suspension were mixed and stirred at 30° C. for 15-60 min. This resulted in a reaction mixture which contained 4 mg/ml of transferring and 20 mg/ml of lipids.

The quantitative analysis of transferrin was performed by the bicinchoninic acid (BCA) assays according to instructions provided by the vendor.

The increase of molecular weight after incorporation of transferrin was investigated by SDS-PAGE (Sodium Dodecyl Sulfate polyacrylamide gel electrophoresis). The analysis of NG-DOPE was performed by high-performance liquid chromatography (HPLC) with evaporative light scattering detector (ELSD2000, Alltech, MD, USA) using a Silicagel column (YMC PVA Silica Column, 4.6×250 mm, 5 µm).

Example 8

Preparation of Oxaliplatin-Containing Liposome (NG-DSPE:Tf-NG-DSPE:DSPC:CH)

The composition of the liposome was as follows:

Distearoyl phosphatidylcholine (1,2-distearoyl-sn-glycero-3-phosphocholine:DSPC) Cholesterol (CH)

N-glutaryl-distearoyl phosphatidyl ethanolamine (N-glutaryl-1,2-distearoyl-sn-glycero-3-phosphoethanolamine, sodium salt:DSPE-$(CH_2)_3$—COOH; hereinafter represented by NG-DSPE)

DSPC:CH:NG-DSPE=2:1:0.2 (mol/mol).

As the aqueous phase, an aqueous solution of l-OHP (8 mg/ml, in a 9% sucrose solution) was used, as described in Example 1.

A mixture of DSPC (MC8080, NOF, Japan), cholesterol (038-03005, Wako Pure Chemical Industries, Ltd., Japan) and NG-DSPE (Dr. Kazuo Maruyama, Teikyo University, Faculty of Pharmaceutical Sciences, Japan) at the ratio of 2:1:0.2 (m/m) was dissolved in chloroform and isopropyl ether.

To the resultant solution, a solution of l-OHP (in a 9% sucrose solution) was added, and then the resulting mixture was sonicated for about 15-30 minutes. The solution was then evaporated by rotary evaporation at 60° C. to remove the solvent and the freeze/thawing was repeated five times. The suspension was frozen (by being immersed in dry-ice/acetone bath) and thawed (by being left to stand and immersed in warm water). This was repeated five times.

Then, the resultant product was sized at 60° C. using EXTRUDER filters (twice at 400 nm and then five times at 100 nm), (Lipex™ Extruder, Model No. T-001, Northern Lipids Inc., Canada) and ultracentrifuged (200,000×g, 60 min, about 4° C.). The precipitate was resuspended in a 9% sucrose solution or MES buffer (pH 5.5) (MES buffer. Cat. No. 345-01625, Dojindo Laboratories, Japan) to obtain l-OHP-encapsulated NG-DSPE:DSPC:CH liposome.

Subsequently, the l-OHP-encapsulated NG-DSPE:DSPC:CH liposome was derivatized with transferrin (Tf). To the thus obtained l-OHP-encapsulated NG-DSPE liposome, 1-ethyl-3-(3-dimethylaminopropyl)carbodiimide hydrochloride (EDC; Cat. No. #22980, Pierce Biotechnology, Inc., USA) (in an amount of 2.7% relative to the weight of the lipid) and N-hydroxysulfosuccinimide (S-NHS; 038-0432, Wako Pure Chemical Industries, Ltd., Japan) (in an amount of 7.3% relative to the weight of the lipid) were added, and the mixture was left at room temperature for 10 minutes.

Then, to the resultant solution, transferrin (Tf) (in an amount of 20% relative to the weight of the lipid; (Cat. No. T4132, SIGMA, USA) was added and stirred at room temperature for 3 hours. A 1 mM PBS (Phosphate buffered saline) solution of transferrin (Tf) ((in an amount of 20% relative to the volume of the total reaction mixture) and 1 mM PBS were added (in an amount of 20% relative to the volume of the total reaction mixture), and the resulting solution stirred at room temperature for 1 hour.

To the thus obtained apo-form of Tf-NG-DSPE liposome, 10-40 eq. (vs. transferrin) of iron citrate-sodium citrate (Wako Pure Chemical Industries, Ltd., Japan) was added to the suspension and stirred at room temperature for 15 minutes. The resultant solution was ultrafiltrated as above. The precipitate was then resuspended in a 9% sucrose solution, whereby a holo-form of Tf-NG-DSPE liposome was obtained. The solution was ultrafiltrated (200,000×g, 60 min, about 4° C.) and then the precipitate was resuspended in a 9% sucrose solution.

The quantitative analysis of transferrin was performed by the bicinchoninic acid (BCA) assays, performed in accordance with the vendor's instruction (Cat. No. 23227, BCA™ Protein Assay Kit, Pierce Biotechnology, Inc., USA).

The increase in molecular weight upon derivatization was investigated by SDS-PAGE (Sodium Dodecyl Sulfate polyacrylamide gel electrophoresis). The analysis of NG-DSPE was performed by high-performance liquid chromatography (HPLC) with evaporative light scattering detector (ELSD2000, Alltech, MD, USA) using a Silicagel column (YMC PVA Silica Column, 4.6×250 mm, 5 μm).

Example 9

Preparation of PEGylated Oxaliplatin-Containing Liposomes

Following the experimental protocol in Example 8, DSPC:cholesterol:DSPE-PEG(2K)-OMe:DSPE-PEG(3.4K)-COOH liposomes (Tf-PEG-liposomes) were prepared. In these liposomes the ratio of components was as follows: DSPC:cholesterol:DSPE-PEG(2K)-OMe:DSPE-PEG(3.4K)-COOH=2:1:0.16:0.03.

This liposome contained 6% by mole of PEG-lipid and 1% by mole of PEG-COOH-lipid, and Tf is bound to the liposome through PEG-COOH.

Also made by the method of Example 8 were Tf/PEG-DSPE liposomes (Tf/PEG-NG-DSPE liposomes).

In these liposomes the ratio of components was as follows: DSPC:cholesterol:DSPE-PEG(2K)-OMe:NG-DSPE=2:1:0.16:0.03.

This liposome is derivatized with PEG, and the Tf was bound to the liposome through NG-DSPE. PEG-derivatized liposomes can also be produced by the methods described in U.S. Pat. App. Pub. Nos. 2003/0224037 and 2004/0022842, the disclosures of which are hereby incorporated in their entirety.

Example 10

Preparation of Blank Liposome

A mixture of DMPC, Chol (Wako Pure Chemical Industries, Ltd., Japan), NG-DOPE (NOF Corporation, Japan) and NHS-NG-DOPE (NOF Corporation, Japan) (at the mole ratio of 50:45:4:1; 410 g of DMPC, 211 g of Chol, 43 g of NG-DOPE and 12 g of NHS-NG-DOPE, respectively) was dissolved in 4 v/w (vs. total lipid weight) of warm ethanol/t-butanol/water solvent. The resulting suspension with a volume of 20 L was incubated at 45° C. with stirring and passed through an Extruder (Stevested Machinery & Engineering Ltd., Canada) that was lapped with five stacking of polycarbonate 100 nm filters (Cat. No. 112105, Whatman plc, UK) under pressure of about 200-800 psi at about 45° C. The liposomes were thus obtained, having an average diameter in the vicinity of 100 nm. Liposome diameter was determined by QELS.

The liposome suspension, PBS buffer (pH 7.9) and PBS solution of transferrin (Cat. No. 4455, Selorogicals, GA, USA) (pH 7.0) were mixed at the ratio of 3:1:1 (v/v/v), then stirred for 15-60 min. at 30° C. Approximately 6 L blank liposome was thus obtained.

20 g (about 19 mL) of liposome solution was poured into a vial and frozen for about 8 hours on a shelf at −40° C. It was depressurized to about 0.1 mmHg and kept in the reduced pressure for 2 days with rising temperature from −40° C. to 25° C. stepwise over the 2-day period. At the completion of this process about 3.5 g of lyophilized blank liposome was thus obtained. The liposomes were subsequently stored at 4° C.

Example 11

Encapsulation of Oxaliplatin in Pre-Prepared Blank Liposome

An aqueous solution of l-OHP (8 mg/mL, in a 300 mM sucrose solution) was added to about 3.5 g of lyophilized blank liposome and rehydrated by stirring for 2 hours at 40° C. After stirring, liposomal l-OHP was separated from free l-OHP by fractionation using Sephadex G-25 (φ1×45 cm). The liposome l-OHP and free l-OHP were monitored by VIS 600 nm and UV 210 nm respectively.

The amount of l-OHP and cholesterol was measured. The l-OHP concentration was calculated for the case of condensing the liposome fraction to the original cholesterol concentration finally, the yield of l-OHP was measured by comparison of the l-OHP concentration of liposome and a feeding concentration of l-OHP.

Total l-OHP concentration for the case of condensing the liposome fraction to the origin cholesterol concentration was 210 μg/mL. And the yield of l-OHP was 2.6%.

This indicates 210 μg/mL of l-OHP was encapsulated into the lyophilized blank liposome.

Example 12

Comparison of Liposome Levels in Blood and Organs

A comparative study was carried out to evaluate the blood retention and accumulation in organs of l-OHP-encapsulated Tf-modified liposome compositions in tumor-bearing mice. Male BALB/c mice aged 5 weeks were used as the animal models, and Colon 26 cells (derived from mouse colon cancer) were used as the tumor cells. The cells were obtained from Laboratory of Biopharmaceutics, Teikyo University School of Pharmaceutical Sciences, Japan.

Colon 26 cells (2×10$^6$ cells) subcultured in vitro were subcutaneously implanted into the dorsal region of the mice. A mouse bearing a tumor with a diameter of about 8 to 10 mm (after 8 to 10 days growth on average) was used as the colon cancer-bearing mouse. A solution of each of the liposomes prepared in Examples 8 and 9 or l-OHP (8 mg/ml in a 9% sucrose solution) was injected into the tail vein. The concentration of oxaliplatin was adjusted at 5 mg l-OHP/kg body weight in each case. As the liposomes, Tf-NG-DSPE liposome ((■); Example 8), Tf/PEG-NG-DSPE liposome ((▲); Example 9) and Tf-PEG-DSPE liposome ((♦); Example 9) were used.

Figure 9:
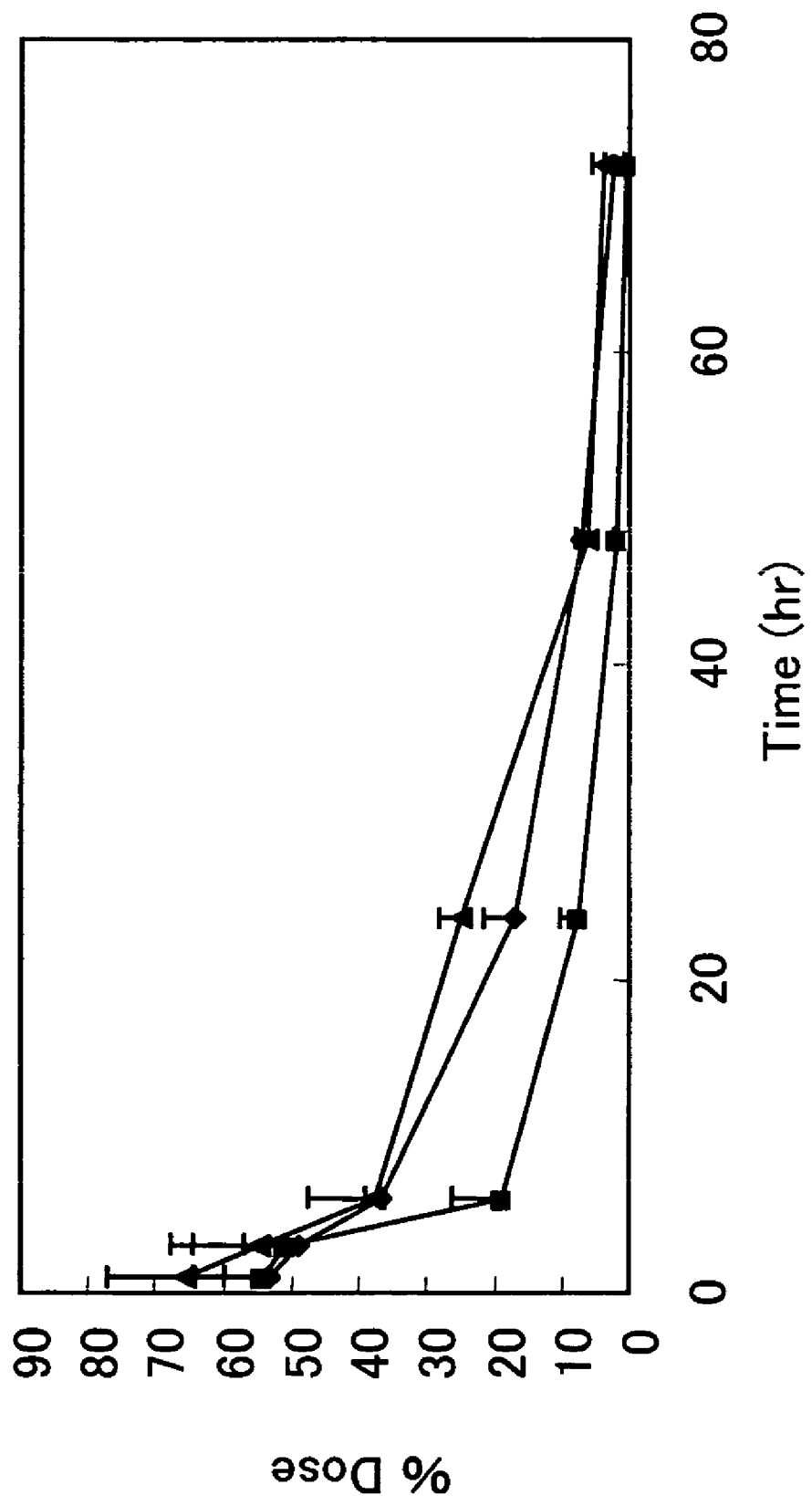
FIG. 9 shows the concentrations of liposomes in the blood, where (◆) indicates the Tf-PEG-liposomes prepared in Example 9, (■) indicates the Tf-NG-DSPE:NG-DSPE:DSPC:CH liposomes prepared in Example 8, and (▲) indicates the Tf/PEG-NG-DSPE liposomes prepared in Example 9.

Blood, plasma, liver, spleen, kidney, heart, lung and tumor tissues were collected from 3 mice at each time point for each group at 1, 3, 6, 24, 48 and 72 hours after the administration. The Pt concentration in the blood, each organ and tumor tissues were determined using atomic absorption (AA), and the l-OHP concentration was calculated and reported as the ratio (%) to the dose. The concentrations in the blood are shown in FIG. 9.

Figure 10:
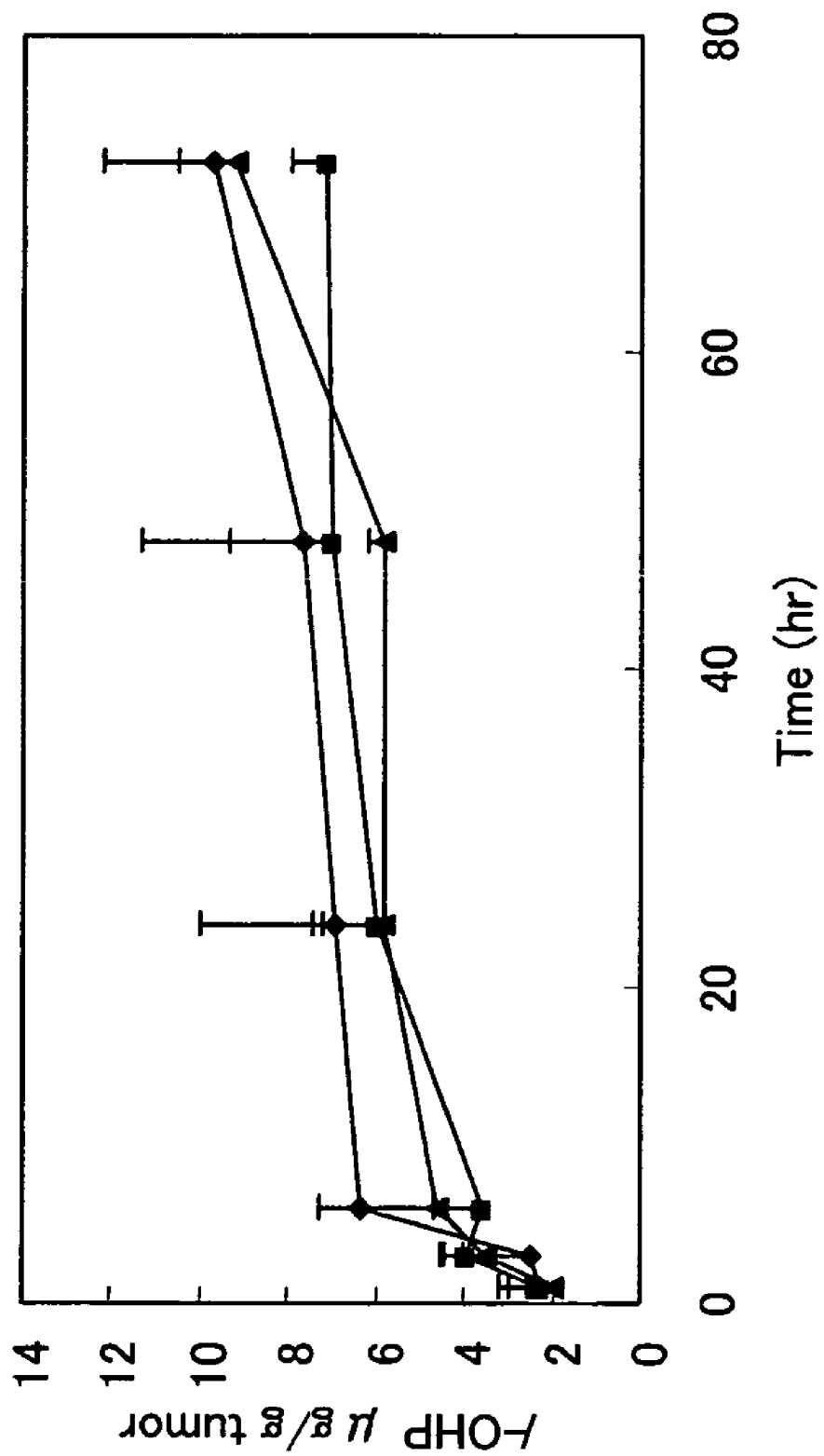
FIG. 10 shows the concentrations of liposomes in cancer tissues; where (◆) indicates the Tf-PEG-liposomes prepared in Example 9, (■) indicates the Tf-NG-DSPE:NG-DSPE:DSPC:CH liposomes prepared in Example 8, and (▲) indicates the Tf/PEG-NG-DSPE liposomes prepared in Example 9.

Tf-NG-DSPE liposome showed substantially the same blood retention until 3 hours after the administration compared with Tf-PEG-DSPE liposome and Tf/PEG-NG-DSPE liposome. However, after 6 hours, Tf-NG-DSPE liposome showed some blood retention, but it disappeared more quickly from the blood compared with the PEG liposomes. The concentrations in the tumor tissues are shown in FIG. 10. Tf-NG-DSPE liposome showed substantially the same accumulation to tumor tissues as Tf-PEG-DSPE liposome and Tf/PEG-NG-DSPE liposome, despite being retained at a lower concentration in the blood over time.

From the above results, it was found that about 6 hours of retention time in the blood after administration is necessary and sufficient deliver a sufficient concentration of a drug to tumor tissue at a significant level or higher in mice. It is considered that a retention time in the blood longer than this may increase the possibility of causing an adverse effect on a normal tissue.

Example 13

Preparation of Diagnostic Liposome and Accumulation of $^{125}$I in Tumor Tissue Liposomes were prepared in the same manner as in Example 7 with the exception that [$^{125}$I]-Tyraminyl inulin (in PBS solution) replaced l-OHP and DMPC/CH/NG-DOPE/Tf-NG-DOPE/[$^{125}$I]-Tyraminyl inulin liposomes were obtained. Lipid components were obtained also as described in Example 7. Two liposome formulations were prepared, with the components as shown below. The liposome lacking Tf-NG-DOPE served as a control for non-targeted distribution of the liposome.

Targeted Liposome: DMPC/CH/NG-DOPE/Tf-NG-DOPE (63.3/31.7/4/1 (m/m))

Non-Targeted Liposome (control): DMPC/CH/NG-DOPE (63.3/31.7/5 (m/m))

$^{125}$I was bound to tyraminyl inulin by combining Na-$^{125}$I (PerkinElmer Japan Co., Ltd., Japan) and tyraminyl inulin (Dr. Kazuo Maruyama, Teikyo University, Faculty of Pharmaceutical Sciences, Japan) using the iodogen method (Biochem. Biophys. Res. Commun., 122, 319-325 (1984), incorporated by reference in its entirety). $^{125}$I-Tyraminyl inulin was thus obtained. $^{125}$I-Tyraminyl inulin/PBS(−) solution at a concentration of about 1 mg/mL was then encapsulated into the liposome as described in Example 7.

100 μl of each of the liposome solutions was injected into the tail vein of murine colon cancer-bearing mice described in Example 12. Tumor tissue and tail were collected from 5 mice at each time point for each group at 1, 6, 24 and 48 hours after the administration. The weight of the tumor tissue was measured and the radioactivity (unit: cpm) in the tumor tissue and the tail was measured using a gamma counter (Aloka Auto Gamma System ARC-300, Japan). Results were evaluated as the distribution amount in the tumor tissue (% of dose/g-tumor)=[(count value in the tumor tissue)−(value of b.g.)]× 100/[(count value of Std.)−(count value in the tail)]/(weight of tumor tissue (g)). The half-life radioactive of $^{125}$I is approximately 60 days.

Figure 11:
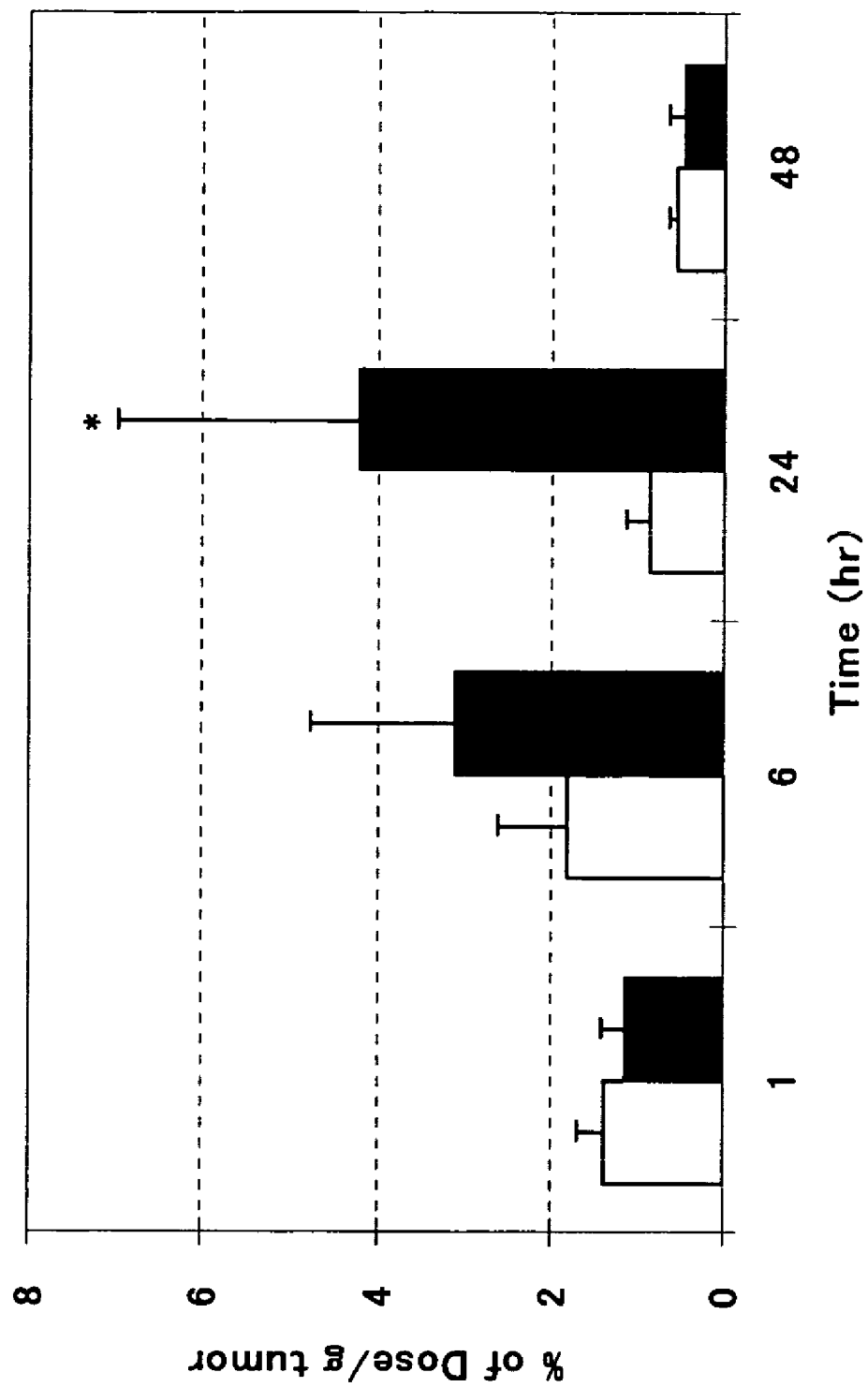
FIG. 11 shows the accumulation in tumor tissue of NG-PE liposomes, prepared as described in Example 13, after intravenous injection, where NGPE liposomes encapsulated tyraminyl inulin labeled with $^{125}I$ were injected into Colon 26 tumor-bearing mice. Data shown as mean. Data shown as mean±SD (n=5). (□) 0 mol % (−); (■) 1 mol % (+) Tf-NG-DOPE. * Significant difference from 0 mol % (−).

The radioactivity of 100 μl of the administered solution (standard: Std.) was defined as 100% and the count value of an empty test tube was defined as the value of the background (b.g.). The results are shown in FIG. 11. As is apparent from FIG. 11 Tf-modified liposome shows high accumulation to a tumor tissue, while non-targeted liposomes do not show a high accumulation. These results demonstrate that a liposome encapsulating a radioactive compound are useful for the detection of tumor tissue.

Example 14

Comparison of Antitumor Effects of Liposomes

A comparative study was carried out to evaluate the antitumor effects on colon cancer Colon 26-bearing mice for l-OHP-encapsulated Tf-modified liposome compositions (Tf-PEG-liposomes prepared in Example 9, Tf-NG-DSPE: NG-DSPE:DSPC:CH liposomes prepared in Example 8, Tf/PEG-NG-DSPE liposomes prepared in Example 9; 9 mice in each group) and for each of the liposome compositions to which transferrin is not bound ((−)TF; 6 mice in each group).

The tumor-bearing mice were prepared in the same manner as in Example 12. As the control, a solution of l-OHP (8 mg/ml in a 9% sucrose solution) was used. The date when l-OHP was administered at doses of 5 mg/kg was defined as the start date, and on day 4, l-OHP was administered at doses of 5 mg/kg again. The size of the tumor on day 0 was defined as 1, and the size was shown as the ratio based on this starting size. The size of the tumor was measured on day 0, 2, 5, 7, 10, 13, 15, 18 and 21, and the survival days were surveyed.

Figure 12:
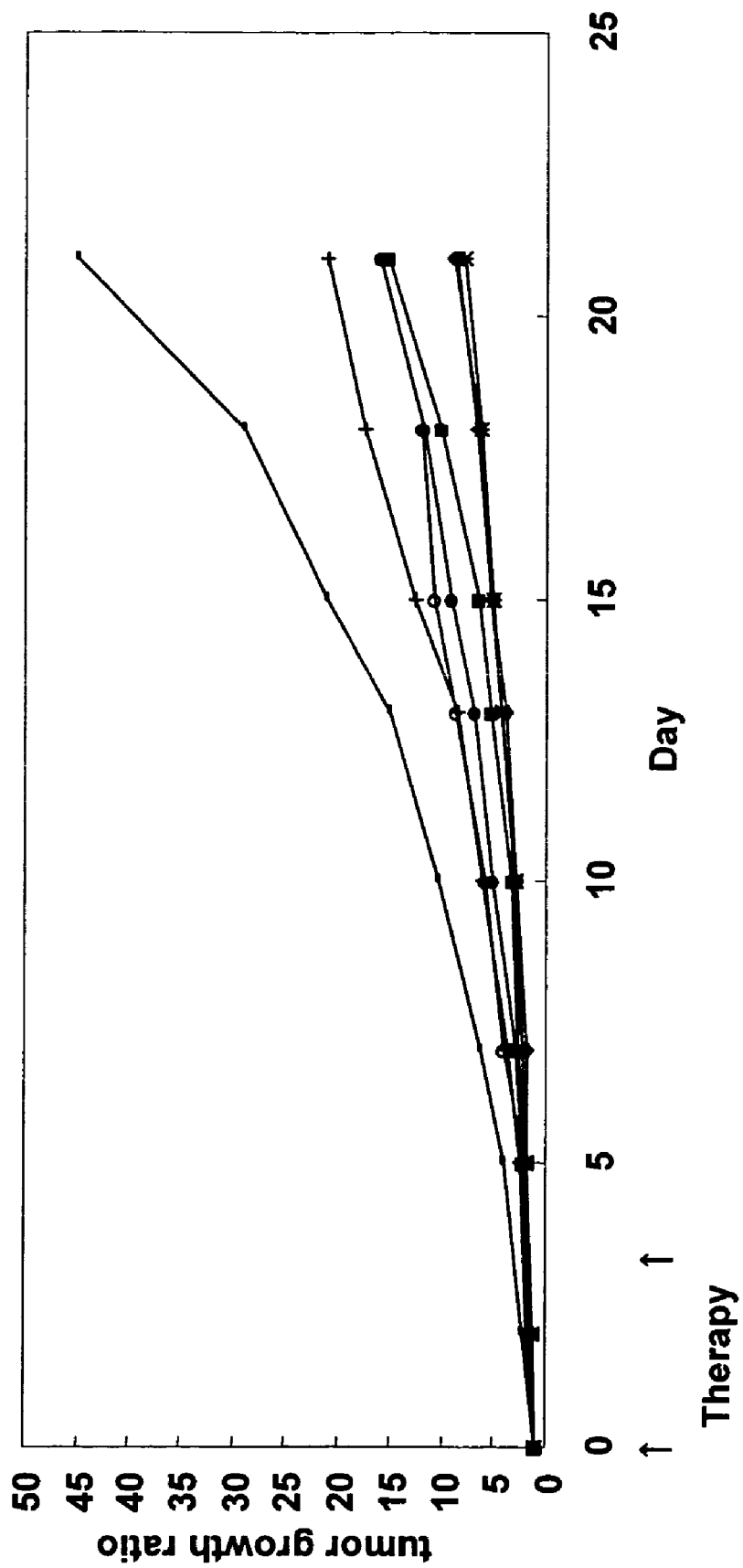
FIG. 12 shows the inhibitory effects of liposomes on tumor growth by plotting the tumor growth ratio vs. days after initial treatment, where (◆) indicates the Tf-PEG-liposomes prepared in Example 9; (■) indicates the PEG-liposomes prepared in Example 9 without Tf; (▲) indicates the Tf-NG-DSPE:NG-DSPE:DSPC:CH liposomes prepared in Example 8; (○) indicates the NG-DSPE:NG-DSPE:DSPC:CH liposomes prepared in Example 8, without Tf; (*) indicates the Tf/PEG-NG-DSPE liposomes prepared in Example 9; (●) indicates the PEG-NG-DSPE liposomes prepared in Example 9, without Tf; (+) indicates l-OHP solution; and (−) indicates no treatment.

The results are shown in FIG. 12.

As can be seen in FIG. 12, the liposome compositions to which transferrin is bound exhibited an inhibitory effect on tumor growth. On the other hand, the liposome compositions to which transferrin is not bound had a weaker inhibitory effect on tumor growth compared with that of the liposome compositions to which transferrin was bound. From the results depicted in FIGS. 9 and 10, it was found that about 6 hours of retention time in the blood after administration is necessary and sufficient for a liposome to which transferrin is bound to have an inhibitory effect on tumor growth and to make the concentration of a drug accumulating to a tumor tissue be significant and substantially the same level. It is considered that a retention time in the blood longer than this may increase the possibility of causing an adverse effect on a normal tissue.

Example 15

Optimization of NG-DSPE Content

In order to determine the optimal blending ratio of NG-DSPE in a liposome, the blood retention of NG-DSPE in which an anticancer agent was not encapsulated was investigated in normal mice. Liposome compositions in which an anticancer agent was not encapsulated were prepared in the same manner as in Example 8, but using water instead of a solution of l-OHP as the aqueous phase, with differing amounts of NG-DSPE.

The total molar amount of the total lipid components constituting a liposome is defined as 100% and the contents of NG-DSPE are shown as the ratio (% by mole) of NG-DSPE to the total lipid components. In addition, a liposome containing 6% by mole of MPB lipid (MPB-DSPE) or PDP lipid (PDP-DSPE) as the constituent lipid was also prepared. MPB liposome is obtained by forming a liposome by binding maleimide-phenylbutyrate (MPB) to the amino group of the ethanolamine of the lipid, and binding Tf to the liposome through MPB (870013(16:0), Avanti Polar Lipids, Inc, USA). PDP (870205(16:0, Avanti Polar Lipids, Inc, USA) liposome is obtained by forming a liposome by binding 2-pyridylthio propionate (PDP) to the amino group of ethanolamine of the lipid, and binding Tf to the liposome through PDP.

In the experiment, 105 mice (ICR male, 6 weeks of age) (Tokyo Laboratory Animal Science Co., Ltd., Japan) were used. As the tracer, $^{125}I$ was bound to tyraminyl-inulin, (prepared as described in Example 13) and this inulin solution at a concentration of about 1 mg/ml was encapsulated into the liposome. The weight of the collected blood and organs for each case was measured, and the radioactivity (unit: cpm) of the liposome marker was measured using a gamma counter (Aloka Auto Gamma System ARC-300, Japan). In addition, the radioactivity of each administered solution (100 μl) to the tail vein was measured. The radioactivity of 100 μl of the administered solution (standard: Std.) was defined as 100%, and the value (% of dose) for each organ was expressed as a percentage. The total blood amount was estimated to be 7.3% of the body weight, and the liposome amount in the blood was expressed as the amount in the total blood. The count value of an empty test tube was defined as the value of the background (b.g.), which was subtracted from the count value for each sample.

Distribution amount in the blood (%)=[(count value of the blood)−(value of b.g.)]×(body weight of mouse (g))×0.073× 100/[(count value of Std.)−(count value of tail)×(weight of blood (g))].

Figure 13:
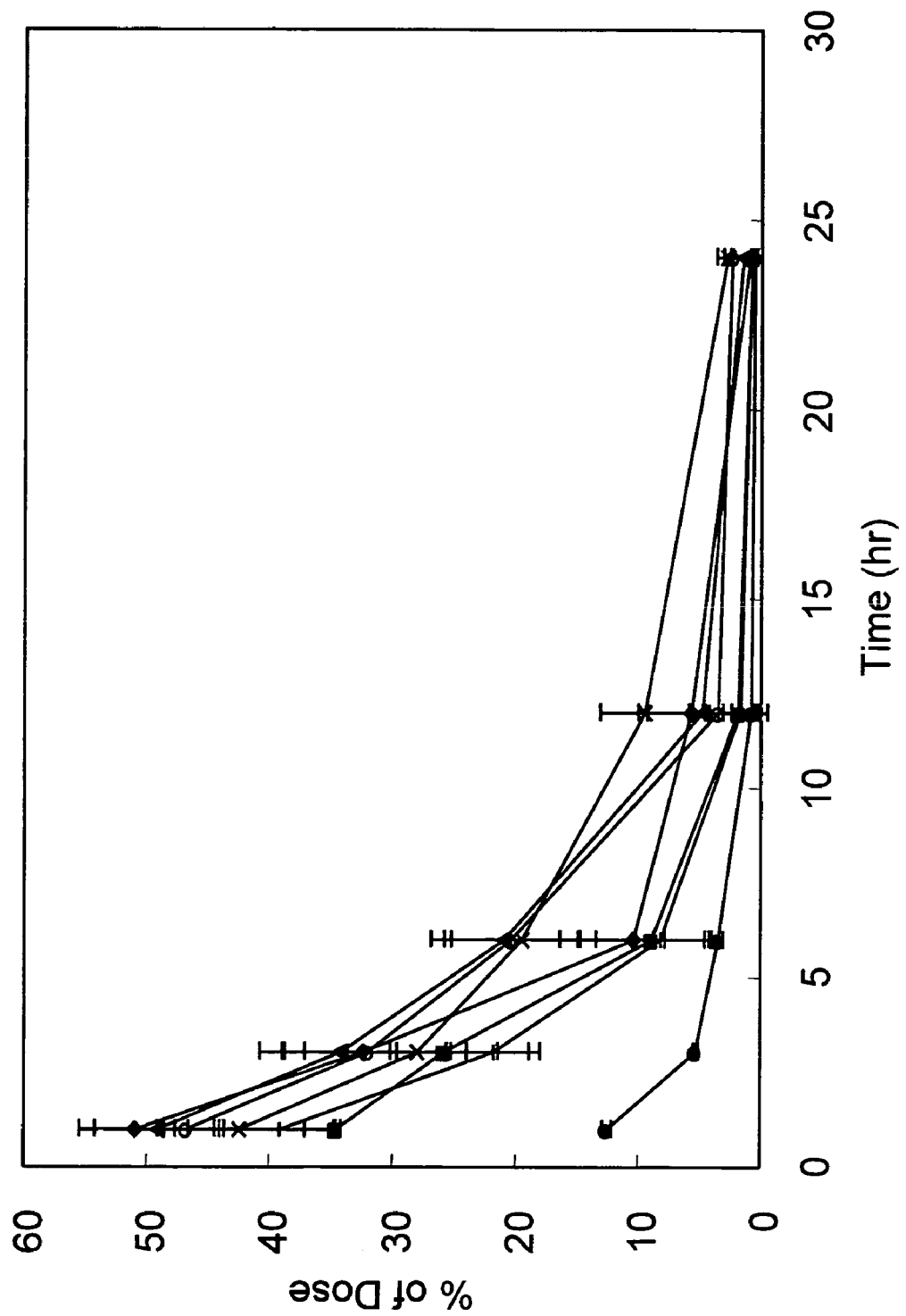
FIG. 13 shows the effect of varying concentration of NG-PE (NG-DSPE) on the percentage of drug dose detected in blood, where concentration (% of total lipid content) of NG-DSPE is as follows: (◆) 0%, (■) 1%; (▲) 3%; (x) 6%; (○) 12%; and with the following lipids: (●) MPB 6%; (+) PDP 6%.

The results are shown in FIG. 13. With regard to the concentration in the blood after 6 hours, NG-DSPE liposome shows high blood retention when the lipid content is 3% by mole or higher. As for the maleimide-liposome (MPB 6%), the blood retention was low.

Example 16

Effect of Tf and Dicarboxylic Acid on Blood Retention

In order to investigate the effects of the presence or absence of the liposome-bound transferrin and the types of dicarboxylic acids (e.g., glutaryl, succinyl, etc.), the blood retention of a transferrin-bound liposome in which an anticancer agent was not encapsulated was examined in normal mice. The experimental method was the same as described in Example 15.

A liposome containing a phospholipid to which succinic acid was bound instead of glutaric acid was prepared.

NG-DSPE (glutaric) was prepared as follows. In the dark under a nitrogen gas stream, DSPE (ME-8080, NOF Corporation, Japan) was suspended in dehydrated chloroform of 10 times the volume of DSPE. Then, 1.3 equivalent amounts of triethylamine (208-02643, Wako Pure Chemical Industries, Ltd., Japan) were added, and a dehydrated chloroform solution of glutaric acid anhydrous (G0071, Tokyo Chemical Industry, Japan) (dissolved in dehydrated chloroform of the same volume as DSPE) was added dropwise at room temperature. After completion, the solution was reacted at 30° C. for 2 hours while stirring.

Then, the reaction solution was washed 3 times with an acetate buffer (pH 4.5), and the organic layer was dehydrated with magnesium sulfate and filtrated by suction filtration with a water flow aspirator. Then, the filtrate was concentrated under reduced pressure at 30° C. When it became oily (about 2 times the volume of DSPE), methanol was added to form crystals, and then filtered. It was dissolved in chloroform again, and this procedure was repeated twice. Then, the crystal was dried under reduced pressure at room temperature, whereby a target product was obtained as white crystal. NG-DSPE liposome was prepared by the same method as in Example 8.

Figure 14:
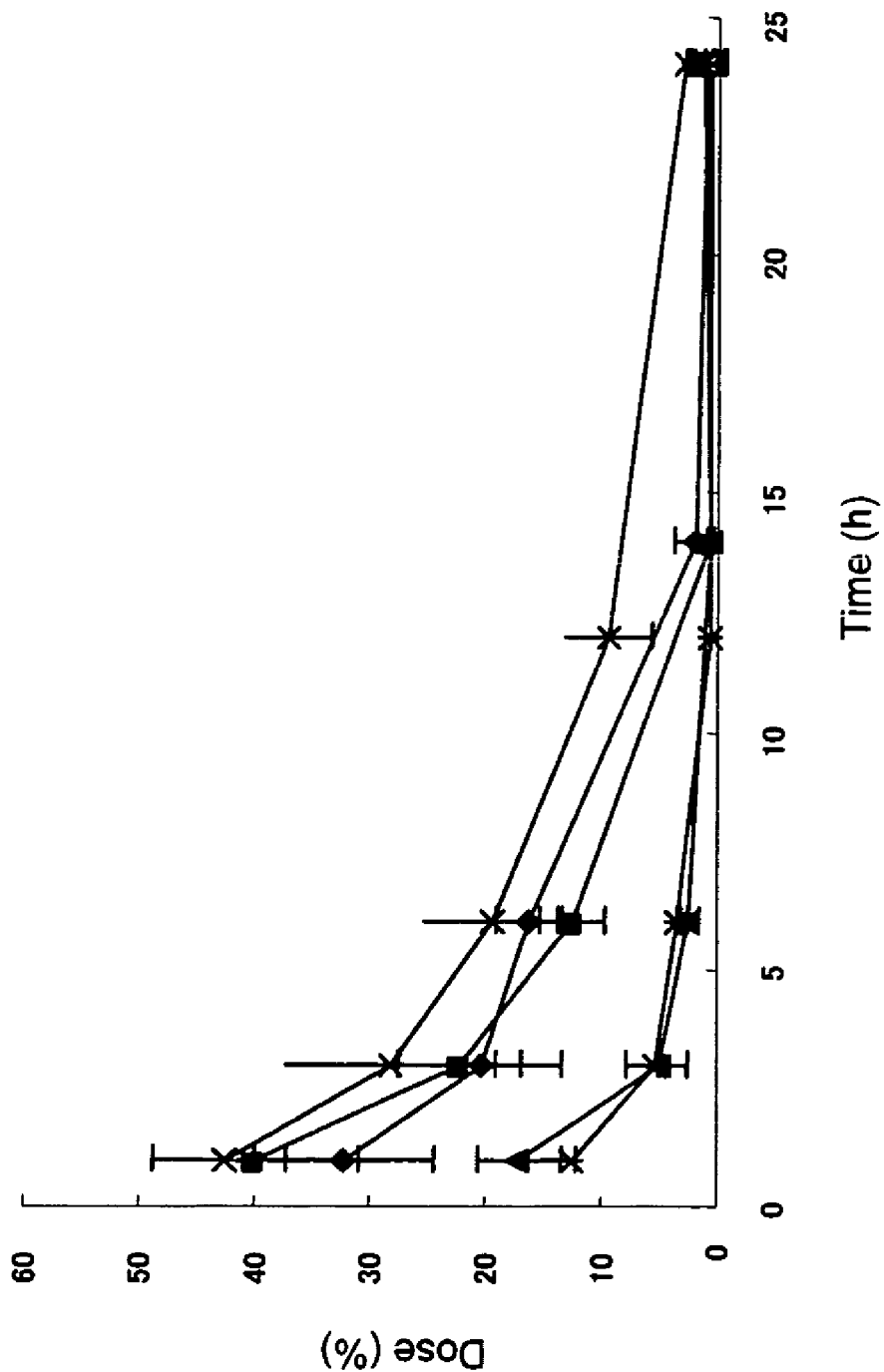
FIG. 14 shows the blood retention of liposomes with various dicarboxylic acid linkers, with and without Tf; where (◆) Tf-NGPE, (■) Tf-NSPE; (▲) TF-MPB; (x) NGPE (no Tf), (*) MPB (no Tf).

The results are shown in FIG. 14. The liposome to which transferrin is bound through dicarboxylic acid (NG-DSPE:N-glutaryl-distearoyl phosphatidyl ethanolamine, NS-DSPE: N-succinyl-distearoyl phosphatidyl ethanolamine) shows high blood retention. However, in the case of the liposome to which transferrin is bound through an S—S bond by maleimide (MPB), the blood retention was low even though the same ligand, transferrin, was bound.

Example 17

Electrophoretic Analysis of Liposomes

As one example of analytical methods for characterizing the liposomes, an example of electrophoresis is shown. Liposome was dissolved and denatured at 95° C. for 5 min in sample buffer containing 2.5% of SDS and 5% of 2-mercaptoethanol. By using about 7.5% to 10% polyacrylamide gel (Funakoshi, Easy gel (II), precast gel, Japan), 5 µl of each sample was applied on the gel, and electrophoresis was carried out under a constant current of 20 mA for 1 to 2 hours.

Figure 15:
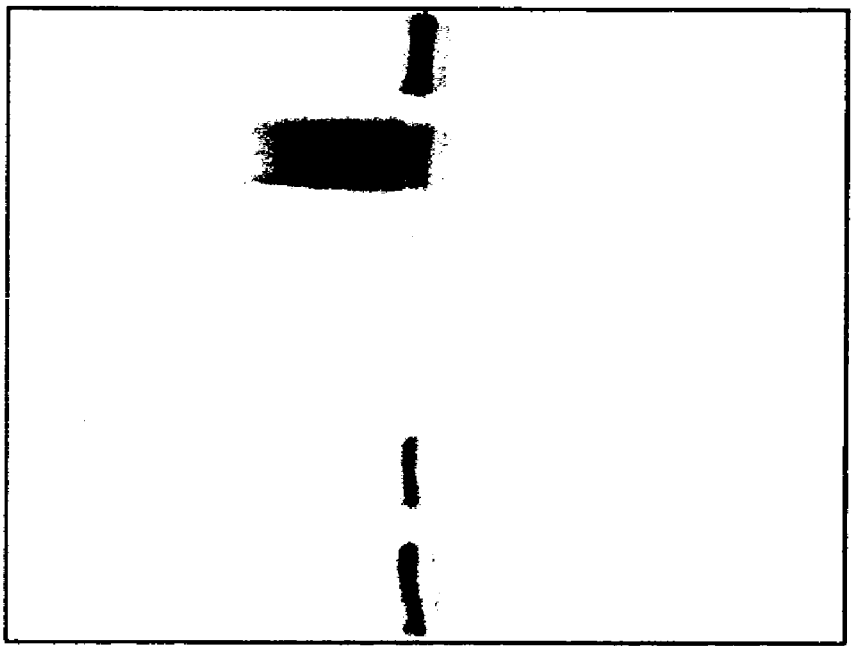
FIG. 15 shows exemplary analysis of liposomes by electrophoresis: lane 6 (transferrin-N-glutaryl-distearoyl phosphatidyl ethanolamine-liposome (Tf-NG-DSPE liposome)); lane 5 (transferrin-polyethyleneglycol-distearoyl phosphatidyl ethanolamine-liposome (Tf-PEG-DSPE liposome)) are shown. Lanes 1-4, contain h-apo-Tf (240 ng), h-apo-Tf (120 ng), h-apo-Tf (60 ng), and h-apo-Tf (30 ng), respectively.

After the electrophoresis, the gel was silver stained with a silver staining kit (Wako Pure Chemical Industries, Silver Staining II Kit Wako, Japan). The results are shown in FIG. 15 for the following liposomes: lane 6 (transferrin-N-glutaryl-distearoyl phosphatidyl ethanolamine-liposome (Tf-NG-DSPE liposome)); lane 5 (transferrin-polyethyleneglycol-distearoyl phosphatidyl ethanolamine-liposome (Tf-PEG-DSPE liposome)) are shown. Lanes 1-4, contain h-apo-Tf (240 ng), h-apo-Tf (120 ng), h-apo-Tf (60 ng), and h-apo-Tf (30 ng), respectively.

In the case of the comparative example, Tf-PEG-DSPE liposome, since polyethyleneglycol has some molecular weight distribution, a complicated electrophoresis image with several bands appeared. In the case of Tf-NG-DSPE liposome, a single band appeared, which is much more easily analyzed and enhances the ability to purify the liposome. These results indicate that, for the liposome composition according to the present invention, an analytical assay method is simpler than that for a PEG-derivatized liposome composition.

Example 18

Effect of Free PE on Liposome Compositions

In order to investigate the effects of the presence of free phosphatidyl ethanolamine (non-NG-PE) in a liposome, the binding ability of Tf was measured for Tf-NG-DSPE liposome and a liposome prepared by adding distearoyl phosphatidyl ethanolamine (DSPE) (no NG present). Tf-NG-DSPE liposome was prepared from DSPC (64 parts), CH (32 parts) and NG-DSPE (4 parts), and Tf-NG-DSPE+DSPE liposome was prepared from DSPC (64 parts), CH (32 parts), NG-DSPE (4 parts) and DSPE (10 parts) in the same manner as in Example 8.

Subsequently, Tf was bound to NG-DSPE by using 10 equivalent amounts of NHS and ECD/HCl and 0.05 equivalent amounts of Tf. Then, the liposome samples in an amount corresponding to 1 mg of lipid were separated by SDS-PAGE, and the bands were visualized by silver staining as described in Example 17.

Figure 16:
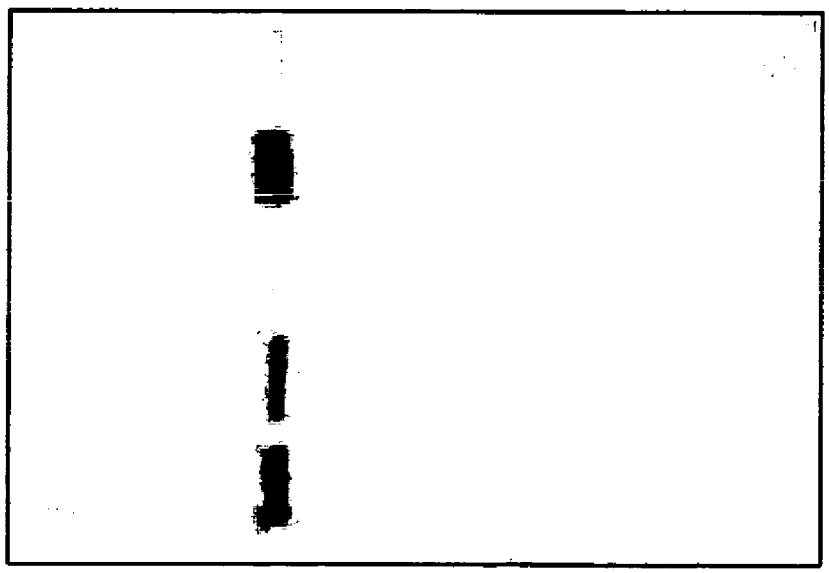
FIG. 16 shows the amount of transferrin binding to Tf-NG-DSPE liposomes with (lane 5) and without (lane 4) non-NG-DSPE incorporated into the liposome. Lanes 1-3, contain h-apo-Tf (400 ng), h-apo-Tf (200 ng), and h-apo-Tf (50 ng), respectively.

The results are shown in FIG. 16. It was found that, in the case of NG-DSPE+DSPE liposome to which 10% by mole of DSPE was added, the bound amount of Tf was significantly low compared with that of NG-DSPE liposome that contained no non-NG-DSPE. It is likely that this is because the amino group of Tf and the amino group of DSPE compete each other in the reaction where Tf is bound to the carboxyl group of NG-DSPE.

Example 19

Comparison of Liposome Levels in Blood and Organs

Using the protocols described in Example 12, the levels of NG-DOPE:Tf-NG-DOPE:DMPC:CH (Tf-NG-DOPE:NG-DOPE) liposomes (prepared as in Example 7) and Tf-PEG-DSPE liposomes (prepared as in Example 9) in blood and tumor were compared. The results for the amount of liposome retained in blood are depicted in FIG. 17 and the amount of liposome detected in tumors is shown in FIG. 18.

Figure 17:
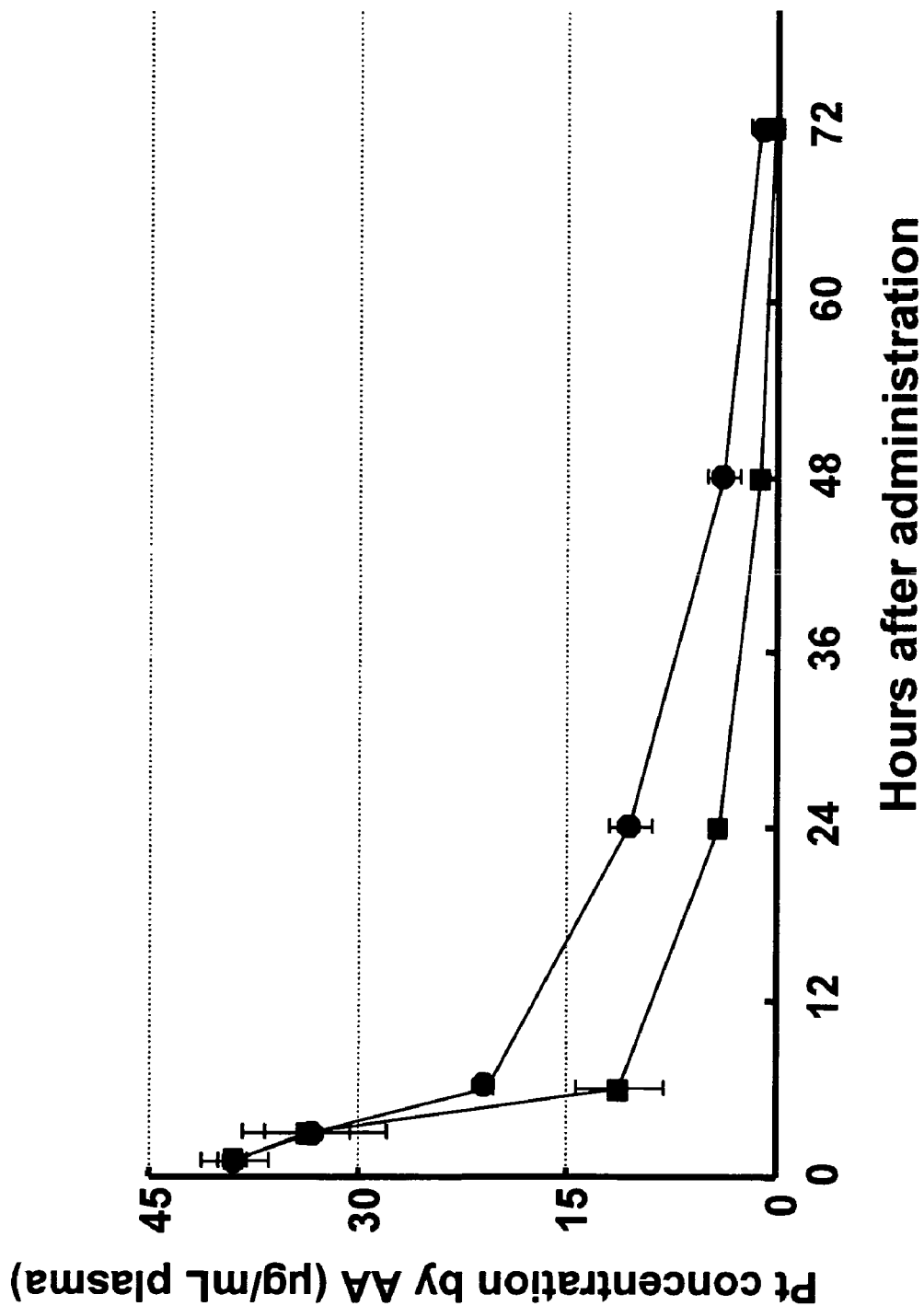
FIG. 17 shows the accumulation oxaliplatin in blood after administration of (■) NG-DOPE:Tf-NG-DOPE:DMPC:CH liposomes at 5 mg/kg and (●) Tf-PEG liposomes at 5 mg/kg.
Figure 18:
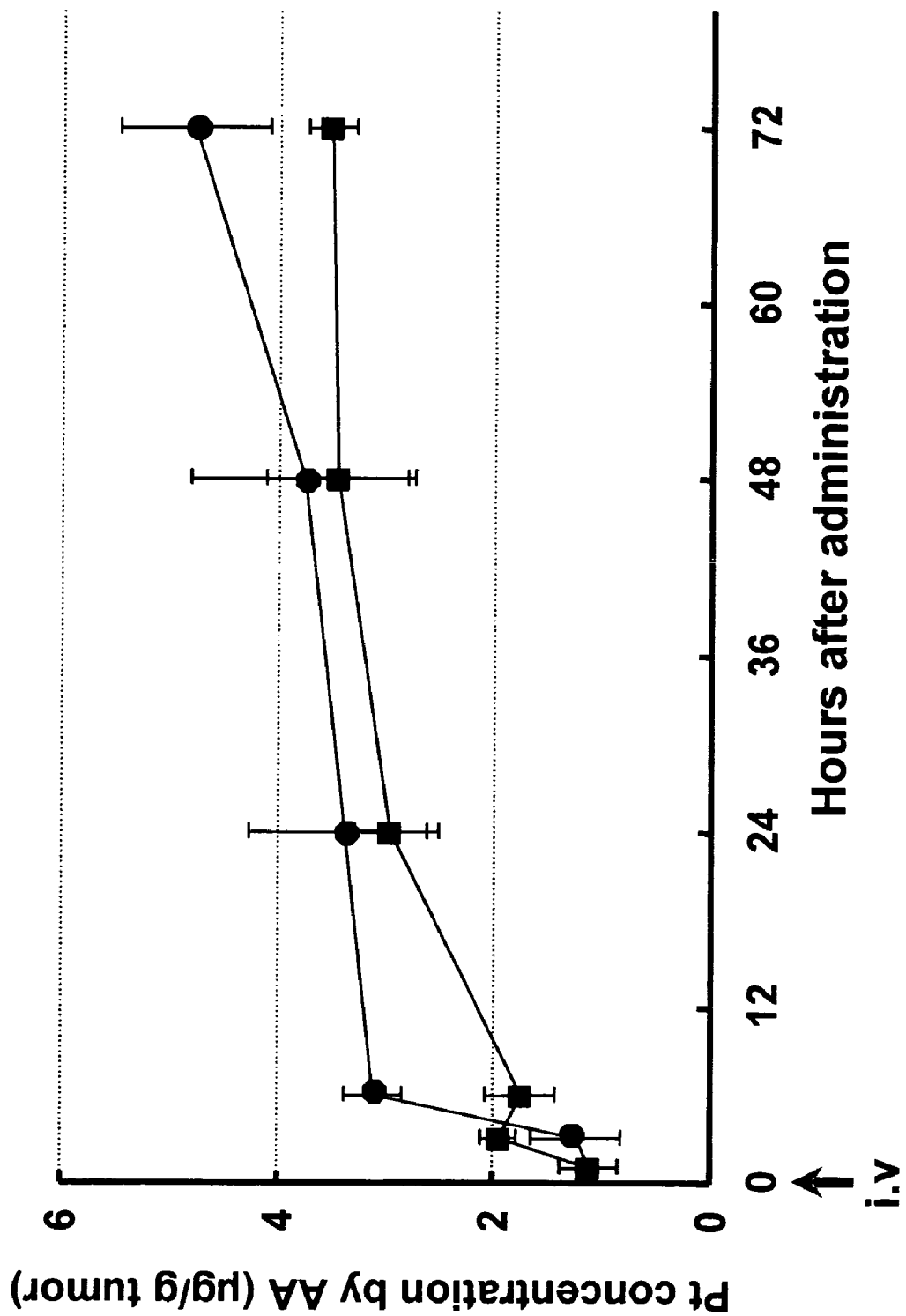
FIG. 18 shows the accumulation oxaliplatin in colon 26 tumors after administration of (■) NG-DOPE:Tf-NG-DOPE:DMPC:CH liposomes at 5 mg/kg and (●) Tf-PEG liposomes at 5 mg/kg in mouse colon 26 tumors.

The results in FIGS. 17 and 18 show that while the Tf-NG-DOPE:NG-DOPE liposomes show a lower accumulation in the blood (FIG. 17) than the Tf-PEG-DSPE liposomes, they were able to deliver a greater amount of oxaliplatin to the tumor (FIG. 18). Lower accumulation of liposomes in the blood is likely to reduce the adverse systemic effects of the oxaliplatin.

Example 20

Comparison of Liposome Antitumor Effects in Colon 26 Tumor-Bearing Mice

Using the protocols described in Example 14, the effect of NG-DOPE:Tf-NG-DOPE:DMPC:CH liposomes (prepared as in Example 7) and Tf-PEG-DSPE liposomes (prepared as in Example 9) on colon 26 tumors in mice were compared. The results are depicted in FIG. 19.

Figure 19:
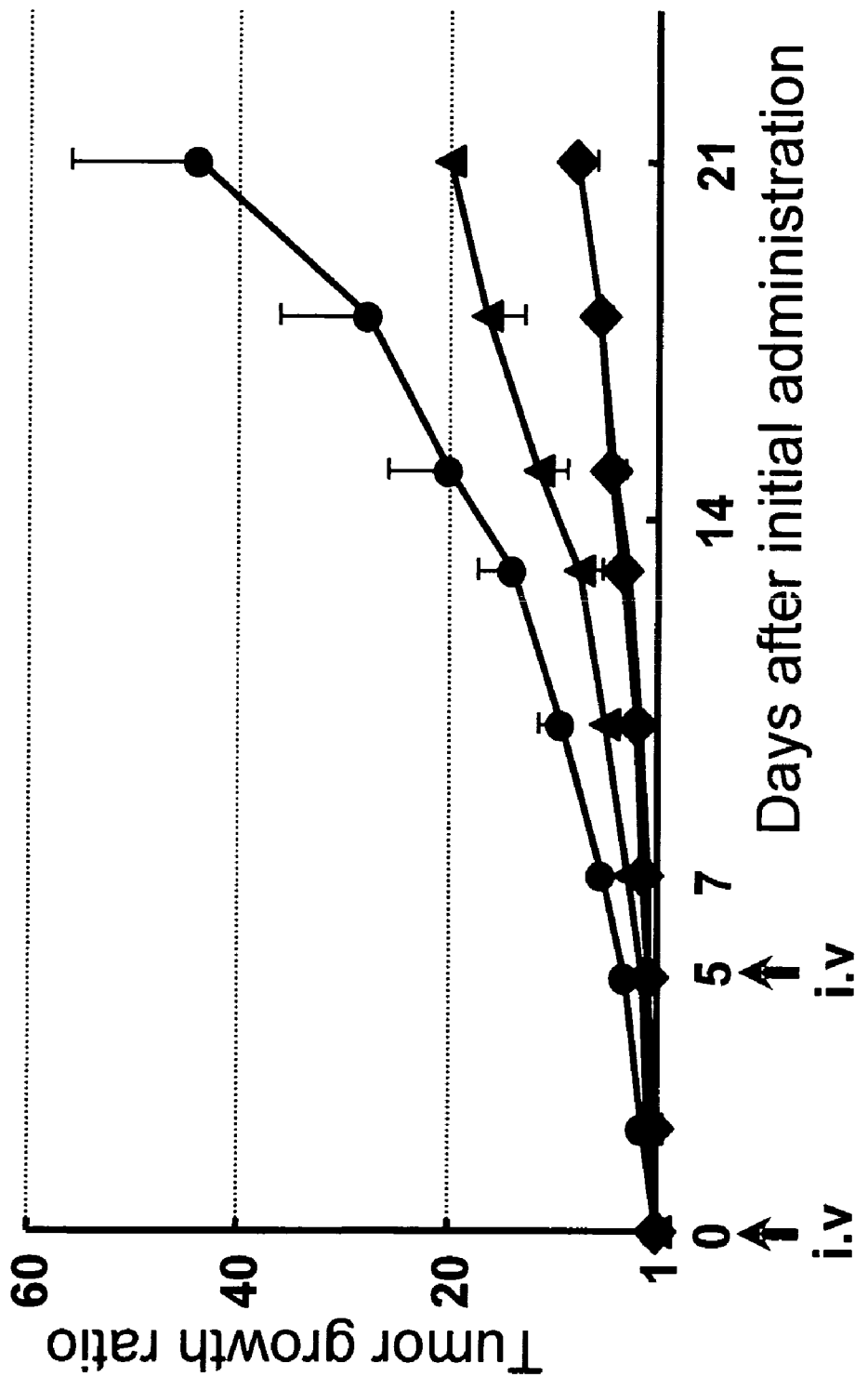
FIG. 19 shows the antitumor effect in colon 26 tumor-bearing mice of NG-DOPE:Tf-NG-DOPE:DMPC:CH liposomes, where (●) indicates vehicle control (9% sucrose); (▲) indicates l-OHP solution at 5 mg/kg, (◆) indicates NG-DOPE:Tf-NG-DOPE:DMPC:CH liposomes at 5 mg/kg and (■) indicates Tf-PEG liposomes at 5 mg/kg.

As can be seen in FIG. 19, both liposomes show an inhibition of tumor growth compared to oxaliplatin solution, however, as noted in Example 19, the accumulation of less of the NG-DOPE:Tf-NG-DOPE:DMPC:CH in blood (plasma) will likely mean that these liposomes are better tolerated by the individuals to whom they are administered.

Example 21

Liposome Antitumor Effects on Xenograft HCT-116 Colon Tumor Model

Figure 20:
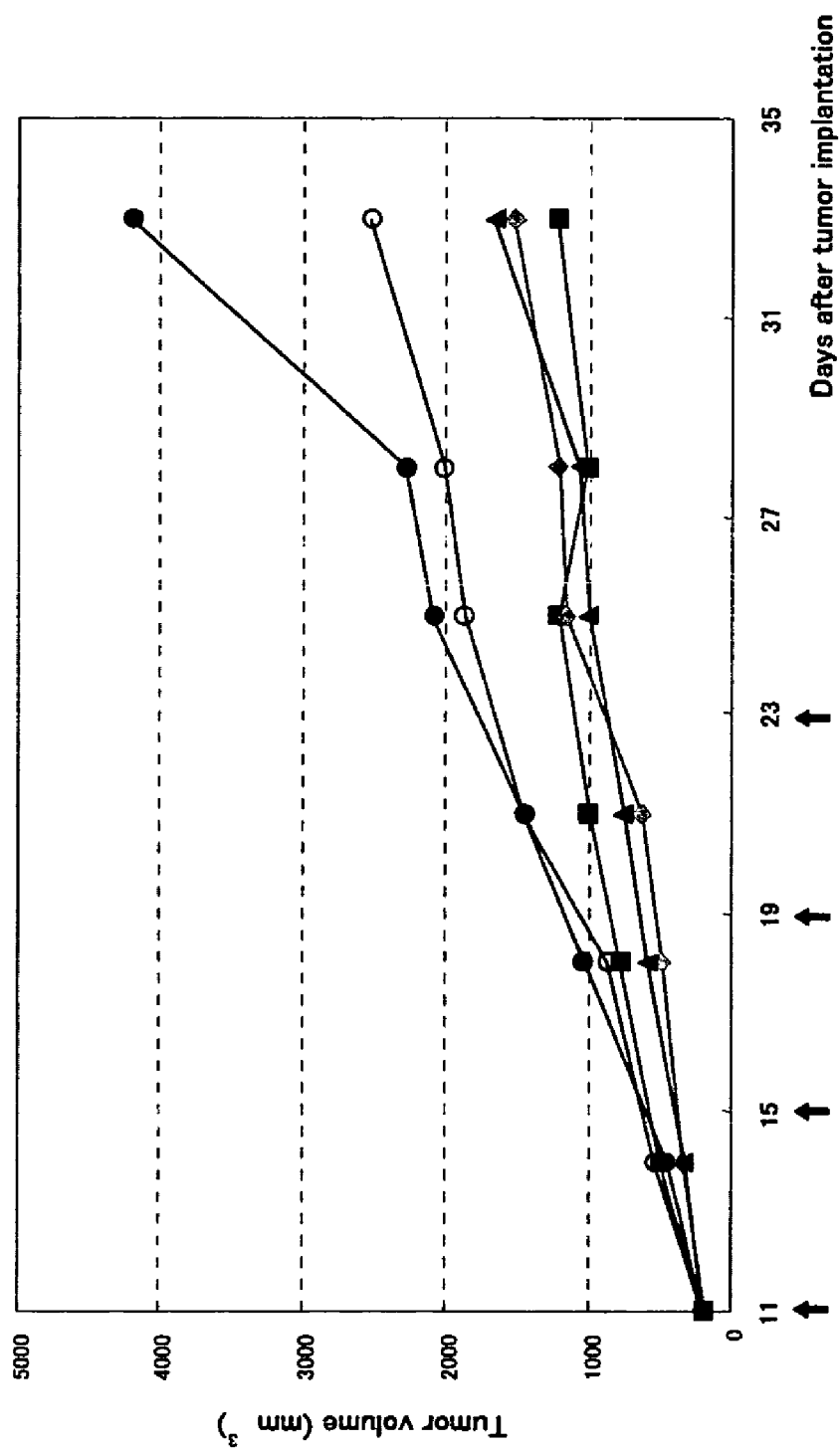
FIG. 20 shows the antitumor effect in HCT-116 human colon tumor xenograft-bearing mice of NG-DOPE:Tf-NG-DOPE:DMPC:CH liposomes, where (●) indicates vehicle control (300 mM (10.27%) sucrose); (○) indicates blank (no drug) liposomes, (▲) indicates l-OHP solution at 15 mg/kg, (◆) indicates NG-DOPE:Tf-NG-DOPE:DMPC:CH liposomes at 10 mg/kg and (■) indicates NG-DOPE:Tf-NG-DOPE:DMPC:CH liposomes at 15 mg/kg. All liposomes were administered by exact body weight with an injection volume of 0.103 mL/10 g body weight.

The antitumor efficacy of the NG-DOPE:Tf-NG-DOPE:DMPC:CH liposomes (prepared as in Example 7) when administered against subcutaneously implanted HCT-116 human colon tumor xenografts. The test was performed at Southern Research Institute, AL, USA] in male athymic NCr-nu mice (02/A/08F17T9, Frederick Cancer Research and Development Center, MD, USA; 50 mice) was studied, with oxaliplatin in solution used as a reference compound. The antitumor activity of NG-DOPE:Tf-NG-DOPE:DMPC:CH liposomes is summarized in FIG. 20.

NG-DOPE:Tf-NG-DOPE:DMPC:CH liposomes were administered intravenously (i.v.) every four days for four injections (q4d×4) as doses of 15 and 10 mg/kg/injection. Oxaliplatin was administered on the same schedule at a dose of 15 mg/kg/injection. Vehicle (about 10.3% sucrose) and blank liposome control groups were injected on the same schedule.

Mean tumor volume for the HCT-116 colon tumor model, following treatment with NG-DOPE:Tf-NG-DOPE:DMPC:CH liposomes every 4 days was 28.9% of the control tumor volume for the 15 mg/kg group and 35.9% of the control tumor volume for the 10 mg/kg group. The antitumor activity of NG-DOPE:Tf-NG-DOPE:DMPC:CH liposomes was also compared to non-liposomal oxaliplatin in the HCT-116 model, where NG-DOPE:Tf-NG-DOPE:DMPC:CH liposomes showed greater efficacy in terms of relative tumor volume, when administered at 15 mg/kg (28.9% of the control tumor volume) every four days (4×). Non-liposomal oxaliplatin delivered at 15 mg/kg every four days (4×) yielded 39.3% of the control tumor volume.

Example 22

Liposome Antitumor Effects on Xenograft HT-29 Colon Tumor Model

Figure 21:
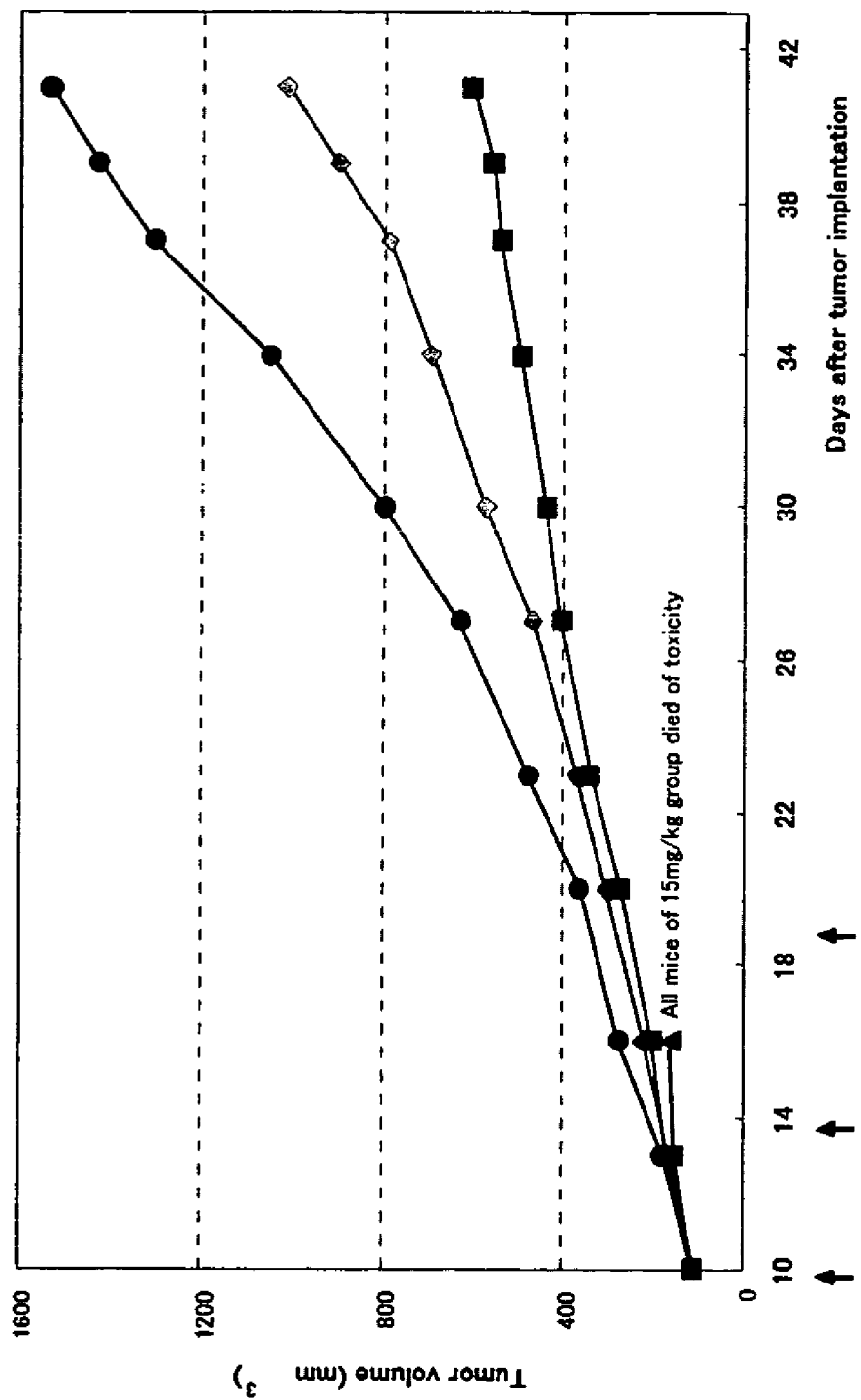
FIG. 21 shows the antitumor effect in HT-29 human colon tumor xenograft-bearing mice of NG-DOPE:Tf-NG-DOPE:DMPC:CH liposomes, where (●) indicates vehicle control (300 mM (10.27%) sucrose), (▲) indicates NG-DOPE:Tf-NG-DOPE:DMPC:CH liposomes at 15 mg/kg, (■) indicates NG-DOPE:Tf-NG-DOPE:DMPC:CH liposomes at 10 mg/kg, and (◆) indicates NG-DOPE:Tf-NG-DOPE:DMPC:CH liposomes at 6.7 mg/kg.

The antitumor efficacy of NG-DOPE:Tf-NG-DOPE:DMPC:CH liposomes (prepared as in Example 7) when administered against subcutaneously implanted HT-29 human colon tumor xenografts. The test was performed at Panapharm Laboratories Co., Ltd., Japan in female athymic BALB/cA Jcl-nu mice (CLEA Japan, Inc., Japan; 50 mice) and the results are summarized in FIG. 21. Groups of 4 mice were administered NG-DOPE:Tf-NG-DOPE:DMPC:CH liposomes at doses of 6.7, 10 or 15 mg/kg, or vehicle control. The vehicle and 6.7 and 10 mg/kg treated groups were injected on days 10, 14 and 19 and the 15 mg/kg treated group was injected on days 10 and 14.

The mean tumor volume for the HT-29 colon tumor model, following treatment with NG-DOPE:Tf-NG-DOPE:DMPC:CH liposomes was 66.3% of the control tumor volume for the 6.7 mg/kg group and 39.5% of the control tumor volume for the 10 mg/kg group (p value$\leq$0.01).

Example 23

Liposome Antitumor Effects on Xenograft MKN45 Gastric Tumor Model

Figure 22:
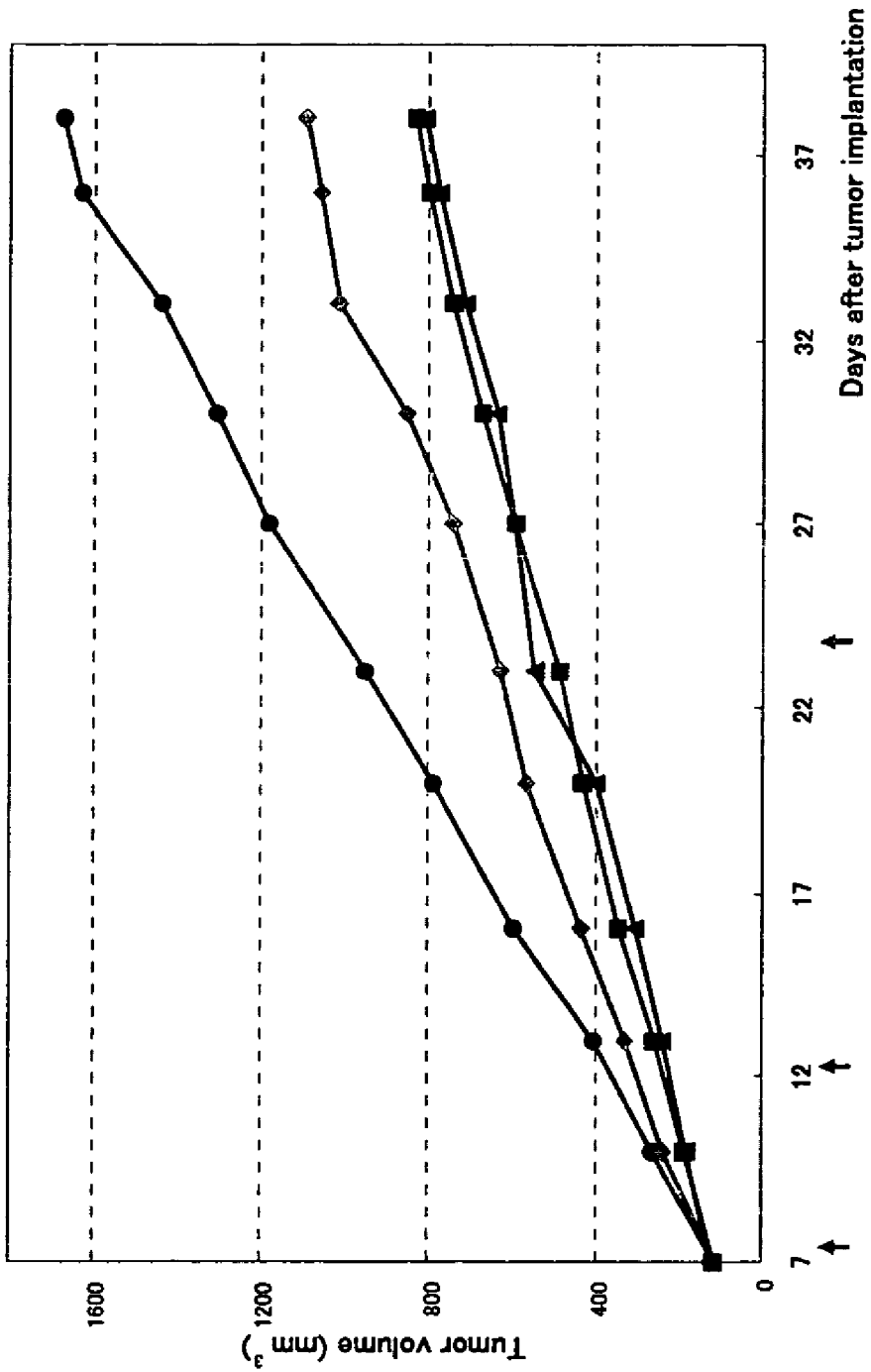
FIG. 22 shows the antitumor effect in MKN45 gastric human tumor xenograft-bearing mice of NG-DOPE:Tf-NG-DOPE:DMPC:CH liposomes, where (●) indicates vehicle control (300 mM (10.27%) sucrose), (▲) indicates NG-DOPE:Tf-NG-DOPE:DMPC:CH liposomes at 15 mg/kg, (■) indicates NG-DOPE:Tf-NG-DOPE:DMPC:CH liposomes at 10 mg/kg, and (◆) indicates NG-DOPE:Tf-NG-DOPE:DMPC:CH liposomes at 6.7 mg/kg.

The antitumor efficacy of NG-DOPE:Tf-NG-DOPE:DMPC:CH liposomes (prepared as in Example 7) when administered against subcutaneously implanted MKN45 human gastric tumor xenografts. The test was performed at Panapharm Laboratories Co., Ltd., Japan in male athymic BALB/cA Jcl-nu mice (CLEA Japan, Inc., Japan; 50 mice) was studied and is summarized FIG. 22.

Groups of 4 mice were administered NG-DOPE:Tf-NG-DOPE:DMPC:CH liposomes at doses of 6.7, 10 or 15 mg/kg, or vehicle control. The vehicle and 6.7 and 10 mg/kg treated groups were injected on days 7, 12 and 24 and the 15 mg/kg treated group was injected on days 7 and 24. The mean tumor volume for the MKN45 gastric tumor model following treatment with NG-DOPE:Tf-NG-DOPE:DMPC:CH liposomes was 65.4% of the control tumor volume for the 6.7 mg/kg group (p value$\leq$0.05), 49.6% of the control tumor volume for the 10 mg/kg group (p value$\leq$0.01), and 48.5% of the control tumor volume for the 15 mg/kg group (p value$\leq$0.01; delivered every 17 days).

Example 24

Liposome Antitumor Effects on Xenograft COLO 205 Colon Tumor Model

Figure 23:
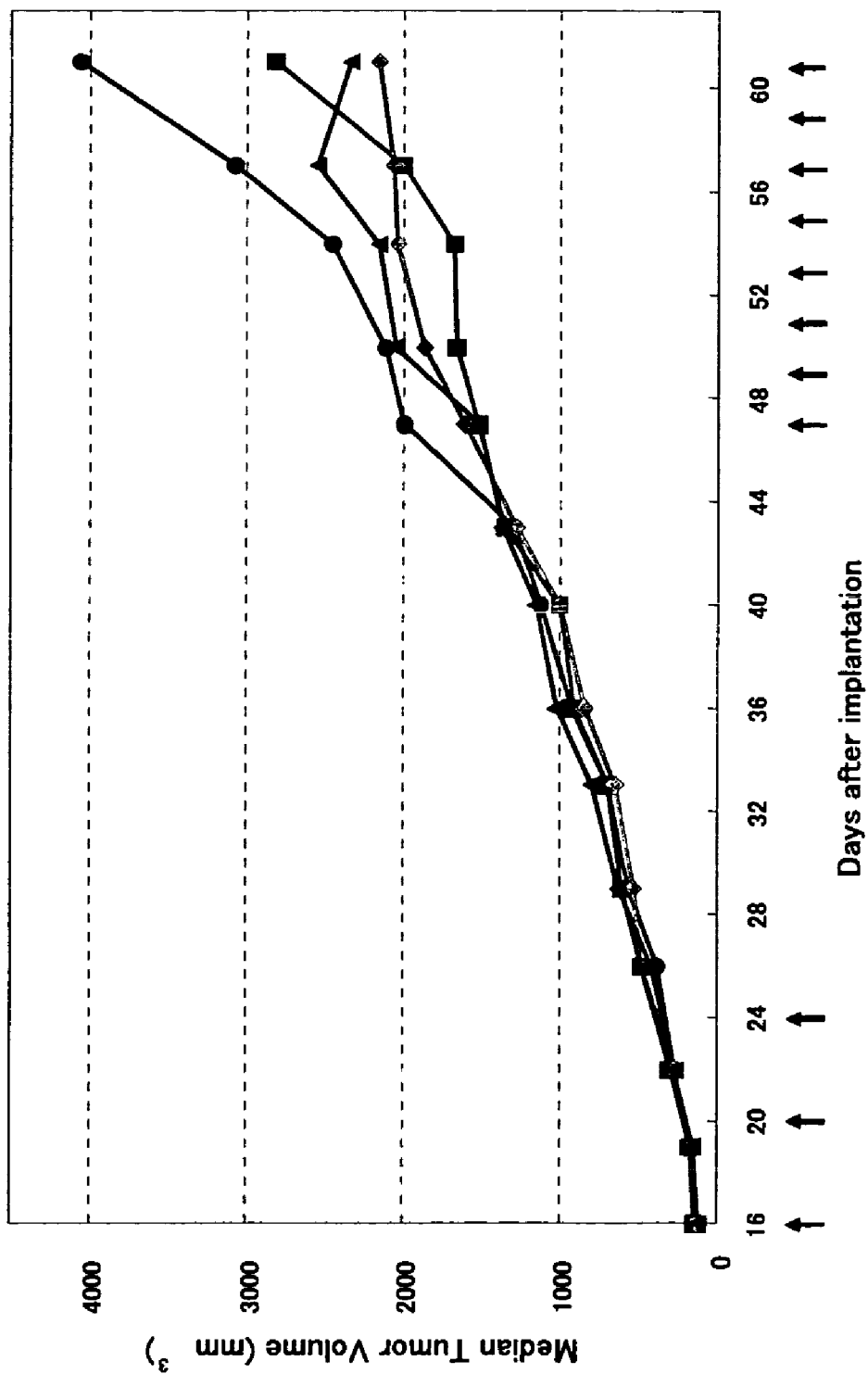
FIG. 23 shows the antitumor effect in COLO 205 human tumor xenograft-bearing mice of NG-DOPE:Tf-NG-DOPE:DMPC:CH liposomes, where (●) indicates vehicle control (9% sucrose); (▲) indicates l-OHP solution at 5 mg/kg q4d×3 (day 16), 10 mg/kg q2d×2 (day 47), 2 mg/kg q2d×6 (day 51); (◆) indicates NG-DOPE:Tf-NG-DOPE:DMPC:CH liposomes at 5 mg/kg q4d×3 (day 16), 10 mg/kg q2d×2 (day 47), 2 mg/kg q2d×6 (day 51); and (■) indicates NG-DOPE:Tf-NG-DOPE:DMPC:CH liposomes at 10 mg/kg q4d×3 (day 16), 15 mg/kg q2d×2 (day 47), 4 mg/kg q2d×6 (day 51).

The antitumor efficacy of NG-DOPE:Tf-NG-DOPE:DMPC:CH liposomes (prepared as in Example 7) when administered against subcutaneously implanted COLO 205 human colon tumor xenografts The test was performed at Southern Research Institute, AL, USA in male athymic NCr-nu mice (01/A/09F3T8, Federic Cancer Research and Development Center, MD, USA) was studied, with oxaliplatin in solution used as a reference compound and is summarized in FIG. 23.

Into 40 mice NG-DOPE:Tf-NG-DOPE:DMPC:CH liposomes were administered by i.v. injection every four days for three injections (q4d×3) at doses of 10 and 5 mg/kg/injection. Oxaliplatin was administered at a dose of 5 mg/kg/injection on the same schedule. The control group was injected on the same schedule. Advanced-stage tumors were retreated beginning on day 47 for all groups.

NG-DOPE:Tf-NG-DOPE:DMPC:CH liposomes were administered every other day for two injections at doses of 15 and 10 mg/kg/injection followed by treatment every other day for six injections at doses of 4 and 2 mg/kg/injection, respectively. Oxaliplatin was administered on the same schedule at doses of 10 and 2 mg/kg/injection. The control group was treated on the same schedule.

The mean tumor volume for the COLO 205 colon tumor model following treatment with NG-DOPE:Tf-NG-DOPE:DMPC:CH liposomes administered initially at doses of 10 and 5 mg/kg, with subsequent treatment of advanced stage, previously treated tumor with NG-DOPE:Tf-NG-DOPE:DMPC:CH liposomes at doses of 15 and 10 mg/kg, followed by NG-DOPE:Tf-NG-DOPE:DMPC:CH liposomes at doses of 4 and 2 mg/kg using various treatment schedules, was between 53.2% and 69.5% of the control tumor volume (p value$\leq$0.05 or 0.01).

Example 25

Encapsulation of Oxaliplatin in Targeted Liposomes

In order to measure the proportion of oxaliplatin encapsulated in NG-DOPE:Tf-NG-DOPE:DMPC:CH (Tf-NG-DOPE:NG-DOPE) liposomes prepared as in Example 7, the following procedure was used.

The extent of encapsulation was determined by passing an aliquot of the sample down a 3,000 MWCO (molecular weight cut-off) spin column (30K MWCO cellulose ultrafilter membrane column, Cat. No. 42410, Millipore Corp., USA) and measuring oxaliplatin concentration in the eluent using HPLC with isocratic elution of 1% acetonitrile in diluted phosphoric acid water solution (pH 3.0).

The level of oxaliplatin was determined following membrane filtration using HPLC analysis to quantify the levels of unencapsulated (free) drug. The trapping efficiencies of 3 batches, prepared as in Example 7, were greater than 98% (see Table 1).

TABLE 1

The Ratio of Encapsulation of Oxaliplatin in Lipsome

| | Lot | | |
|---|---|---|---|
| | I | II | III |
| % of encapsulation | 98.8 | 99.6 | 99.1 |

Example 26 pH of Targeted Liposomes

The pH of targeted liposomes can be determined by place the liposomes of the invention in distilled water and measuring with a standard pH meter as described below.

The pH of NG-DOPE:Tf-NG-DOPE:DMPC:CH liposomes (prepared as in Example 7) was determined by pH meter (VWR Model 8000), with an Ag/AgCl gel-filled electrode. The pH values for 4 lots of liposome ranged from pH 7.17-7.23, as shown in Table 2 below.

TABLE 2 pH of Liposome

| | Lot | | | |
|---|---|---|---|---|
| | 1 | 2 | 3 | 4 |
| pH | 7.17 | 7.17 | 7.23 | 7.20 |

The appearance of the liposomes at varying pHs are summarized in Table 3. These results indicate that a low pH led to aggregation, sedimentation, and precipitation, which may be due to protonation of NG-DOPE and Tf followed by aggregation of the bilayer and denaturation of transferrin.

TABLE 3

Condition of Liposome at Various pH Values

| pH | Observations |
|---|---|
| 7.19 | Liquid, translucent, light pink |
| 6.98 | Liquid, translucent, no change as compared to no addition, light pink |
| 6.83 | Liquid, translucent, no change as compared to no addition, light pink |
| 6.37 | Liquid, small white precipitates upon addition, clears within a minute to as compared to no addition, light pink |
| 5.53 | Liquid, white precipitates upon addition, clears within a minute but is slightly more cloudy, slightly white in color |
| 5.07 | Liquid, small white precipitates, cloudy, white in color |
| 4.33 | Increased viscosity, significant amount of white precipitates, very cloudy, white in color |
| 3.72 | Very viscous, sample does not move when the microcentrifuge tube is turned, white in color upside down, opaque, white in color |

Example 27

Identification of Conjugated Transferrin and SDS-PAGE Pattern of Transferrin in Targeted Liposomes This study was performed to confirm transferrin conjugation to NG-DOPE in the NG-DOPE:Tf-NG-DOPE:DMPC:CH liposomes prepared as in Example 7. When transferrin is conjugated to NG-DOPE, the complex shows a higher molecular weight than non-conjugated transferrin in this method.

Liposome was dissolved and denatured at 95° C. for 5 min in sample buffer containing 2.5% of SDS and 5% of 2-mercaptoethanol. The samples were then applied to 5-10% gradient polyacrylamide gel and then they were electrophoresed in the presence of SDS. Migrated protein bands were visualized by using a brilliant blue G-colloidal (B2025, SIGMA, USA).

Figure 24:
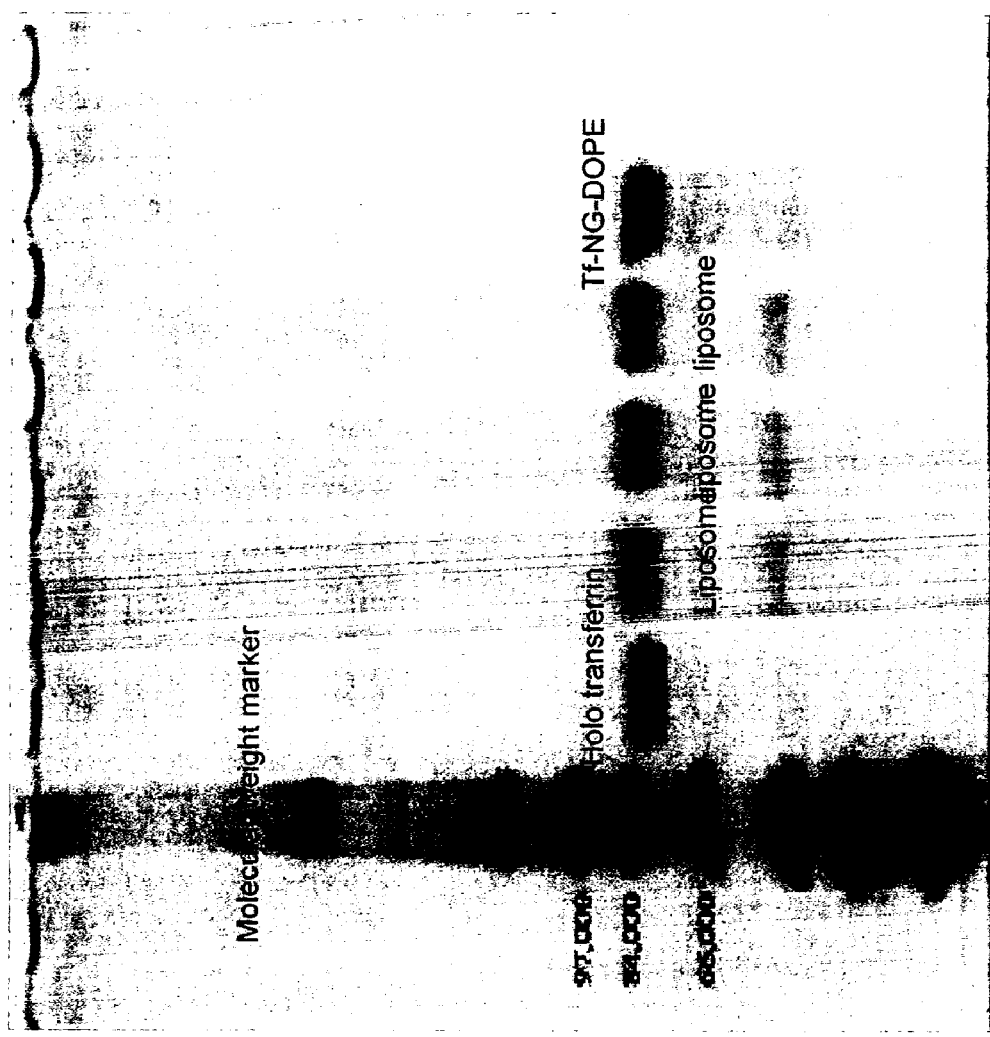
FIG. 24 shows the pattern of SDS-PAGE after reduction with 2-mercaptoethanol, where lane 1 is the molecular weight markers, lane 2 is holo-transferrin, lanes 3-5 are NG-DOPE:Tf-NG-DOPE:DMPC:CH liposomes, and lane 6 is Tf-NG-DOPE.
Figure 25:
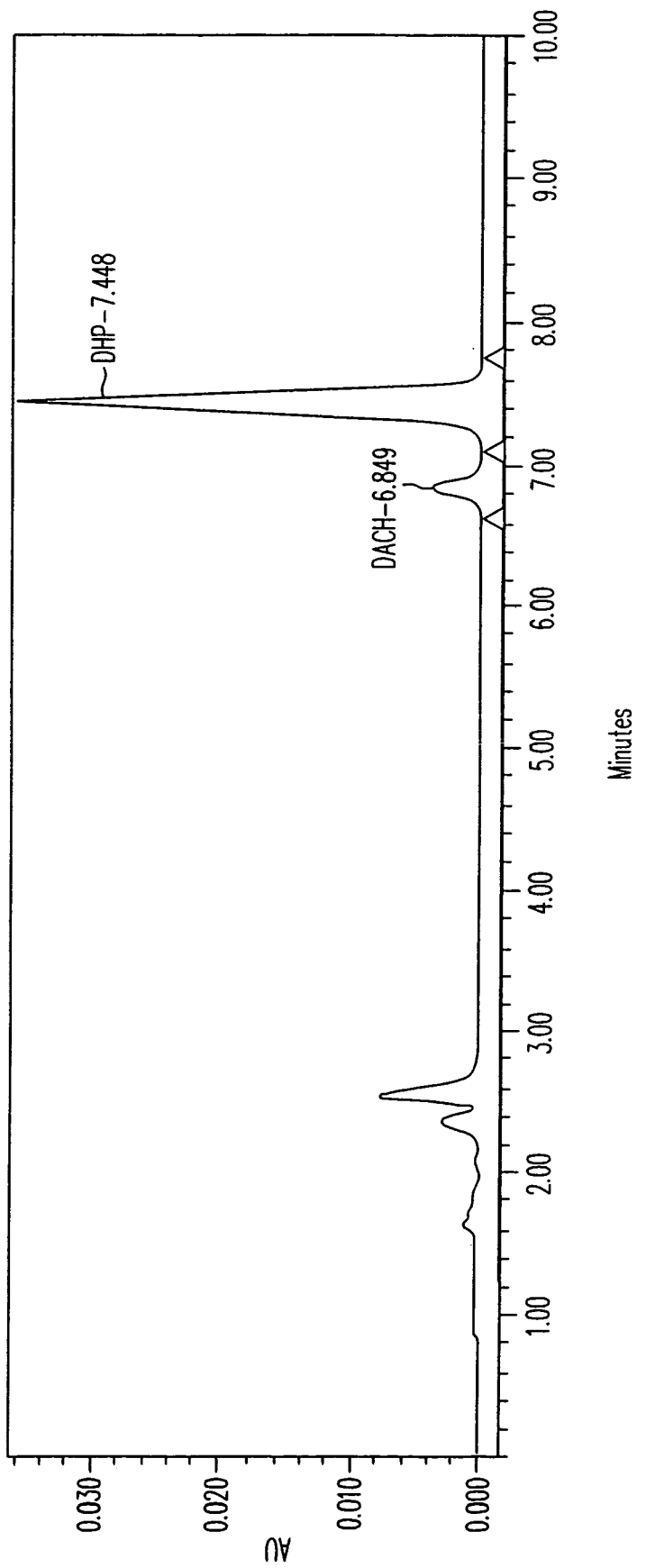
FIG. 25 shows an exemplary HPLC chromatogram of system suitability.

The transferrin in the liposome was detected as transferrin conjugated to NG-DOPE, which showed a higher molecular weight than that of intact transferrin (see FIG. 24). A minor band with a lower molecular weight was detected as free transferrin.

The ratio of free transferrin to transferrin conjugated to NG-DOPE on the SDS-PAGE (FIG. 24) was calculated as the area of the peak using Scion Image soft ware (freely available at www.microsoft.com.DirectX). The ratio of free Tf in total Tf of NG-DOPE:Tf-NG-DOPE:DMPC:CH liposome was approximately 4.7%.

Example 28

Analysis of Osmotic Pressure

The osmotic pressure at a given temperature depends on sucrose and salts such as sodium chloride and phosphate buffer. It does not depend on the solute, but on the total ion density and the size of the molecules within the solution. Normally osmotic pressure can be measured using an instrument known as an osmometer, which measures osmotic pressure in suitable pressure units.

The osmotic pressure NG-DOPE:Tf-NG-DOPE:DMPC:CH liposomes prepared as in Example 7 at room temperature was measured using an osmometer (Vapro Vapor Pressure Osmometer Model5520, Wescor, Inc., USA). The osmolarity values for 3 preparations of liposomes ranged from 360-370 mOsm/kg, as reported in Table 4.

TABLE 4

Osmolarity Pressure

| | Lot | | |
|---|---|---|---|
| | A | B | C |
| Osmolarity (mOsm/Kg) | 360 | 370 | 368 |

Example 29

Isolation of Tf-NG-DOPE 900 mL of EtOH was added to 100 mL of blank liposome (DMPC/Chol/NG-DOPE/Tf-NG-DOPE) (as prepared in Example 10 prior to lyophilization) and stirred fully. The mixture was then centrifuged (9,000 rpm, 10 min, 20° C.; CF16RX, Hitachi Koki Co., Ltd., Japan) and a pellet was obtained.

100 mL of EtOH was then added to this pellet and stirred fully. The mixture was centrifuged (9,000 rpm, 10 min, 20° C.; CF16RX, Hitachi Koki Co., Ltd., Japan) again and off-white (light orange) pellet was obtained. This washing process was repeated once more.

The obtained pellet above was dried with $N_2$ gas for 30 min. The dried material was then dissolved in 10 mL of distilled water and passed through a sterile filter (0.22 μm) (Millipore Corp., USA).

The filtrate was poured into a vial and frozen for about 8 hours on a shelf at −40° C. The was depressurized to about 0.1 mmHg and kept under reduced pressure for 2 days with rising temperature from −40° C. to 25° C. stepwise. Approximately 444 mg of Tf-NG-DOPE (about 45% of transferrin content of the blank liposome was thus obtained.

Example 30

Preparation of Tf-NG-DSPE

200 μL of NHS (Wako Pure Chemical Industries, Ltd., Japan) aqueous solution (0.1 mol/L), 200 μL of EDC (N-ethyl-N'-(3-dimethylaminopropyl)-carbodiimide hydrochloride) (Tokyo Chemical Industry Co., Ltd., Japan) aqueous solution (0.25 mol/L) and 1 mL of NG-DSPE solution (2 mmol/L) containing 2% (w/v) of OG (n-octyl-D-glucopyranoside) (Wako Pure Chemical Industries, Ltd., Japan) in 50 mmol/L MES buffer (pH 5.5) were mixed and stirred for 10 minutes.

Surplus reagents were eliminated by Sephadex G-15 column (1.5 cm×20 cm, 0.1% (w/v) of OG in 50 mmol/L HEPES buffer (pH 8.0), GE Healthcare Bio-Sciences Corp., USA) and fractioned to about 1 mL/tube.

5 mL of 1% transferrin (Sigma, USA) aqueous solution was added dropwise to the fractions containing NG-DSPE and stirred gently for 20 hours at 4° C. Identification was by MS determination of each fraction.

The reaction product was then fractioned to about 1.7 mL/tube by TOYOPEARL HW-55S column (1.5 cm×45 cm, 0.9% NaCl, Tosoh Bioscience LLC, USA). Tf-NG-DSPE was estimated by mass spectrometry (MALDI-TOF/MS) and SDS-PAGE with CBB (Coomasie Brilliant Blue, Wako Pure Chemical Industries, Ltd., Japan) staining.

What is claimed is:

1. A targeted liposome comprising one or more phosphatidylcholines, an N-(ω)-dicarboxylic acid-derivatized phosphatidyl ethanolamine, a targeting factor-modified N-(ω)-dicarboxylic acid-derivatized phosphatidyl ethanolamine, an encapsulated drug, and at least one additional lipid, which is cholesterol,
wherein the mol % of the phosphatidylcholines is 40-60 mol %, the mol % of the cholesterol is 35-55 mol %, and the mol % of the total of the N-(ω)-dicarboxylic acid-derivatized phosphatidyl ethanolamine plus targeting factor-modified N-(ω)-dicarboxylic acid-derivatized phosphatidyl ethanolamine is 2-8 mol %, where the total mol % of the phosphatidylcholines, the cholesterol, and the derivatized phosphatidylethanolamines is 100%
wherein the targeting factor-modified N-(ω)-dicarboxylic acid-derivatized phosphatidyl ethanolamine comprises transferrin linked to a second N-(ω)-dicarboxylic acid-derivatized phosphatidyl ethanolamine; and
wherein
the N-(ω)-dicarboxylic acid-derivatized phosphatidyl ethanolamine is represented by Formula 1, Formula 1
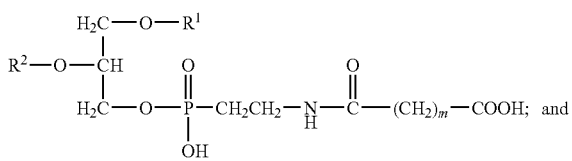

the second N-(ω)-dicarboxylic acid-derivatized phosphatidyl ethanolamine is represented by Formula 3, Formula 3
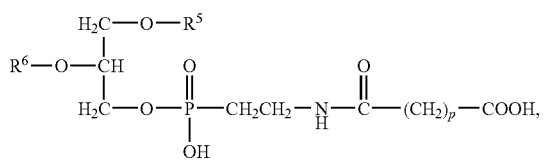

wherein $R^1$, $R^2$, $R^5$ and $R^6$ are each an acyl group,
wherein the acyl groups are acyl groups from saturated or unsaturated aliphatic carboxylic acids having 18-22 carbon atoms, and
wherein $R^1$ and $R^2$ are the same, and $R^5$ and $R^6$ are the same; and
m and p are, independently, an integer from 1 to 10; and,
wherein the targeted liposomes contains from about 10 μg transferrin/mg lipid to about 50 μg transferrin/mg lipid; and,
wherein the liposome does not comprise a non-derivatized phosphatidyl ethanolamine, egg phosphatidylcholine, or a hydrophilic polymer used to enhance the circulatory half-life of liposomes.

2. The targeted liposome of claim 1, wherein the targeted liposome contains from about 10 μg transferrin/mg lipid to about 25 μg transferrin/mg lipid.

3. The targeted liposome of claim 1, wherein the total mol % of N-(ω)-dicarboxylic acid-derivatized phosphatidyl ethanolamine and targeting factor-modified N-(ω)-dicarboxylic acid-derivatized phosphatidyl ethanolamine is 2-6 mol % of total lipid content.

4. The targeted liposome of claim 1, wherein the phosphatidylcholine includes a moiety of a saturated fatty acid.

5. The targeted liposome of claim 1, wherein the one or more phosphatidylcholines is DMPC, DSPC, POPC or DPPC.

6. The targeted liposome of claim 1, wherein the liposome comprises DMPC.

7. The targeted liposome according to claim 1, wherein the transferrin is in a holo-form but not in an apo-form.

8. The targeted liposome according to claim 1, wherein the mean diameter of the liposome is from about 9 nm to about 250 nm.

9. The targeted liposome of claim 1, wherein $R^1$, $R^2$, $R^5$ and $R^6$ are oleoyl or stearoyl, and m and p are 3.

10. The targeted liposome of claim 9, wherein the drug is an anticancer agent.

11. The targeted liposome of claim 9, wherein the one or more phosphatidylcholines is DMPC or DSPC.

12. The targeted liposome of claim 9, wherein $R^1$, $R^2$, $R^5$ and $R^6$ are oleoyl.

13. The targeted liposome of claim 1, wherein m and p are each, independently, an integer from 2 to 4.

14. The targeted liposome of claim 1, wherein m and p are equal and are an integer from 2 to 4.

15. The targeted liposome of claim 13, wherein m and p are equal and are 3.

16. The targeted liposome of claim 1, wherein $R^1$, $R^2$, $R^5$ and $R^6$ are oleoyl or stearoyl.

17. The targeted liposome of claim 1, wherein $R^1$, $R^2$, $R^5$ and $R^6$ are the same.

18. The targeted liposome of claim 1, wherein the drug is oxaliplatin.

19. The targeted liposome according to claim 1, wherein the drug is an anticancer agent.

20. The targeted liposome according to claim 1, wherein the drug is a cytotoxic drug.

21. The targeted liposome according to claim 1, wherein the drug is a topoisomerase I inhibitor.

22. The targeted liposome according to claim 21, wherein the topoisomerase I inhibitor is topotecan or irinotecan.

23. The targeted liposome according to claim 1, wherein the drug is a vinca alkaloid.

24. The targeted liposome according to claim 23, wherein the vinca alkaloid is vincristine, vinblastine, vinleurosine, vinrodisine, vinorelbine or vindesine.

25. The targeted liposome according to claim 1, wherein the drug is a nucleic acid.

26. The targeted liposome according to claim 25, wherein the nucleic acid is an antisense oligonucleotide or a ribozyme.

27. The targeted liposome according to claim 1, wherein the drug is a platinum compound.

28. The targeted liposome according to claim 17, wherein the platinum compound is biplatin, cisplatin, carboplatin, ormaplatin, oxaliplatin, zeniplatin, enloplatin, lobaplatin or spiroplatin.

29. The targeted liposome according to claim 28, wherein the platinum compound is oxaliplatin.

30. The targeted liposome according to claim 29, wherein $R^1$, $R^2$, $R^5$ and $R^6$ are oleoyl, m and p are 3, and the one or more phosphatidylcholines is DMPC.

31. The targeted liposome of claim 30, wherein the targeted liposome contains from about 10 μg transferrin/mg lipid to about 25 μg transferrin/mg lipid.

32. The targeted liposome of claim 30, wherein the total mol % of N-(ω)-dicarboxylic acid-derivatized phosphatidyl ethanolamine and targeting factor-modified N-(ω)-dicarboxylic acid-derivatized phosphatidyl ethanolamine is 2-6 mol % of total lipid content.

33. The targeted liposome according to claim 1, wherein the drug is an alkylating agent.

34. The targeted liposome according to claim 1, wherein the drug is a taxane.

35. The targeted liposome according to claim 1, wherein the drug is a metabolic antagonist.

36. The targeted liposome according to claim 1, wherein the drug is an antitumour antibiotic.

37. The targeted liposome according to claim 1, wherein the drug is a hormone therapy drug.

38. The targeted liposome according to claim 1, wherein the drug is a molecular target drug.

39. The targeted liposome according to claim 29, wherein the oxaliplatin is dissolved in an aqueous solution of a sugar selected from the group consisting of trehalose, maltose, sucrose, mannose, lactose, mannitol, glycerol and dextrose.

40. The targeted liposome of claim 39, wherein the sugar is at a concentration of about 300 mM sugar.

41. The targeted liposome of claim 39, wherein the concentration of oxaliplatin is from about 0.1 mg/ml to about 25 mg/ml within the liposome.

42. The targeted liposome of claim 29, wherein the transferrin is in a holo-form.

43. The targeted liposome claim 1, wherein the liposome does not comprise a cationic lipid.

44. The targeted liposome of claim 1, wherein the liposome does not comprise an anionic lipid.

45. A targeted liposome comprising one or more phosphatidylcholines, an N-(ω)-dicarboxylic acid-derivatized phosphatidyl ethanolamine, a targeting factor-modified N-(ω)-dicarboxylic acid-derivatized phosphatidyl ethanolamine, an encapsulated drug, and, at least one additional lipid which is cholesterol,
wherein the mol % of the phosphatidylcholines is 40-60 mol %, the mol % of the cholesterol is 35-55 mol %, and the mol % of the total of the N-(ω)-dicarboxylic acid-derivatized phosphatidyl ethanolamine plus targeting factor-modified N-(ω)-dicarboxylic acid-derivatized phosphatidyl ethanolamine is 2-8 mol %, where the total mol % of the phosphatidylcholines, the cholesterol, and the derivatized phosphatidylethanolamines is 100% wherein the targeting factor-modified N-(ω)-dicarboxylic acid-derivatized phosphatidyl ethanolamine comprises a transferrin linked to a second N-(ω)-dicarboxylic acid-derivatized phosphatidyl ethanolamine; and wherein the N-(ω)-dicarboxylic acid-derivatized phosphatidyl ethanolamine is represented by Formula 1, Formula 1

$$\begin{array}{c} H_2C-O-R^1 \\ R^2-O-CH \quad O \quad\quad O \\ H_2C-O-\overset{\|}{\underset{OH}{P}}-O-CH_2CH_2-\underset{H}{N}-\overset{\|}{C}-(CH_2)_m-COOH; \end{array}$$ and the second N-(ω)-dicarboxylic acid-derivatized phosphatidyl ethanolamine is represented by Formula 3, Formula 3

$$\begin{array}{c} H_2C-O-R^5 \\ R^6-O-CH \quad O \quad\quad O \\ H_2C-O-\overset{\|}{\underset{OH}{P}}-O-CH_2CH_2-\underset{H}{N}-\overset{\|}{C}-(CH_2)_p-COOH, \end{array}$$

wherein $R^1$, $R^2$, $R^5$ and $R^6$ are each an acyl group,
wherein $R^1$ and $R^2$ are the same, and $R^5$ and $R^6$ are the same,
wherein $R^1$, $R^2$, $R^5$ and $R^6$ are not palmitoyl or myristoyl; and
m and p are, independently, an integer from 1 to 10; and,
wherein the targeted liposomes contains from about 10 μg transferrin/mg lipid to about 50 μg transferrin/mg lipid; and,
wherein the liposome does not comprise a non-derivatized phosphatidyl ethanolamine, egg phosphatidylcholine, or a hydrophilic polymer used to enhance the circulatory half-life of liposomes.

46. The targeted liposome of claim 45, wherein the targeted liposome contains from about 10 μg transferrin/mg lipid to about 25 μg transferrin/mg lipid.

47. The targeted liposome of claim 45, wherein the total mol % of N-(ω)-dicarboxylic acid-derivatized phosphatidyl ethanolamine and targeting factor-modified N-(ω)-dicarboxylic acid-derivatized phosphatidyl ethanolamine is from about 2 to about 6 mol % of total lipid content.

48. A pharmaceutical formulation comprising a targeted liposome according to claim 1 and one or more pharmaceutically acceptable carriers, excipients, diluents, stabilizers, or preservatives.

* * * * *